(12) United States Patent
Kreutzer et al.

(10) Patent No.: US 7,829,693 B2
(45) Date of Patent: Nov. 9, 2010

(54) COMPOSITIONS AND METHODS FOR INHIBITING EXPRESSION OF A TARGET GENE

(75) Inventors: Roland Kreutzer, Weidenberg (DE); Stefan Limmer, Kulmbach (DE); Sylvia Limmer, Kulmbach (DE); Philipp Hadwiger, Altenkunstadt (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1791 days.

(21) Appl. No.: 10/384,339

(22) Filed: Mar. 7, 2003

(65) Prior Publication Data

US 2004/0175703 A1    Sep. 9, 2004

Related U.S. Application Data

(63) Continuation-in-part of application No. 09/889,802, filed as application No. PCT/DE00/00244 on Jan. 29, 2000, now abandoned, application No. 10/384,339, which is a continuation-in-part of application No. PCT/EP02/00152, filed on Jan. 9, 2002.

(30) Foreign Application Priority Data

| Nov. 24, 1999 | (DE) | ................................ | 199 56 568 |
| Jan. 9, 2001 | (DE) | ................................ | 101 00 586 |
| Oct. 26, 2001 | (DE) | ................................ | 101 55 280 |
| Nov. 29, 2001 | (DE) | ................................ | 101 58 411 |
| Dec. 7, 2001 | (DE) | ................................ | 101 60 151 |

(51) Int. Cl.
C12Q 1/68 (2006.01)
C12N 15/88 (2006.01)
C07H 21/02 (2006.01)
C07H 21/04 (2006.01)

(52) U.S. Cl. .......................... 536/24.5; 435/6; 435/91.1; 435/91.31; 435/455; 435/458; 536/23.1; 536/24.31

(58) Field of Classification Search .................... 435/6, 435/91.1, 91.31, 455, 458; 536/23.1, 24.5, 536/24.31; 514/44

See application file for complete search history.

(56) References Cited

U.S. PATENT DOCUMENTS

| 4,309,492 | A | 1/1982 | Bernard | ....................... | 429/161 |
| 5,112,734 | A | 5/1992 | Kramer et al. | | |
| 5,225,347 | A | 7/1993 | Goldberg et al. | | |
| 5,246,921 | A | 9/1993 | Reddy et al. | | |
| 5,340,318 | A | 8/1994 | Kunihiro | ....................... | 439/66 |
| 5,472,802 | A | 12/1995 | Holland et al. | ................. | 429/54 |
| 5,496,698 | A | 3/1996 | Draper et al. | | |
| 5,525,468 | A | 6/1996 | McSwiggen | | |
| 5,574,142 | A | 11/1996 | Meyer, Jr. et al. | | |
| 5,616,459 | A | 4/1997 | Kramer et al. | | |
| 5,635,385 | A | 6/1997 | Leopold et al. | | |
| 5,639,655 | A | 6/1997 | Thompson et al. | | |
| 5,712,257 | A | 1/1998 | Carter | | |
| 5,811,275 | A | 9/1998 | Wong-Staal et al. | | |
| 5,811,300 | A | 9/1998 | Sullivan et al. | | |
| 5,814,500 | A | 9/1998 | Dietz | | |
| 5,824,519 | A | 10/1998 | Norris et al. | | |
| 5,837,510 | A | 11/1998 | Goldsmith et al. | | |
| 5,854,067 | A | 12/1998 | Newgard et al. | | |
| 5,864,028 | A | 1/1999 | Sioud | | |
| 5,866,701 | A | 2/1999 | Hampel et al. | | |
| 5,891,717 | A | 4/1999 | Newgard et al. | | |
| 5,898,031 | A | 4/1999 | Crooke | | |
| 5,908,779 | A | 6/1999 | Carmichael et al. | | |
| 5,939,262 | A | 8/1999 | Pasloske et al. | | |
| 5,968,737 | A | 10/1999 | Ali-Osman et al. | | |
| 5,985,620 | A | 11/1999 | Sioud | | |
| 6,057,156 | A | 5/2000 | Akhtar et al. | | |
| 6,071,890 | A | 6/2000 | Scheule et al. | | |
| 6,077,705 | A | 6/2000 | Duan et al. | | |

(Continued)

FOREIGN PATENT DOCUMENTS

CA    2334951    12/1999

(Continued)

OTHER PUBLICATIONS

Agrawal, S. et al., Molecular Med. Today, vol. 6, pp. 72-81 (2002).*

(Continued)

*Primary Examiner*—Jane Zara
(74) *Attorney, Agent, or Firm*—Fenwick & West LLP

(57) ABSTRACT

The present invention relates to a double-stranded ribonucleic acid (dsRNA) having a nucleotide sequence which is substantially identical to at least a part of a target gene and which is no more than 49, preferably less than 25, nucleotides in length, and which comprises a complementary (antisense) RNA strand having a 1 to 4 nucleotide overhang at the 3'-end and a blunt 5'-end. The invention further relates to a pharmaceutical composition comprising the dsRNA and a pharmaceutically acceptable carrier. The pharmaceutical compositions are useful for inhibiting the expression of a target gene, as well as for treating diseases caused by expression of the target gene, at low dosages (i.e., less than 5 milligrams, preferably less than 25 micrograms, per kg body weight per day). The invention also relates to methods for inhibiting the expression of a target gene, as well as methods for treating diseases caused by the expression of the gene.

6 Claims, 20 Drawing Sheets

U.S. PATENT DOCUMENTS

| | | | |
|---|---|---|---|
| 6,080,851 A | 6/2000 | Pachuk et al. | |
| 6,087,164 A | 7/2000 | Hochberg et al. | |
| 6,087,172 A | 7/2000 | Veerapaneni et al. | |
| 6,099,823 A | 8/2000 | Falb | |
| 6,100,087 A | 8/2000 | Rossi et al. | |
| 6,100,444 A | 8/2000 | Frelinger et al. | |
| 6,107,094 A | 8/2000 | Crooke | |
| 6,183,959 B1 | 2/2001 | Thompson | |
| 6,187,585 B1 * | 2/2001 | Bennett et al. | 435/375 |
| 6,224,868 B1 * | 5/2001 | Wong et al. | 424/184.1 |
| 6,225,291 B1 | 5/2001 | Lewin et al. | |
| 6,245,560 B1 | 6/2001 | Lisziewicz | |
| 6,245,748 B1 | 6/2001 | Wellstein et al. | |
| 6,255,071 B1 | 7/2001 | Beach et al. | |
| 6,346,398 B1 | 2/2002 | Pavco et al. | |
| 6,355,415 B1 | 3/2002 | Wagner et al. | |
| 6,410,176 B1 | 6/2002 | Genc et al. | 429/13 |
| 6,423,489 B1 | 7/2002 | Anderson et al. | 435/6 |
| 6,482,803 B1 | 11/2002 | Roth et al. | |
| 6,486,299 B1 | 11/2002 | Shimkets | 530/350 |
| 6,506,559 B1 | 1/2003 | Driver et al. | 435/6 |
| 6,573,046 B1 | 6/2003 | Kmiec et al. | |
| 2002/0086356 A1 | 7/2002 | Tuschl et al. | 435/69.1 |
| 2002/0114784 A1 | 8/2002 | Li et al. | 424/93.2 |
| 2002/0123034 A1 | 9/2002 | Canaani et al. | 435/4 |
| 2002/0132346 A1 | 9/2002 | Cibelli | 435/455 |
| 2002/0162126 A1 | 10/2002 | Beach et al. | 800/8 |
| 2002/0173478 A1 | 11/2002 | Gewirtz | 514/44 |
| 2003/0027783 A1 | 2/2003 | Zernicka-Goetz et al. | 514/44 |
| 2003/0108923 A1 | 6/2003 | Tuschl et al. | 435/6 |
| 2003/0125281 A1 | 7/2003 | Lewis et al. | 514/44 |
| 2003/0143732 A1 | 7/2003 | Fosnaugh et al. | 435/325 |
| 2003/0148341 A1 | 8/2003 | Sin et al. | 435/6 |
| 2003/0157030 A1 | 8/2003 | Davis et al. | 424/46 |
| 2003/0176671 A1 | 9/2003 | Reed et al. | 536/23.1 |
| 2003/0180756 A1 | 9/2003 | Shi et al. | 435/6 |
| 2003/0190635 A1 | 10/2003 | McSwiggen | 435/6 |
| 2003/0198627 A1 | 10/2003 | Arts et al. | 424/93.21 |

FOREIGN PATENT DOCUMENTS

| | | |
|---|---|---|
| DE | 196 18 797 | 11/1997 |
| DE | 196 31 919 | 7/1998 |
| DE | 199 56 568 A1 | 11/1999 |
| DE | 200 23 125 U1 | 1/2000 |
| DE | EP 1 214 945 A2 | 1/2000 |
| DE | 19956568 | 8/2000 |
| DE | 101 00 588 A1 | 1/2001 |
| DE | 10100586 | 1/2001 |
| DE | 10155280 | 10/2001 |
| DE | 10158411 | 11/2001 |
| DE | 101 63 098 A1 | 12/2001 |
| DE | 101 00 586 C1 | 4/2002 |
| DE | 102 30 966 A1 | 7/2002 |
| DE | 102 30 997 A1 | 7/2002 |
| DE | 101 00 587 C1 | 11/2002 |
| DE | 10163098 | 4/2003 |
| EP | 1 001 666 A2 | 5/2000 |
| EP | 00126325.0 | 1/2001 |
| EP | 1 107 340 A2 | 6/2001 |
| WO | WO 92/19732 | 11/1992 |
| WO | WO 94/01550 | 1/1994 |
| WO | WO 98/05770 | 2/1998 |
| WO | WO 98/53083 | 11/1998 |
| WO | WO 99/15682 | 4/1999 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 00/01846 | 1/2000 |
| WO | WO 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A2 | 2/2002 |
| WO | WO 02/26780 A2 | 4/2002 |
| WO | WO 02/44321 * | 6/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A2 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A2 | 2/2003 |
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |

OTHER PUBLICATIONS

Branch, A.D., Trends in Biochem. Sci., vol. 23, pp. 45-50 (1998).*
Crooke, S.T., Antisense Research & Application, Chapter 1, pp. 1-50, Ed. by S. Crooke, Publ. by Springer-Verlag (1998).*
Peracchi, A., Rev. Med. Virol., vol. 14, pp. 47-64 (2003).*
Chirila, T.V. et al., Biomaterials, vol. 23, pp. 321-342 (2002).*
Opalinska, J.B. et al., Nature Reviews, vol. 1, pp. 503-514 (2002).*
Zamore et al., Cell, vol. 101, pp. 25-33 (2000).*
Elbashir et al (Nature, vol. 411, pp. 494-498 (2001).*
Z-Axis Connector Company, Silver STAX, www.z-axiscc.com/prodstax.htm, Accessed Jul. 19, 2001.
Z-Axis Connector Company, LCD Connectors, www.z-axiscc.com/prodlcd.htm, Accessed Jul. 19, 2001.
Holen, T. et al., (2002), "Positional effects of short interfering RNAs targeting the human coagulation trigger Tissue Factor", *Nucleic Acids Research*, 30(8):1757-1766.
Ambros, V., (2001), "Dicing Up RNAs", *Science*, 293:811-813.
Elbashir, S.M. et al., (2001), "Duplexes of 21-nucleotide RNAs mediate RNA interference in cultured mammalian cells", *Nature*, 411:494-498.
Gautschi, O. et al., (2001), "Activity of a Novel bcl-2/bcl-xL-Bispecific Antisense Oligonucleotide Against Tumors of Diverse Histologic Origins", *Journal of the National Cancer Institute*, 93(6):463-471.
Lipardi, C. et al., (2001), "RNAi as Random Degradative PCR: siRNA Primers Convert mRNA into dsRNAs that Are Degraded to Generate New siRNAs", *Cell*, 107:297-307.
Sharp, P.A., (2001), "RNA interference—2001", *Genes & Development*, 15:485-490.
Sijen, T. et al., (2001), "On the Role of RNA Amplification in dsRNA-Triggered Gene Silencing", *Cell*, 107:465-476.

Bass, B.L., (2000), "Double-Stranded RNA as a Template for Gene Silencing", *Cell*, 101:235-238.

Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.

Hammond, S.M. et al., (2000), "An RNA-directed nuclease mediates post-transcriptional gene silencing in Drosophila cells", *Nature*, 404:293-296.

Yang, D. et al., (2000), "Evidence that processed small dsRNAs may mediate sequence-specific mRNA degradation during RNAi in Drosophila embryos", *Current Biology*, 10:1191-1200.

Wianny, F. et al., (2000), "Specific interference with gene function by double-stranded RNA in early mouse development", *Nature Cell Biology*, 2:70-75.

Zamore, P.D. et al., (2000), "RNAi: Double-Stranded RNA Directs the ATP-Dependent Cleavage of mRNA at 21 to 23 Nucleotide Intervals", *Cell*, 101:25-33.

Fire, A., (1999), "RNA-triggered gene silencing", *TIG*, 15(9):358-363.

Tuschl, T. et al., (1999), "Targeted mRNA degradation by double-stranded RNA in vitro", *Genes & Development*, 13:3191-3197.

Wild, K. et al., (1999), "The 2 Å structure of helix 6 of the human signal recognition particle RNA", *Structure*, (11):1345-1352.

Montgomery, M.K. et al., (1998), "Double-stranded RNA as a mediator in sequence-specific genetic silencing and co-suppression", *TIG*, 14(7):255-258.

Lowy, D.R. et al., (1993), "Function and Regulation of RAS", *Annu. Rev. Biochem.*, 62:851-891.

Downward, J. et al., (1990), "Identification of a nucleotide exchange-promoting activity for p21$^{ras}$", *Proc. Natl. Acad. Sci. USA*, 87:5998-6002.

Gibbs, J.B. et al., (1988), "Purification of ras GTPase activating protein from bovine brain", *Proc. Natl. Acad. Sci. USA*, 85:5026-5030.

Caplen, N.J., (2002), "A new approach to the inhibition of gene expression", *TRENDS in Biotechnology*, 20(2):49-51.

Caplen, N.J. et al., (2001), "Specific inhibition of gene expression by small double-stranded RNAs in invertebrate and vertebrate systems", *Proc. Natl. Acad. Sci. USA*, 98(17):9742-9747.

Doench, J.G. et al., (2003), "siRNAs can function as miRNAs", *Genes & Development*, 17:438-442.

Donzé, O. et al., (2002), "RNA interference in mammalian cells using siRNAs synthesized with T7 RNA Polymerase", *Nucleic Acids Research*, 30(10):e46(4pages).

Elbashir, S.M. et al., (2001), "RNA interference is mediated by 21- and 22-nucleotide RNAs", *Genes & Development*, 15:188-200.

Elbashir, S.M. et al., (2001), "Functional anatomy of siRNAs for mediating efficient RNAi in Drosophila melanogaster embryo lysate", *The EMBO Journal*, 20(23):6877-6888.

Fire, A. et al., (1998), "Potent and specific genetic interference by double-stranded RNA in Caenorhabditis elegans", *Nature*, 391:806-811.

Harborth, J. et al., (2001), "Identification of essential genes in cultured mammalian cells using small interfering RNAs", *Journal of Cell Science*, 114(24):4557-4565.

Lewis, D.L. et al., (2002), "Efficient delivery of siRNA for inhibition of gene expression in postnatal mice", *Nature Genetics*, 32:107-108.

Manche, L. et al., (1992), "Interactions between Double-Stranded DNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ngô, H. et al., (1998), "Double-stranded RNA induces mRNA degradation in Trypanosoma brucei", *Proc. Natl. Acad. Sci.*, 95:14687-14692.

Paddison, P.J. et al., (2002), "Short hairpin RNAs (shRNAs) induce sequence-specific silencing in mammalian cells", *Genes & Development*, 16:948-958.

Randall, G. et al., (2003), "Clearance of replicating hepatitis C virus replicon RNAs in cell culture by small interfering RNAs", *PNAS*, 100(1):235-240.

Tijsterman, M. et al., (2002), "The Genetics of RNA Silencing", *Annu. Rev. Genet.*, 36:489-519.

Yu, J. et al., (2002), "RNA interference by expression of short-interfering RNAs and hairpin RNAs in mammalian cells", *PNAS*, 99(9):6047-6052.

English Abstract of DE 101 00 587 C1.

Uhlmann, E. et al. Jun. 1, 1990, "Antisense Nucleotides: A New Therapeutic Principal" Chemical Reviews, American Chemical Society, Easton, US vol. 90, No. 4, pp. 543-584, ISSN:0009-2665.

Parrish S. et al. Nov. 2000, Functional Anatomy of a dsRNA Trigger: Differential Requirement for the Two Trigger Strands in RNA Interference, Molecular Cell, vol. 6, 1077-87.

Jiang and Milner, "Selective silencing of viral gene expression in HPV-positive human cervical carcinoma cells treated with siRNA, a primer of RNA interference" *Oncogene* 21:6041-6048 (2002).

Martinez et al., "Synthetic small inhibiting RNAs: Efficient tools to inactivate oncogenic mutations and restore p53 pathways" *Proc. Nat. Acad. Sc.* 99:14849-14854 (2002).

Reynolds et al., "Rational siRNA Design for RNA Interference" *Nature Biotechnology* 22:326-330 (2004).

Spänkuch-Schmitt et al., "Effect of RNA Silencing of Polo-Like Kinase-1 (PLK1) on Apoptosis and Spindle Formation in Human Cancer Cells" *J. Nat. Cancer Inst.* 94:1863-1877 (2002).

Agrawal et al., "Self-Stabilized Oligonucleotides as Novel Antisense Agents," *Delivery Strategies for Antisense Oligonucleotide Therapeutics*, Edited by Saghir Akhtar, CRC Press, pp. 105-121 (1995).

Alfonzo et al., "The mechanism of U insertion/deletion RNA editing in kinetoplastid mitochondria" *Nucleic Acids Res.* 25:3751-3759 (1997).

Anderson et al., "Human gene therapy" *Nature* 392:25-30 (1998).

Asanuma et al., "Photoregulation of the Formation and Dissociation of a DNA Duplex by Using the *cis-trans* Isomerization of Azobenzene" *Angew. Chem. Int. Ed.* 38:2393-2395 (1999).

Azhayeva et al., "Inhibitory properties of double helix forming circular oligonucleotides" *Nucleic Acids Res.* 25:4954-4961 (1997).

Bahramian et al., "Transcriptional and Posttranscriptional Silencing of Rodent α1(I) Collagen by a Homologous Transcriptionally Self-Silenced Transgene" *Mol. Cell. Biol.* 19:274-283 (1999).

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras" *Proc. Natl. Acad. Sci. USA* 95:11047-11052 (1998).

Bhan et al., "2',5'-Linked oligo-3'-deoxyribonucleoside phosphorothioate chimeras: thermal stability and antisense inhibition of gene expression" *Nucleic Acids Res.* 25:3310-3317 (1997).

Billy et al., "Specific interference with gene expression induced by long, double-stranded RNA in mouse embryonal teratocarcinoma cell lines" *Proc. Natl. Acad. Sci. USA* 98:14428-14433 (2001).

Borecky et al., "Therapeutic use of double-stranded RNAs in man" *Tex. Rep. Biol. Med.* 41:575-581 (1981-1982) (Abstract only).

Braich et al., "Regiospecific Solid-Phase Synthesis of Branched Oligonucleotides. Effect of Vicinal 2',5'- (or 2',3'-) and 3',5'-Phosphodiester Linkages on the Formation of Hairpin DNA" *Bioconjug. Chem.* 8:370-377 (1997).

Castelli et al., "The 2-5A system in viral infection and apoptosis" *Biomed. Pharmacother*. 52:386-390 (1998).

Czauderna et al., "Structural variations and stabilizing modifications of synthetic siRNAs in mammalian cells," *Nucleic Acids Res.*, 31(1):1-12 (2003).

Dolinnaya et al., "Oligonucleotide circularization by template-directed chemical ligation" *Nucleic Acids Res.*, 21:5403-5407 (1993).

Expert-Bezançon et al., "Precise localization of several covalent RNA-RNA cross-link in *Escherichia coli* 16S RNA" *Eur. J. Biochem.* 136:267-274 (1983).

Fire et al., "Production of antisense RNA leads to effective and specific inhibition of gene expression in *C. elegans* muscle" *Development* 113:503-514 (1991).

Gao et al., "Circularization of oligonucleotides by disulfide bridge formation" *Nucleic Acids Res.*, 23:2025-2029 (1995).

Grasby et al., "Purine Functional Groups in Essential Residues of the Hairpin Ribozyme Required for Catalytic Cleavage of RNA" *Biochemistry* 34:4068-4076 (1995).

Griffey et al., "2'-O-Aminopropyl Ribonucleotides: A Zwitterionic Modification That Enhances the Exonuclease Resistance and Biological Activity of Antisense Oligonucleotides" *J. Med. Chem.* 39:5100-5109 (1996).

Gryaznov et al., "Template controlled coupling and recombination of oligonucleotide blocks containing thiophosphoryl groups" *Nucleic Acids Res.* 21:1403-1408 (1993).

Ha et al., "A bulged *lin-4/lin-14* RNA duplex is sufficient for *Caenorhabditis elegans lin-14* temporal gradient formation" *Genes & Development* 10:3041-3050 (1996).

Hamilton et al., "A Species of Small Antisense RNA in Post-transcriptional Gene Silencing in Plants" *Science* 286:950-952 (1999).

Harfe et al., "Analysis of a *Caenorhabditis elegans* Twist homolog identifies conserved and divergent aspects of mesodermal patterning" *Genes Dev.* 12:2623-2635 (1998).

Hoke et al., "Effects of phosphorothioate capping on antisense oligonucleotide stability, hybridization and antiviral efficacy versus herpes simplex infection" *Nucleic Acids Res.* 19:5743-5748 (1991).

Horn et al., "Chemical synthesis and characterization of branched oligodeoxyribonucleotides (bDNA) for use as signal amplifiers in nucleic acid quantification assays" *Nucleic Acids Res.* 25:4842-4849 (1997).

Hunter, "Genetics: A touch of elegance with RNAi" *Curr. Biol.* 9:R440-R442 (1999).

"Introduction of DNA into Mammalian Cells," *Current Protocols in Molecular Biology*, Supplement 48, Edited by Frederick M. Ausubel et al., John Wiley & Sons, Inc., pp. 9.4.7-9.4.8 (1999).

Iwase et al., "Gene regulation by decoy approach (I): synthesis and properties of photo-crosslinked oligonucleotides" *Nucleic Acids Symp. Ser.* 37:203-204 (1997).

Jacobs et al., "When Two Strands Are Better Than One: The Mediators and Modulators of the Cellular Responses to Double-Stranded RNA" *Virology* 219:339-349 (1996).

Jäschke et al., "Synthesis and Analytical Characterization of RNA-Polyethylene Glycol Conjugates" *Nucleosides & Nucleotides* 15:1519-1529 (1996).

Kaufman, "Double-stranded RNA-activated protein kinase mediates virus-induced apoptosis: A new role for an old actor" *Proc. Natl. Acad. Sci. USA* 96:11693-11695 (1999).

Kennerdell et al., "Use of dsRNA-Mediated Genetic Interference to Demonstrate that *frizzled* and *frizzled 2* Act in the Wingless Pathway" *Cell* 95:1017-1026 (1998).

Kreutzer et al., "Specific inhibition of viral gene expression by double-stranded RNA in vitro" *Annual Fall Meeting of the GBH*, Abstract for Poster Paper No. 328, p. S169 (1999).

Kumar et al., "Antisense RNA: function and fate of duplex RNA in cells of higher eukaryotes" *Microbiol. Mol. Biol. Rev.* 62:1415-1434 (1998).

Lee et al., "The *C. elegans* Heterochronic Gene *lin-4* Encodes Small RNAs with Antisense Complementarity to *lin-14*" *Cell* 75:843-854 (1993).

Li et al., "Double-stranded RNA injection produces null phenotypes in zebrafish" *Dev. Biol.* 210:238, Abstract No. 346 (1999).

Lin et al., "Policing rogue genes" *Nature* 402:128-129 (1999).

Lipinski et al., "Experimental and computational approaches to estimate solubility and permeability in drug discovery and development settings" *Adv. Drug Deliv. Rev.* 23:3-25 (1997).

Lipson et al., "Psoralen Cross-Linking of Ribosomal RNA" *Methods Enzymol.* 164:330-341 (1988).

Liu et al., "Detection of a Novel ATP-Dependent Cross-Linking Protein at the 5' Splice-Site U1 Small Nuclear RNA Duplex by Methylene Blue-Mediated Photo-Cross-Linking" *Mol. Cell. Biol.* 18:6910-6920 (1998).

Ma et al., "Design and Synthesis of RNA Miniduplexes via a Synthetic Linker Approach", *Biochemistry* 32:1751-1758 (1993).

Majumdar et al., "Targeted gene knockout mediated by triple helix forming oligonucleotides" *Nat. Genet.* 20:212-214 (1998).

Micura et al., "Cyclic Oligoribonucleotides (RNA) by Solid-Phase Synthesis" *Chem. Eur. J.* 5:2077-2082 (1999).

Milhaud et al., "Free and Liposome-Encapsulated Double-Stranded RNAs as Inducers of Interferon, Interleukin-6, and Cellular Toxicity" *J. Interferon Res.*, 11:261-265 (1991).

Minks et al., "Structural Requirements of Double-stranded RNA for the Activation of 2',5'Oligo(A) Polymerase and Protein Kinase of Interferon-treated HeLa Cells" *J. Biol. Chem.* 254(20):10180-10183 (1979).

Misquitta et al., "Targeted disruption of gene function in *Drosophila* by RNA interference (RNA-i): A role for *nautilus* in embryonic somatic muscle formation" *Proc. Natl. Acad. Sci. USA* 96:1451-1456 (1999).

Montgomery et al., "RNA as a target of double-stranded RNA-mediated genetic interference in *Caenorhabditis elegans*" *Proc. Natl. Acad. Sci. USA* 95:15502-15507 (1998).

Moss et al., "The Cold Shock Domain Protein LIN-28 Controls Developmental Timing in *C. elegans* and Is Regulated by the *lin-4* RNA" *Cell* 88:637-646 (1997).

Nielsen et al., "A novel class of conformationally restricted oligonucleotide analogues: synthesis of 2',3'-bridged monomers and RNA-selective hybridization" *Chem. Commun.* pp. 825-826 (1997).

Nikiforov et al., "Oligodeoxynucleotides containing 4-thiothymidine and 6-thiodeoxyguanosine as affinity labels for the Eco RV restriction endonuclease and modification methylase" *Nucleic Acids Res.* 20:1209-1214 (1992).

Pegram et al., "Phase II Study of Receptor-Enhanced Chemosensitivity Using Recombinant Humanized Anti-p185$^{HER2}$/*neu* Monoclonal Antibody Plus Cisplatin in Patients With HER2/*neu*-Overexpressing Metastatic Breast Cancer Refractory to Chemotherapy Treatment" *J. Clin. Oncol.* 16:2659-2671 (1998).

Seydoux et al., "Repression of gene expression in the embryonic germ lineage of *C. elegans*" *Nature* 382:713-716 (1996).

Sharp et al., "RNAi and double-strand RNA" *Genes Dev.* 13:139-141 (1999).

Shi et al., "A CBP/p300 homolog specifies multiple differentiation pathways in *Caenorhabditis elegans*" *Genes Dev.* 12:943-955 (1998).

Skripkin et al., "Psoralen crosslinking between human immunodeficiency virus type 1 RNA and primer tRNA$_3^{Lys}$" *Nucleic Acids Res.* 24:509-514 (1996).

Strauss, "Candidate 'Gene Silencers' Found" *Science* 286:886 (1999).

Thompson, "Shortcuts from gene sequence to function" *Nature* 17:1158-1159 (1999).

Timmons et al., "Specific interference by ingested dsRNA" *Nature* 395:854 (1998).

Verma et al., "Gene therapy—promises, problems and prospects" *Nature* 389:239-242 (1997).

Voinnet et al., "Systemic signalling in gene silencing" *Nature* 389:553 (1997).

Wagner et al., "Double-stranded RNA poses puzzle" *Nature* 391:744-745 (1998).

Wang et al., "Circular RNA oligonucleotides. Synthesis, nucleic acid binding properties, and a comparison with circular DNAs" *Nucleic Acids Res.* 22:2326-2333 (1994).

Wang et al., "RNA Conformation in the Tat—TAR Complex Determined by Site-Specific Photo-Cross-Linking" *Biochemistry* 35:6491-6499 (1996).

Wargelius et al., "Double-Stranded RNA Induces Specific Developmental Defects in Zebrafish Embryos" *Biochem. Biophys. Res. Commun.* 263:156-161 (1999).

Waterhouse et al., "Virus resistance and gene silencing in plants can be induced by simultaneous expression of sense and antisense RNA" *Proc. Natl. Acad. Sci. USA* 95:13959-13964 (1998).

Watkins et al., "In vivo UV cross-linking of U snRNAs that participate in trypanosome *trans*-splicing" *Genes Dev.* 5:1859-1869 (1991).

Wengel, "Synthesis of 3'-*C*- and 4'-*C*-Branched Oligodeoxynucleotides and the Development of Locked Nucleic Acid (LNA)" *Acc. Chem. Res.* 32:301-310 (1999).

Zwieb et al., "Evidence for RNA-RNA cross-link formation in *Escherichia coli* ribosomes" *Nucleic Acids Res.* 5:2705-2720 (1978).

Notice of Opposition by SIRNA Therapeutics, Inc. against EP application No. 02710786.1 (Feb. 28, 2007).

Patentees Observations filed in opposition proceedings for EP application No. 02710786.1 (Oct. 15, 2007).

Summons to Attend oral proceedings in the opposition proceedings for EP application No. 02710786.1 (Mar. 17, 2009).

Boutla et al., "Short 5'-Phosphorylated double-stranded RNAs induce RNA interference in *Drosophila*" Current Biol. 11:1776-80, 2001.

Bumcrot et al., "RNAi Therapeutics: a potential new class of pharmaceutical drugs" Nature Chem. Biol. 2:711-719, 2006.

Gewirtz et al., "Nucleic Acid Therapeutics: State of the Art and future prospects" Blood 92:712-736, 1998.

Hanazawa et al., "Use of cDNA subtraction and RNA interference screens in combination reveals genes required for germ-line development in *Caenorhabditis elegans*" Proc. Natl. Acad. Sci. 97:8686-91, 2001.

Hornung et al., "Sequence-specific potent induction of IFN-alpha by short interfering RNA in plasmacytoid dendritic cells through TLR7" Nature medicine 11:263-70, 2005.

Huang et al., "Epidermal growth factor receptor inhibition in cancer therapy: biology, rationale and preliminary clinical results" Investig. New Drugs 17:259-69, 1999.

Judge et al., "Sequence-dependent stimulation of the mammalian innate immune response by synthetic siRNA" Nature Biotech 23:457-62, 2005.

Marques et al., "Activation of the mammalian immune system by siRNAs" Nature Biotech 11:139-1405, 2005.

Nykanen, "ATP Requirements and small interfering RNA structure in the RNA interference pathway" Cell 107:309-21, 2001.

Park et al., "Specific inhibition of HIV-1 gene expression by double-stranded RNA" Nucleic Acids Res. Suppl. No. 1:219-20, 2001.

Sharp et al., "RNA Interference" Science 287:2432-33, 2000.

Sledz et al., "Activation of interferon system by short-interfering RNAs" Nature Cell Biol. 5:834-839, 2003.

Veal et al., "Sequence-specific RNAse cleavage of gag mRNA from HIV-1 infected cells by an antisense oligonucleotide in vitro" Nucleic Acids Res. 26:5670-75, 1998.

Wess et al., "Early days of RNAi" BioCentury vol. 11, No. 12, 2003.

Zamore, "RNA interference: listening to the sound of silence" Nature Struc. Biol. 8:748-750, 2001.

Petition by Sirna Therapeutics in opposition proceedings for European Patent No. 1352061 (May 14, 2009).

Schlingensiepen et al., Blackwell Science Ltd., vol. 6, 1997, "Antisense—From Technology to Therapy".

Submission and Auxiliary Request by Sirna Therapeutics in opposition proceedings for European Patent No. 1352061 (May 13, 2009).

Minutes of the oral proceedings of the Opposition Division, Opposition Application No. 02710786.1 for European Patent No. EP1352061, Aug. 25, 2009, 11 Pages.

Decision on Rejection of the Opposition, Opposition Application No. 02710786.1 for European Patent No. EP1352061, Aug. 25, 2009, 40 Pages.

Annex to Decision on Reject of the Opposition, Opposition Application No. 02710786.1 for European Patent No. EP1352061, Aug. 25, 2009, 20 Pages (English translation of claims included within document).

Response to Grounds of Appeal Filed by Opponent in opposition to European Patent No. EP1352061, filed by Alnylam Europe AG on May 21, 2010, 15 Pages.

Grounds for Appeal in opposition to European Patent No. EP1352061, filed by SIRNA Therapeutics, filed on Jan. 4, 2010, 39 Pages.

Notice of Appeal in opposition to European Patent No. EP1352061, filed by SIRNA Therapeutics, filed on Oct. 23, 2009, 39 Pages.

Lima, W., et al., "Cleavage of Single Strand RNA Adjacent to RNA-DNA Duplex Regions by *Escherichia coli* RNase H1," The Journal of Biological Chemistry, Oct. 31, 1997, pp. 27513-27516, vol. 272, No. 44.

Wu, H., et al., "Properties of Clones and Expressed Human RNase H1," The Journal of Biological Chemistry, Oct. 1, 1999, pp. 28270-28278, vol. 274, No. 40.

Communication from the European Patent Office including Response to Patentee's Submission of May 21, 2010, filed by SIRNA Therapeutics on Sep. 7, 2010, in opposition to European Patent No. 1352061, 15 Pages.

\* cited by examiner

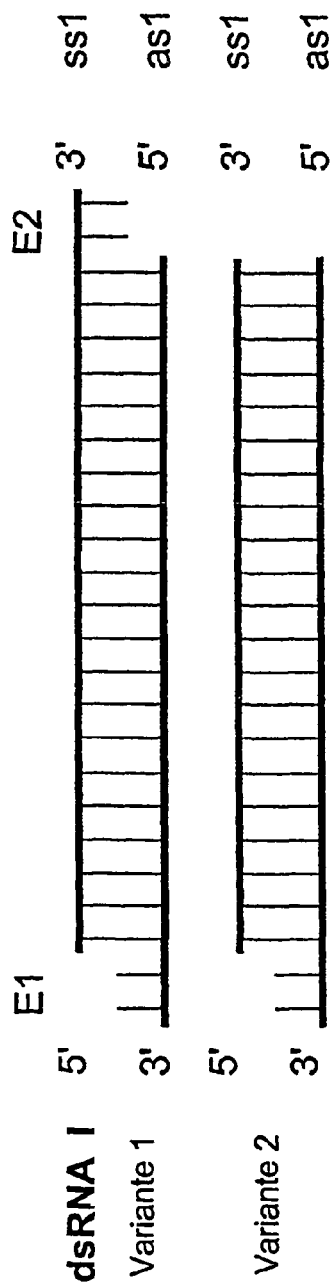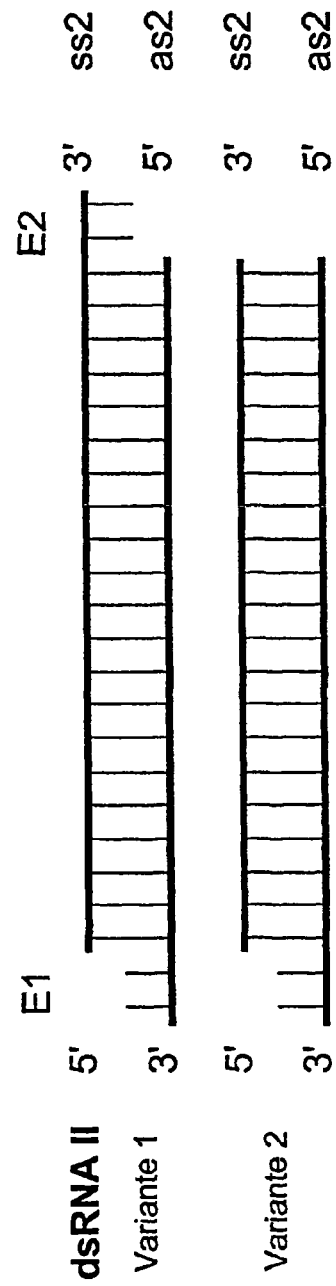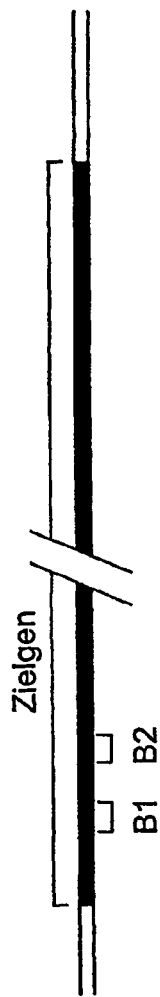

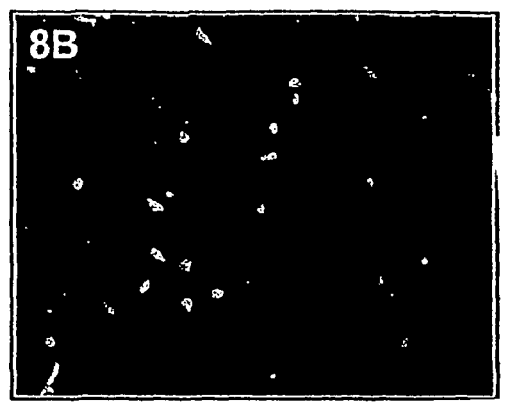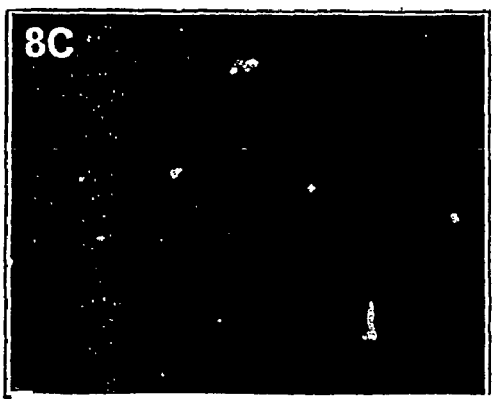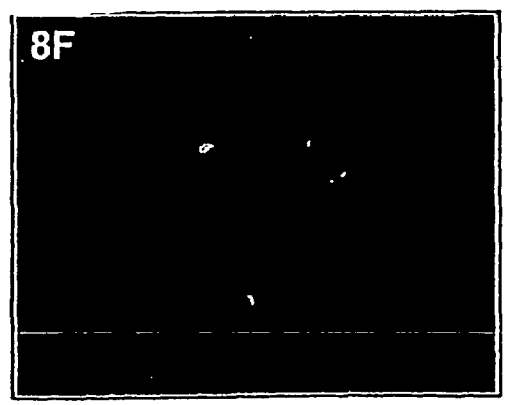
Fig. 8

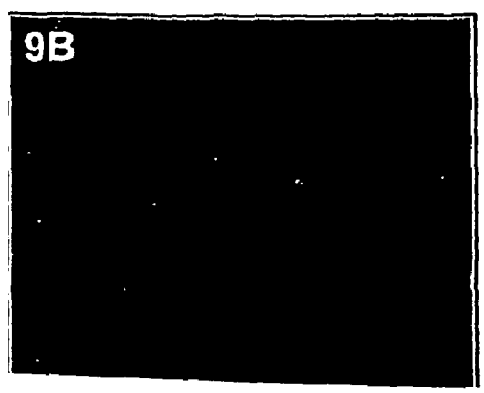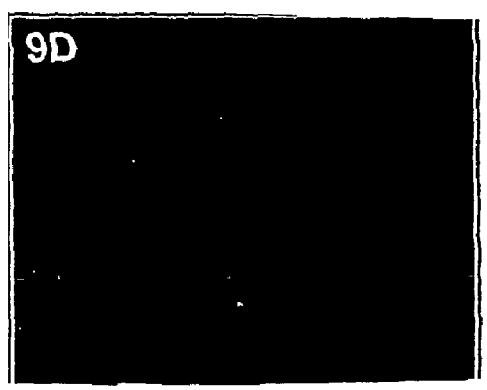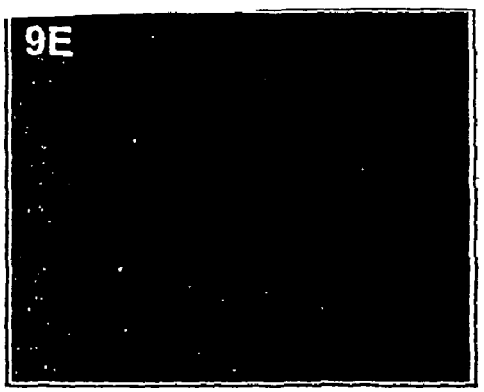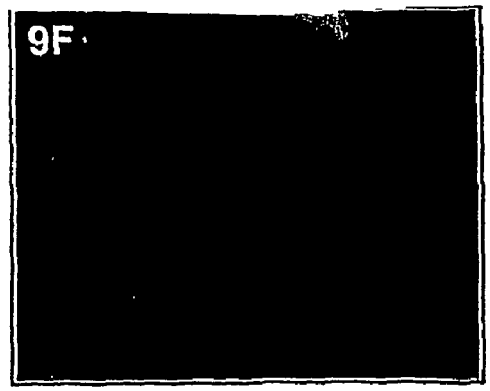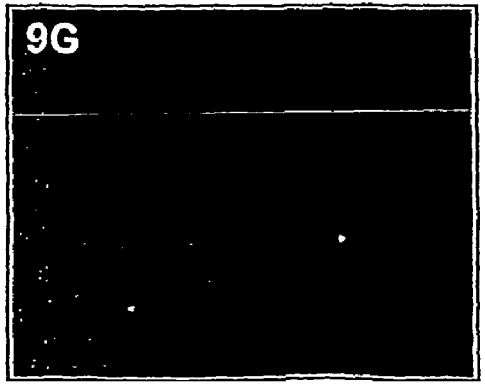
Fig. 9

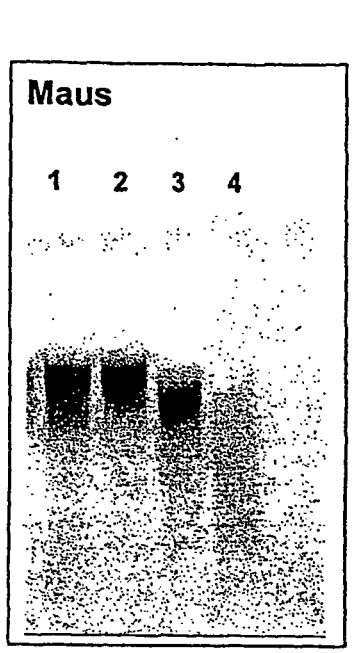
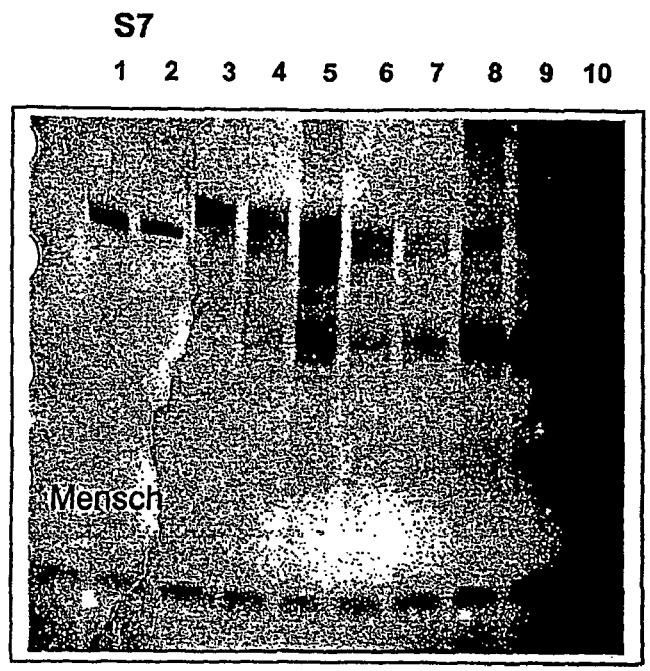
Fig. 12                               Fig. 13
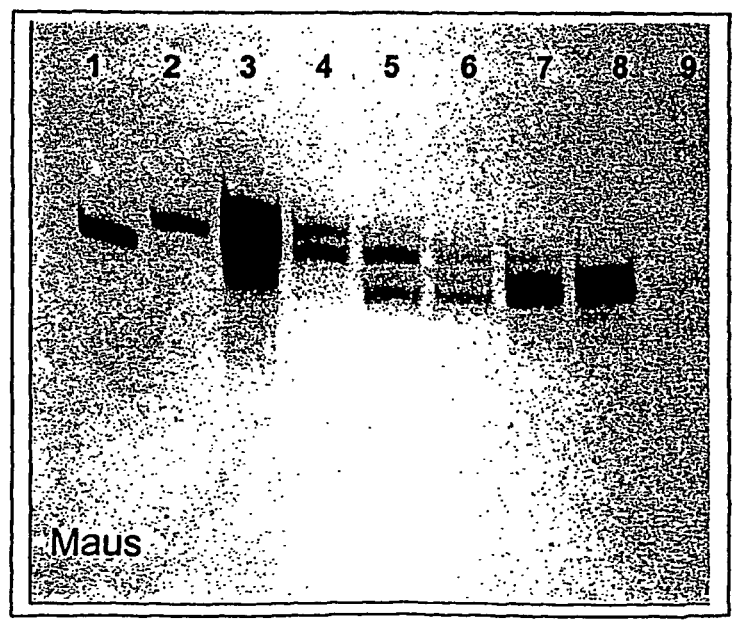
Fig. 14

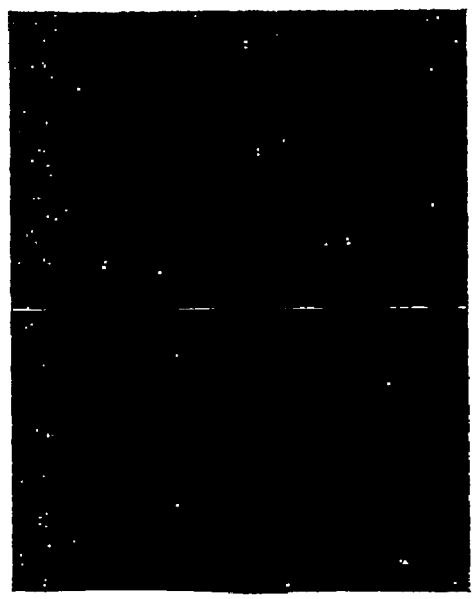
Fig. 27

US 7,829,693 B2

COMPOSITIONS AND METHODS FOR INHIBITING EXPRESSION OF A TARGET GENE

RELATED APPLICATIONS

This application is a continuation-in-part of U.S. application Ser. No. 09/889,802, filed Sep. 17, 2001, now abandoned which claims priority to under 35 U.S.C. 371 to PCT/DE00/00244 filed Jan. 29, 2000, which in turn claims priority to DE19903713.2, filed Jan. 30, 1999, and DE19956568.6, filed Nov. 24, 1999. This application also claims priority as a continuation-in-part of International Application No. PCT/EP02/00152, which designated the United States and was filed on Jan. 9, 2002, which claims the benefit of German Patent No. 101 00 586.5, filed on Jan. 9, 2001, German Patent No. 101 55 280.7, filed on Oct. 26, 2001, German Patent No. 101 58 411.3, filed Nov. 29, 2001, and German Patent No. 101 60 151.4, filed Dec. 7, 2001. The entire teachings of the above application(s) are incorporated herein by reference.

FIELD OF THE INVENTION

This invention relates to double-stranded ribonucleic acid (dsRNA), and its use in mediating RNA interference in vitro and in vivo.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. The therapeutic benefits of being able to selectively silence these abnormal or foreign genes is obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and I. Gibson, *Blood* (1998) 91:371). However, both of these agents have inherent limitations. Antisense approaches, using either single-stranded RNA or DNA, act in a 1:1 stoichiometric relationship and thus have low efficacy (Skorski et al., supra). For example, Jansen et al. report that, in a small percentage of patients, relatively high doses (2 mg/kg body weight per day) of antisense RNA resulted in biologically significant levels (i.e., long-term plasma concentrations above 1 mg/L) of encoded protein (Jansen, B., et al., *The Lancet* (2000) 356:1728-1733). However, no detectable level of plasma protein was observed at lower dosages (e.g., 0.6 mg). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). Briefly, the RNAse III Dicer enzyme processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.) and *Drosophilia* (see, e.g.,Yang, D., et al., *Curr. Biol.* (2000) 10:1191-1200). Despite successes in these organisms, until recently the general perception in the art has been that RNAi cannot be made to work in mammals. It was believed that protocols used for invertebrate and plant systems would not be effective in mammals due to the interferon response, which leads to an overall block to translation and the onset of apoptosis (see, e.g., Wianny, F., et al., *Nature Cell Biol.* (2000) 2:70-75); Fire, A., *Trends Genet.* (1999) 15:358-363; and Tuschl, T., et al., *Genes Dev.* (1999) 13(24):3191-97). At least one group of scientists believed that RNAi could only be made to work in mammals if the PKR response could be neutralized or some way avoided, although no suggestions were given as to how this might be achieved (Fire, *Trends Genet.* (1999), supra; and Montgomery and Fire, *Trends Genet.* (1998) 14:255-258). However, WO 00/44895 (Limmer) demonstrated for the first time that dsRNA can induce RNAi in mammalian cells, provided that the dsRNA meets certain structural requirements, including a defined length limitation.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target gene at a low dose, would be highly desirable. Compositions comprising such agents would be useful for treating diseases caused by abnormal expression or activity of a gene.

SUMMARY OF THE INVENTION

The present invention discloses double-stranded ribonucleic acid (dsRNA), as well as compositions and methods for inhibiting the expression of a target gene in a cell using the dsRNA. The present invention also discloses compositions and methods for treating diseases caused by the expression or activity of the target gene. The dsRNA of the invention, which is no more than 49 nucleotides in length, comprises an RNA strand (complementary RNA strand) having a region which is complementary to an RNA transcript of at least a part of a target gene. The 3'-end of the complementary RNA strand comprises a nucleotide overhang of 1 to 4 nucleotides; the 5'-end of the complementary RNA strand is blunt.

In one aspect, the invention relates to a double-stranded ribonucleic acid (dsRNA), which is no more than 49 nucleotides in length, comprises a sense RNA strand and a complementary RNA strand. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be an oncogene, a cytokine gene, an idiotype protein gene, a prion gene, a gene that encodes a protein that induces angiogenesis, a gene that encodes an adhesion protein, a gene that encodes a cell surface receptor, a gene that encodes a protein involved in a metastasizing and/or invasive process, a gene that encodes a proteinase, a gene that encodes a protein that regulates apoptosis, a gene that encodes a EGF receptor, a MDR1 gene, a gene of a human papilloma virus, a hepatitis C virus, or a human immunodeficiency virus. In one embodiment, the target gene comprises a sequence of SEQ ID NO:1-140.

In another aspect, the invention relates to a method of inhibiting the expression of a target gene in a cell. The method comprises introducing a double-stranded ribonucleic acid (dsRNA) into the cell, and maintaining the cell for a time sufficient to obtain degradation of the mRNA transcript of the target gene, thereby inhibiting expression of the target gene. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be any gene whose expression is to be inhibited, such as the target genes described above.

In yet another aspect, the invention relates to a pharmaceutical composition for inhibiting the expression of a target gene in a mammal. The pharmaceutical composition comprises a dsRNA, as described above, and a pharmaceutically acceptable carrier. The dosage unit of dsRNA may be in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression is to be inhibited, such as the target genes described above. The pharmaceutically acceptable carrier may be an aqueous solution, such as phosphate buffered saline, and may comprise a micellar structure, such as a liposome, capsid, capsoid, polymeric nanocapsule, or polymeric microcapsule. The pharmaceutical composition may be formulated to be administered by inhalation, infusion, injection, or orally, preferably by intravenous or intraperitoneal injection.

In another aspect, the invention relates to a method for treating a disease caused by the expression of a target gene in a mammal. The method comprises administering a pharmaceutical composition, as described above, comprising a double-stranded ribonucleic acid (dsRNA) and a pharmaceutically acceptable carrier. The dosage unit of dsRNA may be in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression causes a disease in an organism, such as the target genes described elsewhere herein.

The details of once or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1 is a diagram of a first dsRNA (A) and a second dsRNA (B).

FIG. 2 is a diagram of a target gene.

FIG. 8 fluorescence microscopic imaging of NIH/3T3 cells after transfection with pcDNA-YFP or after cotransfection with pcDNA-YFP and various dsRNAs.

FIG. 9 fluorescence microscopic imaging of HeLa-S3 cells after transfection with pcDNA-YFP or after cotransfection with pcDNA-YFP and various dsRNAs.

FIG. 12 is a gel electrophoretic separation of S7 after incubation in mouse serum.

FIG. 13 is a gel electrophoretic separation of S7 after incubation in human serum.

FIG. 14 is a gel electrophoretic separation of K3 after incubation in mouse serum.

FIG. 27 shows a comparison of a transmitted light- and fluorescence microscopic imaging of a transfection with 175 nM dsRNA (Sequence R1 in Table 4).

DETAILED DESCRIPTION OF THE INVENTION

Figure 3:
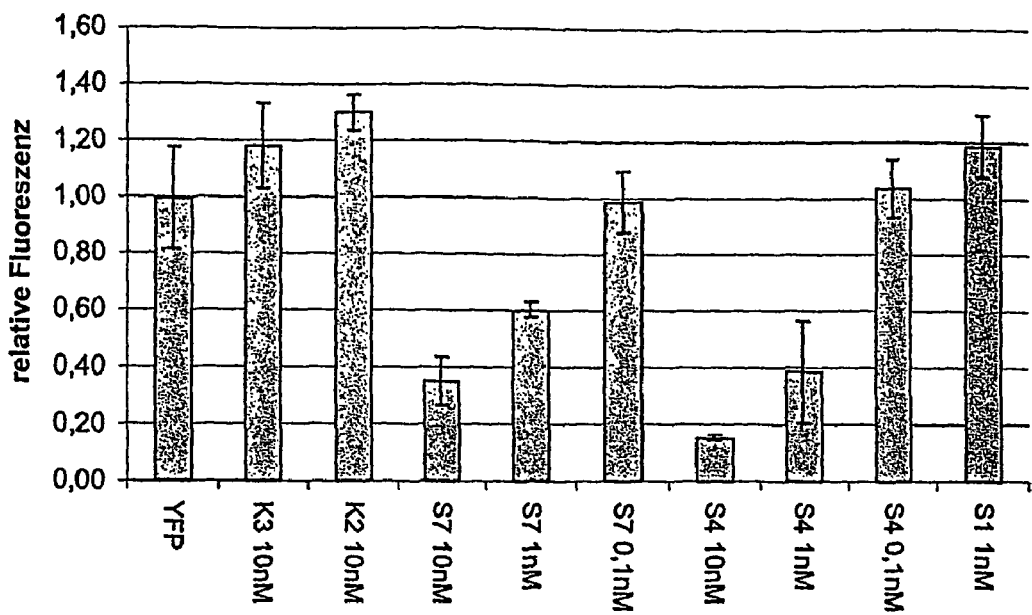
FIG. 3 relative YFP fluorescence after application of various dsRNAs in NIH/3T3 cells (first experiment).
Figure 4:
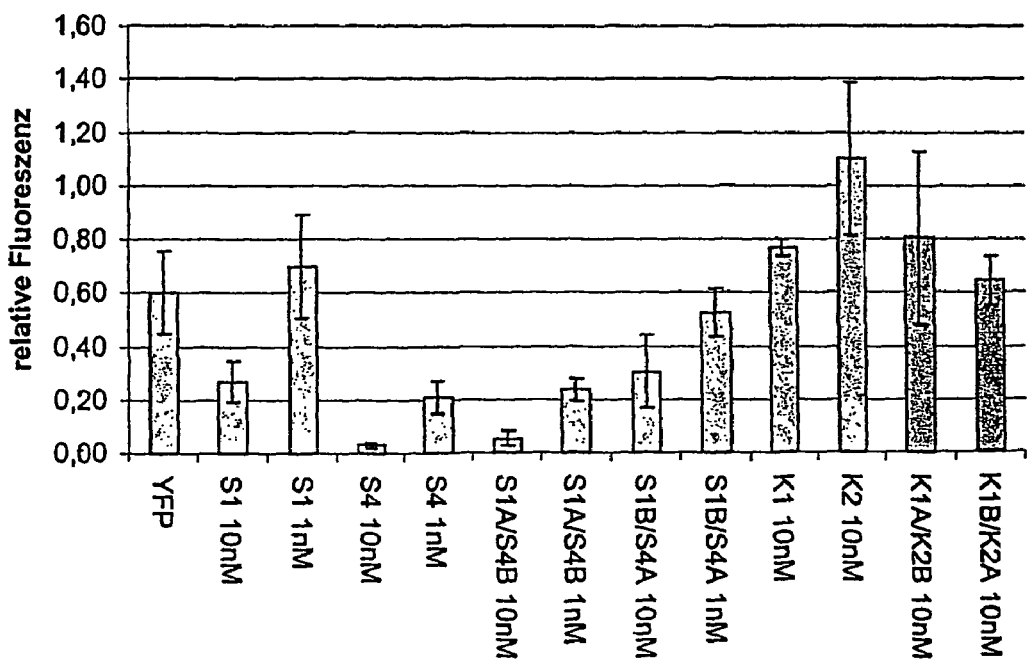
FIG. 4 relative YFP fluorescence after application of various dsRNAs in NIH/3T3 cells (second experiment).
Figure 5:
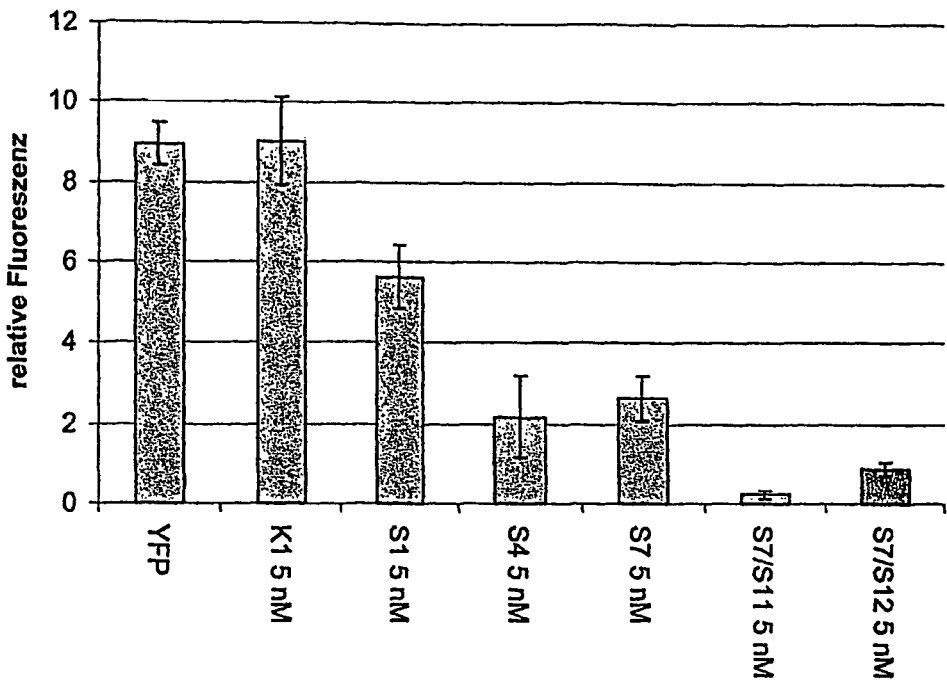
FIG. 5 relative YFP fluorescence after application of various dsRNAs in NIH/3T3 cells (third experiment).
Figure 6:
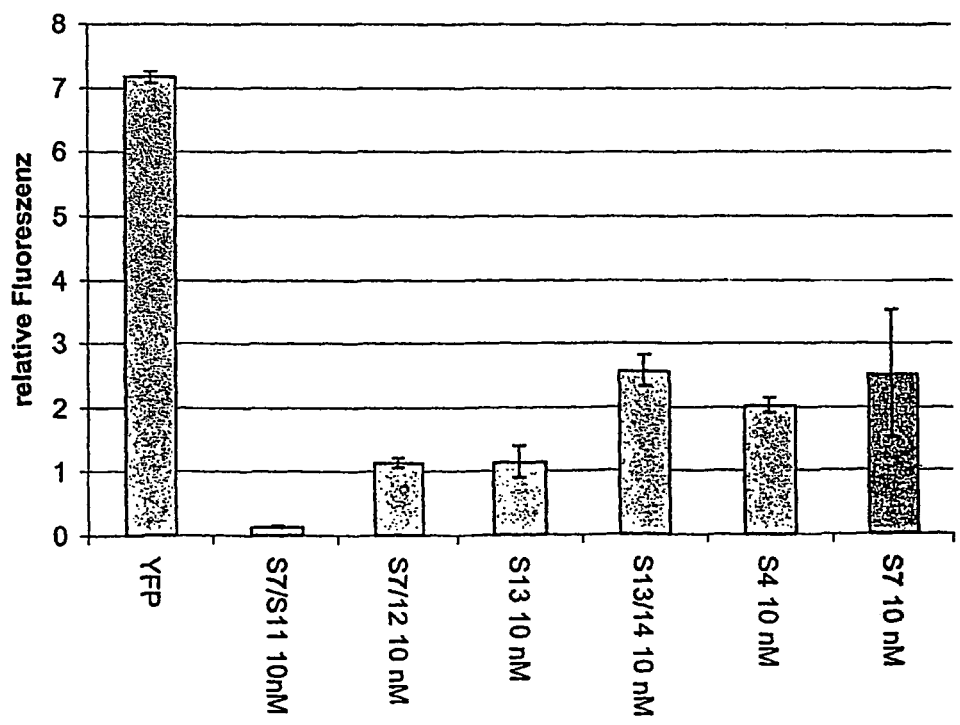
FIG. 6 relative YFP fluorescence after application of various dsRNAs in NIH/3T3 cells (fourth experiment).
Figure 7:
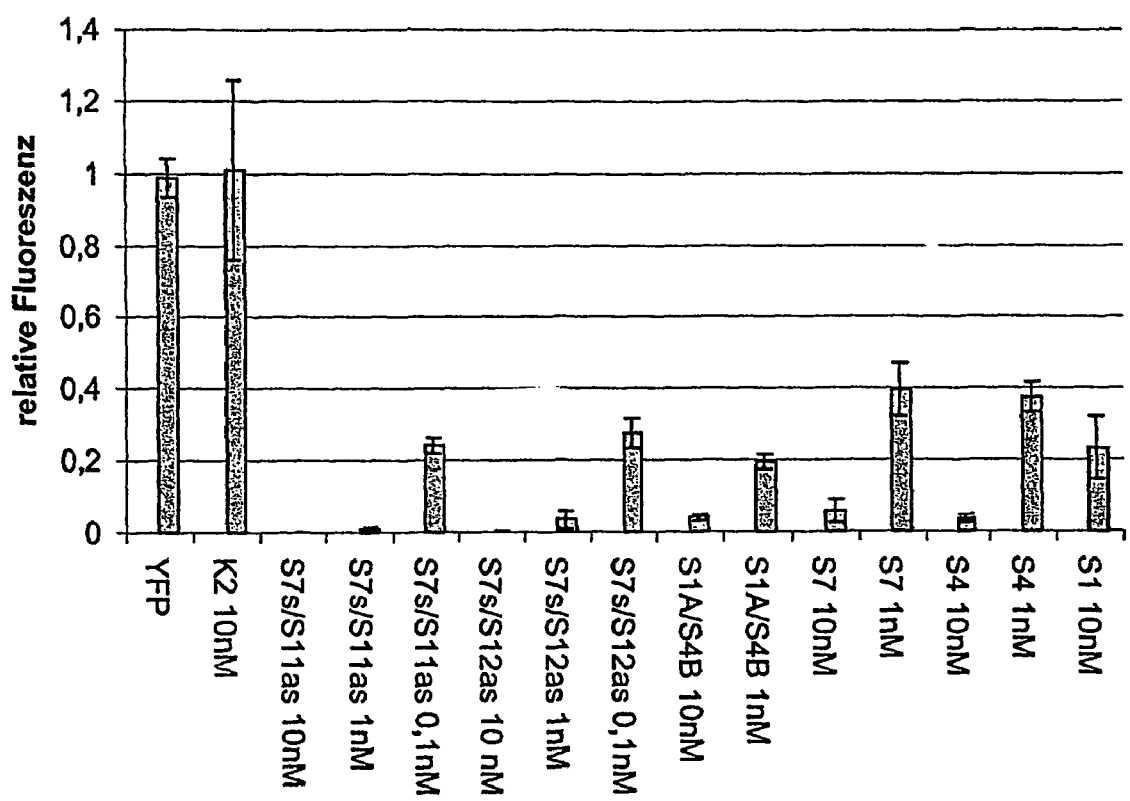
FIG. 7 relative YFP fluorescence after application of various dsRNAs in NIH/3T3 cells (fifth experiment).
Figure 10:
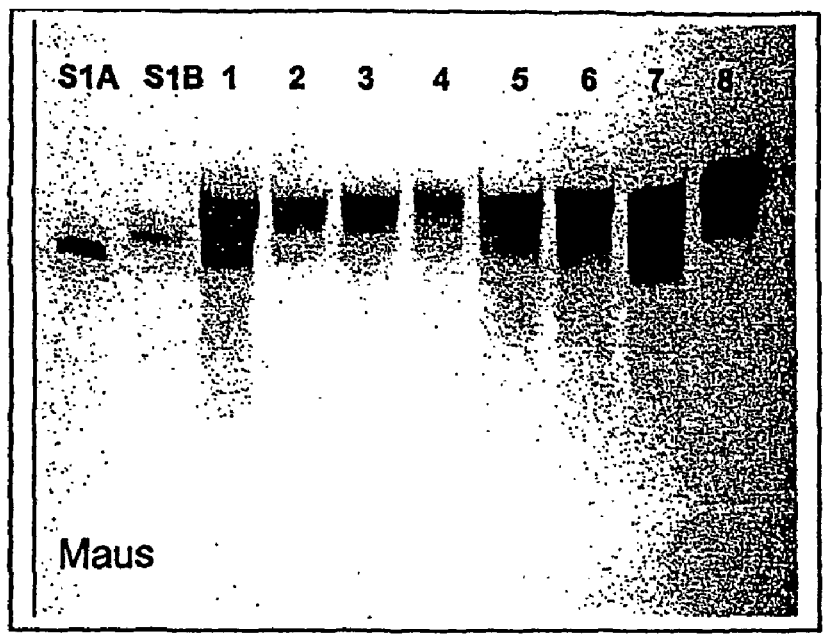
FIG. 10 is a gel electrophoretic separation of S1 after incubation in mouse serum.
Figure 11:
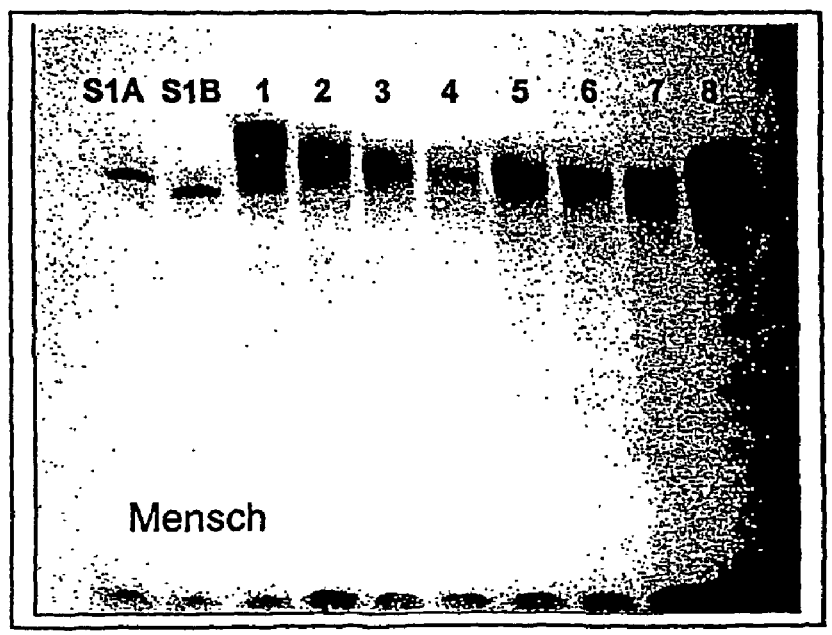
FIG. 11 is a gel electrophoretic separation of S1 after incubation in human serum.
Figure 15:
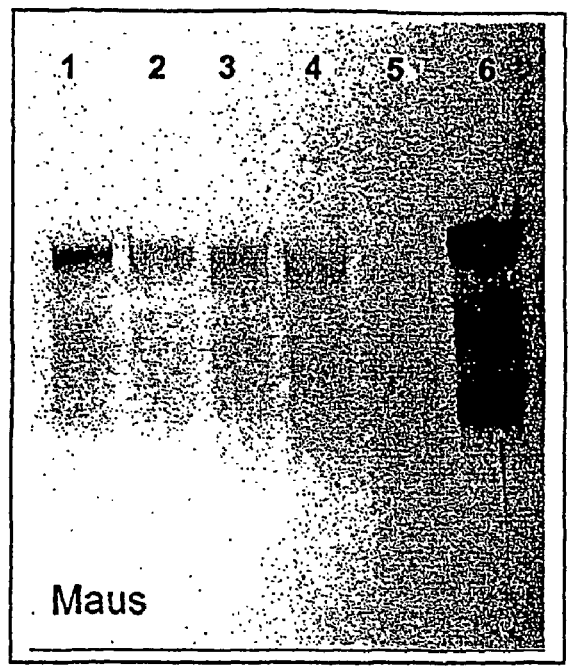
FIG. 15 is a gel electrophoretic separation of PKCl/2 after incubation in mouse serum.
Figure 16:
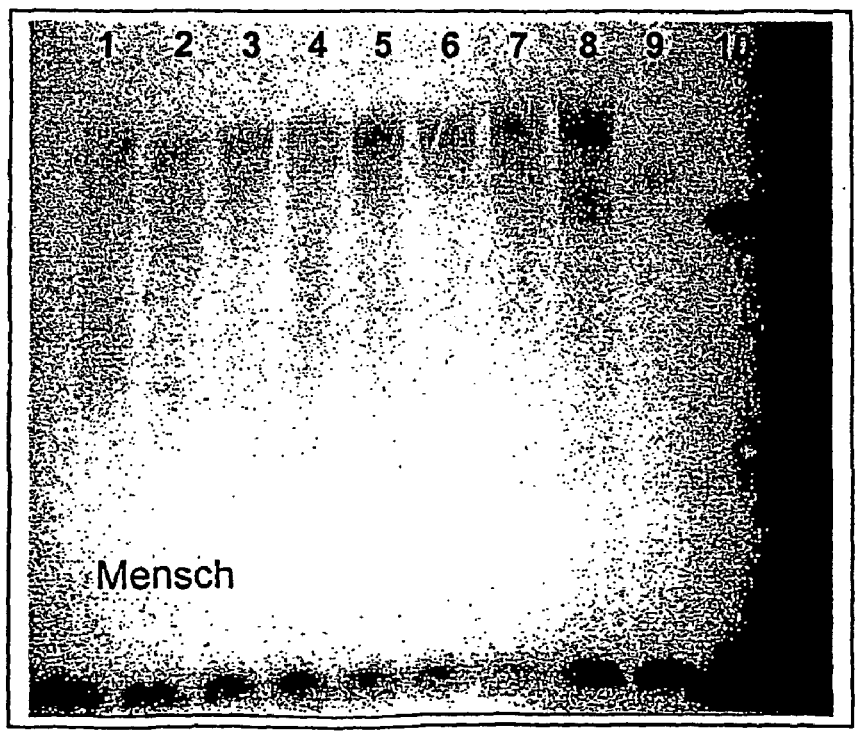
FIG. 16 is a gel electrophoretic separation of S1A/S4B after incubation in human serum.
Figure 17:
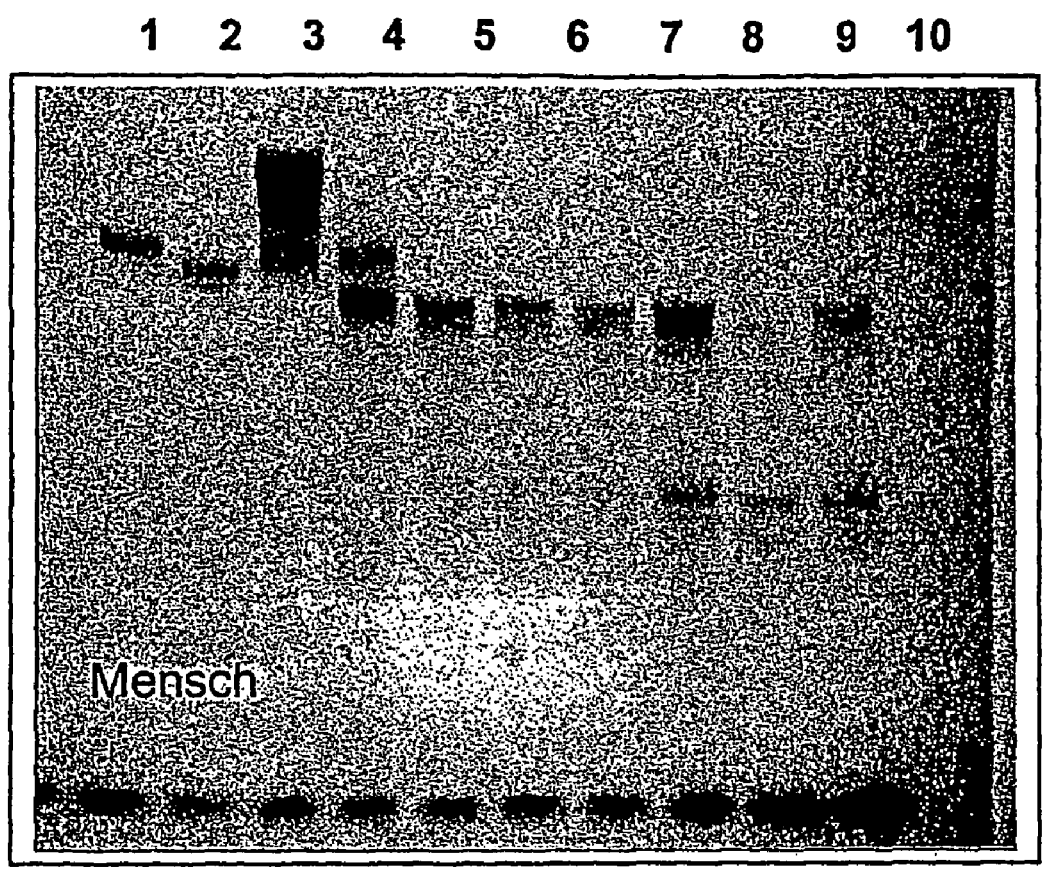
FIG. 17 is a gel electrophoretic separation of K2 after incubation in human serum.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by expression of a target gene using dsRNA. dsRNA directs the sequence-specific degradation of mRNA through a process known as RNA interference (RNAi). The process occurs in a wide variety of organisms, including mammals and other vertebrates. The dsRNA of the invention is no more than 49 nucleotides in length, and comprises an RNA strand (complementary RNA strand) having a region that is complementary to an RNA transcript of at least a portion of a target gene. The complementary RNA strand has a nucleotide overhang of 1 to 4 nucleotides at the 3'-end; the 5'-end is blunt. Using transgenic mice, the present inventors have demonstrated that very low dosages of these dsRNA can specifically and efficiently mediate RNAi, resulting in significant inhibition of expression of the target gene. The present invention encompasses these dsRNAs and compositions comprising dsRNA and their use for specifically inactivating gene function. The use of these dsRNAs enables the targeted degradation of mRNAs of genes that are implicated in a wide variety of disease processes, including cellular proliferative disorders, hematopoietic disorders, immune disorders, and certain infectious diseases. Thus, the methods and compositions of the present invention comprising these dsRNAs are useful for treating diseases and disorders caused by the expression or activity of a particular gene.

The following detailed description discloses how to make and use the dsRNA and compositions containing dsRNA to inhibit the expression of a target gene, as well as compositions and methods for treating diseases and disorders caused by the expression of the gene. The pharmaceutical compositions of the present invention comprise a dsRNA having a nucleotide sequence of no more than 49 nucleotides in length, preferably less than 25 nucleotides in length, and which is substantially identical to at least a part of the target gene, together with a pharmaceutically acceptable carrier. The dsRNA has a single-stranded nucleotide overhang of 1 to 4 nucleotides at the 3'-end of the complementary RNA strand; the 5'-end is blunt.

Accordingly, certain aspects of the present invention relate to pharmaceutical compositions comprising the dsRNA of the present invention together with a pharmaceutically acceptable carrier, methods of using the compositions to inhibit expression of a target gene, and methods of using the pharmaceutical compositions to treat diseases caused by the expression or activity of a particular gene.

I. Definitions

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a matrix for transcription, as well as a section of an RNA strand of a (+) strand RNA virus. A target gene, usually the sense strand, is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or plasmodium).

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); a cytokine gene (Rubinstein, M., et al., *Cytokine Growth Factor Rev*. (1998) 9(2):175-81); a idiotype (Id) protein gene (Benezra, R., et al., *Oncogene* (2001) 20(58):8334-41; Norton, J. D., *J. Cell Sci.* (2000) 113(22):3897-905); a prion gene (Prusiner, S. B., et al., *Cell* (1998) 93(3):337-48; Safar, J., and S. B. Prusiner, *Prog. Brain Res*. (1998) 117:421-34); a gene that expresses molecules that induce angiogenesis (Gould, V. E. and B. M. Wagner, *Hum. Pathol*. (2002) 33(11):1061-3); adhesion molecules (Chothia, C. and E. Y. Jones, *Annu. Rev. Biochem*. (1997) 66:823-62; Parise, L. V., et al., *Semin. Cancer Biol*. (2000) 10(6):407-14); cell surface receptors (Deller, M. C., and Y. E. Jones, *Curr. Opin. Struct. Biol*. (2000) 10(2):213-9); genes of proteins that are involved in metastasizing and/or invasive processes (Boyd, D., *Cancer Metastasis Rev*. (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20): R776-8; Krepela, E., *Neoplasma* (2001) 48(5):332-49; Basbaum and Werb, *Curr. Opin. Cell Biol*. (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol*. (1993) 9:541-573; Brinkerhoff, E., and L. M. Matrisan, *Nature Reviews* (2002) 3:207-214; Strasser, A., et al., *Annu. Rev. Biochem*. (2000) 69:217-45; Chao, D. T. and S. J. Korsmeyer, *Annu. Rev. Immunol*. (1998) 16:395-419; Mullauer, L., et al., *Mutat. Res.* (2001) 488(3):211-31; Fotedar, R., et al., *Prog. Cell Cycle Res*. (1996) 2:147-63; Reed, J. C., *Am. J. Pathol*. (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci*. (2001) 6:D685-707); and the multi-drug resistance 1 gene, MDR1 gene (Childs, S., and V. Ling, *Imp. Adv. Oncol*. (1994) 21-36).

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to an mRNA transcript of a portion of the target gene. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. The dsRNA is no more than 49, preferably less than 25, and most preferably between 19 and 23, nucleotides in length. dsRNAs of this length are particularly efficient in inhibiting the expression of the target gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math.* (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, the terms "pathogen" and "pathogenic organism" refer to an organism capable of producing disease, including, without limitation, a virus, viroid, or plasmodium. As used herein, the term "pathogen" includes organisms capable of causing disease in animals and/or plants.

As used herein, a "transformed cell" is a cell into which a dsRNA molecule has been introduced by means of recombinant DNA techniques.

II. Double-stranded Ribonucleic Acid (dsRNA)

In one embodiment, the invention relates to a double-stranded ribonucleic acid (dsRNA) having a nucleotide sequence which is substantially identical to at least a portion of a target gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA transcript of the target (DNA) gene or a gene of a (+) strand RNA virus. The dsRNA has no more than 49 nucleotides, preferably less than 25 nucleotides, and most preferably 23 nucleotides in length. The dsRNA can be synthesized by standard methods known in the art, e.g., by use of an automated DNA synthesizer, such as are commercially available from Biosearch, Applied Biosystems, Inc. In specific embodiments, the dsRNA can comprise the sequence set forth in SEQ ID NO:141-173, or a complement or equivalent thereof.

At least one end of the dsRNA has a single-stranded nucleotide overhang of 1 to 4, preferably 1 or 2 nucleotides. The single-stranded overhang is located at the 3'-terminal end of the complementary (antisense) RNA strand, and the 5'-end of the complementary RNA strand is blunt (i.e., no overhang). Such dsRNAs have improved stability and inhibitory activity, thus allowing administration at low dosages, i.e., less than 5 mg/kg body weight of the recipient per day. In another embodiment, one or more of the nucleotides in the overhang is replaced with a nucleoside thiophosphate. dsRNAs having a nucleotide overhang at the 3'-end of the antisense have unexpectedly superior inhibitory properties than their blunt-ended counterparts. Moreover, the present inventors have discovered that the presence of a nucleotide overhang at the 3'-overhang of the antisense strand strengthens the interference activity of the dsRNA, without effecting its overall stability. Such dsRNAs have proven particularly stable and effective in vivo, as well as in a variety of cells, cell culture mediums, blood, and serum.

In another embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (e.g., Williams, D. J., and K. B. Hall, *Biochem.* (1996) 35:14665-14670). In a preferred embodiment, the 5'-end of the complementary (antisense) RNA strand and the 3'-end of the second (sense) RNA strand are chemically linked via a hexa-ethylene glycol linker.

In yet another embodiment, the target gene is an oncogene; a cytokinin gene; an idiotype protein gene (Id protein gene); a prion gene; a gene that expresses a protein that induces angiogenesis, an adhesion molecule; a cell surface receptor; a gene of a protein involved in a metastasizing and/or invasive process; a gene of a proteinase; a gene of a protein that regulates apoptosis and the cell cycle; a gene that expresses the EGF receptor; or a MDR1 gene, all of which are described elsewhere herein.

In one embodiment, the target gene is the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J. Natl. Cancer Inst.* (1989) 81:1683-1685) also may render MDR.

In yet another embodiment, the invention relates to a method for treating viral diseases, including but not limited to hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of a target gene.

In another embodiment, the invention relates to a pharmaceutical composition comprising at least two dsRNAs, both designed to target the same gene, and a pharmaceutically acceptable carrier. Because of the duplicative targeting of mRNA by a plurality of dsRNAs, pharmaceutical compositions comprising multiple dsRNAs provide improved efficiency of inhibition as compared to compositions comprising a single dsRNA. In this embodiment, the individual dsRNAs are prepared as described in the preceding section, which is incorporated by reference herein. One dsRNA (referred to herein as "dsRNA I") has a nucleotide sequence ("complementary region I") which is substantially identical to at least a portion of the target gene (referred to herein as "region A" of the target gene). Additional dsRNAs are prepared, each of which has a nucleotide sequence that is substantially identical to a different region of the target gene. For example, a second dsRNA ("dsRNA II") may have a nucleotide sequence ("complementary region II") that is substantially identical to a "region B" of the target gene. Region A and region B, which reflect distinct regions of the same target gene, may overlap each other, be adjacent to one another, or be physically separated within the target gene. dsRNA I and dsRNA II may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to two dsRNAs (dsRNA I and dsRNA II) which target two regions (region A and region B) of the target gene, the present invention encompasses any number of dsRNAs, each of which targets a distinct region of the target gene.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y., *Int. J. Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A. W., et al, *J. Exp. Med.* (1988) 167(2):353-71; Zeng X X et al., *Blood.* (1988) 92(10):3529-36; Eriksson, B., et al., *Exp. Hematol.* (1999) 27(4):682-8; and Kovalchuk, A., et al., *J. Exp. Med.* (2000) 192(8): 1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Diseases Caused by Expression of a Target Gene

In one embodiment, the invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoictic origin, e.g., arising from myeloid, lymphoid or erythroid lineages, or precursor cells thereof.

The pharmaceutical compositions of the present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyclitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

Examples of genes which can be targeted for treatment include, without limitation, an oncogene; a cytokine gene; a idiotype (Id) protein; a prion gene; a gene that expresses molecules that induce angiogenesis; an adhesion molecule; a cell surface receptor; a gene of a protein involved in a metastasizing and/or invasive process; a gene of a proteases as or a protein that regulates apoptosis and the cell cycle; a gene that expresses the EGF receptor; and the multi-drug resistance 1 gene, MDR1 gene, all of which are described elsewhere herein.

In one embodiment, a pharmaceutical compositions comprising dsRNA is used to inhibit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J. Natl. Cancer Inst.* (1989) 81:1683-1685) also may render MDR.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of a Target Gene

In yet another aspect, the invention relates to a method for inhibiting the expression of a target gene in an organism. The method comprises administering a composition of the invention to the organism such that expression of the target gene is silenced. The organism may be an animal or a plant. Because of their high specificity, the dsRNAs of the present invention specifically target RNAs (primary or processed) of target genes, and at surprisingly low dosages. Compositions and methods for inhibiting the expression of a target gene using dsRNAs can be performed as described elsewhere herein.

In one embodiment, the comprises administering a composition comprising a dsRNA, wherein the dsRNA comprises a nucleotide sequence which is complementary to at least a part of an RNA transcript of the target gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any gene one wishes to silence, thereby specifically inhibiting its expression. Examples of human genes which can be targeted for silencing include, without limitation, an oncogene; cytokinin gene; idiotype protein gene (Id protein gene); prion gene; gene that expresses molecules that induce angiogenesis, adhesion molecules, and cell surface receptors; genes of proteins that are involved in metastasizing and/or invasive processes; genes of proteases as well as of molecules that regulate apoptosis and the cell cycle; genes that express the EGF receptor; the multi-drug resistance 1 gene (MDR1 gene); a gene or component of a virus, particularly a human pathogenic virus, that is expressed in pathogenic organisms, preferably in plasmodia.

The methods for inhibition the expression of a target gene can also be applied to any plant gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

RNA Interference in a Mouse Model

In this Example, double stranded siRNAs are used to inhibit GFP gene expression in transgenic mice.

Synthesis and Preparation of dsRNAs

Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 mM $NaClO_4$, pH 6.8, 10% acetonitrile; the high-salt buffer was: 20 mM Tris, 400 mM NaClO4, pH 6.8, 10% acetonitrile. flow rate: 3 ml/min). Formation of double stranded siRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours, In addition, dsRNA molecules with linkers may be produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

| Name | Sequence ID No. | DsRNA sequence | Nucleotide number (overhang at the 3'-end of the S1 double-stranded region - overhang at the 3'-end of S2)] |
|---|---|---|---|
| S1 | SEQ ID NO. 148 (S2) | 5'-CCACAUGAAGCAGCACGACUUC-3' | 0-22-0 |
|  | SEQ ID NO. 149 (S1) | 3'-GGUGUACUUCGUCGUGCUGAAG-5' |  |

-continued

| Name | Sequence ID No. | DsRNA sequence | Nucleotide number (overhang at the 3'-end of the S1 double-stranded region - overhang at the 3'-end of S2)] |
|---|---|---|---|
| S7 | SEQ ID NO. 150 (S2)<br>SEQ ID NO. 151 (S1) | 5'-CCACAUGAAGCAGCACGACUU-3'<br>3'-CUGGUGUACUUCGUCGUGCUG-5' | 2-19-2 |
| K1 | SEQ ID NO. 153 (S2)<br>SEQ ID NO. 154 (S1) | 5'-ACAGGAUGAGGAUCGUUUCGCA-3'<br>3'-UGUCCUACUCCUAGCAAAGCGU-5' | 0-22-0 |
| K3 | SEQ ID NO. 155 (S2)<br>SEQ ID NO. 156 (S1) | 5'-GAUGAGGAUCGUUUCGCAUGA-3'<br>3'-UCCUACUCCUAGCAAAGCGUA-5' | 2-19-2 |
| K4 | SEQ ID NO. 155 (S2)<br>SEQ ID NO. 156 (S1) | 5'-GAUGAGGAUCGUUUCGCAUGA-3'<br>3'-UCCUACUCCUAGCAAAGCGUACU-5' | 2-21-0 |
| S7/S11 | SEQ ID NO. 150 (S2)<br>SEQ ID NO. 159 (S1) | 5'-CCACAUGAAGCAGCACGACUU-3'<br>3'-CUGGUGUACUUCGUCGUGCUGAA-5' | 2-21-0 |

RNAi Administration

DsRNA are administered systemically either orally, by means of inhalation, infusion, or injection, preferably by intravenous or intraperitoneal infusion or injection in combination with pharmaceutically acceptable carriers. Examples of suitable carriers are found in standard pharmaceutical texts, e.g. "Remington's Pharmaceutical Sciences", 16th edition, Mack Publishing Company, Easton, Pa., 1980. A preparation that is suitable for inhalation, infusion, or injection preferably consists of dsRNA and a physiologically tolerated solvent, preferably a physiological saline solution or a physiologically tolerated buffer, preferably a phosphate buffered saline solution. The invention anticipates the use of a double-stranded ribonucleic acid in a dosage of a maximum of 5 mg/kg body weight per day.

GFP Laboratory Mice:

The transgenic laboratory mouse strain TgN (GFPU) 5Nagy (Jackson Laboratory, Bar Harbor, Me.), which expresses GFP in all cells studied to date (with the help of a beta actin promoter and a CMV intermediate early enhancer) (Hadjantonakis A K. et al., 1998, Nature Genetics 19: 220-222), was used. The GFP transgenic mice may be clearly differentiated on the basis of fluorescence (using a UV lamp) from the corresponding wild types (WT). The following experiments were carried out using GFP-heterozygote animals that were bred by mating a WT animal each with a heterozygote GFP-type animal. The animals were kept under controlled conditions in groups of 3-5 animals in Type III Makrolon cages (Ehret Co., Emmendingen, Germany) at a constant temperature of 22° C. and a light-to-dark rhythm of 12 hours. Granulated softwood (8/15, Altromin Co., Lage, Germany) was strewn on the bottom of the cages. The animals received tap water and Altromin 1324 pelleted standard feed (Altromin Co.) ad libitum.

In vivo Experiment:

Heterozygote GFP animals were placed in cages as described above in groups of 3. DsRNA solution was injected intravenously (i.v.) into the caudal vein in 12-hour rotation (between 5:30 and 7:00 and between 17:30 and 19:00) over 5 days. Injection volume was 60 µl per 10 g body weight, and dosage was 2.5 mg dsRNA or 50 µg per kg body weight. The groups were organized as follows:

Group A: PBS (phosphate buffered saline) 60 µl per 10 g body weight each,

Group B: 2.5 mg per kg body weight of a non-specific control dsRNA (K1 control with smooth ends and a double-stranded region of 22 nucleotide pairs), Group C: 2.5 mg per kg body weight of another non-specific control dsRNA (K3 control with 2 nucleotide [nt] overhangs and both 3'-ends and a double-stranded region of 19 nucleotide pairs), Group D: 2.5 mg per kg body weight of dsRNA (directed specifically against GFP, henceforth designated as S1, with smooth ends and a double-stranded region of 22 nucleotide pairs), Group E: 2.5 mg dsRNA per kg body weight (directed specifically against GFP, henceforth designated as S7, with 2 nt overhangs and the 3'-ends of both strands, and a double-stranded region of 19 nucleotide pairs), Group F: 50 µg S1 dsRNA per kg body weight (in other words 1/50 the dosage of Group D).

After the last injection of a series of 10 injections, the animals were sacrificed after 14-20 hours, and the organs and blood were removed as described below.

Organ Removal:

Immediately after the animals were killed by CO2 inhalation, the blood and various organs were removed (thymus, lungs, heart, spleen, stomach, intestines, pancreas, brain, kidneys, and liver). The organs were quickly rinsed in cold sterile PBS and dissected with a sterile scalpel. A portion was fixed for 24 hours for immunohistochemical staining in methyl Carnoy (MC, 60% methanol, 30% chloroform, 10% glacial acetic acid); another portion was immediately flash-frozen in liquid nitrogen for freeze sections and protein isolation, and stored at −80° C.; and another smaller portion was frozen for RNA isolation at −80° C. in RNAeasy Protect (QIAGEN GmbH, Max Volmer Str. 4, 40724 Hilden). Immediately after removal, the blood was kept on ice for 30 minutes, mixed, centrifuged for 5 minutes at 2000 rpm (Mini Spin, Eppendorf AG, Barkhausenweg 1, 22331, Hamburg, Germany), and the supernatant fluid was drawn off and stored at −80° C. (designated here as plasma).

Processing the Biopsies:

After fixing the tissue for 24 hours in MC, the tissue pieces were dehydrated in an ascending alcohol series at room temperature: 40 minutes each 70% methanol, 80% methanol, 2×96% methanol and 3×100% isopropanol. After that the tissue was warmed up in 100% isopropanol at 60° C. in an incubator, after which it was incubated for 1 hour in an isopropanol/paraffin mixture at 60° C. and 3× for 2 hours in paraffin, and then embedded in paraffin. Tissue sections 3 µm in thickness were prepared for immunoperoxidase staining, using a rotation microtome (Leica Microsystems Nussloch GmbH, Heidelberger Str. 17-19, 69226 Nussloch, Germany), placed on microscopic slides (Superfrost, Vogel GmbH & Co. KG, Medical Technology and Electronics, Marburger Str. 81, 35396 Giessen, Germany), and incubated for 30 minutes at 60° C.

Immunoperoxidase Staining for GFP:

The sections were deparaffinized for 3×5 minutes in xylol, rehydrated in a descending alcohol series (3×3 min. 100% ethanol, 2×2 min. 95% ethanol), and then incubated for 20 minutes in 3% H2O2/methanol to block endogenous peroxidases. Next, all incubation steps were carried out in a moist chamber. After 3×3 min. washing with PBS, the sections were incubated with a first antibody (goat anti-GFP antibody, sc-5384, Santa Cruz Biotechnology, Inc., Berheimer Str. 89-2, 69115 Heidelberg, Germany) 1:500 in 1% BSA/PBS overnight at 4° C. The sections were then incubated with the biotinylated secondary antibody (donkey anti-goat IgG; Santa Cruz Biotechnology; 1:2000 dilution) for 30 minutes at room temperature, after which they were incubated for 30 minutes with Avidin D peroxidase (1:2000 dilution, Vector Laboratories, 30 Ingold Road, Burlingame, Calif. 94010). After each antibody incubation, the sections were washed in PBS for 3×3 min., and buffer residue was removed from the sections along with cell material. All antibodies were diluted with 1% bovine serum albumin (BSA)/PBS. The sections were stained with 3,3'-diamino benzidine (DAB) using the DAB Substrate Kit (Vector Laboratories) in accordance with the manufacturer's instructions. Gill's Hematoxylin III (Merck KgaA, Frankfurter Str. 250, 64293 Darmstadt) was used as the nuclear counterstain. After dehydration in an ascending alcohol series and 3×5 minutes xylol, the sections were covered with Entellan (Merck). Microscopic evaluation of the stains was accomplished using a IX50 microscope from OLYMPUS Optical Co. (Europe) GmbH, Wendenstr. 14-18 20097 Hamburg, Germany, fitted with a CCD camera (Hamamatsu Photonics K.K., Systems Division, 8012 Jokocho Hamamatsu City, 431-3196 Japan).

Protein Isolation from Tissue Pieces:

Frozen tissue samples were added to 800 µl isolation buffer (50 m HEPES, pH 7.5; 150 mM NaCl; 1 mM EDTA; 2.5 mM EGTA; 10% glycerol; 0.1% Tween; 1 mM DTT; 10 mM β-glycerol phosphate; 1 mM NaF; 0.1 mM Na3VO4 with a "complete" protease inhibitor tablet from Roche Diagnostics GmbH, Roche Applied Science, Sandhofer Str. 116, 68305 Mannheim), and homogenized for 2×30 seconds with an ultraturrax (DIAX 900, Dispersion Tool 6G, HEIDOLPH Instruments GmbH & Co. KG, Walpersdorfer Str. 12, 91126 Schwabach), and cooled on ice in between steps. After incubation for 30 minutes on ice, the homogenate was mixed and centrifuged for 20 minutes at 10,000 g, 4° C. (3K30, SIGMA Laboratory Centrifuge GmbH, An der Unteren Söse 50, 37507 Osterode am Harz). The supernatant fluid was again incubated for 10 minutes on ice, mixed, and centrifuged for 20 minutes at 15,000 g, 4° C. Protein determination of the supernatant fluid was determined according to Bradford, 1976, modified according to Zor & Selinger, 1996, using the Roti-Nanoquant system (Carl Roth GmbH & Co., Schoemperlenstr. 1-5, 76185 Karlsruhe, Germany) in accordance with manufacturer's instructions. BSA was used for protein calibration in a concentration range of 10 to 100 µg/ml.

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS; 3.3 ml distilled water; 250 µl ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µl 1 M tris/HCl, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DTT (dithiotreithol), 0.02% bromophenol blue, 20% glycerin) was then added to the proteins, which were then denatured on a heat block at 100° C., centrifuged on ice after cooling off, and then applied to the gel. The same plasma and protein quantities were used in each lane (3 µl plasma or 25 µg total protein each). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Proteins separated by SDS-PAGE were transferred to a PVDF (polyvinyl difluoride) membrane (Hybond-P, Amersham Biosciences Europe GmbH, Munzinger Str. 9, 79111 Freiburg, Germany) using the semidry transfer method according to Kyhse-Anderson (J. Biochem. Biophys. Methods 10: 203-210, 1984) at room temperature and constant amperage of 0.8 mA/cm2 for 1.5 hours in Tris/Glycerin transfer buffer (39 mM glycerin, 46 mM tris, 0.1% SDS, and 20% methanol). After immunodetection both the gels and the blots, as well as the blot membranes, were stained with Coomassie (0.1% Coomassie G250, 45% methanol, 10% glacial acetic acid) in order to check for electrophoretic transfer. The blot membranes were incubated after transfer in 1% skim milk powder/PBS for 1 hour at room temperature to saturate nonspecific bonds. Next, each membrane was washed three times for 3 minutes with 0.1% Tween-20/PBS. All subsequent antibody incubations and wash steps were done in 0.1% Tween-20/PBS. The primary antibody (goat anti-GFP antibody, sc-5384, Santa Cruz Biotechnology) was incubated for one hour at room temperature at a dilution of 1:1000. After washing 3×5 minutes, the membranes were incubated with a horseradish peroxidase coupled secondary antibody (donkey anti-goat IgG, Santa Cruz Biotechnology), at a dilution of 1:10,000. Detection of horseradish peroxidase was then achieved using the ECL system (Amersham) in accordance with the manufacturer's instructions.

Figure 18:
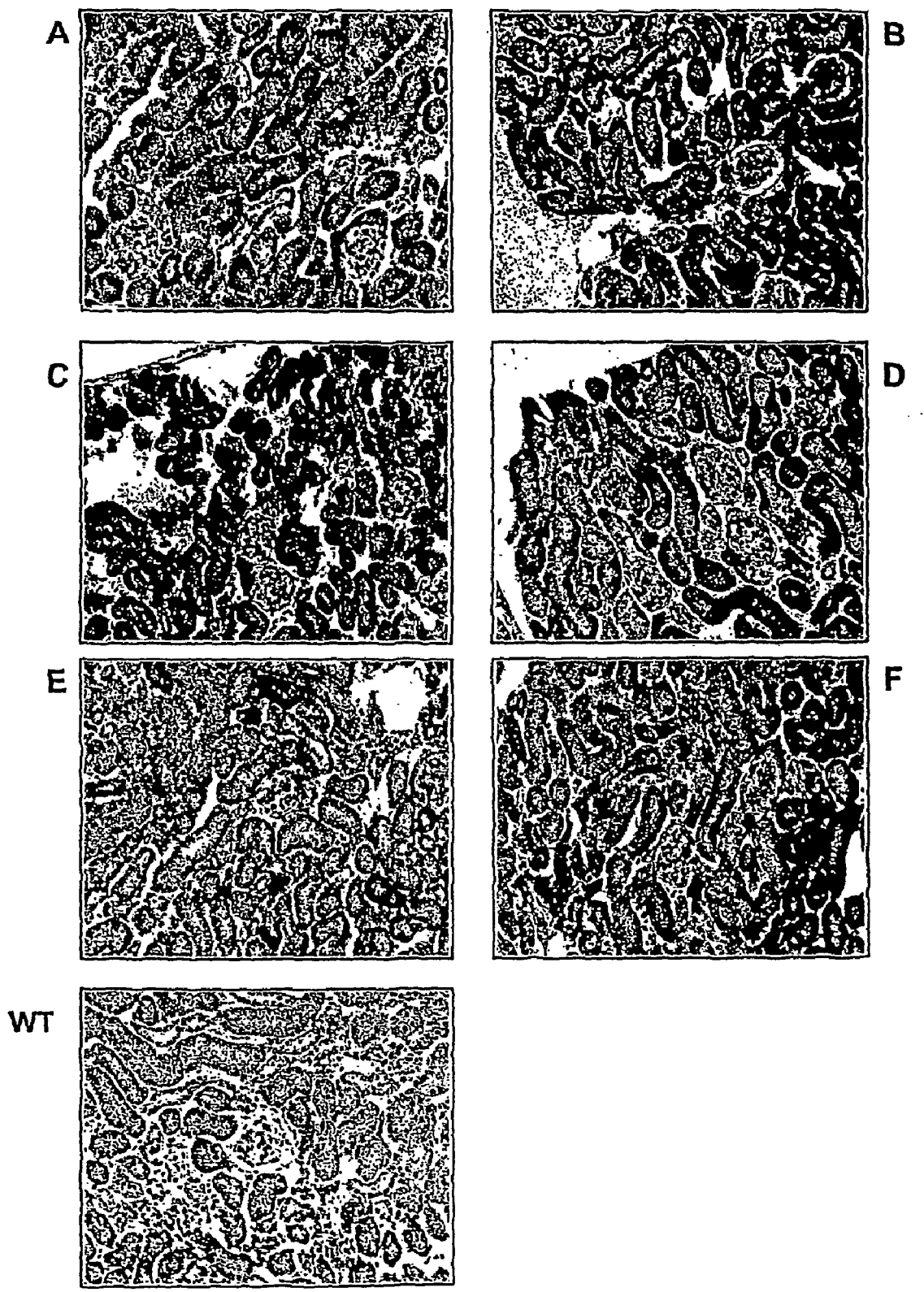
FIG. 18 is a GFP-specific immunoperoxidase staining of kidney paraffin sections from transgenic GFP mice.
Figure 19:
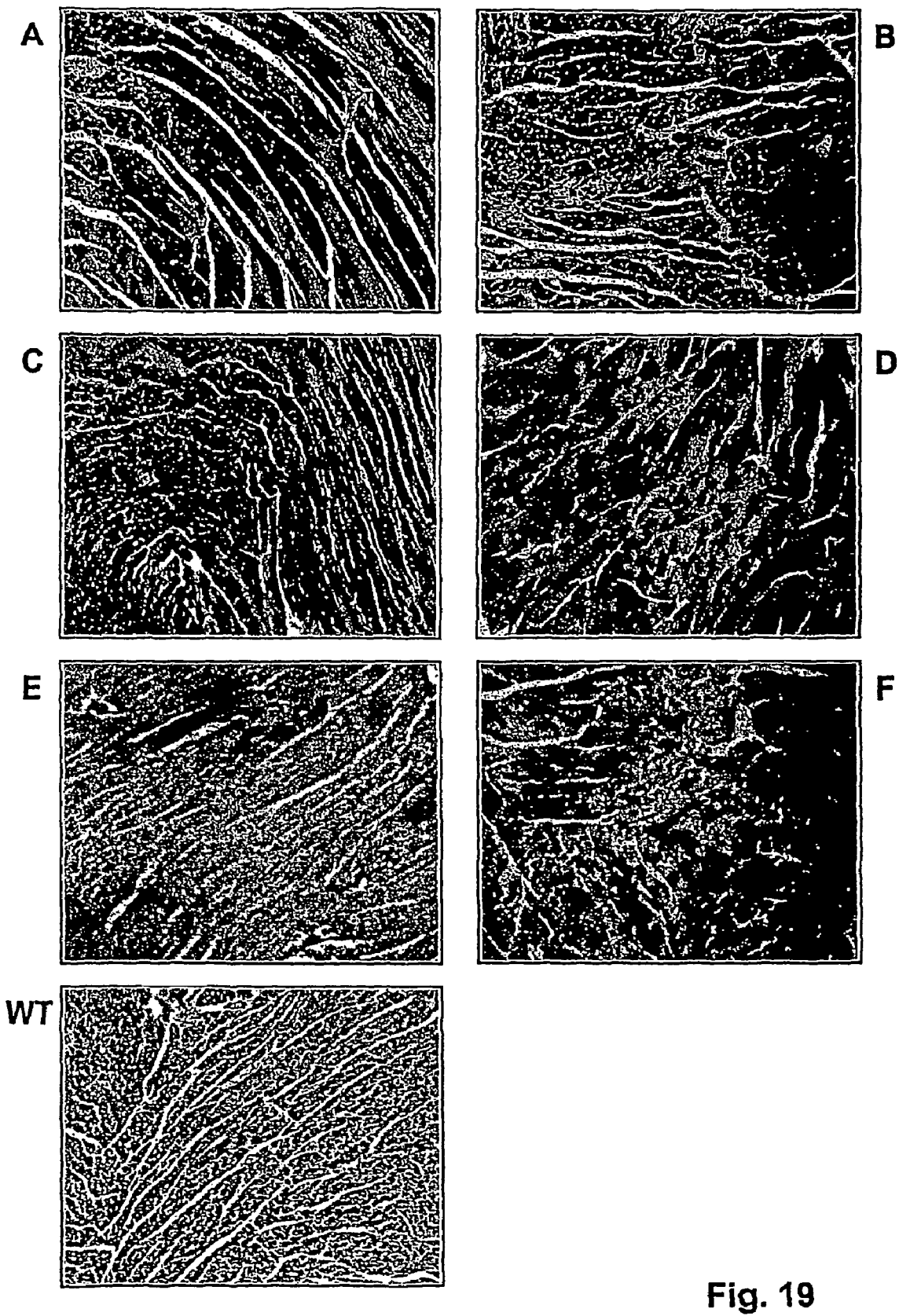
FIG. 19 is a GFP-specific immunoperoxidase staining of heart paraffin sections from transgenic GFP mice.
Figure 20:
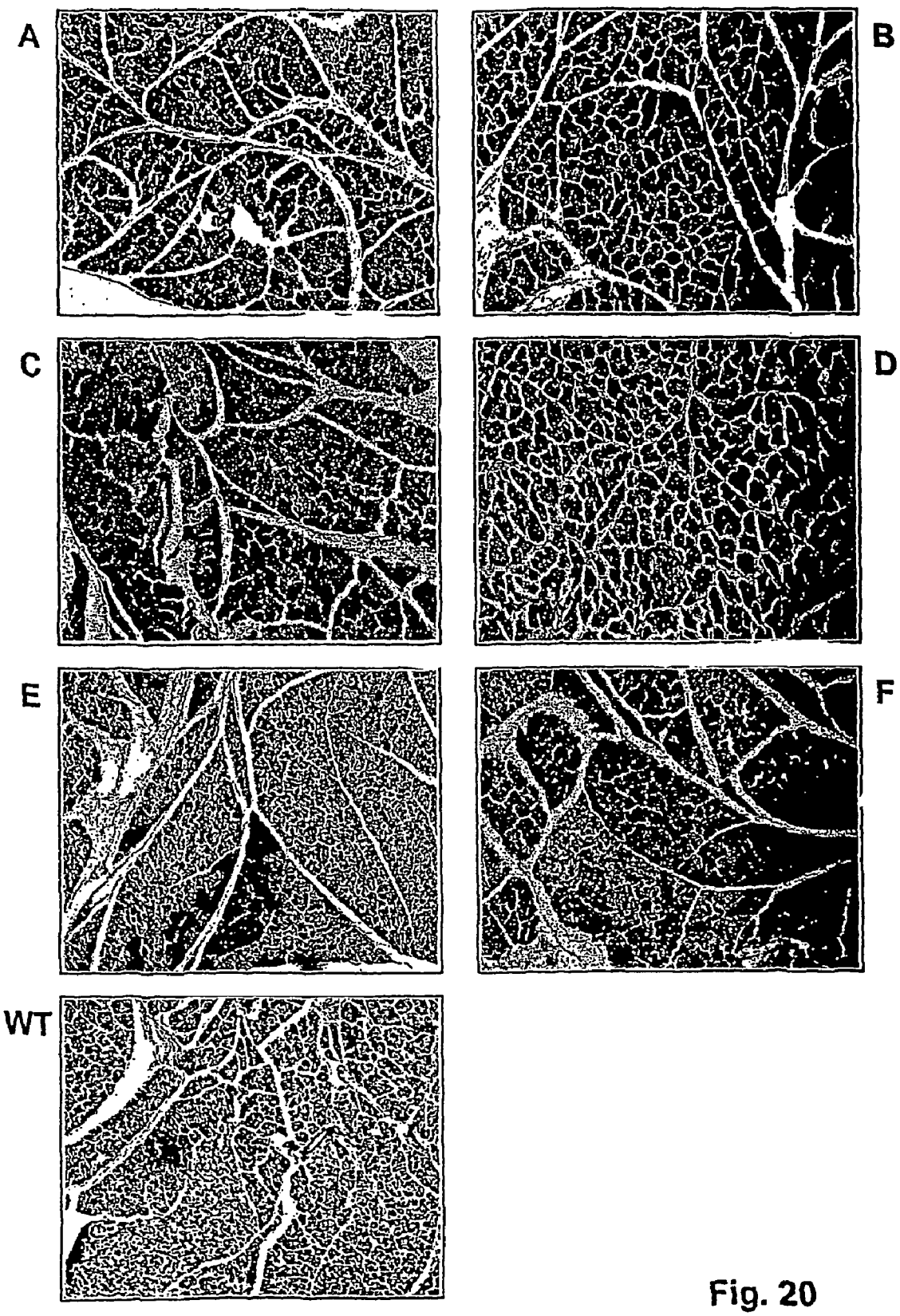
FIG. 20 is a GFP-specific immunoperoxidase staining of pancreas paraffin sections from transgenic GFP mice.
Figure 21:
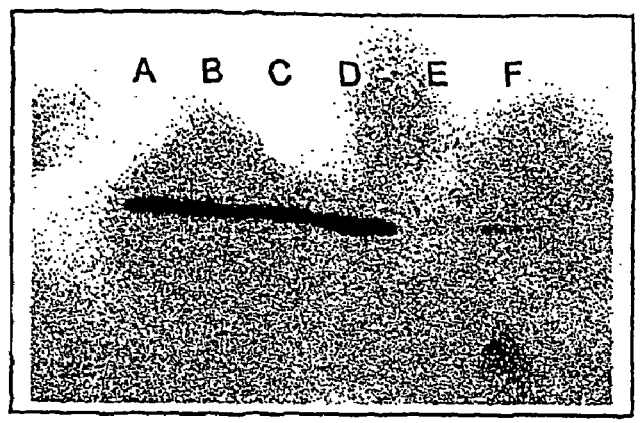
FIG. 21 is a Western blot analysis of GFP expression in plasma.
Figure 22:
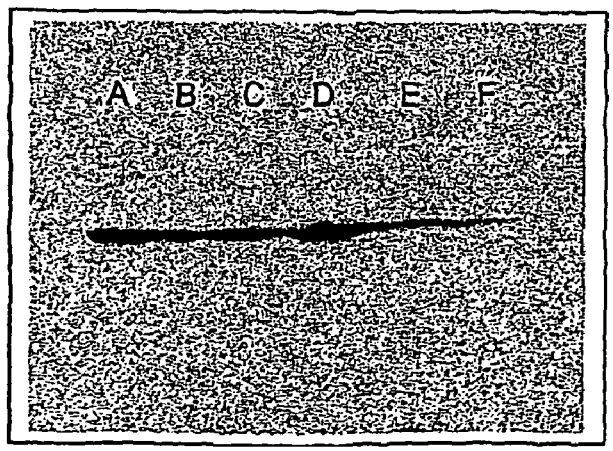
FIG. 22 is a Western blot analysis of GFP expression in kidney.
Figure 23:
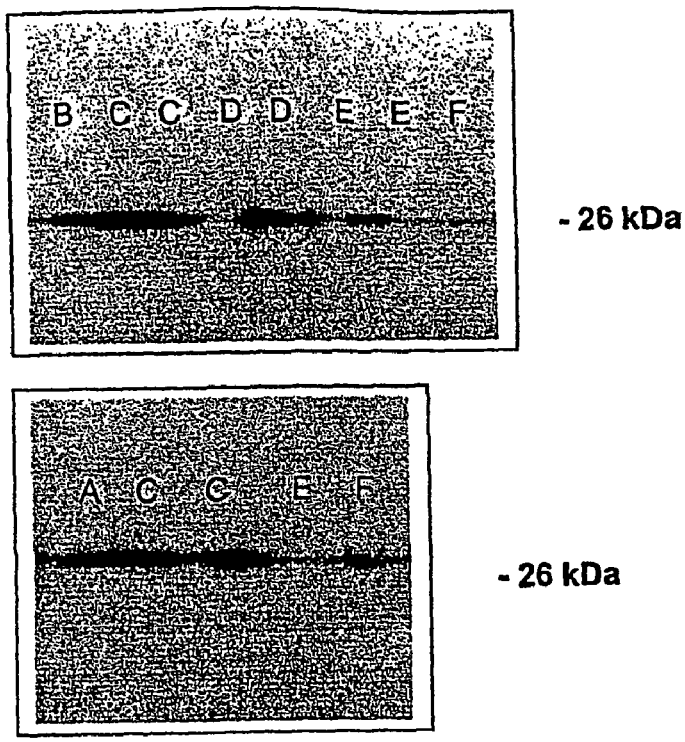
FIG. 23 is a Western blot analysis of GFP expression in heart.

FIGS. 18 to 20 show inhibition of GFP expression after intravenous injection of specific anti-GFP dsRNA, by means of immunoperoxidase GFP staining of 3 µm paraffin sections. Over the course of the experiment, the anti-GFP dsRNA, with a double-stranded region of 22 nucleotide (nt) pairs without overhangs at the 3'-ends (D) and the corresponding non-specific control dsRNA (B), as well as the specific anti-GFP dsRNA, with a double-stranded region consisting of 19 nucleotide pairs with 2 nt overhangs at the 3'-ends (E), and the corresponding non-specific control dsRNA (C) were applied in 12-hour rotation over 5 days. (F) received 1/50 the dosage of Group (D). Animals not administered dsRNA (A) and WT animals were used as further controls. FIG. 18 shows the inhibition of GFP expression in kidney sections; FIG. 19 in heart sections; and FIG. 20 in pancreas tissue. FIGS. 21 to 23 show Western blot analyses of GFP expression in plasma and tissues. FIG. 21 shows the inhibition of GFP expression in plasma; FIG. 22 in kidney; and FIG. 23 in heart. FIG. 23 shows the total protein isolate from various animals. The same quantities of total protein were used for each track. In the animals that were given non-specific control dsRNA (animals in Groups B and C), GFP is not reduced in comparison with animals that received no dsRNA. Animals that received the specific anti-GFP dsRNA with 2 nt overhangs at the 3'-ends of both strands and a double-stranded region consisting of 19 nucleotide pairs showed significantly inhibited GFP expression in the tissues studied (heart, kidneys, pancreas, and blood), compared with untreated animals (FIGS. 18-23). Of the animals in Groups D and F, who were given specific anti-GFP dsRNA, with blunt ends and a double-stranded region consisting of 22 nucleotide pairs, only those animals that received the dsRNA at a dosage of 50 µg/kg body weight per day demonstrated specific inhibition of GFP expression. However, the degree of inhibition was less marked than that seen with the animals in Group E.

A summary evaluation of GFP expression in tissue sections and Western blot shows that the inhibition of GFP expression is greatest in blood and in kidneys (FIGS. 18, 21 and 22).

Example 2

Inhibition of EGFR Gene Expression with EGFR-specific siRNA

The epidermal growth factor (=EGF) receptor (=EGFR) belongs to the tyrosin kinase receptors, transmembrane proteins with an intrinsic tyrosin kinase activity that are involved in the control of a series of cellular processes such as cell growth, cell differentiation, migratory processes, and cell vitality (reviewed in: Van der Geer et al., 1994). The EGFR family consists of 4 members, EGFR (ErbB1), HER2 (ErbB2), HER3 (ErbB3), and HER4 (ErbB4) with a transmembrane domain, a cysteine-rich extracellular domain, and a catalytic intracellular domain. The EGFR sequence, a 170-kDa protein, was first described by Ullrich et al., 1984.

EGFR is activated by peptide growth factors such as EGF, TGFα (transforming growth factor), amphiregulin, betacellulin, HB-EGF (heparin binding EGF-like growth factor), and neuregulins. Ligand binding induces the formation of homodimers or heterodimers with subsequent autophosphorylation of cytoplasmic tyrosine (Ullrich & Schlessinger, 1990; Alroy & Yarden, 1997). The phosphorylated amino acids form the binding sites of numerous proteins that are involved in the initial steps of a complex signal transduction pathway. EGFR is involved in many cancers, and is therefore an appropriate target for therapeutic approaches (Huang & Harari, 1999). The mechanisms that lead to aberrant EGFR activity may be related to overexpression, amplification, constitutive activation of mutant receptor forms, or autocrine loops (Voldberg et al., 1997). Overexpression of EGFR has been described for a series of tumors such as breast cancer (Walker & Dearing, 1999), non-minor lung cancer (Fontaninii et al., 1998), pancreatic cancer, colon cancer (Salomon et al., 1995), and glioblastoma (Rieske et al., 1998). For malignant glioblastoma, in particular, there have to date been no effective and specific therapeutic agents.

Example 3

Efficacy of Inhibition of EGFR Gene Expression

To test the effectiveness of dsRNA for the specific inhibition of EGFR gene expression, U-87 MG cells (human glioblastoma cells), ECCAC (European Collection of Animal Cell Culture) No. 89081402 were transfected with the specific anti-EGF receptor-directed dsRNA (sequence identification SEQ ID NO. 51). After approximately 72 hours of incubation, the cells were harvested, the protein was isolated, and EGFR expression was analyzed by Western blot.

Test Protocol:

Synthesis and Preparation of dsRNAs

Oligoribonucleotides were synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM tris, 10 mM $NaClO_4$, pH 6.8, 10% acetonitrile; flow rate: 3 ml/min). Formation of double stranded siRNAs was then achieved by heating a stoichiometric mixture of the individual complementary strands (10 M) to 95° C. for 5 minutes in 25 mM Tris-HCl, pH 7.5, and 100 mM NaCl, followed by subsequent cooling for 6 hours to room temperature dsRNA molecules with linkers were produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) was coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite was comparable to the incorporation of nucleoside phosphoramidites.

Seeding the Cells:

All cells were cultured under sterile conditions at an appropriate workstation (HS18/Hera Safe, Kendro, Heraeus). U-87 MG cells were incubated in a $CO_2$-incubator (T20, Hera Cell, Kendro, Heraeus) at 37° C., 5% $CO_2$ and saturated atmospheric humidity in DMEM (Dulbecco's modified eagle medium, Biochrom) with 10% FCS (fetal calf serum, Biochrom), 2 mM L-glutamine (Biochromone) mM sodium pyruvate (Biochrom), 1×NEAA (nonessential amino acids, Biochrom), and penicillin/streptomycin (100 IU/100 µg/ml, Biochrom). In order to maintain the cells in an exponential growth state, the cells were passaged every 3 days. 24 hours before dsRNA application by means of transfection, the cells were trypsinized (10× trypsin/EDTA, Biochrom, Germany) and placed in a 6-well plate (6-well plates, Schubert & Weiss Laboratories, GmbH) in 1.5 µl growth medium.

DsRNA Application in Cultured U-87 MG Cells:

Cells were transfected with dsRNA using the OLIGO-FECTAMINE™ reagent (Life Technologies) in accordance with the manufacturer's instructions. Total transfection volume was 1 ml. First, the dsRNA was diluted in serum-free medium: 0.5 µl of a 20 µM stock solution of specific anti-EGFR directed dsRNA and 9.5 µl of a 20 µM stock solution of nonspecific dsRNA (K1A/K2B) diluted with 175 µl serum-free medium in the transfection incubate or 10 nM specific EGFR-dsRNA) per well. The OLIGO-FECTAMINE™ reagent was also diluted in serum-free medium: 3 µl with 12 µl medium per well and then incubated for 10 minutes at room temperature. Then the diluted OLIGOFECTAMINE™ reagent was added to the medium of diluted dsRNA, mixed, and incubated for a further 20 minutes at room temperature. The medium was changed during incubation. The cells were washed 1× with 1 ml serum-free medium and further incubated with 800 µl serum-free medium until the dsRNA/OLIGOFECTAMINE™ reagent was added. After the addition of 200 µl dsRNA/OLIGOFECTAMINE™ reagent per well, the cells incubated up until protein isolation.

Protein Isolation:

Approximately 72 hours after transfection, the cells were harvested and total protein was isolated. The medium was removed, and the cell monolayer was washed once with PBS. After the addition of 200 µl protein isolation buffer (1× "Complete" protease inhibitor, Roche, 50 mM HEPES, pH 7.5, 150 mM NaCl, 1 mM EDTA, 2.5 mM EGTA, 10% glycerin, 0.1% Tween-20, 1 mM DTT, 10 mM β-glycerine phosphate, 1 mM NaF, 0.1 mM $Na_3VO_4$) the cells were removed with the help of a cell scraper, incubated for 10 minutes on ice, transferred to an Eppendorf reagent vessel, and stored at −80° C. for at least 30 minutes. After thawing, the lysate was homogenized at the third setting for 10 seconds with a disperser (DIAX 900, 6G disperser, Heidolph Instruments GmbH, Schwabach), incubated on ice for 10 minutes, and then centrifuged for 15 minutes at 14,000×g at 4° C. (3K30, Sigma). Quantitation of total protein in the supernatant was determined according to Bradford using the Roti-Nanoquant system from Roth (Roth GmbH, Karlsruhe) in accordance with the manufacturer's instructions. 200 µl protein solution at a suitable dilution is mixed with 800 µl 1× working solution, and extinction was measured in semi-microcuvettes at 450 nm and 590 nm against distilled water in a Beckman spectrophotometer (DU 250). BSA dilutions were used for calibration (beaded BSA, Sigma).

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS; 3.3 ml distilled water; 250 µl ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µl 1 M tris/HCl, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DTT (dithiotreithol), 0.02% bromophenol blue, 20% glycerin) was then added to the proteins, which were then denatured on a heat block at 100° C., centrifuged on ice after cooling off, and then applied to the gel (35 µg total protein/lane). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Transfer of the proteins from SDS-PAGE to a PVDF (polyvinyl difluoride) membrane (Hybond-P, Amersham) was done using a semidry method according to Kyhse-Anderson (J. Biochem. Biophys. Methods 10:203-210, 1984) at room temperature and a constant 0.8 mA/cm² for 1.5 hours. A cathode buffer (30 mM Tris, 40 mM glycine, 10% methanol, and 0.1% SDS, pH 9.4), anode buffer I (300 mM Tris, pH 10.4, 10% methanol), and anode buffer II (30 mM Tris, pH 10.4, 10% methanol) were used as the transfer buffers. Before assembling the blot stack with 3MM Whatman paper (Schleicher & Schüll) the gel was incubated in cathode buffer, and the PVDF membrane (previously for 30 seconds in 100% methanol) in anode buffer II (5 minutes): 2 layers of 3MM paper (anode buffer I), 1 layer 3MM paper (anode buffer II), PVDF membrane, gel, 3 layers 3MM paper (cathode buffer). To analyze electrophoretic transfer, both the post-blot gels and the blot membranes were stained after immunodetection using Coomassie (0.1% Coomassie G250, 45% methanol, 10% glacial acetic acid).

After transfer, the blot membrane was incubated in 1% skim milk powder/PBS/0.1% Tween-20 for one hour at room temperature. After that, the membrane was washed three times for 3 minutes with 0.1% Tween-20/PBS. All subsequent antibody incubations and washings were done using 0.1% Tween-20/PBS. The primary antibody (human EGFR extracellular domain, specific goat IgG, Catalogue No. AF231, R&D Systems) was incubated with shaking for two hours at room temperature at a concentration of 1.5 µg/ml. After washing 3×5 minutes, the membrane was incubated for one hour at room temperature with the secondary antibody (labeled donkey anti-goat IgG horseradish peroxidase, Santa Cruz Biotechnology) at a dilution of 1:10,000. After washing (3×3 minutes in PBS/0.1% Tween-20) horseradish peroxidase was detected by ECL reaction (enhanced chemoluminescence). To 18 ml of distilled water, 200 µl Solution A (250 mM luminol, Roth, dissolved in DMSO), 89 µl Solution B (90 mM p-coumaric acid, Sigma, dissolved in DMSO), and 2 ml 30% $H_2O_2$ solution were added. Depending on membrane size, 4-6 ml were pipetted directly onto the membrane, incubated for 1 minute at room temperature, and then placed immediately on X-Ray film (Biomax MS, Kodak).

The sequences used here are depicted in Table 3 below, as well as in sequence protocols SEQ ID NOS. 153, 157, 158, 168-173.

TABLE 3

| ES-7 | SEQ ID NO. 168 (A) | 5'-AACACCGCAGCAUGUCAAGAU-3' | 2-19-2 |
|---|---|---|---|
| | SEQ ID NO. 169 (B) | 3'-UUUUGUGGCGUCGUACAGUUC-5' | |
| ES-8 | SEQ ID NO. 170 (A) | 5'-AAGUUAAAAUUCCCGUCGCUAU-3' | $2^5$-19-$2^5$ |
| | SEQ ID NO. 171 (B) | 3'-CAAUUUUAAGGGCAGCGAUAGU-5' | |

TABLE 3-continued

| | | | |
|---|---|---|---|
| ES2A/ES5B | SEQ ID NO. 172 (A) | 5'-AGUGUGAUCCAAGCUGUCCCAA-3' | 0-22-2 |
| | SEQ ID NO. 173 (B) | 3'-UUUCACACUAGGUUCGACAGGGUU-5' | |
| K2 | SEQ ID NO. 157 (A) | 5'-ACAGGAUGAGGAUCGUUUCGCAUG-3' | 2-22-2 |
| | SEQ ID NO. 158 (B) | 3'-UCUGUCCUACUCCUAGCAAAGCGU-5' | |
| K1A/K2B | SEQ ID NO. 153 (A) | 5'-ACAGGAUGAGGAUCGUUUCGCA-3' | 0-22-2 |
| | SEQ ID NO. 158 (B) | 3'-UCUGUCCUACUCCUAGCAAAGCGU-5' | |

Example 4

Figure 24:
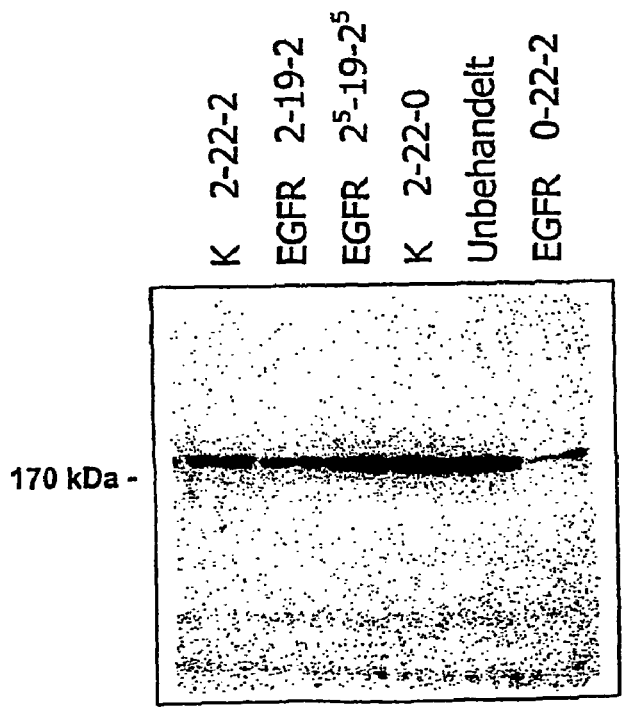
FIG. 24 is a Western blot analysis of EGFR expression in U-87 MG glioblastoma cells.

Inhibition of EGFR Expression in U-87 MG Glioblastoma Cells 24 hours after seeding the cells, U-87 MG glioblastoma cells were transfected with 10 nM dsRNA and oligofectamine. After 72 hours, the cells were harvested and total protein isolated and loaded on to a 7.5% SDS-PAGE gel. 35 µg total protein was applied to each lane. The corresponding Western blot analysis (see FIG. 24) shows that with the specific anti-EGFR-directed dsRNA with a 2 nt overhang at the 3'-end of the antisense strand, EGFR expression in U-87 MG cells is significantly inhibited in comparison to the corresponding controls. This inhibition of expression of an endogenous gene by means of specific dsRNA confirms the results noted in Example II. The inhibition of EGFR expression mediated by ES-7 and ES-8 is notably smaller. The dsRNAs used in FIG. 24 are shown in Table 3.

Example 5

Treatment of a Breast Cancer Patient with EGFR siRNA

In this Example, EGFR-specific double stranded siRNA is injected into a breast cancer patient and shown to specifically inhibit EGFR gene expression.

SiRNA Synthesis

EGFR-specific siRNAs directed against the fusion sequence of EGFR are chemically synthesized with or without a hexaethylene glycol linker as described above siRNA Administration and Dosage The present example provides for pharmaceutical compositions for the treatment of human breast cancer patients comprising a therapeutically effective amount of a EGFR-specific siRNA as disclosed herein, in combination with a pharmaceutically acceptable carrier or excipient. SiRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare siRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa., 1980.

The dosage of the siRNAs will vary depending on the form of administration. In the case of an injection, the therapeutically effective dose of siRNA per injection is in a dosage range of approximately 1-500 g/kg body weight, preferably 100 g/kg body weight. In addition to the active ingredient, the compositions usually also contain suitable buffers, for example phosphate buffer, to maintain an appropriate pH and sodium chloride, glucose or mannitol to make the solution isotonic. The administering physician will determine the daily dosage which will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The siRNAs of the present invention may be administered alone or with additional siRNA species or in combination with other pharmaceuticals.

RNA Purification and Analysis

Efficacy of the siRNA treatment is determined at defined intervals after the initiation of treatment using real time PCR or RNAse protection assays on total RNA extracted tissue bipsies. Cytoplasmic RNA from whole blood, taken prior to and during treatment, is purified with the help of the RNeasy Kit (Qiagen, Hilden) and Bcr-abl mRNA levels are quantitated by real time RT-PCR. Real-time Taqman-RT-PCR is performed as described previously (Eder M et al. Leukemia 1999; 13: 1383-1389; Scherr M et al. BioTechniques. 2001; 31: 520-526). Analysis by real time PCR at regular intervals, for example every 1-2 weeks, provides the attending physician with a rapid and accurate assessment of treatment efficacy as well as the opportunity to modify the treatment regimen in response to the patient's symptoms and disease progression.

Example 6

EGFR-Specific siRNA Expression Vectors

In another aspect of the invention, siRNA molecules that interact with target RNA molecules and modulate gene expression activity are expressed from transcription units inserted into DNA or RNA vectors (see for example Couture et A, 1996, TIG., 12, 510, Skillern et A, International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292).

The individual strands of a siRNA can be transcribed by promoters on two separate expression vectors and cotransfected into a target cell. Alternatively each individual strand of the siRNA can be transcribed by promoters both of which are located on the same expression plasmid. In a preferred embodiment, the siRNA is expressed as an inverted repeat joined by a linker polynucleotide sequence such that the siRNA has a stem and loop structure.

The recombinant siRNA expression vectors are preferably DNA plasmids or viral vectors. siRNA expressing viral vectors can be constructed based on, but not limited to, adeno-associated virus (for a review, see Muzyczka et al. (1992, Curr. Topics in Micro. and Immunol. 158:97-129)), adenovirus (see, for example, Berkner et al. (1988, BioTechniques 6:616), Rosenfeld et al. (1991, Science 252:431-434), and Rosenfeld et al. (1992, Cell 68:143-155)), or alphavirus as well as others known in the art. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254: 1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving siRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268276); the endothelin regulatory sequence for endothelial cells (Lee, 1990, J. Biol. Chem. 265:10446-50); the keratin regulatory sequence for epidennis; the myosin light chain-2 regulatory sequence for heart (Lee et al., 1992, J. Biol. Chem. 267: 15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since NMC expression is induced by cytokines, expression of a test gene operably linked to this promoter can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the siRNA transgene.

Preferably, recombinant vectors capable of expressing siRNA molecules are delivered as described below, and persist in target cells. Alternatively, viral vectors can be used that provide for transient expression of siRNA molecules. Such vectors can be repeatedly administered as necessary. Once expressed, the siRNAs bind to target RNA and modulate its function or expression. Delivery of siRNA expressing vectors can be systemic, such as by intravenous or intramuscular administration, by administration to target cells ex-planted from the patient followed by reintroduction into the patient, or by any other means that allows for introduction into a desired target cell.

SiRNA expression DNA plasmids are typically transfected into target cells as a complex with cationic lipid carriers (e.g. Oligofectamine) or non-cationic lipid-based carriers (e.g. Transit-TKO™). Multiple lipid transfections for siRNA-mediated knockdowns targeting different regions of a single target gene or multiple target genes over a period of a week or more are also contemplated by the present invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

For a review of techniques that can be used to generate and assess transgenic animals, skilled artisans can consult Gordon (IwL Rev. CytoL 115:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., Bio/Technology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Scieizce, 244:1281, 1986; Wagner et al., U.S. Pat. No. 5,175,385; and Krimpenfort et al., U.S. Pat. No. 5,175,384.

The EGFR-specific siRNAs described above can also be generally inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 7

Method of Determining an Effective Dose of a siRNA

A therapeutically effective amount of a composition containing a sequence that encodes an EGFR-specific siRNA, (i.e., an effective dosage), is an amount that inhibits expression of the polypeptide encoded by the EGFR target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the siRNA may be desired. When an inducible promoter is included in the construct encoding an siRNA, expression is assayed upon delivery to the subject of an appropriate dose of the substance used to induce expression.

Appropriate doses of a composition depend upon the potency of the molecule (the sequence encoding the siRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). In addition, the attending physician will monitor the symptoms associated with the disease or disorder afflicting the patient and compare with those symptoms recorded prior to the initiation of siRNA treatment.

Example 8

Inhibiting Expression of Multi-drug Resistance Gene 1 (MDR1) Using a MDR-1 Specific siRNA Inhibition of MDR1 expression by MDR-1 specific siRNA was tested using the colon cancer cell line LS174T (ATCC—American Type Culture Collection; Tom et al., 1976). Expression of MDR1 in this cell line is inducible by adding rifampicin to the culture medium (Geick et al., 2001). Cells were transfected with MDR-1 specific siRNA using a variety of commercially available transfection kits (Lipofectamine, Oligofectamine, both from Invitrogen; TransMessenger, Qiagen), of which the TransMessenger kit proved to be the most suitable for this cell line.

Four short double-stranded ribonucleic acids (R1-R4) were tested (see Table 4). The ribonucleic acids are homologous with segments of the coding sequence ofMDR1 (sequence protocol SEQ ID NO. 30). Sequences R1-R3 consist of a 22-mer sense strand and a 24mer antisense strand, whereby the resulting double strand exhibits a 2-nucleotide overhang at its 3'-end (0-22-2).

Sequence R4 corresponds to R1; however it consists of a 19-mer double-stranded, each with 2-nucleotide overhangs at each 3'-end (2-19-2).

TABLE 4

| Name | Sequence ID No. | Sequence | Position in Data bank-# AF016535 |
|---|---|---|---|
| Seq R1 | SEQ ID NO. 141 | 5'- CCA UCU CGA AAA GAA GUU AAG A-3' | 1320-1342 |
|  | SEQ ID NO. 142 | 3'-UG GGU AGA GCU UUU CUU CAA UUC U-5' | 1335-1318 |
| Seq R2 | SEQ ID NO. 143 | 5'- UAU AGG UUC CAG GCU UGC UGU A-3' | 2599-2621 |
|  | SEQ ID NO. 152 | 3'-CG AUA UCC AAG GUC CGA ACG ACA U-5' | 2621-2597 |
| Seq R3 | SEQ ID NO. 144 | 5'- CCA GAG AAG GCC GCA CCU GCA U-3' | 3778-3799 |
|  | SEQ ID NO. 145 | 3'-UC GGU CUC UUC CGG CGU GGA CGU A-5' | 3799-3776 |
| Seq R4 | SEQ ID NO. 146 | 5'- CCA UCU CGA AAA GAA GUU AAG-3' | 1320-1341 |
|  | SEQ ID NO. 147 | 3'-UG GGU AGA GCU UUU CUU CAA U-5' | 1339-1318 |
|  |  |  | Position in Data bank-# AF402779 |
| K1A/K2B | SEQ ID NO. 153 | 5'- ACA GGA UGA GGA UCG UUU CGC A-3' | 2829-2808 |
|  | SEQ ID NO. 158 | 3'-UC UGU CCU ACU CCU AGC AAA GCG U-5' | 2808-2831 |

The sequences shown in Table 4 are designated as sequences SEQ ID NOS. 141-147, 152, 153, and 158 in the sequence protocol. Cells were first seeded in 12-well plates at 3.8×105 cells/well. A day later, dsRNA was transfected into the cells in duplicate at a concentration of 175 nM. For each transfection assay, 93.3 III EC-R buffer (TransMessenger kits, Qiagen, Hilden) was mixed with 3.2 III Enhancer R prior to the addition of 3.5 III of the particular 20 J1M dsRNA, mixed well, and incubated for 5 minutes at room temperature. After the addition of 6J11 TransMessenger transfection reagent, the transfection assay was mixed vigorously for 10 seconds, and then incubated for a further 10 minutes at room temperature. The cells were then washed once with PBS (phosphate-buffered saline), and 200 µl fresh medium without FCS was added to the cells in each well. After 10-minute incubation, 100 µl FCS-free medium was pipetted into each transfection assay, mixed, and the mixture was then pipetted drop by drop onto the cells (the dsRNA concentration of 175 µM relates to 400 µl medium total volume). The dsRNA/TransMessenger complexes were incubated with the cells for 4 hours at 37° C. in FCS-free medium. The medium was then changed and replaced with fresh medium containing 10 µM rifampin and 10% FCS. A non-specific dsRNA sequence that exhibits no homologies with the MDR1 gene sequence was used (K) as a control, and a MOCK transfection was conducted that contained all reagents except for dsRNA.

The cells were harvested after 24, 48, and 72 hours, and total RNA was extracted with the RNeasy mini kit from Qiagen. 10 µg total protein from each sample was then separated by electrophoresis on a 1% agarose-formaldehyde gel, blotted on a nylon membrane, and then hybridized as an internal control with specific probes that had been randomly-marked with 5'-$\alpha^{32}$p-dCTP, first against MDR1, and after the blot had been stripped, against GAPDH, and then exposed on x-ray film. The x-ray film was digitized (Image Master, VDS, Pharmacia) and quantified using Image-Quant software and standardized against the GAPDH signal.

Figure 25A:
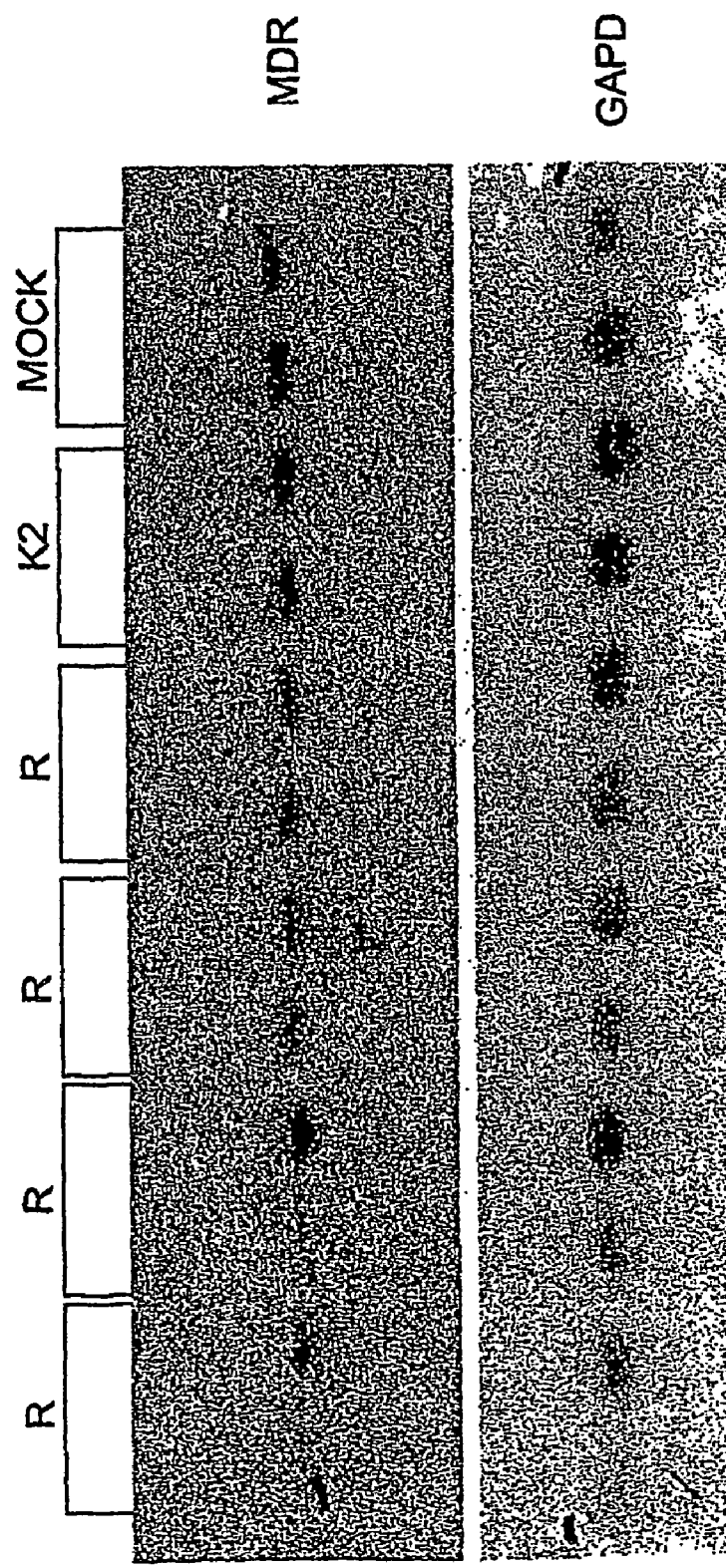
FIG. 25 show a Northern blot analysis of the MDRI mRNA level in colon carcinoma cell line LS174T, whereby the cells were harvested after 74 hours (FIG. 25a); and quantification of the bands in FIG. 25a, whereby the averages are represented by two values (FIG. 25b).
Figure 25B:
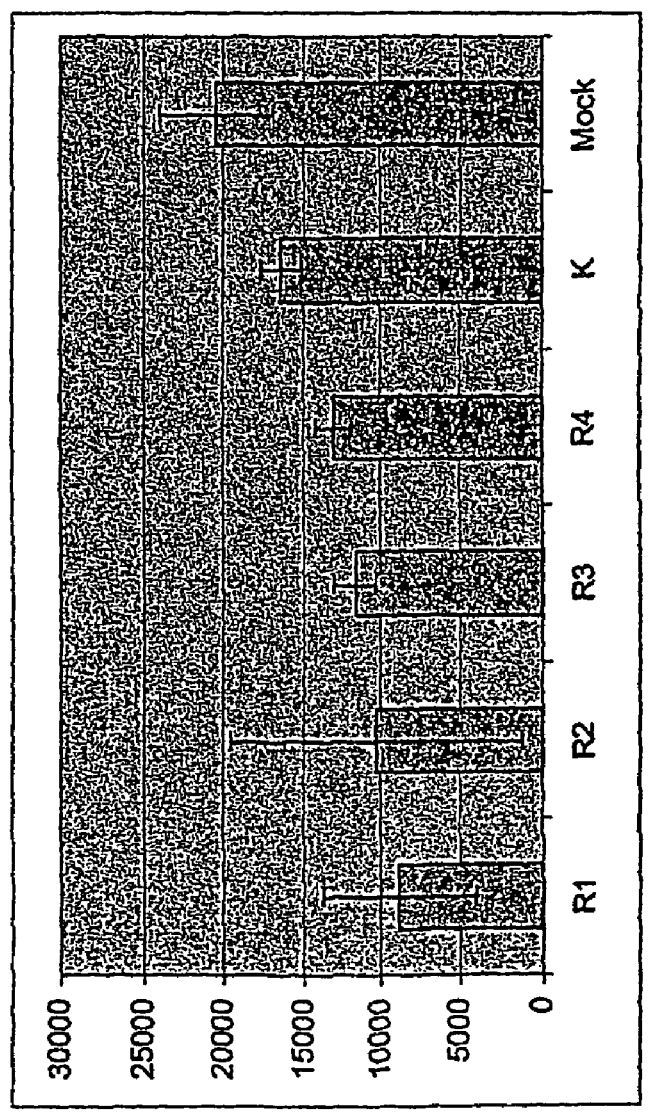
Figure 26A:
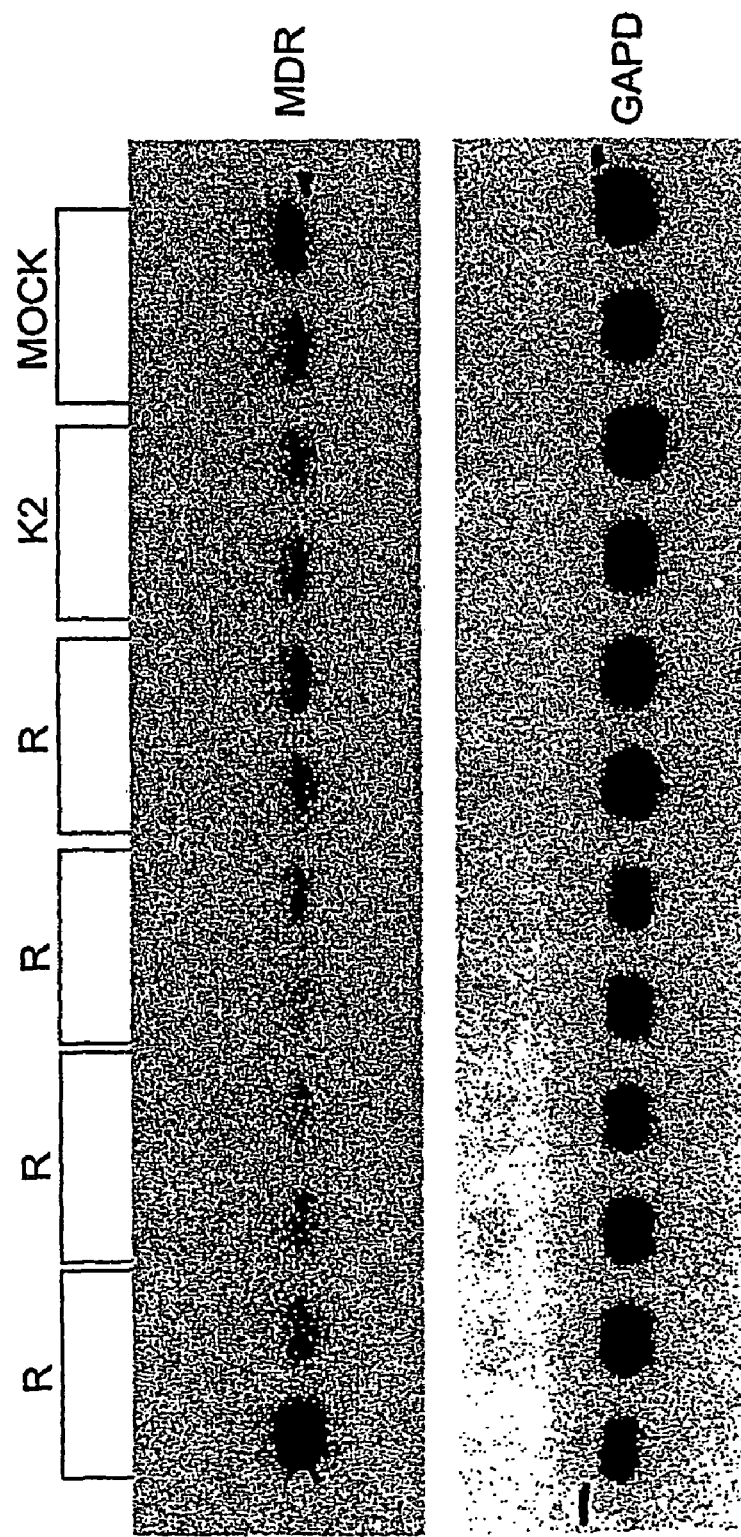
FIG. 26 shows a Northern blot analysis of the MDRI mRNA level in colon carcinoma cell line LS174T, whereby the cells were harvested after 48 hours (FIG. 26a); and quantification of the bands in FIG. 26a, whereby the averages of two values are represented (FIG. 26b).
Figure 26B:
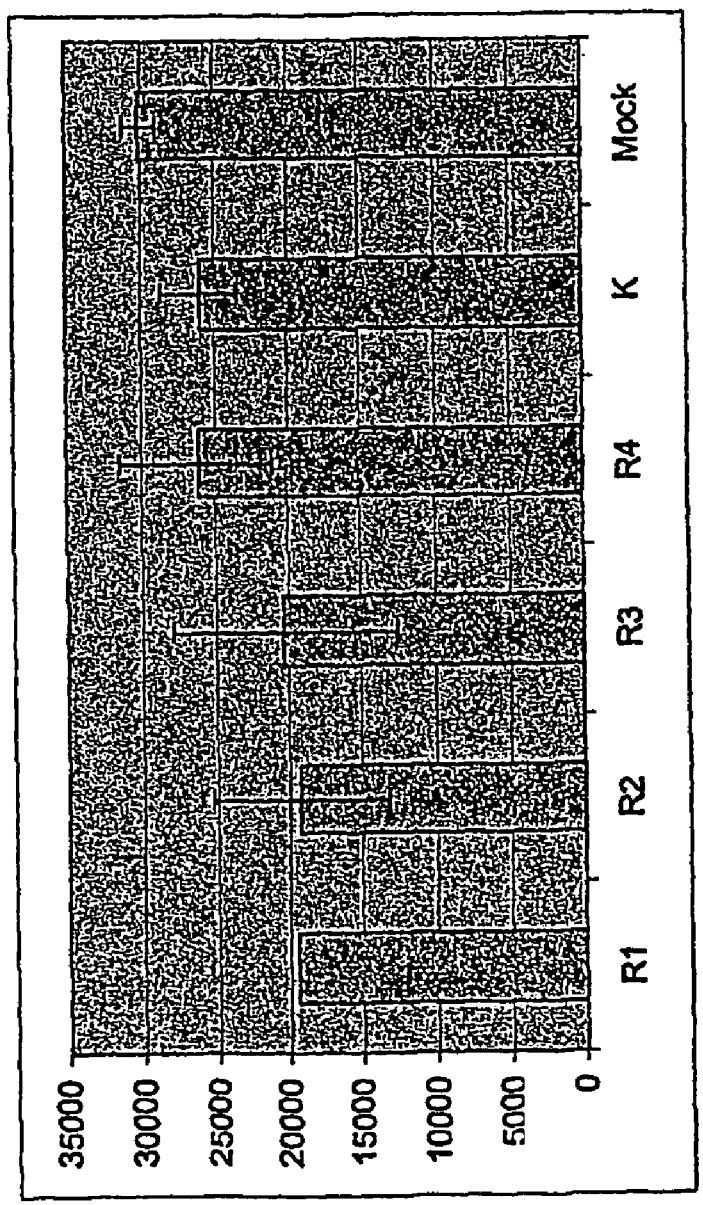

FIGS. 25 and 26 show Northern blots (FIGS. 26a, 26a) with quantitative analysis of the MDR1-specific signal after adjustment with the corresponding GAPDH values (FIGS. 25b, 26p). A reduction in the MDR1 mRNA by as much as 55% was observed in comparison to the MOCK transfection, and by as much as 45% in comparison to the non-specific control transfection. After 48 hours there was a significant reduction in the MDR1-mRNA level in the dsRNA constructs designated as R1, R2, and R3 (Table 4). With the R4 dsRNA constructs, no significant reduction compared to controls was observed after 48 hours (FIGS. 26a and 26b). After 74 hours, there was an even stronger reduction in MDR1-mRNA levels in the presence of R1, R2, and R3 as compared to the values observed at 48 hours (FIGS. 25a and 26b). A significant decrease in the MDR1-mRNA level was seen at this time with R4 as well. Thus, the constructs with a 2 nt overhang at the 3'-end of the antisense strand and a double-stranded region consisting of 22 nucleotide pairs reduces the MDR1-mRNA level more efficiently than do constructs with 2 nt overhangs at the 3'-end of both strands (antisense strand and sense strand) and a double-stranded region consisting of 19 nucleotide pairs, apparently independent of the sequence region homologous to the MDR1 gene in each case (after 48 hours; FIG. 26b). The results strengthen the findings in Example IV, which describe the inhibition of EGFR gene expression by means of specific dsRNAs after transfection in U-87 MG cells.

Transfection efficiency was determined in a separate experiment with the help of a DNA oligonucleotide marked with Texas red (TexRed-A[GATC]$_5$T; also transfected with 175 nM) (FIGS. 27a, 27b; 400× enlargement, 48 hours after transfection). Transfection efficiency was approximately 50% on the basis of red fluorescent cells in comparison to total cell number. If one takes the transfection rate of cells of approximately 50% into consideration, then the observed decrease in the MDR1-mRNA level by approximately 45-55% (compared with the controls) indicates that MDR1-mRNA was almost completely and specifically broken down in all cells that were successfully transfected with specific dsRNA.

SEQUENCE LISTING

```
<160> NUMBER OF SEQ ID NOS: 173

<210> SEQ ID NO 1
<211> LENGTH: 2955
<212> TYPE: DNA
<213> ORGANISM: Homo sapiens
<300> PUBLICATION INFORMATION:
<302> TITLE: Eph A1
<310> PATENT DOCUMENT NUMBER: NM00532

<400> SEQUENCE: 1
atggagcggc gctggcccct ggggctaggg ctggtgctgc tgctctgcgc cccgctgccc      60 ccggggggcgc gcgccaagga agttactctg atggacacaa gcaaggcaca gggagagctg     120
ggctggctgc tggatccccc aaaagatggg tggagtgaac agcaacagat actgaatggg     180 acaccctct acatgtacca ggactgccca atgcaaggac gcagagacac tgaccactgg      240
cttcgctcca attggatcta ccgcggggag gaggcttccc gcgtccacgt ggagctgcag     300
ttcaccgtgc gggactgcaa gagtttcccct gggggagccg ggcctctggg ctgcaaggag    360
accttcaacc ttctgtacat ggagagtgac caggatgtgg gcattcagct ccgacggcc      420
```

-continued

```
ttgttccaga aggtaaccac ggtggctgca gaccagagct tcaccattcg agaccttgcg     480
tctggctccg tgaagctgaa tgtggagcgc tgctctctgg gccgcctgac ccgccgtggc     540
ctctacctcg ctttccacaa cccgggtgcc tgtgtggccc tggtgtctgt ccgggtcttc     600
taccagcgct gtcctgagac cctgaatggc ttggcccaat tcccagacac tctgcctggc     660
cccgctgggt tggtggaagt ggcgggcacc tgcttgcccc acgcgcgggc cagccccagg     720
ccctcaggtg caccccgcat gcactgcagc cctgatggcg agtggctggt gcctgtagga     780
cggtgccact gtgagcctgg ctatgaggaa ggtggcagtg gcgaagcatg tgttgcctgc     840
cctagcggct cctaccggat ggacatggac acacccatt gtctcacgtg cccccagcag     900
agcactgctg agtctgaggg ggccaccatc tgtacctgtg agagcggcca ttacagagct     960
cccgggggagg gccccaggt ggcatgcaca ggtcccccct cggcccccg aaacctgagc    1020
ttctctgcct cagggactca gctctccctg cgttgggaac cccagcaga tacgggggga    1080
cgccaggatg tcagatacag tgtgaggtgt tcccagtgtc agggcacagc acaggacggg    1140
gggccctgcc agccctgtgg ggtgggcgtg cacttctcgc cgggggcccg ggcgctcacc    1200
acacctgcag tgcatgtcaa tggccttgaa ccttatgcca actacacctt taatgtggaa    1260
gcccaaaatg gagtgtcagg gctgggcagc tctggccatg ccagcacctc agtcagcatc    1320
agcatggggc atgcagagtc actgtcaggc ctgtctctga actggtgaa gaaagaaccg    1380
aggcaactag agctgacctg gcggggtcc cggccccgaa gccctggggc gaacctgacc    1440
tatgagctgc acgtgctgaa ccaggatgaa gaacggtacc agatggttct agaacccagg    1500
gtcttgctga cagagctgca gcctgacacc acatacatcg tcagagtccg aatgctgacc    1560
ccactgggtc ctggcccttt ctccctgat catgagtttc ggaccagccc accagtgtcc    1620
aggggcctga ctggaggaga gattgtagcc gtcatctttg ggctgctgct tggtgcagcc    1680
ttgctgcttg ggattctcgt tttccggtcc aggagagccc agcggcagag gcagcagagg    1740
cacgtgaccg cgccaccgat gtggatcgag aggacaagct gtgctgaagc cttatgtggt    1800
acctccaggc atacgaggac cctgcacagg gagccttgga ctttacccgg aggctggtct    1860
aatttttcctt cccgggagct tgatccagcg tggctgatgg tggacactgt cataggagaa    1920
ggagagtttg gggaagtgta tcgagggacc ctcaggctcc ccagccagga ctgcaagact    1980
gtggccatta agaccttaaa agacacatcc ccaggtggcc agtggtggaa cttccttcga    2040
gaggcaacta tcatgggcca gtttagccac ccgcatattc tgcatctgga aggcgtcgtc    2100
acaaagcgaa agccgatcat gatcatcaca gaatttatgg agaatgcagc cctggatgcc    2160
ttcctgaggg agcgggagga ccagctggtc cctgggcagc tagtggccat gctgcagggc    2220
atagcatctg gcatgaacta cctcagtaat acaattatg tccaccggga cctggctgcc    2280
agaaacatct tggtgaatca aaacctgtgc tgcaaggtgt ctgactttgg cctgactcgc    2340
ctcctggatg actttgatgg cacatacgaa acccaggag gaaagatccc tatccgttgg    2400
acagcccctg aagccattgc ccatcggatc ttcaccacag ccagcgatgt gtggagcttt    2460
gggattgtga tgtgggaggt gctgagcttt ggggacaagc ttatgggga gatgagcaat    2520
caggaggtta tgaagagcat tgaggatggg taccggttgc cccctcctgt ggactgccct    2580
gcccctctgt atgagctcat gaagaactgc tgggcatatg accgtgcccg ccggccacac    2640
ttccagaagc ttcaggcaca tctggagcaa ctgcttgcca ccccccactc cctgcggacc    2700
attgccaact ttgaccccag ggtgactctt cgcctgccca gcctgagtgg ctcagatggg    2760
atcccgtatc gaaccgtctc tgagtggctc gagtccatac gcatgaaacg ctacatcctg    2820
```

| | |
|---|---|
| cacttccact cggctgggct ggacaccatg gagtgtgtgc tggagctgac cgctgaggac | 2880 |
| ctgacgcaga tgggaatcac actgcccggg caccagaagc gcattctttg cagtattcag | 2940 |
| ggattcaagg actga | 2955 |

<210> SEQ ID NO 2
<211> LENGTH: 3042
<212> TYPE: DNA
<213> ORGANISM: Homo sapiens
<300> PUBLICATION INFORMATION:
<302> TITLE: ephrin A2
<310> PATENT DOCUMENT NUMBER: XM002088

<400> SEQUENCE: 2

| | |
|---|---|
| gaagttgcgc gcaggccggc gggcgggagc ggacaccgag gccggcgtgc aggcgtgcgg | 60 |
| gtgtgcggga gccgggctcg gggggatcgg accgagagcg agaagcgcgg catggagctc | 120 |
| caggcagccc gcgcctgctt cgccctgctg tgggctgtg cgctggccgc ggccgcggcg | 180 |
| gcgcagggca aggaagtggt actgctggac tttgctgcag ctggagggga gctcggctgg | 240 |
| ctcacacacc cgtatggcaa agggtgggac ctgatgcaga acatcatgaa tgacatgccg | 300 |
| atctacatgt actccgtgtg caacgtgatg tctggcgacc aggacaactg gctccgcacc | 360 |
| aactgggtgt accgaggaga ggctgagcgt atcttcattg agctcaagtt tactgtacgt | 420 |
| gactgcaaca gcttccctgg tggcgccagc tcctgcaagg agactttcaa cctctactat | 480 |
| gccgagtcgg acctggacta cggcaccaac ttccagaagc gcctgttcac caagattgac | 540 |
| accattgcgc ccgatgagat caccgtcagc agcgacttcg aggcacgcca cgtgaagctg | 600 |
| aacgtggagg agcgctccgt ggggccgctc acccgcaaag gcttctacct ggccttccag | 660 |
| gatatcggtg cctgtgtggc gctgctctcc gtccgtgtct actacaagaa gtgccccgag | 720 |
| ctgctgcagg gcctggccca cttccctgag accatcgccg gctctgatgc accttccctg | 780 |
| gccactgtgg ccggcacctg tgtggaccat gccgtggtgc caccgggggg tgaagagccc | 840 |
| cgtatgcact gtgcagtgga tggcgagtgg ctggtgccca ttgggcagtg cctgtgccag | 900 |
| gcaggctacg agaaggtgga ggatgcctgc caggcctgct cgcctggatt ttttaagttt | 960 |
| gaggcatctg agagccctg cttggagtgc cctgagcaca cgctgccatc ccctgagggt | 1020 |
| gccacctcct gcgagtgtga ggaaggcttc ttccgggcac ctcaggaccc agcgtcgatg | 1080 |
| ccttgcacac gaccccctc cgccccacac tacctcacag ccgtgggcat gggtgccaag | 1140 |
| gtggagctgc gctggacgcc ccctcaggac agcggggggcc gcgaggacat tgtctacagc | 1200 |
| gtcacctgcg aacagtgctg gcccgagtct ggggaatgcg gccgtgtga ggccagtgtg | 1260 |
| cgctactcgg agcctcctca cggactgacc cgcaccagtg tgacagtgag cgacctggag | 1320 |
| ccccacatga actacacctt caccgtggag gcccgcaatg gcgtctcagg cctggtaacc | 1380 |
| agccgcagct ccgtactgc cagtgtcagc atcaaccaga cagagccccc caaggtgagg | 1440 |
| ctggagggcc gcagcaccac ctcgcttagc gtctcctgga gcatccccccc gccgcagcag | 1500 |
| agccgagtgt ggaagtacga ggtcacttac cgcaagaagg gagactccaa cagctacaat | 1560 |
| gtgcgccgca cgagggtttt ctccgtgacc ctggacgacc tggcccccaga caccacctac | 1620 |
| ctggtccagg tgcaggcact gacgcaggag gccaggggg ccggcagcaa ggtgcacgaa | 1680 |
| ttccagacgc tgtccccgga gggatctggc aacttggcgg tgattggcgg cgtggctgtc | 1740 |
| ggtgtggtcc tgcttctggt gctggcagga gttggcttct ttatccaccg caggaggaag | 1800 |
| aaccagcgtg cccgccagtc cccggaggac gtttacttcc ccaagtcaga acaactgaag | 1860 |

-continued

| | |
|---|---|
| cccctgaaga catacgtgga cccccacaca tatgaggacc ccaaccaggc tgtgttgaag | 1920 |
| ttcactaccg agatccatcc atcctgtgtc actcggcaga aggtgatcgg agcaggagag | 1980 |
| tttggggagg tgtacaaggg catgctgaag acatcctcgg ggaagaagga ggtgccggtg | 2040 |
| gccatcaaga cgctgaaagc cggctacaca gagaagcagc gagtggactt cctcggcgag | 2100 |
| gccggcatca tgggccagtt cagccaccac aacatcatcc gcctagaggg cgtcatctcc | 2160 |
| aaatacaagc ccatgatgat catcactgag tacatggaga atggggccct ggacaagttc | 2220 |
| cttcgggaga aggatggcga gttcagcgtg ctgcagctgg tgggcatgct gcggggcatc | 2280 |
| gcagctggca tgaagtacct ggccaacatg aactatgtgc accgtgacct ggctgcccgc | 2340 |
| aacatcctcg tcaacagcaa cctggtctgc aaggtgtctg actttggcct gtcccgcgtg | 2400 |
| ctggaggacg accccgaggc cacctacacc accagtggcg gcaagatccc catccgctgg | 2460 |
| accgccccgg aggccatttc ctaccggaag ttcacctctg ccagcgacgt gtggagcttt | 2520 |
| ggcattgtca tgtgggaggt gatgacctat ggcgagcggc cctactggga gttgtccaac | 2580 |
| cacgaggtga tgaaagccat caatgatggc ttccggctcc ccacacccat ggactgcccc | 2640 |
| tccgccatct accagctcat gatgcagtgc tggcagcagg agcgtgcccg ccgccccaag | 2700 |
| ttcgctgaca tcgtcagcat cctggacaag ctcattcgtg ccctgactc cctcaagacc | 2760 |
| ctggctgact ttgaccccg cgtgtctatc cggctcccca gcacgagcgg ctcggagggg | 2820 |
| gtgcccttcc gcacggtgtc cgagtggctg agtccatca agatgcagca gtatacggag | 2880 |
| cacttcatgg cggccggcta cactgccatc gagaaggtgg tgcagatgac caacgacgac | 2940 |
| atcaagagga ttggggtgcg gctgcccggc caccagaagc gcatcgccta cagcctgctg | 3000 |
| ggactcaagg accaggtgaa cactgtgggg atccccatct ga | 3042 |

<210> SEQ ID NO 3
<211> LENGTH: 2953
<212> TYPE: DNA
<213> ORGANISM: Homo sapiens
<300> PUBLICATION INFORMATION:
<302> TITLE: ephrin A3
<310> PATENT DOCUMENT NUMBER: NM005233

<400> SEQUENCE: 3

| | |
|---|---|
| atggattgtc agctctccat cctcctcctt ctcagctgct ctgttctcga cagcttcggg | 60 |
| gaactgattc cgcagccttc caatgaagtc aatctactgg attcaaaaac aattcaaggg | 120 |
| gagctgggct ggatctctta tccatcacat gggtgggaag agatcagtgg tgtggatgaa | 180 |
| cattacacac ccatcaggac ttaccaggtg tgcaatgtca tggaccacag tcaaaacaat | 240 |
| tggctgagaa caaactgggt ccccaggaac tcagctcaga agatttatgt ggagctcaag | 300 |
| ttcactctac gagactgcaa tagcattcca ttggttttag aacttgcaa ggagacattc | 360 |
| aacctgtact acatggagtc tgatgatgat catggggtga aatttcgaga gcatcagttt | 420 |
| acaaagattg acaccattgc agctgatgaa agtttcactc aaatggatct ggggaccgt | 480 |
| attctgaagc tcaacactga gattagagaa gtaggtcctg tcaacaagaa gggatttta | 540 |
| ttggcatttc aagatgttgg tgcttgtgtt gccttggtgt ctgtgagagt atacttcaaa | 600 |
| aagtgcccat ttcagtgaa gaatctggct atgtttccag acacgtacc catgactcc | 660 |
| cagtccctgg tggaggttag agggtcttgt gtcaacaatt ctaaggagga agatcctcca | 720 |
| aggatgtact gcagtacaga aggcgaatgg cttgtaccca ttggcaagtg ttcctgcaat | 780 |
| gctggctatg aagaagagg ttttatgtgc caagcttgtc gaccaggttt ctacaaggca | 840 |

-continued

```
ttggatggta atatgaagtg tgctaagtgc ccgcctcaca gttctactca ggaagatggt     900
tcaatgaact gcaggtgtga gaataattac ttccgggcag acaaagaccc tccatccatg     960
gcttgtaccc gacctccatc ttcaccaaga aatgttatct ctaatataaa cgagacctca    1020
gttatcctgg actggagttg gcccctggac acaggaggcc ggaaagatgt taccttcaac    1080
atcatatgta aaaatgtgg gtggaatata aacagtgtg agccatgcag cccaaatgtc      1140
cgcttcctcc ctcgacagtt tggactcacc aacaccacgg tgacagtgac agaccttctg    1200
gcacatacta actacaccti tgagattgat gccgttaatg gggtgtcaga gctgagctcc    1260
ccaccaagac agtttgctgc ggtcagcatc acaactaatc aggctgctcc atcacctgtc    1320
ctgacgatta agaagatcg gacctccaga aatagcatct ctttgtcctg caagaacct     1380
gaacatccta atgggatcat attggactac gaggtcaaat actatgaaaa gcaggaacaa    1440
gaaacaagtt ataccattct gagggcaaga ggcacaaatg ttaccatcag tagcctcaag    1500
cctgacacta tatacgtatt ccaaatccga gcccgaacag ccgctggata tgggacgaac    1560
agccgcaagt ttgagtttga aactagtcca gactctttct ccatctctgg tgaaagtagc    1620
caagtggtca tgatcgccat ttcagcggca gtagcaatta ttctcctcac tgttgtcatc    1680
tatgttttga ttgggaggtt ctgtggctat aagtcaaaac atggggcaga tgaaaaaaga    1740
cttcattttg gcaatgggca tttaaaactt ccaggtctca ggacttatgt tgacccacat    1800
acatatgaag accctaccca agctgttcat gagtttgcca aggaattgga tgccaccaac    1860
atatccattg ataaagttgt tggagcaggt gaatttggag aggtgtgcag tggtcgctta    1920
aaacttcctt caaaaaaaga gatttcagtg gccattaaaa ccctgaaagt tggctacaca    1980
gaaaagcaga ggagagactt cctgggagaa gcaagcatta tgggacagtt tgaccacccc    2040
aatatcattc gactggaagg agttgttacc aaaagtaagc cagttatgat tgtcacagaa    2100
tacatggaga atggttcctt ggatagtttc ctacgtaaac acgatgccca gtttactgtc    2160
attcagctag tggggatgct tcgagggata gcatctggca tgaagtacct gtcagacatg    2220
ggctatgttc accgagacct cgctgctcgg aacatcttga tcaacagtaa cttggtgtgt    2280
aaggtttctg atttcggact ttcgcgtgtc ctggaggatg acccagaagc tgcttataca    2340
acaagaggag ggaagatccc aatcaggtgg acatcaccag aagctatagc ctaccgcaag    2400
ttcacgtcag ccagcgatgt atggagttat gggattgttc tctgggaggt gatgtcttat    2460
ggagagagac atactgggga gatgtccaat caggatgtaa ttaaagctgt agatgagggc    2520
tatcgactgc cacccccat ggactgccca gctgccttgt atcagctgat gctggactgc    2580
tggcagaaag acaggaacaa cagacccaag tttgagcaga ttgttagtat tctgacaag     2640
cttatccgga atcccggcag cctgaagatc atcaccagtg cagccgcaag gccatcaaac    2700
cttcttctgg accaaagcaa tgtggatatc tctaccttcc gcacaacagg tgactggctt    2760
aatggtgtcc ggacagcaca ctgcaaggaa atcttcacgg gcgtggagta cagttcttgt    2820
gacacaatag ccaagatttc cacagatgac atgaaaaagg ttggtgtcac cgtggttggg    2880
ccacagaaga agatcatcag tagcattaaa gctctagaaa cgcaatcaaa gaatgggcca    2940
gttcccgtgt aaa                                                       2953
```

<210> SEQ ID NO 4
<211> LENGTH: 2784
<212> TYPE: DNA
<213> ORGANISM: Homo sapiens
<300> PUBLICATION INFORMATION:

<302> TITLE: ephrin A4
<310> PATENT DOCUMENT NUMBER: XM002578

<400> SEQUENCE: 4

| | | | | | |
|---|---|---|---|---|---:|
| atggatgaaa | aaaatacacc | aatccgaacc | taccaagtgt | gcaatgtgat | ggaacccagc | 60 |
| cagaataact | ggctacgaac | tgattggatc | acccgagaag | gggctcagag | ggtgtatatt | 120 |
| gagattaaat | tcaccttgag | ggactgcaat | agtcttccgg | cgtcatggg | gacttgcaag | 180 |
| gagacgttta | acctgtacta | ctatgaatca | gacaacgaca | aagagcgttt | catcagagag | 240 |
| aaccagtttg | tcaaaattga | caccattgct | gctgatgaga | gcttcaccca | agtggacatt | 300 |
| ggtgacagaa | tcatgaagct | gaacaccgag | atccggatg | tagggccatt | aagcaaaaag | 360 |
| gggttttacc | tggcttttca | ggatgtgggg | gcctgcatcg | ccctggtatc | agtccgtgtg | 420 |
| ttctataaaa | agtgtccact | cacagtccgc | aatctggccc | agtttcctga | caccatcaca | 480 |
| ggggctgata | cgtcttccct | ggtggaagtt | cgaggctcct | gtgtcaacaa | ctcagaagag | 540 |
| aaagatgtgc | caaaaatgta | ctgtgggca | gatggtgaat | ggctggtacc | cattggcaac | 600 |
| tgcctatgca | cgctgggca | tgaggagcgg | agcggagaat | gccaagcttg | caaaattgga | 660 |
| tattcaagg | ctctctccac | ggatgccacc | tgtgccaagt | gcccacccca | cagctactct | 720 |
| gtctgggaag | gagccacctc | gtgcacctgt | gaccgaggct | ttttcagagc | tgacaacgat | 780 |
| gctgcctcta | tgccctgcac | ccgtccacca | tctgctcccc | tgaacttgat | ttcaaatgtc | 840 |
| aacgagacat | ctgtgaactt | ggaatggagt | agccctcaga | atacaggtgg | ccgccaggac | 900 |
| atttcctata | atgtggtatg | caagaaatgt | ggagctggtg | accccagcaa | gtgccgaccc | 960 |
| tgtggaagtg | gggtccacta | cacccccacag | cagaatggct | tgaagaccac | caaagtctcc | 1020 |
| atcactgacc | tcctagctca | taccaattac | acctttgaaa | tctgggctgt | gaatggagtg | 1080 |
| tccaaatata | accctaaccc | agaccaatca | gtttctgtca | ctgtgaccac | caaccaagca | 1140 |
| gcaccatcat | ccattgcttt | ggtccaggct | aaagaagtca | agatacag | tgtggcactg | 1200 |
| gcttggctgg | aaccagatcg | gcccaatggg | gtaatcctgg | aatatgaagt | caagtattat | 1260 |
| gagaaggatc | agaatgagcg | aagctatcgt | atagttcgga | cagctgccag | gaacacagat | 1320 |
| atcaaaggcc | tgaaccctct | cacttcctat | gttttccacg | tgcgagccag | acagcagct | 1380 |
| ggctatggag | acttcagtga | gcccttggag | gttacaacca | acacagtgcc | ttcccggatc | 1440 |
| attggagatg | gggctaactc | cacagtcctt | ctggtctctg | tctcgggcag | tgtggtgctg | 1500 |
| gtggtaattc | tcattgcagc | ttttgtcatc | agccggagac | ggagtaaata | cagtaaagcc | 1560 |
| aaacaagaag | cggatgaaga | gaaacatttg | aatcaaggtg | taagaacata | tgtggacccc | 1620 |
| tttacgtacg | aagatcccaa | ccaagcagtg | cgagagtttg | ccaaagaaat | tgacgcatcc | 1680 |
| tgcattaaga | ttgaaaaagt | tataggagtt | ggtgaatttg | gtgaggtatg | cagtgggcgt | 1740 |
| ctcaaagtgc | ctggcaagag | agagatctgt | gtggctatca | agactctgaa | agctggttat | 1800 |
| acagacaaac | agaggagaga | cttcctgagt | gaggccagca | tcatgggaca | gtttgaccat | 1860 |
| ccgaacatca | ttcacttgga | aggcgtggtc | actaaatgta | aaccagtaat | gatcataaca | 1920 |
| gagtacatgg | agaatggctc | cttggatgca | ttcctcagga | aaaatgatgg | cagatttaca | 1980 |
| gtcattcagc | tggtgggcat | gcttcgtggc | attgggtctg | ggatgaagta | tttatctgat | 2040 |
| atgagctatg | tgcatcgtga | tctggccgca | cggaacatcc | tggtgaacag | caacttggtc | 2100 |
| tgcaaagtgt | ctgattttgg | catgtcccga | gtgcttgagg | atgatccgga | agcagcttac | 2160 |
| accaccaggg | gtggcaagat | tcctatccgg | tggactgcgc | cagaagcaat | tgcctatcgt | 2220 |

-continued

| | |
|---|---|
| aaattcacat cagcaagtga tgtatggagc tatggaatcg ttatgtggga agtgatgtcg | 2280 |
| tacggggaga ggccctattg ggatatgtcc aatcaagatg tgattaaagc cattgaggaa | 2340 |
| ggctatcggt tacccctcc aatggactgc cccattgcgc tccaccagct gatgctagac | 2400 |
| tgctggcaga aggagaggag cgacaggcct aaatttgggc agattgtcaa catgttggac | 2460 |
| aaactcatcc gcaaccccaa cagcttgaag aggacaggga cggagagctc cagacctaac | 2520 |
| actgccttgt tggatccaag ctcccctgaa ttctctgctg tggtatcagt gggcgattgg | 2580 |
| ctccaggcca ttaaaatgga ccggtataag gataacttca cagctgctgg ttataccaca | 2640 |
| ctagaggctg tggtgcacgt gaaccaggag gacctggcaa gaattggtat cacagccatc | 2700 |
| acgcaccaga ataagatttt gagcagtgtc caggcaatgc gaacccaaat gcagcagatg | 2760 |
| cacggcagaa tggttcccgt ctga | 2784 |

<210> SEQ ID NO 5
<211> LENGTH: 2997
<212> TYPE: DNA
<213> ORGANISM: Homo sapiens
<300> PUBLICATION INFORMATION:
<302> TITLE: ephrin A7
<310> PATENT DOCUMENT NUMBER: XM004485

<400> SEQUENCE: 5

| | |
|---|---|
| atggttttc aaactcggta cccttcatgg attattttat gctacatctg ctgctccgc | 60 |
| tttgcacaca caggggaggc gcaggctgcg aaggaagtac tactgctgga ttctaaagca | 120 |
| caacaaacag agttggagtg gatttcctct ccacccaatg ggtgggaaga aattagtggt | 180 |
| ttggatgaga actataccc gatacgaaca taccaggtgt gccaagtcat ggagcccaac | 240 |
| caaaacaact ggctgcggac taactggatt tccaaaggca atgcacaaag gatttttgta | 300 |
| gaattgaaat tcaccctgag ggattgtaac agtcttcctg gagtactggg aacttgcaag | 360 |
| gaaacattta atttgtacta ttatgaaaca gactatgaca ctggcaggaa tataagagaa | 420 |
| aacctctatg taaaaataga caccattgct gcagatgaaa gttttaccca aggtgacctt | 480 |
| ggtgaaagaa agatgaagct taacactgag gtgagagaga ttggaccttt gtccaaaaag | 540 |
| ggattctatc ttgcctttca ggatgtaggg gcttgcatag cttggtttc tgtcaaagtg | 600 |
| tactacaaga agtgctggtc cattattgag aacttagcta tctttccaga tacagtgact | 660 |
| ggttcagaat tttcctcttt agtcgaggtt cgagggacat gtgtcagcag tgcagaggaa | 720 |
| gaagcggaaa acgcccccag gatgcactgc agtgcagaag gagaatggtt agtgcccatt | 780 |
| ggaaaatgta tctgcaaagc aggctaccag caaaaggag acacttgtga accctgtggc | 840 |
| cgtgggttct acaagtcttc ctctcaagat cttcagtgct ctcgttgtcc aactcacagt | 900 |
| ttttctgata agaaggctc ctccagatgt gaatgtgaag atgggtatta cagggctcca | 960 |
| tctgacccac catacgttgc atgcacaagg cctccatctg caccacagaa cctcattttc | 1020 |
| aacatcaacc aaaccacagt aagtttggaa tggagtcctc ctgcagacaa tgggggaaga | 1080 |
| aacgatgtga cctacagaat attgtgtaag cggtgcagtt gggagcaggg cgaatgtgtt | 1140 |
| ccctgtggga gtaacattgg atacatgccc cagcagactg gattagagga taactatgtc | 1200 |
| actgtcatgg acctgctagc ccacgctaat tatacttttg aagttgaagc tgtaaatgga | 1260 |
| gtttctgact taagccgatc ccagaggctc tttgctgctg tcagtatcac cactggtcaa | 1320 |
| gcagctccct cgcaagtgag tggagtaatg aaggagagag tactgcagcg gagtgtcgag | 1380 |
| cttttcctggc aggaaccaga gcatcccaat ggagtcatca cagaatatga aatcaagtat | 1440 |

```
tacgagaaag atcaaaggga acggacctac tcaacagtaa aaaccaagtc tacttcagcc      1500
tccattaata atctgaaacc aggaacagtg tatgttttcc agattcgggc ttttactgct      1560
gctggttatg gaaattacag tcccagactt gatgttgcta cactagagga agctacaggt      1620
aaaatgtttg aagctacagc tgtctccagt gaacagaatc tgttattat cattgctgtg      1680 gttgctgtag ctgggaccat cattttggtt tcatggtct ttggcttcat cattgggaga      1740
aggcactgtg gttatagcaa agctgaccaa gaaggcgatg aagagcttta ctttcatttt      1800
aaatttccag gcaccaaaac ctacattgac cctgaaacct atgaggaccc aaatagagct      1860
gtccatcaat tcgccaagga gctagatgcc tcctgtatta aaattgagcg tgtgattggt      1920
gcaggagaat tcggtgaagt ctgcagtggc cgtttgaaac ttccagggaa aagagatgtt      1980
gcagtagcca taaaaacccct gaaagttggt tacacagaaa acaaaggag agactttttg      2040 tgtgaagcaa gcatcatggg gcagtttgac cacccaaatg ttgtccattt ggaagggtt      2100 gttacaagag ggaaaccagt catgatagta atagagttca tggaaaatgg agccctagat      2160
gcatttctca ggaaacatga tgggcaattt acagtcattc agttagtagg aatgctgaga      2220
ggaattgctg ctggaatgag atatttggct gatatgggat atgttcacag gaccttgca      2280 gctcgcaata ttcttgtcaa cagcaatctc gtttgtaaag tgtcagattt tggcctgtcc      2340
cgagttatag aggatgatcc agaagctgtc tatacaacta ctggtggaaa aattccagta      2400
aggtggacag cacccgaagc catccagtac cggaaattca catcagccag tgatgtatgg      2460
agctatggaa tagtcatgtg ggaagttatg tcttatggag aaagacctta ttgggacatg      2520
tcaaatcaag atgttataaa agcaatagaa gaaggttatc gtttaccagc acccatggac      2580
tgcccagctg gccttcacca gctaatgttg gattgttggc aaaaggagcg tgctgaaagg      2640
ccaaaatttg aacagatagt tggaattcta gacaaaatga ttcgaaaccc aaatagtctg      2700
aaaactcccc tgggaacttg tagtaggcca ataagccctc ttctggatca aaacactcct      2760
gatttcacta cctttttgttc agttggagaa tggctacaag ctattaagat ggaaagatat      2820
aaagataatt tcacggcagc tggctacaat tcccttgaat cagtagccag gatgactatt      2880
gaggatgtga tgagtttagg gatcacactg gttggtcatc aaaagaaaat catgagcagc      2940
attcagacta tgagagcaca aatgctacat ttacatggaa ctggcattca agtgtga       2997
```

<210> SEQ ID NO 6
<211> LENGTH: 3018
<212> TYPE: DNA
<213> ORGANISM: Homo sapiens
<220> FEATURE:
<221> NAME/KEY: CDS
<222> LOCATION: (1)..(3018)

<400> SEQUENCE: 6

```
atg gcc ccc gcc cgg ggc cgc ctg ccc cct gcg ctc tgg gtc gtc acg        48
Met Ala Pro Ala Arg Gly Arg Leu Pro Pro Ala Leu Trp Val Val Thr
1               5                   10                  15 gcc gcg gcg gcg gcg gcc acc tgc gtg tcc gcg gcg cgc ggc gaa gtg        96
Ala Ala Ala Ala Ala Ala Thr Cys Val Ser Ala Ala Arg Gly Glu Val
                20                  25                  30 aat ttg ctg gac acg tcg acc atc cac ggg gac tgg ggc tgg ctc acg       144
Asn Leu Leu Asp Thr Ser Thr Ile His Gly Asp Trp Gly Trp Leu Thr
            35                  40                  45 tat ccg gct cat ggg tgg gac tcc atc aac gag gtg gac gag tcc ttc       192
Tyr Pro Ala His Gly Trp Asp Ser Ile Asn Glu Val Asp Glu Ser Phe
        50                  55                  60
```

```
cag ccc atc cac acg tac cag gtt tgc aac gtc atg agc ccc aac cag    240
Gln Pro Ile His Thr Tyr Gln Val Cys Asn Val Met Ser Pro Asn Gln
 65              70                  75                  80 aac aac tgg ctg cgc acg agc tgg gtc ccc cga gac ggc gcc cgg cgc    288
Asn Asn Trp Leu Arg Thr Ser Trp Val Pro Arg Asp Gly Ala Arg Arg
                 85                  90                  95 gtc tat gct gag atc aag ttt acc ctg cgc gac tgc aac agc atg cct    336
Val Tyr Ala Glu Ile Lys Phe Thr Leu Arg Asp Cys Asn Ser Met Pro
            100                 105                 110 ggt gtg ctg ggc acc tgc aag gag acc ttc aac ctc tac tac ctg gag    384
Gly Val Leu Gly Thr Cys Lys Glu Thr Phe Asn Leu Tyr Tyr Leu Glu
        115                 120                 125 tcg gac cgc gac ctg ggg gcc agc aca caa gaa agc cag ttc ctc aaa    432
Ser Asp Arg Asp Leu Gly Ala Ser Thr Gln Glu Ser Gln Phe Leu Lys
130                 135                 140 atc gac acc att gcg gcc gac gag agc ttc aca ggt gcc gac ctt ggt    480
Ile Asp Thr Ile Ala Ala Asp Glu Ser Phe Thr Gly Ala Asp Leu Gly
145                 150                 155                 160 gtg cgg cgt ctc aag ctc aac acg gag gtg cgc agt gtg ggt ccc ctc    528
Val Arg Arg Leu Lys Leu Asn Thr Glu Val Arg Ser Val Gly Pro Leu
                165                 170                 175 agc aag cgc ggc ttc tac ctg gcc ttc cag gac ata ggt gcc tgc ctg    576
Ser Lys Arg Gly Phe Tyr Leu Ala Phe Gln Asp Ile Gly Ala Cys Leu
            180                 185                 190 gcc atc ctc tct ctc cgc atc tac tat aag aag tgc cct gcc atg gtg    624
Ala Ile Leu Ser Leu Arg Ile Tyr Tyr Lys Lys Cys Pro Ala Met Val
        195                 200                 205 cgc aat ctg gct gcc ttc tcg gag gca gtg acg ggg gcc gac tcg tcc    672
Arg Asn Leu Ala Ala Phe Ser Glu Ala Val Thr Gly Ala Asp Ser Ser
    210                 215                 220 tca ctg gtg gag gtg agg ggc cag tgc gtg cgg cac tca gag gag cgg    720
Ser Leu Val Glu Val Arg Gly Gln Cys Val Arg His Ser Glu Glu Arg
225                 230                 235                 240 gac aca ccc aag atg tac tgc agc gcg gag ggc gag tgg ctc gtg ccc    768
Asp Thr Pro Lys Met Tyr Cys Ser Ala Glu Gly Glu Trp Leu Val Pro
                245                 250                 255 atc ggc aaa tgc gtg tgc agt gcc ggc tac gag gag cgg cgg gat gcc    816
Ile Gly Lys Cys Val Cys Ser Ala Gly Tyr Glu Glu Arg Arg Asp Ala
            260                 265                 270 tgt gtg gcc tgt gag ctg ggc ttc tac aag tca gcc cct ggg gac cag    864
Cys Val Ala Cys Glu Leu Gly Phe Tyr Lys Ser Ala Pro Gly Asp Gln
        275                 280                 285 ctg tgt gcc cgc tgc cct ccc cac agc cac tcc gca gct cca gcc gcc    912
Leu Cys Ala Arg Cys Pro Pro His Ser His Ser Ala Ala Pro Ala Ala
    290                 295                 300 caa gcc tgc cac tgt gac ctc agc tac tac cgt gca gcc ctg gac ccg    960
Gln Ala Cys His Cys Asp Leu Ser Tyr Tyr Arg Ala Ala Leu Asp Pro
305                 310                 315                 320 ccg tcc tca gcc tgc acc cgg cca ccc tcg gca cca gtg aac ctg atc    1008
Pro Ser Ser Ala Cys Thr Arg Pro Pro Ser Ala Pro Val Asn Leu Ile
                325                 330                 335 tcc agt gtg aat ggg aca tca gtg act ctg gag tgg gcc cct ccc ctg    1056
Ser Ser Val Asn Gly Thr Ser Val Thr Leu Glu Trp Ala Pro Pro Leu
            340                 345                 350 gac cca ggt ggc cgc agt gac atc acc tac aat gcc gtg tgc cgc cgc    1104
Asp Pro Gly Gly Arg Ser Asp Ile Thr Tyr Asn Ala Val Cys Arg Arg
        355                 360                 365 tgc ccc tgg gca ctg agc cgc tgc gag gca tgt ggg agc ggc acc cgc    1152
Cys Pro Trp Ala Leu Ser Arg Cys Glu Ala Cys Gly Ser Gly Thr Arg
    370                 375                 380
```

```
ttt gtg ccc cag cag aca agc ctg gtg cag gcc agc ctg ctg gtg gcc    1200
Phe Val Pro Gln Gln Thr Ser Leu Val Gln Ala Ser Leu Leu Val Ala
385                 390                 395                 400 aac ctg ctg gcc cac atg aac tac tcc ttc tgg atc gag gcc gtc aat    1248
Asn Leu Leu Ala His Met Asn Tyr Ser Phe Trp Ile Glu Ala Val Asn
            405                 410                 415 ggc gtg tcc gac ctg agc ccc gag ccc cgg gcc gct gtg gtc aac        1296
Gly Val Ser Asp Leu Ser Pro Glu Pro Arg Arg Ala Ala Val Val Asn
        420                 425                 430 atc acc acg aac cag gca gcc ccg tcc cag gtg gtg gtg atc cgt caa    1344
Ile Thr Thr Asn Gln Ala Ala Pro Ser Gln Val Val Val Ile Arg Gln
                435                 440                 445 gag cgg gcg ggg cag acc agc gtc tcg ctg ctg tgg cag gag ccc gag    1392
Glu Arg Ala Gly Gln Thr Ser Val Ser Leu Leu Trp Gln Glu Pro Glu
            450                 455                 460 cag ccg aac ggc atc atc ctg gag tat gag atc aag tac tac gag aag    1440
Gln Pro Asn Gly Ile Ile Leu Glu Tyr Glu Ile Lys Tyr Tyr Glu Lys
465                 470                 475                 480 gac aag gag atg cag agc tac tcc acc ctc aag gcc gtc acc acc aga    1488
Asp Lys Glu Met Gln Ser Tyr Ser Thr Leu Lys Ala Val Thr Thr Arg
                485                 490                 495 gcc acc gtc tcc ggc ctc aag ccg ggc acc cgc tac gtg ttc cag gtc    1536
Ala Thr Val Ser Gly Leu Lys Pro Gly Thr Arg Tyr Val Phe Gln Val
            500                 505                 510 cga gcc cgc acc tca gca ggc tgt ggc cgc ttc agc cag gcc atg gag    1584
Arg Ala Arg Thr Ser Ala Gly Cys Gly Arg Phe Ser Gln Ala Met Glu
            515                 520                 525 gtg gag acc ggg aaa ccc cgg ccc cgc tat gac acc agg acc att gtc    1632
Val Glu Thr Gly Lys Pro Arg Pro Arg Tyr Asp Thr Arg Thr Ile Val
530                 535                 540 tgg atc tgc ctg acg ctc atc acg ggc ctg gtg gtg ctt ctg ctc ctg    1680
Trp Ile Cys Leu Thr Leu Ile Thr Gly Leu Val Val Leu Leu Leu Leu
545                 550                 555                 560 ctc atc tgc aag aag agg cac tgt ggc tac agc aag gcc ttc cag gac    1728
Leu Ile Cys Lys Lys Arg His Cys Gly Tyr Ser Lys Ala Phe Gln Asp
                565                 570                 575 tcg gac gag gag aag atg cac tat cag aat gga cag gca ccc cca cct    1776
Ser Asp Glu Glu Lys Met His Tyr Gln Asn Gly Gln Ala Pro Pro Pro
            580                 585                 590 gtc ttc ctg cct ctg cat cac ccc ccg gga aag ctc cca gag ccc cag    1824
Val Phe Leu Pro Leu His His Pro Pro Gly Lys Leu Pro Glu Pro Gln
        595                 600                 605 ttc tat gcg gaa ccc cac acc tac gag gag cca ggc cgg gcg ggc cgc    1872
Phe Tyr Ala Glu Pro His Thr Tyr Glu Glu Pro Gly Arg Ala Gly Arg
610                 615                 620 agt ttc act cgg gag atc gag gcc tct agg atc cac atc gag aaa atc    1920
Ser Phe Thr Arg Glu Ile Glu Ala Ser Arg Ile His Ile Glu Lys Ile
625                 630                 635                 640 atc ggc tct gga gac tcc ggg gaa gtc tgc tac ggg agg ctg cgg gtg    1968
Ile Gly Ser Gly Asp Ser Gly Glu Val Cys Tyr Gly Arg Leu Arg Val
                645                 650                 655 cca ggg cag cgg gat gtg ccc gtg gcc atc aag gcc ctc aaa gcc ggc    2016
Pro Gly Gln Arg Asp Val Pro Val Ala Ile Lys Ala Leu Lys Ala Gly
            660                 665                 670 tac acg gag aga cag agg cgg gac ttc ctg agc gag gcg tcc atc atg    2064
Tyr Thr Glu Arg Gln Arg Arg Asp Phe Leu Ser Glu Ala Ser Ile Met
        675                 680                 685 ggg caa ttc gac cat ccc aac atc atc cgc ctc gag ggt gtc gtc acc    2112
Gly Gln Phe Asp His Pro Asn Ile Ile Arg Leu Glu Gly Val Val Thr
```

-continued

```
         690              695             700
cgt ggc cgc ctg gca atg att gtg act gag tac atg gag aac ggc tct      2160
Arg Gly Arg Leu Ala Met Ile Val Thr Glu Tyr Met Glu Asn Gly Ser
705                 710                 715                 720 ctg gac acc ttc ctg agg acc cac gac ggg cag ttc acc atc atg cag      2208
Leu Asp Thr Phe Leu Arg Thr His Asp Gly Gln Phe Thr Ile Met Gln
                725                 730                 735 ctg gtg ggc atg ctg aga gga gtg ggt gcc ggc atg cgc tac ctc tca      2256
Leu Val Gly Met Leu Arg Gly Val Gly Ala Gly Met Arg Tyr Leu Ser
            740                 745                 750 gac ctg ggc tat gtc cac cga gac ctg gcc gcc cgc aac gtc ctg gtt      2304
Asp Leu Gly Tyr Val His Arg Asp Leu Ala Ala Arg Asn Val Leu Val
        755                 760                 765 gac agc aac ctg gtc tgc aag gtg tct gac ttc ggg ctc tca cgg gtg      2352
Asp Ser Asn Leu Val Cys Lys Val Ser Asp Phe Gly Leu Ser Arg Val
770                 775                 780 ctg gag gac gac ccg gat gct gcc tac acc acc acg ggc ggg aag atc      2400
Leu Glu Asp Asp Pro Asp Ala Ala Tyr Thr Thr Thr Gly Gly Lys Ile
785                 790                 795                 800 ccc atc cgc tgg acg gcc cca gag gcc atc gcc ttc cgc acc ttc tcc      2448
Pro Ile Arg Trp Thr Ala Pro Glu Ala Ile Ala Phe Arg Thr Phe Ser
                805                 810                 815 tcg gcc agc gac gtg tgg agc ttc ggc gtg gtc atg tgg gag gtg ctg      2496
Ser Ala Ser Asp Val Trp Ser Phe Gly Val Val Met Trp Glu Val Leu
            820                 825                 830 gcc tat ggg gag cgg ccc tac tgg aac atg acc aac cgg gat gtc atc      2544
Ala Tyr Gly Glu Arg Pro Tyr Trp Asn Met Thr Asn Arg Asp Val Ile
        835                 840                 845 agc tct gtg gag gag ggg tac cgc ctg ccc gca ccc atg ggc tgc ccc      2592
Ser Ser Val Glu Glu Gly Tyr Arg Leu Pro Ala Pro Met Gly Cys Pro
850                 855                 860 cac gcc ctg cac cag ctc atg ctc gac tgt tgg cac aag gac cgg gcg      2640
His Ala Leu His Gln Leu Met Leu Asp Cys Trp His Lys Asp Arg Ala
865                 870                 875                 880 cag cgg cct cgc ttc tcc cag att gtc agt gtc ctc gat gcg ctc atc      2688
Gln Arg Pro Arg Phe Ser Gln Ile Val Ser Val Leu Asp Ala Leu Ile
                885                 890                 895 cgc agc cct gag agt ctc agg gcc acc gcc aca gtc agc agg tgc cca      2736
Arg Ser Pro Glu Ser Leu Arg Ala Thr Ala Thr Val Ser Arg Cys Pro
            900                 905                 910 ccc cct gcc ttc gtc cgg agc tgc ttt gac ctc cga ggg ggc agc ggt      2784
Pro Pro Ala Phe Val Arg Ser Cys Phe Asp Leu Arg Gly Gly Ser Gly
        915                 920                 925 ggc ggt ggg ggc ctc acc gtg ggg gac tgg ctg gac tcc atc cgc atg      2832
Gly Gly Gly Gly Leu Thr Val Gly Asp Trp Leu Asp Ser Ile Arg Met
930                 935                 940 ggc cgg tac cga gac cac ttc gct gcg ggc gga tac tcc tct ctg ggc      2880
Gly Arg Tyr Arg Asp His Phe Ala Ala Gly Gly Tyr Ser Ser Leu Gly
945                 950                 955                 960 atg gtg cta cgc atg aac gcc cag gac gtg cgc gcc ctg ggc atc acc      2928
Met Val Leu Arg Met Asn Ala Gln Asp Val Arg Ala Leu Gly Ile Thr
                965                 970                 975 ctc atg ggc cac cag aag aag atc ctg ggc agc att cag acc atg cgg      2976
Leu Met Gly His Gln Lys Lys Ile Leu Gly Ser Ile Gln Thr Met Arg
            980                 985                 990 gcc cag ctg acc agc acc cag ggg  ccc cgc cgg cac ctc tga             3018
Ala Gln Leu Thr Ser Thr Gln Gly  Pro Arg Arg His Leu
        995                 1000                1005
```

<210> SEQ ID NO 7
<211> LENGTH: 1497
<212> TYPE: DNA
<213> ORGANISM: Homo sapiens
<300> PUBLICATION INFORMATION:
<308> DATABASE ACCESSION NUMBER: U83508
<309> DATABASE ENTRY DATE: 1996-12-31
<300> PUBLICATION INFORMATION:
<302> TITLE: angiopoietin 2
<310> PATENT DOCUMENT NUMBER: U83508

<400> SEQUENCE: 7

```
atgacagttt tcctttcctt tgctttcctc gctgccattc tgactcacat agggtgcagc      60
aatcagcgcc gaagtccaga aacagtggga gaagatataa accggattca acatgggcaa    120
tgtgcctaca ctttcattct tccagaacac gatggcaact gtcgtgagag tacgacagac    180
cagtacaaca caaacgctct gcagagagat gctccacacg tggaaccgga tttctcttcc    240
cagaaacttc aacatctgga acatgtgatg gaaaattata ctcagtggct gcaaaaactt    300
gagaattaca ttgtggaaaa catgaagtcg gagatggccc agatacagca gaatgcagtt    360
cagaaccaca cggctaccat gctggagata ggaaccagcc tcctctctca gactgcagag    420
cagaccagaa agctgacaga tgttgagacc caggtactaa atcaaactc tcgacttgag    480
atacagctgc tggagaattc attatccacc tacaagctag agaagcaact tcttcaacag    540
acaaatgaaa tcttgaagat ccatgaaaaa aacagtttat tagaacataa aatcttagaa    600
atggaaggaa acacaaggaa gagttggac acctttaaagg aagagaaaga gaaccttcaa    660
ggcttggtta ctcgtcaaac atatataatc caggagctgg aaaagcaatt aaacagagct    720
accaccaaca cagtgtcct tcagaagcag caactggagc tgatggacac agtccacaac    780
cttgtcaatc tttgcactaa agaaggtgtt ttactaaagg gaggaaaaag agaggaagag    840
aaaccattta gagactgtgc agatgtatat caagctggtt ttaataaaag tggaatctac    900
actatttata ttaataatat gccagaaccc aaaaaggtgt tttgcaatat ggatgtcaat    960
gggggaggtt ggactgtaat acaacatcgt gaagatggaa gtctagattt ccaaagaggc   1020
tggaaggaat ataaaatggg ttttggaaat ccctccggtg aatattggct ggggaatgag   1080
tttattttg ccattaccag tcagaggcag tacatgctaa gaattgagtt aatggactgg   1140
gaagggaacc gagcctattc acagtatgac agattccaca tggaaatga aaagcaaaac   1200
tataggttgt atttaaaagg tcacactggg acagcaggaa acagagcag cctgatctta   1260
cacggtgctg atttcagcac taaagatgct gataatgaca actgtatgtg caaatgtgcc   1320
ctcatgttaa caggaggatg gtggtttgat gcttgtggcc cctccaatct aaatggaatg   1380
ttctatactg cgggacaaaa accatggaaaa ctgaatggga taaagtggca ctacttcaaa   1440
gggcccagtt actccttacg ttccacaact atgatgattc gacctttaga ttttga       1497
```

<210> SEQ ID NO 8
<211> LENGTH: 3417
<212> TYPE: DNA
<213> ORGANISM: Homo sapiens
<300> PUBLICATION INFORMATION:
<310> PATENT DOCUMENT NUMBER: XM001924
<300> PUBLICATION INFORMATION:
<302> TITLE: Tie1

<400> SEQUENCE: 8

```
atggtctggc gggtgccccc tttcttgctc cccatcctct tcttggcttc tcatgtgggc      60
gcggcggtgg acctgacgct gctggccaac ctgcggctca cggaccccca gcgcttcttc    120
```

```
ctgacttgcg tgtctgggga ggccggggcg gggagggggct cggacgcctg ggggcccgccc   180 ctgctgctgg agaaggacga ccgtatcgtg cgcaccccgc ccgggccacc cctgcgcctg   240
gcgcgcaacg gttcgcacca ggtcacgctt cgcggcttct ccaagccctc ggacctcgtg   300
ggcgtcttct cctgcgtggg cggtgctggg gcgcggcgca cgcgcgtcat ctacgtgcac   360
aacagccctg gagcccacct gcttccagac aaggtcacac acactgtgaa caaaggtgac   420
accgctgtac tttctgcacg tgtgcacaag gagaagcaga cagacgtgat ctggaagagc   480
aacggatcct acttctacac cctggactgg catgaagccc aggatgggcg gttcctgctg   540
cagctcccaa atgtgcagcc accatcgagc ggcatctaca gtgccactta cctggaagcc   600 agcccctgg gcagcgcctt ctttcggctc atcgtgcggg gttgtggggc tgggcgctgg   660
gggccaggct gtaccaagga gtgcccaggt tgcctacatg gaggtgtctg ccacgaccat   720
gacggcgaat gtgtatgccc ccctggcttc actggcaccc gctgtgaaca ggcctgcaga   780
gagggccgtt ttgggcagag ctgccaggag cagtgcccag gcatatcagg ctgccggggc   840
ctcaccttct gcctcccaga cccctatggc tgctcttgtg gatctggctg gagaggaagc   900
cagtgccaag aagcttgtgc ccctggtcat tttggggctg attgccgact ccagtgccag   960
tgtcagaatg gtggcacttg tgaccggttc agtggttgtg tctgcccctc tgggtggcat  1020
ggagtgcact gtgagaagtc agaccggatc ccccagatcc tcaacatggc ctcagaactg  1080
gagttcaact tagagacgat gccccggatc aactgtgcag ctgcagggaa ccccttcccc  1140
gtgcggggca gcatagagct acgcaagcca cacggcactg tgctcctgtc caccaaggcc  1200
attgtggagc cagagaagac cacagctgag ttcgaggtgc ccgcttggt tcttgcggac  1260 agtgggttct gggagtgccg tgtgtccaca tctggcggcc aagacagccg gcgcttcaag  1320
gtcaatgtga aagtgccccc cgtgcccctg gctgcacctc ggctcctgac caagcagagc  1380
cgccagcttg tggtctcccc gctggtctcg ttctctgggg atggacccat ctccactgtc  1440
cgcctgcact accggcccca ggacagtacc atggactggt cgaccattgt ggtggacccc  1500
agtgagaacg tgacgttaat gaacctgagg ccaaagacag gatacagtgt tcgtgtgcag  1560
ctgagccggc caggggaagg aggagagggg gcctgggggc ctcccaccct catgaccaca  1620
gactgtcctg agcctttgtt gcagccgtgg ttggagggct ggcatgtgga aggcactgac  1680
cggctgcgag tgagctggtc cttgcccttg gtgcccgggc cactggtggg cgacggtttc  1740
ctgctgcgcc tgtgggacgg gacacggggg caggagcggc gggagaacgt ctcatccccc  1800
caggcccgca ctgccctcct gacgggactc acgcctggca cccactacca gctggatgtg  1860
cagctctacc actgcacccc ctgggcccg gcctcgcccc ctgcacacgt gcttctgccc  1920
cccagtgggc ctcagccccc ccgacacctc cacgcccagg ccctctcaga ctccgagatc  1980
cagctgacat ggaagcaccc ggaggctctg cctgggccaa tatccaagta cgttgtggag  2040
gtgcaggtgg ctggggtgc aggagaccca ctgtggatag acgtggacag gcctgaggag  2100
acaagcacca tcatccgtgg cctcaacgcc agcacgcgct acctcttccg catgcgggcc  2160
agcattcagg ggctcgggga ctggagcaac acagtagaag agtccaccct gggcaacggg  2220
ctgcaggctg agggcccagt ccaagagagc cgggcagctg aagagggcct ggatcagcag  2280
ctgatcctgg cggtggtggg ctccgtgtct gccacctgcc tcaccatcct ggctgccctt  2340
ttaaccctgg tgtgcatccg cagaagctgc ctgcatcgga gacgcacctt cacctaccag  2400
tcaggctcgg gcgaggagac catcctgcag ttcagctcag ggaccttgac acttacccgg  2460
cggccaaaac tgcagcccga gcccctgagc tacccagtgc tagagtggga ggacatcacc  2520
```

-continued

| | |
|---|---|
| tttgaggacc tcatcgggga ggggaacttc ggccaggtca tccgggccat gatcaagaag | 2580 |
| gacgggctga agatgaacgc agccatcaaa atgctgaaag agtatgcctc tgaaaatgac | 2640 |
| catcgtgact ttgcgggaga actggaagtt ctgtgcaaat tggggcatca ccccaacatc | 2700 |
| atcaacctcc tgggggcctg taagaaccga ggttacttgt atatcgctat tgaatatgcc | 2760 |
| ccctacggga acctgctaga ttttctgcgg aaaagccggg tcctagagac tgacccagct | 2820 |
| tttgctcgag agcatgggac agcctctacc cttagctccc ggcagctgct gcgtttcgcc | 2880 |
| agtgatgcgg ccaatggcat gcagtacctg agtgagaagc agttcatcca cagggacctg | 2940 |
| gctgcccgga atgtgctggt cggagagaac ctggcctcca agattgcaga cttcggcctt | 3000 |
| tctcggggag aggaggttta tgtgaagaag acgatgggc gtctccctgt gcgctggatg | 3060 |
| gccattgagt ccctgaacta cagtgtctat accaccaaga gtgatgtctg gtcctttgga | 3120 |
| gtccttcttt gggagatagt gagccttgga ggtacaccct actgtggcat gacctgtgcc | 3180 |
| gagctctatg aaaagctgcc ccagggctac cgcatggagc agcctcgaaa ctgtgacgat | 3240 |
| gaagtgtacg agctgatgcg tcagtgctgg cgggaccgtc cctatgagcg accccccttt | 3300 |
| gcccagattg cgctacagct aggccgcatg ctggaagcca ggaaggccta tgtgaacatg | 3360 |
| tcgctgtttg agaacttcac ttacgcgggc attgatgcca cagctgagga ggcctga | 3417 |

<210> SEQ ID NO 9
<211> LENGTH: 3375
<212> TYPE: DNA
<213> ORGANISM: Homo sapiens
<300> PUBLICATION INFORMATION:
<302> TITLE: TEK
<310> PATENT DOCUMENT NUMBER: L06139

<400> SEQUENCE: 9

| | |
|---|---|
| atggactctt tagccagctt agttctctgt ggagtcagct tgctcctttc tggaactgtg | 60 |
| gaaggtgcca tggacttgat cttgatcaat tccctacctc ttgtatctga tgctgaaaca | 120 |
| tctctcacct gcattgcctc tgggtggcgc cccatgagc ccatcaccat aggaagggac | 180 |
| tttgaagcct taatgaacca gcaccaggat ccgctggaag ttactcaaga tgtgaccaga | 240 |
| gaatgggcta aaaagttgt ttggaagaga gaaaaggcta gtaagatcaa tggtgcttat | 300 |
| ttctgtgaag ggcgagttcg aggagaggca atcaggatac gaaccatgaa gatgcgtcaa | 360 |
| caagcttcct cctaccagc tactttaact atgactgtgg acaagggaga taacgtgaac | 420 |
| atatctttca aaaggtatt gattaaagaa gaagatgcag tgatttacaa aaatggttcc | 480 |
| ttcatccatt cagtgccccg gcatgaagta cctgatattc tagaagtaca cctgcctcat | 540 |
| gctcagcccc aggatgctgg agtgtactcg gccaggtata taggaggaaa cctcttcacc | 600 |
| tcggccttca ccaggctgat agtccggaga tgtgaagccc agaagtgggg acctgaatgc | 660 |
| aaccatctct gtactgcttg tatgaacaat ggtgtctgcc atgaagatac tggagaatgc | 720 |
| atttgccctc tgggtttat gggaaggacg tgtgagaagg cttgtgaact gcacacgttt | 780 |
| ggcagaactt gtaagaaag gtgcagtgga caagagggat gcaagtctta tgtgttctgt | 840 |
| ctccctgacc cctatgggtg ttcctgtgcc acaggctgga aggtctgca gtgcaatgaa | 900 |
| gcatgccacc ctgttttta cgggccagat tgtaagctta ggtgcagctg caacaatggg | 960 |
| gagatgtgtg atcgcttcca aggatgtctc tgctctccag gatggcaggg gctccagtgt | 1020 |
| gagagagaag gcataccgag gatgaccca agatagtgg atttgccaga tcatatagaa | 1080 |
| gtaaacagtg gtaaatttaa tcccatttgc aaagcttctg gctggccgct acctactaat | 1140 |

```
gaagaaatga ccctggtgaa gccggatggg acagtgctcc atccaaaaga ctttaaccat    1200
acggatcatt tctcagtagc catattcacc atccaccgga tcctcccccc tgactcagga    1260
gtttgggtct gcagtgtgaa cacagtggct gggatggtgg aaaagcccct caacatttct    1320
gttaaagttc ttccaaagcc cctgaatgcc ccaaacgtga ttgacactgg ataaacttt     1380 gctgtcatca acatcagctc tgagccttac tttggggatg gaccaatcaa atccaagaag    1440
cttctataca aacccgttaa tcactatgag gcttggcaac atattcaagt gacaaatgag    1500
attgttacac tcaactattt ggaacctcgg acagaatatg aactctgtgt gcaactggtc    1560
cgtcgtggag agggtgggga agggcatcct ggacctgtga gacgcttcac aacagcttct    1620
atcggactcc ctcctccaag aggtctaaat ctcctgccta aaagtcagac cactctaaat    1680
ttgacctggc aaccaatatt tccaagctcg gaagatgact tttatgttga agtggagaga    1740
aggtctgtgc aaaaaagtga tcagcagaat attaaagttc caggcaactt gacttcggtg    1800
ctacttaaca acttacatcc cagggagcag tacgtggtcc gagctagagt caacaccaag    1860 gcccagggggg aatggagtga agatctcact gcttggaccc ttagtgacat tcttcctcct    1920
caaccagaaa acatcaagat tccaacatt acacactcct cggctgtgat tcttggaca     1980 atattggatg ctattctat ttcttctatt actatccgtt acaaggttca aggcaagaat    2040
gaagaccagc acgttgatgt gaagataaag aatgccacca tcattcagta tcagctcaag    2100
ggcctagagc ctgaaacagc ataccaggtg gacattttg cagagaacaa catagggtca    2160
agcaacccag ccttttctca tgaactgtg acccctccag aatctcaagc accagcggac    2220
ctcggagggg ggaagatgct gcttatagcc atccttggct ctgctggaat gacctgcctg    2280
actgtgctgt tggcctttct gatcatattg caattgaaga gggcaaatgt gcaaggaga     2340 atggcccaag ccttccaaaa cgtgagggaa gaaccagctg tgcagttcaa ctcagggact    2400
ctggccctaa acaggaaggt caaaaacaac ccagatccta caatttatcc agtgcttgac    2460
tggaatgaca tcaaatttca agatgtgatt ggggagggca attttggcca agttcttaag    2520
gcgcgcatca agaaggatgg gttacggatg gatgctgcca tcaaaagaat gaaagaatat    2580
gcctccaaag atgatcacag ggactttgca ggagaactgg aagttctttg taaacttgga    2640
caccatccaa acatcatcaa tctcttagga gcatgtgaac atcgaggcta cttgtacctg    2700
gccattgagt acgcgcccca tggaaaccct ctggacttcc ttcgcaagag ccgtgtgctg    2760
gagacggacc cagcatttgc cattgccaat agcaccgcgt ccacactgtc ctcccagcag    2820
ctccttcact tcgctgccga cgtggcccgg ggcatggact acttgagcca aaaacagttt    2880
atccacaggg atctggctgc cagaaacatt ttagttggtg aaaactatgt ggcaaaaata    2940
gcagattttg gattgtcccg aggtcaagag gtgtacgtga aaaagacaat gggaaggctc    3000
ccagtgcgct ggatggccat cgagtcactg aattacagtg tgtacacaac caacagtgat    3060
gtatggtcct atggtgtgtt actatgggag attgttagct taggaggcac accctactgc    3120
gggatgactt gtgcagaact ctacgagaag ctgcccccagg gctacagact ggagaagccc    3180
ctgaactgtg atgatgaggt gtatgatcta atgagacaat gctggcggga aagccttat     3240 gagaggccat catttgccca gatattggtg tccttaaaca gaatgttaga ggagcgaaag    3300
acctacgtga ataccacgct ttatgagaag tttacttatg caggaattga ctgttctgct    3360
gaagaagcgg cctag                                                     3375
```

<210> SEQ ID NO 10

<211> LENGTH: 2400
<212> TYPE: DNA
<213> ORGANISM: Homo sapiens
<220> FEATURE:
<221> NAME/KEY: CDS
<222> LOCATION: (1)..(2397)
<300> PUBLICATION INFORMATION:
<300> PUBLICATION INFORMATION:
<302> TITLE: beta5 integrin
<310> PATENT DOCUMENT NUMBER: X53002

<400> SEQUENCE: 10

| | | | | | | | | | | | | | | | | |
|---|---|---|---|---|---|---|---|---|---|---|---|---|---|---|---|---|
| atg | ccg | cgg | gcc | ccg | gcg | ccg | ctg | tac | gcc | tgc | ctc | ctg | ggg | ctc | tgc | 48 |
| Met | Pro | Arg | Ala | Pro | Ala | Pro | Leu | Tyr | Ala | Cys | Leu | Leu | Gly | Leu | Cys | |
| 1 | | | 5 | | | | 10 | | | | | 15 | | | | |

| | | | | | | | | | | | | | | | | |
|---|---|---|---|---|---|---|---|---|---|---|---|---|---|---|---|---|
| gcg | ctc | ctg | ccc | cgg | ctc | gca | ggt | ctc | aac | ata | tgc | act | agt | gga | agt | 96 |
| Ala | Leu | Leu | Pro | Arg | Leu | Ala | Gly | Leu | Asn | Ile | Cys | Thr | Ser | Gly | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| gcc | acc | tca | tgt | gaa | gaa | tgt | ctg | cta | atc | cac | cca | aaa | tgt | gcc | tgg | 144 |
| Ala | Thr | Ser | Cys | Glu | Glu | Cys | Leu | Leu | Ile | His | Pro | Lys | Cys | Ala | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| tgc | tcc | aaa | gag | gac | ttc | gga | agc | cca | cgg | tcc | atc | acc | tct | cgg | tgt | 192 |
| Cys | Ser | Lys | Glu | Asp | Phe | Gly | Ser | Pro | Arg | Ser | Ile | Thr | Ser | Arg | Cys | |
| | 50 | | | | | 55 | | | | | 60 | | | | | |

| | | | | | | | | | | | | | | | | |
|---|---|---|---|---|---|---|---|---|---|---|---|---|---|---|---|---|
| gat | ctg | agg | gca | aac | ctt | gtc | aaa | aat | ggc | tgt | gga | ggt | gag | ata | gag | 240 |
| Asp | Leu | Arg | Ala | Asn | Leu | Val | Lys | Asn | Gly | Cys | Gly | Gly | Glu | Ile | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | cca | gcc | agc | agc | ttc | cat | gtc | ctg | agg | agc | ctg | ccc | ctc | agc | agc | 288 |
| Ser | Pro | Ala | Ser | Ser | Phe | His | Val | Leu | Arg | Ser | Leu | Pro | Leu | Ser | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | ggt | tcg | ggc | tct | gca | ggc | tgg | gac | gtc | att | cag | atg | aca | cca | cag | 336 |
| Lys | Gly | Ser | Gly | Ser | Ala | Gly | Trp | Asp | Val | Ile | Gln | Met | Thr | Pro | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| gag | att | gcc | gtg | aac | ctc | cgg | ccc | ggt | gac | aag | acc | acc | ttc | cag | cta | 384 |
| Glu | Ile | Ala | Val | Asn | Leu | Arg | Pro | Gly | Asp | Lys | Thr | Thr | Phe | Gln | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | gtt | cgc | cag | gtg | gag | gac | tat | cct | gtg | gac | ctg | tac | tac | ctg | atg | 432 |
| Gln | Val | Arg | Gln | Val | Glu | Asp | Tyr | Pro | Val | Asp | Leu | Tyr | Tyr | Leu | Met | |
| | 130 | | | | | 135 | | | | | 140 | | | | | |

| | | | | | | | | | | | | | | | | |
|---|---|---|---|---|---|---|---|---|---|---|---|---|---|---|---|---|
| gac | ctc | tcc | ctg | tcc | atg | aag | gat | gac | ttg | gac | aat | atc | cgg | agc | ctg | 480 |
| Asp | Leu | Ser | Leu | Ser | Met | Lys | Asp | Asp | Leu | Asp | Asn | Ile | Arg | Ser | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | acc | aaa | ctc | gcg | gag | gag | atg | agg | aag | ctc | acc | agc | aac | ttc | cgg | 528 |
| Gly | Thr | Lys | Leu | Ala | Glu | Glu | Met | Arg | Lys | Leu | Thr | Ser | Asn | Phe | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| ttg | gga | ttt | ggg | tct | ttt | gtt | gat | aag | gac | atc | tct | cct | ttc | tcc | tac | 576 |
| Leu | Gly | Phe | Gly | Ser | Phe | Val | Asp | Lys | Asp | Ile | Ser | Pro | Phe | Ser | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| acg | gca | ccg | agg | tac | cag | acc | aat | ccg | tgc | att | ggt | tac | aag | ttg | ttt | 624 |
| Thr | Ala | Pro | Arg | Tyr | Gln | Thr | Asn | Pro | Cys | Ile | Gly | Tyr | Lys | Leu | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| cca | aat | tgc | gtc | ccc | tcc | ttt | ggg | ttc | cgc | cat | ctg | ctg | cct | ctc | aca | 672 |
| Pro | Asn | Cys | Val | Pro | Ser | Phe | Gly | Phe | Arg | His | Leu | Leu | Pro | Leu | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | aga | gtg | gac | agc | ttc | aat | gag | gaa | gtt | cgg | aaa | cag | agg | gtg | tcc | 720 |
| Asp | Arg | Val | Asp | Ser | Phe | Asn | Glu | Glu | Val | Arg | Lys | Gln | Arg | Val | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgg | aac | cga | gat | gcc | cct | gag | ggg | ggc | ttt | gat | gca | gta | ctc | cag | gca | 768 |
| Arg | Asn | Arg | Asp | Ala | Pro | Glu | Gly | Gly | Phe | Asp | Ala | Val | Leu | Gln | Ala | |
| | | | | 245 | | | | | 250 | | | | | 255 | | |

| | | | | | | | | | | | | | | | | |
|---|---|---|---|---|---|---|---|---|---|---|---|---|---|---|---|---|
| gcc | gtc | tgc | aag | gag | aag | att | ggc | tgg | cga | aag | gat | gca | ctg | cat | ttg | 816 |
| Ala | Val | Cys | Lys | Glu | Lys | Ile | Gly | Trp | Arg | Lys | Asp | Ala | Leu | His | Leu | |

-continued

```
              260                 265                 270
ctg gtg ttc aca aca gat gat gtg ccc cac atc gca ttg gat gga aaa    864
Leu Val Phe Thr Thr Asp Asp Val Pro His Ile Ala Leu Asp Gly Lys
            275                 280                 285 ttg gga ggc ctg gtg cag cca cac gat ggc cag tgc cac ctg aac gag    912
Leu Gly Gly Leu Val Gln Pro His Asp Gly Gln Cys His Leu Asn Glu
        290                 295                 300 gcc aac gag tac aca gca tcc aac cag atg gac tat cca tcc ctt gcc    960
Ala Asn Glu Tyr Thr Ala Ser Asn Gln Met Asp Tyr Pro Ser Leu Ala
305                 310                 315                 320 ttg ctt gga gag aaa ttg gca gag aac aac atc aac ctc atc ttt gca   1008
Leu Leu Gly Glu Lys Leu Ala Glu Asn Asn Ile Asn Leu Ile Phe Ala
                325                 330                 335 gtg aca aaa aac cat tat atg ctg tac aag aat ttt aca gcc ctg ata   1056
Val Thr Lys Asn His Tyr Met Leu Tyr Lys Asn Phe Thr Ala Leu Ile
            340                 345                 350 cct gga aca acg gtg gag att tta gat gga gac tcc aaa aat att att   1104
Pro Gly Thr Thr Val Glu Ile Leu Asp Gly Asp Ser Lys Asn Ile Ile
        355                 360                 365 caa ctg att att aat gca tac aat agt atc cgg tct aaa gtg gag ttg   1152
Gln Leu Ile Ile Asn Ala Tyr Asn Ser Ile Arg Ser Lys Val Glu Leu
370                 375                 380 tca gtc tgg gat cag cct gag gat ctt aat ctc ttc ttt act gct acc   1200
Ser Val Trp Asp Gln Pro Glu Asp Leu Asn Leu Phe Phe Thr Ala Thr
385                 390                 395                 400 tgc caa gat ggg gta tcc tat cct ggt cag agg aag tgt gag ggt ctg   1248
Cys Gln Asp Gly Val Ser Tyr Pro Gly Gln Arg Lys Cys Glu Gly Leu
                405                 410                 415 aag att ggg gac acg gca tct ttt gaa gta tca ttg gag gcc cga agc   1296
Lys Ile Gly Asp Thr Ala Ser Phe Glu Val Ser Leu Glu Ala Arg Ser
            420                 425                 430 tgt ccc agc aga cac acg gag cat gtg ttt gcc ctg cgg ccg gtg gga   1344
Cys Pro Ser Arg His Thr Glu His Val Phe Ala Leu Arg Pro Val Gly
        435                 440                 445 ttc cgg gac agc ctg gag gtg ggg gtc acc tac aac tgc acg tgc ggc   1392
Phe Arg Asp Ser Leu Glu Val Gly Val Thr Tyr Asn Cys Thr Cys Gly
450                 455                 460 tgc agc gtg ggg ctg gaa ccc aac agc gcc agg tgc aac ggg agc ggg   1440
Cys Ser Val Gly Leu Glu Pro Asn Ser Ala Arg Cys Asn Gly Ser Gly
465                 470                 475                 480 acc tat gtc tgc ggc ctg tgt gag tgc agc ccc ggc tac ctg ggc acc   1488
Thr Tyr Val Cys Gly Leu Cys Glu Cys Ser Pro Gly Tyr Leu Gly Thr
                485                 490                 495 agg tgc gag tgc cag gat ggg gag aac cag agc gtg tac cag aac ctg   1536
Arg Cys Glu Cys Gln Asp Gly Glu Asn Gln Ser Val Tyr Gln Asn Leu
            500                 505                 510 tgc cgg gag gca gag ggc aag cca ctg tgc agc ggg cgt ggg gac tgc   1584
Cys Arg Glu Ala Glu Gly Lys Pro Leu Cys Ser Gly Arg Gly Asp Cys
        515                 520                 525 agc tgc aac cag tgc tcc tgc ttc gag agc gag ttt ggc aag atc tat   1632
Ser Cys Asn Gln Cys Ser Cys Phe Glu Ser Glu Phe Gly Lys Ile Tyr
530                 535                 540 ggg cct ttc tgt gag tgc gac aac ttc tcc tgt gcc agg aac aag gga   1680
Gly Pro Phe Cys Glu Cys Asp Asn Phe Ser Cys Ala Arg Asn Lys Gly
545                 550                 555                 560 gtc ctc tgc tca ggc cat ggc gag tgt cac tgc ggg gaa tgc aag tgc   1728
Val Leu Cys Ser Gly His Gly Glu Cys His Cys Gly Glu Cys Lys Cys
                565                 570                 575 cat gca ggt tac atc ggg gac aac tgt aac tgc tcg aca gac atc agc   1776
```

-continued

| | | | | | | | | | | | | | | |
|---|---|---|---|---|---|---|---|---|---|---|---|---|---|---|
| His | Ala | Gly | Tyr | Ile | Gly | Asp | Asn | Cys | Asn | Cys | Ser | Thr | Asp | Ile | Ser |
| | | | 580 | | | | | 585 | | | | 590 | | |

```
aca tgc cgg ggc aga gat ggc cag atc tgc agc gag cgt ggg cac tgt    1824
Thr Cys Arg Gly Arg Asp Gly Gln Ile Cys Ser Glu Arg Gly His Cys
        595                 600                 605 ctc tgt ggg cag tgc caa tgc acg gag ccg ggg gcc ttt ggg gag atg    1872
Leu Cys Gly Gln Cys Gln Cys Thr Glu Pro Gly Ala Phe Gly Glu Met
610                 615                 620 tgt gag aag tgc ccc acc tgc ccg gat gca tgc agc acc aag aga gat    1920
Cys Glu Lys Cys Pro Thr Cys Pro Asp Ala Cys Ser Thr Lys Arg Asp
625                 630                 635                 640 tgc gtc gag tgc ctg ctg ctc cac tct ggg aaa cct gac aac cag acc    1968
Cys Val Glu Cys Leu Leu Leu His Ser Gly Lys Pro Asp Asn Gln Thr
        645                 650                 655 tgc cac agc cta tgc agg gat gag gtg atc aca tgg gtg gac acc atc    2016
Cys His Ser Leu Cys Arg Asp Glu Val Ile Thr Trp Val Asp Thr Ile
        660                 665                 670 gtg aaa gat gac cag gag gct gtg cta tgt ttc tac aaa acc gcc aag    2064
Val Lys Asp Asp Gln Glu Ala Val Leu Cys Phe Tyr Lys Thr Ala Lys
        675                 680                 685 gac tgc gtc atg atg ttc acc tat gtg gag ctc ccc agt ggg aag tcc    2112
Asp Cys Val Met Met Phe Thr Tyr Val Glu Leu Pro Ser Gly Lys Ser
690                 695                 700 aac ctg acc gtc ctc agg gag cca gag tgt gga aac acc ccc aac gcc    2160
Asn Leu Thr Val Leu Arg Glu Pro Glu Cys Gly Asn Thr Pro Asn Ala
705                 710                 715                 720 atg acc atc ctc ctg gct gtg gtc ggt agc atc ctc ctt gtt ggg ctt    2208
Met Thr Ile Leu Leu Ala Val Val Gly Ser Ile Leu Leu Val Gly Leu
        725                 730                 735 gca ctc ctg gct atc tgg aag ctg ctt gtc acc atc cac gac cgg agg    2256
Ala Leu Leu Ala Ile Trp Lys Leu Leu Val Thr Ile His Asp Arg Arg
        740                 745                 750 gag ttt gca aag ttt cag agc gag cga tcc agg gcc cgc tat gaa atg    2304
Glu Phe Ala Lys Phe Gln Ser Glu Arg Ser Arg Ala Arg Tyr Glu Met
        755                 760                 765 gct tca aat cca tta tac aga aag cct atc tcc acg cac act gtg gac    2352
Ala Ser Asn Pro Leu Tyr Arg Lys Pro Ile Ser Thr His Thr Val Asp
770                 775                 780 ttc acc ttc aac aag ttc aac aaa tcc tac aat ggc act gtg gac tga    2400
Phe Thr Phe Asn Lys Phe Asn Lys Ser Tyr Asn Gly Thr Val Asp
785                 790                 795

<210> SEQ ID NO 11
<211> LENGTH: 2367
<212> TYPE: DNA
<213> ORGANISM: Homo sapiens
<300> PUBLICATION INFORMATION:
<302> TITLE: beta3 integrin
<310> PATENT DOCUMENT NUMBER: NM000212

<400> SEQUENCE: 11
atgcgagcgc ggccgcggcc ccggccgctc tgggcgactg tgctggcgct gggggcgctg     60
gcgggcgttg cgtaggagg gcccaacatc tgtaccacgc gaggtgtgag ctcctgccag    120
cagtgcctgg ctgtgagccc catgtgtgcc tggtgctctg atgaggccct gcctctgggc    180
tcacctcgct gtgacctgaa ggagaatctg ctgaaggata actgtgcccc agaatccatc    240
gagttcccag tgagtgaggc ccgagtacta gaggacaggc ccctcagcga caagggctct    300
ggagacagct cccaggtcac tcaagtcagt cccagagga ttgcactccg gctccggcca    360
gatgattcga agaatttctc catccaagtg cggcaggtgg aggattaccc tgtggacatc    420
```

-continued

```
tactacttga tggacctgtc ttactccatg aaggatgatc tgtggagcat ccagaacctg      480
ggtaccaagc tggccaccca gatgcgaaag ctcaccagta acctgcggat tggcttcggg      540
gcatttgtgg acaagcctgt gtcaccatac atgtatatct ccccaccaga ggccctcgaa      600
aacccctgct atgatatgaa gaccacctgc ttgcccatgt ttggctacaa acacgtgctg      660
acgctaactg accaggtgac ccgcttcaat gaggaagtga agaagcagag tgtgtcacgg      720
aaccgagatg ccccagaggg tggctttgat gccatcatgc aggctacagt ctgtgatgaa      780
aagattggct ggaggaatga tgcatcccac ttgctggtgt ttaccactga tgccaagact      840
catatagcat tggacggaag gctggcaggc attgtccagc taatgacgg gcagtgtcat       900 gttggtagtg acaatcatta ctctgcctcc actaccatgg attatccctc tttgggggctg     960 atgactgaga agctatccca gaaaaacatc aatttgatct ttgcagtgac tgaaaatgta     1020
gtcaatctct atcagaacta tagtgagctc atcccaggga ccacagttgg ggttctgtcc     1080
atggattcca gcaatgtcct ccagctcatt gttgatgctt atgggaaaat ccgttctaaa     1140
gtagagctgg aagtgcgtga cctccctgaa gagttgtctc tatccttcaa tgccacctgc     1200
ctcaacaatg aggtcatccc tggcctcaag tcttgtatgg gactcaagat tggagacacg     1260
gtgagcttca gcattgaggc caaggtgcga ggctgtcccc aggagaagga gaagtccttt     1320
accataaagc ccgtgggctt caaggacagc ctgatcgtcc aggtcacctt tgattgtgac     1380
tgtgcctgcc aggcccaagc tgaacctaat agccatcgct gcaacaatgg caatgggacc     1440
tttgagtgtg gggtatgccg ttgtgggcct ggctggctgg gatcccagtg tgagtgctca     1500
gaggaggact atcgcccttc ccagcaggac gaatgcagcc ccggggaggg tcagcccgtc     1560
tgcagccagc ggggcgagtg cctctgtggt caatgtgtct gccacagcag tgactttggc     1620
aagatcacgg gcaagtactg cgagtgtgac gacttctcct gtgtccgcta caaggggag     1680 atgtgctcag ccatggcca gtgcagctgt ggggactgcc tgtgtgactc cgactggacc     1740
ggctactact gcaactgtac cacgcgtact gacacctgca tgtccagcaa tgggctgctg     1800
tgcagcggcc gcggcaagtg tgaatgtggc agctgtgtct gtatccagcc gggctcctat     1860
ggggacacct gtgagaagtg ccccacctgc ccagatgcct gcacctttaa gaaagaatgt     1920
gtggagtgta aagtttga ccgggagccc tacatgaccg aaaatacctg caaccgttac     1980
tgccgtgacg agattgagtc agtgaaagag cttaaggaca ctggcaagga tgcagtgaat     2040
tgtacctata agaatgagga tgactgtgtc gtcagattcc agtactatga agattctagt     2100
ggaaagtcca tcctgtatgt ggtagaagag ccagagtgtc ccaagggccc tgacatcctg     2160
gtggtcctgc tctcagtgat gggggccatt ctgctcattg ccttgccgc cctgctcatc     2220 tggaaactcc tcatcaccat ccacgaccga aaagaattcg ctaaatttga ggaagaacgc     2280
gccagagcaa aatgggacac agccaacaac ccactgtata agaggccac gtctaccttc     2340 accaatatca cgtaccgggg cacttaa                                         2367
```

<210> SEQ ID NO 12
<211> LENGTH: 3147
<212> TYPE: DNA
<213> ORGANISM: Homo sapiens
<300> PUBLICATION INFORMATION:
<302> TITLE: alpha v intergrin
<310> PATENT DOCUMENT NUMBER: NM0022210

<400> SEQUENCE: 12

```
atggctttc cgccgcggcg acggctgcgc ctcggtcccc gcggcctccc gcttcttctc       60
```

-continued

```
tcgggactcc tgctacctct gtgccgcgcc ttcaacctag acgtggacag tcctgccgag    120
tactctggcc ccgagggaag ttacttcggc ttcgccgtgg atttcttcgt gcccagcgcg    180
tcttcccgga tgtttcttct cgtgggagct cccaaagcaa acaccaccca gcctgggatt    240
gtggaaggag ggcaggtcct caaatgtgac tggtcttcta cccgccggtg ccagccaatt    300
gaatttgatg caacaggcaa tagagattat gccaaggatg atccattgga atttaagtcc    360
catcagtggt ttggagcatc tgtgaggtcg aaacaggata aaattttggc ctgtgcccca    420
ttgtaccatt ggagaactga gatgaaacag gagcgagagc tgttggaaac atgctttctt    480
caagatggaa caaagactgt tgagtatgct ccatgtagat cacaagatat tgatgctgat    540
ggacagggat tttgtcaagg aggattcagc attgatttta ctaaagctga cagagtactt    600
cttggtggtc ctggtagctt ttattggcaa ggtcagctta tttcggatca agtggcagaa    660
atcgtatcta aatacgaccc caatgtttac agcatcaagt ataataacca attagcaact    720
cggactgcac aagctatttt tgatgacagc tatttgggtt attctgtggc tgtcggagat    780
ttcaatggtg atggcataga tgactttgtt tcaggagttc caagagcagc aaggactttg    840
ggaatggttt atatttatga tgggaagaac atgtcctcct tatacaattt tactggcgag    900
cagatggctg catatttcgg attttctgta gctgccactg acattaatgg agatgattat    960
gcagatgtgt ttattggagc acctctcttc atggatcgtg gctctgatgg caaactccaa    1020
gaggtggggc aggtctcagt gtctctacag agagcttcag agacttcca gacgacaaag    1080 ctgaatggat ttgaggtctt tgcacggttt ggcagtgcca tagctccttt gggagatctg    1140
gaccaggatg gtttcaatga tattgcaatt gctgctccat atggggtga agataaaaaa    1200 ggaattgttt atatcttcaa tggaagatca acaggcttga acgcagtccc atctcaaatc    1260
cttgaagggc agtgggctgc tcgaagcatg ccaccaagct ttggctattc aatgaaagga    1320
gccacagata tagacaaaaa tggatatcca gacttaattg taggagcttt tggtgtagat    1380
cgagctatct tatacagggc cagaccagtt atcactgtaa atgctggtct tgaagtgtac    1440
cctagcattt taaatcaaga caataaaacc tgctcactgc ctggaacagc tctcaaagtt    1500
tcctgtttta atgttaggtt ctgcttaaag gcagatggca aggagtact tcccaggaaa    1560 cttaatttcc aggtggaact tcttttggat aaactcaagc aaaagggagc aattcgacga    1620
gcactgtttc tctacagcag gtccccaagt cactccaaga acatgactat ttcaagggg    1680 ggactgatgc agtgtgagga attgatacg tatctgcggg atgaatctga atttagagac    1740
aaactcactc caattactat ttttatggaa tatcggttgg attatagaac agctgctgat    1800
acaacaggct tgcaacccat tcttaaccag ttcacgcctg ctaacattag tcgacaggct    1860
cacattctac ttgactgtgg tgaagacaat gtctgtaaac ccaagctgga agtttctgta    1920
gatagtgatc aaaagaagat ctatattggg gatgacaacc ctctgacatt gattgttaag    1980
gctcagaatc aaggagaagg tgcctacgaa gctgagctca tcgtttccat tccactgcag    2040
gctgatttca tcgggttgt ccgaaacaat gaagccttag caagactttc ctgtgcattt    2100
aagacagaaa accaaactcg ccaggtggta tgtgaccttg aaacccaat gaaggctgga    2160 actcaactct tagctggtct tcgtttcagt gtgcaccagc agtcagagat ggatacttct    2220
gtgaaatttg acttacaaat ccaaagctca aatctatttg acaaagtaag cccagttgta    2280
tctcacaaag ttgatcttgc tgttttagct gcagttgaga taagaggagt ctcgagtcct    2340
gatcatatct ttcttccgat tccaaactgg gagcacaagg agaaccctga gactgaagaa    2400
```

-continued

```
gatgttgggc cagttgttca gcacatctat gagctgagaa acaatggtcc aagttcattc    2460
agcaaggcaa tgctccatct tcagtggcct tacaaatata ataataacac tctgttgtat    2520
atccttcatt atgatattga tggaccaatg aactgcactt cagatatgga gatcaaccct    2580
ttgagaatta agatctcatc tttgcaaaca actgaaaaga atgacacggt tgccgggcaa    2640
ggtgagcggg accatctcat cactaagcgg gatcttgccc tcagtgaagg agatattcac    2700
actttgggtt gtggagttgc tcagtgcttg aagattgtct gccaagttgg gagattagac    2760
agaggaaaga gtgcaatctt gtacgtaaag tcattactgt ggactgagac ttttatgaat    2820
aaagaaaatc agaatcattc ctattctctg aagtcgtctg cttcatttaa tgtcatagag    2880
tttccttata agaatcttcc aattgaggat atcaccaact ccacattggt taccactaat    2940
gtcacctggg gcattcagcc agcgcccatg cctgtgcctg tgtgggtgat catttttagca   3000 gttctagcag gattgttgct actggctgtt ttggtatttg taatgtacag gatgggcttt    3060
tttaaacggt tccggccacc tcaagaagaa caagaaaggg agcagcttca acctcatgaa    3120
aatggtgaag gaaactcaga aacttaa                                        3147
```

<210> SEQ ID NO 13
<211> LENGTH: 402
<212> TYPE: DNA
<213> ORGANISM: Homo sapiens
<300> PUBLICATION INFORMATION:
<302> TITLE: CaSm (cancer associated SM-like oncogene)
<310> PATENT DOCUMENT NUMBER: AF000177

<400> SEQUENCE: 13

```
atgaactata tgcctggcac cgccagcctc atcgaggaca ttgacaaaaa gcacttggtt      60
ctgcttcgag atggaaggac acttataggc ttttttaagaa gcattgatca atttgcaaac   120
ttagtgctac atcagactgt ggagcgtatt catgtgggca aaaaatacgg tgatattcct    180
cgagggattt ttgtggtcag aggagaaaat gtggtcctac taggagaaat agacttggaa    240
aaggagagtg acacacccct ccagcaagta tccattgaag aaattctaga gaacaaagg    300 gtggaacagc agaccaagct ggaagcagag aagttgaaag tgcaggccct gaaggaccga    360
ggtctttcca ttcctcgagc agatactctt gatgagtact aa                       402
```

<210> SEQ ID NO 14
<211> LENGTH: 1923
<212> TYPE: DNA
<213> ORGANISM: Homo sapiens
<300> PUBLICATION INFORMATION:
<302> TITLE: c-myb
<310> PATENT DOCUMENT NUMBER: NM005375

<400> SEQUENCE: 14

```
atggcccgaa gaccccggca cagcatatat agcagtgacg aggatgatga ggactttgag      60
atgtgtgacc atgactatga tgggctgctt cccaagtctg aaagcgtca cttggggaaa     120 acaaggtgga cccgggaaga ggatgaaaaa ctgaagaagc tggtggaaca gaatggaaca    180
gatgactgga aagttattgc caattatctc ccgaatcgaa cagatgtgca gtgccagcac    240
cgatggcaga aagtactaaa ccctgagctc atcaagggtc cttggaccaa gaagaagat    300 cagagagtga tagagcttgt acagaaatac ggtccgaaac gttggtctgt tattgccaag    360
cacttaaagg ggagaattgg aaaacaatgt agggagaggt ggcataacca cttgaatcca    420
gaagttaaga aaacctcctg gacagaagag gaagacagaa ttatttacca ggcacacaag    480
agactgggga acagatggc agaaatcgca aagctactgc ctggacgaac tgataatgct    540
```

-continued

```
atcaagaacc actggaattc tacaatgcgt cggaaggtcg aacaggaagg ttatctgcag      600
gagtcttcaa aagccagcca gccagcagtg gccacaagct tccagaagaa cagtcatttg      660
atgggttttg ctcaggctcc gcctacagct caactccctg ccactggcca gcccactgtt      720
aacaacgact attcctatta ccacatttct gaagcacaaa atgtctccag tcatgttcca      780
taccctgtag cgttacatgt aaatatagtc aatgtccctc agccagctgc cgcagccatt      840
cagagacact ataatgatga agaccctgag aaggaaaagc gaataaagga attagaattg      900
ctcctaatgt caaccgagaa tgagctaaaa ggacagcagg tgctaccaac acagaaccac      960
acatgcagct accccgggtg gcacagcacc accattgccg accacaccag acctcatgga     1020
gacagtgcac ctgtttcctg tttgggagaa caccactcca ctccatctct gccagcggat     1080
cctggctccc tacctgaaga aagcgcctcg ccagcaaggt gcatgatcgt ccaccagggc     1140
accattctgg ataatgttaa gaacctctta gaatttgcag aaacactcca atttatagat     1200
tctttcttaa acacttccag taaccatgaa aactcagact tggaaatgcc ttctttaact     1260 tccaccccc tcattggtca caaattgact gttacaacac catttcatag agaccagact     1320
gtgaaaactc aaaaggaaaa tactgttttt agaaccccag ctatcaaaag gtcaatctta     1380
gaaagctctc caagaactcc tacaccattc aaacatgcac ttgcagctca agaaattaaa     1440
tacggtcccc tgaagatgct acctcagaca ccctctcatc tagtagaaga tctgcaggat     1500
gtgatcaaac aggaatctga tgaatctgga tttgttgctg agtttcaaga aaatggacca     1560
cccttactga gaaaatcaa acaagaggtg gaatctccaa ctgataaatc aggaaacttc     1620
ttctgctcac accactggga aggggacagt ctgaataccc aactgttcac gcagacctcg     1680
cctgtgcgag atgcaccgaa tattcttaca agctccgttt taatggcacc agcatcagaa     1740
gatgaagaca atgttctcaa agcatttaca gtacctaaaa acaggtccct ggcgagcccc     1800 ttgcagccctt gtagcagtac ctgggaacct gcatcctgtg gaaagatgga ggagcagatg     1860
acatcttcca gtcaagctcg taaatacgtg aatgcattct cagcccggac gctggtcatg     1920
tga                                                                   1923
```

<210> SEQ ID NO 15
<211> LENGTH: 544
<212> TYPE: DNA
<213> ORGANISM: Homo sapiens
<300> PUBLICATION INFORMATION:
<302> TITLE: c-myc
<310> PATENT DOCUMENT NUMBER: J00120

<400> SEQUENCE: 15

```
gaccccgag ctgtgctgct cgcggccgcc accgcgggc cccggccgtc cctggctccc        60
ctcctgcctc gagaagggca gggcttctca gaggcttggc gggaaaaaga acggagggag      120
ggatcgcgct gagtataaaa gccggttttc ggggctttat ctaactcgct gtagtaattc      180
cagcgagagg cagagggagc gagcgggcgg ccggctaggg tggaagagcc gggcgagcag      240
agctgcgctg cgggcgtcct gggaaggag atcggagcg aataggggc ttcgcctctg        300 gcccagccct cccgctgatc ccccagccag cggtccgcaa ccttgccgc atccacgaaa       360 ctttgcccat agcagcgggc gggcactttg cactggaact acaacacccc gagcaaggac      420
gcgactctcc cgacgcgggg aggctattct gcccatttgg ggacacttcc ccgccgctgc     480
caggacccgc ttctctgaaa ggctctcctt gcagctgctt agacgctgga ttttttcgg     540 gtag                                                                   544
```

<210> SEQ ID NO 16
<211> LENGTH: 618
<212> TYPE: DNA
<213> ORGANISM: Homo sapiens
<300> PUBLICATION INFORMATION:
<302> TITLE: ephrin-A1
<310> PATENT DOCUMENT NUMBER: NM004428

<400> SEQUENCE: 16

| | | | | | |
|---|---|---|---|---|---|
| atggagttcc | tctgggcccc | tctcttgggt | ctgtgctgca | gtctggccgc | tgctgatcgc | 60 |
| cacaccgtct | tctggaacag | ttcaaatccc | aagttccgga | atgaggacta | caccatacat | 120 |
| gtgcagctga | atgactacgt | ggacatcatc | tgtccgcact | atgaagatca | ctctgtggca | 180 |
| gacgctgcca | tggagcagta | catactgtac | ctggtggagc | atgaggagta | ccagctgtgc | 240 |
| cagccccagt | ccaaggacca | agtccgctgg | cagtgcaacc | ggcccagtgc | caagcatggc | 300 |
| ccggagaagc | tgtctgagaa | gttccagcgc | ttcacacctt | tcaccctggg | caaggagttc | 360 |
| aaagaaggac | acagctacta | ctacatctcc | aaacccatcc | accagcatga | agaccgctgc | 420 |
| ttgaggttga | aggtgactgt | cagtggcaaa | atcactcaca | gtcctcaggc | ccatgtcaat | 480 |
| ccacaggaga | agagacttgc | agcagatgac | ccagaggtgc | gggttctaca | tagcatcggt | 540 |
| cacagtgctg | ccccacgcct | cttcccactt | gcctggactg | tgctgctcct | tccacttctg | 600 |
| ctgctgcaaa | ccccgtga | | | | | 618 |

<210> SEQ ID NO 17
<211> LENGTH: 642
<212> TYPE: DNA
<213> ORGANISM: Homo sapiens

<400> SEQUENCE: 17

| | | | | | |
|---|---|---|---|---|---|
| atggcgcccg | cgcagcgccc | gctgctcccg | ctgctgctcc | tgctgttacc | gctgccgccg | 60 |
| ccgcccttcg | cgcgcgccga | ggacgccgcc | cgcgccaact | cggaccgcta | cgccgtctac | 120 |
| tggaaccgca | gcaaccccag | gttccacgca | ggcgcggggg | acgacggcgg | gggctacacg | 180 |
| gtggaggtga | gcatcaatga | ctacctggac | atctactgcc | cgcactatgg | ggcgccgctg | 240 |
| ccgccggccg | agcgcatgga | gcgctacgtg | ctgtacatgg | tcaacggcga | gggccacgcc | 300 |
| tcctgcgacc | accgccagcg | cggcttcaag | cgctgggagt | gcaaccggcc | cgcggcgccc | 360 |
| gggggggccgc | tcaagttctc | ggagaagttc | cagctcttca | cgcccttctc | cctgggcttc | 420 |
| gagttccggc | ccgccacga | gtattactac | atctctgcca | cgcctcccaa | tgctgtggac | 480 |
| cggccctgcc | tgcgactgaa | ggtgtacgtg | cggccgacca | acgagaccct | gtacgaggct | 540 |
| cctgagccca | tcttcaccag | caataactcg | tgtagcagcc | cgggcggctg | ccgcctcttc | 600 |
| ctcagcacca | tccccgtgct | ctggaccctc | ctgggttcct | ag | | 642 |

<210> SEQ ID NO 18
<211> LENGTH: 717
<212> TYPE: DNA
<213> ORGANISM: Homo sapiens
<300> PUBLICATION INFORMATION:
<302> TITLE: ephrin-A3
<310> PATENT DOCUMENT NUMBER: XM001787

<400> SEQUENCE: 18

| | | | | | |
|---|---|---|---|---|---|
| atggcggcgg | ctccgctgct | gctgctgctg | ctgctcgtgc | ccgtgccgct | gctgccgctg | 60 |
| ctggcccaag | ggcccggagg | ggcgctggga | aaccggcatg | cggtgtactg | gaacagctcc | 120 |

```
aaccagcacc tgcggcgaga gggctacacc gtgcaggtga acgtgaacga ctatctggat    180
atttactgcc cgcactacaa cagctcgggg gtgggcccg gggcgggacc ggggcccgga    240
ggcggggcag agcagtacgt gctgtacatg gtgagccgca acggctaccg cacctgcaac    300
gccagccagg gcttcaagcg ctgggagtgc aaccggccgc acgcccgca cagccccatc    360 aagttctcgg agaagttcca gcgctacagc gccttctctc tgggctacga gttccacgcc    420
ggccacgagt actactacat ctccacgccc actcacaacc tgcactggaa gtgtctgagg    480
atgaaggtgt tcgtctgctg cgcctccaca tcgcactccg gggagaagcc ggtccccact    540
ctcccccagt tcaccatggg ccccaatatg aagatcaacg tgctggaaga ctttgaggga    600
gagaaccctc aggtgcccaa gcttgagaag agcatcagcg ggaccagccc caaacgggaa    660
cacctgcccc tggccgtggg catcgccttc ttcctcatga cgttcttggc ctcctag      717

<210> SEQ ID NO 19
<211> LENGTH: 606
<212> TYPE: DNA
<213> ORGANISM: Homo sapiens
<300> PUBLICATION INFORMATION:
<302> TITLE: ephrin-A3
<310> PATENT DOCUMENT NUMBER: XM001784

<400> SEQUENCE: 19
atgcggctgc tgcccctgct gcggactgtc ctctgggccg cgttcctcgg ctcccctctg     60 cgcggggct ccagcctccg ccacgtagtc tactggaact ccagtaaccc caggttgctt   120
cgaggagacg ccgtggtgga gctgggcctc aacgattacc tagacattgt ctgccccac    180 tacgaaggcc cagggccccc tgagggcccc gagacgtttg ctttgtacat ggtggactgg   240
ccaggctatg agtcctgcca ggcagagggc ccccgggcct acaagcgctg ggtgtgctcc   300
ctgccctttg ccatgttca attctcagag aagattcagc gcttcacacc cttctccctc    360
ggctttgagt tcttacctgg agagacttac tactacatct cggtgcccac tccagagagt   420
tctggccagt gcttgaggct ccaggtgtct gtctgctgca aggagaggaa gtctgagtca   480
gcccatcctg ttgggagccc tggagagagt ggcacatcag ggtggcgagg gggggacact   540
cccagccccc tctgtctctt gctattactg ctgcttctga ttcttcgtct tctgcgaatt   600
ctgtga                                                              606

<210> SEQ ID NO 20
<211> LENGTH: 687
<212> TYPE: DNA
<213> ORGANISM: Homo sapiens
<300> PUBLICATION INFORMATION:
<302> TITLE: ephrin-A5
<310> PATENT DOCUMENT NUMBER: NM001962

<400> SEQUENCE: 20
atgttgcacg tggagatgtt gacgctggtg tttctggtgc tctggatgtg tgtgttcagc     60
caggacccgg gctccaaggc cgtcgccgac cgctacgctg tctactggaa cagcagcaac   120
cccagattcc agaggggtga ctaccatatt gatgtctgta tcaatgacta cctggatgtt   180
ttctgccctc actatgagga ctccgtccca gaagataaga ctgagcgcta tgtcctctac   240
atggtgaact tgatggctac agtgcctgc gaccacactt ccaaagggtt caagagatgg   300
gaatgtaacc ggcctcactc tccaaatgga ccgctgaagt tctctgaaaa attccagctc   360
ttcactccct ttctctaggg atttgaattc aggccaggcc gagaatatt  tctacatctcc    420 tctgcaatcc cagataatgg aagaaggtcc tgtctaaagc tcaaagtctt tgtgagacca   480
```

-continued

| | |
|---|---|
| acaaatagct gtatgaaaac tataggtgtt catgatcgtg ttttcgatgt taacgacaaa | 540 |
| gtagaaaatt cattagaacc agcagatgac accgtacatg agtcagccga gccatcccgc | 600 |
| ggcgagaacg cggcacaaac accaaggata cccagccgcc ttttggcaat cctactgttc | 660 |
| ctcctggcga tgcttttgac attatag | 687 |

<210> SEQ ID NO 21
<211> LENGTH: 2955
<212> TYPE: DNA
<213> ORGANISM: Homo sapiens

<400> SEQUENCE: 21

| | |
|---|---|
| atggccctgg attatctact actgctcctc ctggcatccg cagtggctgc gatggaagaa | 60 |
| acgttaatgg acaccagaac ggctactgca gagctgggct ggacggccaa tcctgcgtcc | 120 |
| gggtgggaag aagtcagtgg ctacgatgaa aacctgaaca ccatccgcac ctaccaggtg | 180 |
| tgcaatgtct tcgagcccaa ccagaacaat tggctgctca ccaccttcat caaccggcgg | 240 |
| ggggcccatc gcatctacac agagatgcgc ttcactgtga gagactgcag cagcctccct | 300 |
| aatgtcccag atcctgcaa ggagaccttc aacttgtatt actatgagac tgactctgtc | 360 |
| attgccacca gaagtcagc cttctggtct gaggccccct acctcaaagt agacaccatt | 420 |
| gctgcagatg agagcttctc ccaggtggac tttggggaa ggctgatgaa ggtaaacaca | 480 |
| gaagtcagga gctttgggcc tcttactcgg aatggttttt acctcgcttt tcaggattat | 540 |
| ggagcctgta tgtctcttct ttctgtccgt gtcttcttca aaagtgtcc cagcattgtg | 600 |
| caaaattttg cagtgtttcc agagactatg acaggggcag agagcacatc tctggtgatt | 660 |
| gctcggggca catgcatccc caacgcagag gaagtggacg tgcccatcaa actctactgc | 720 |
| aacggggatg gggaatggat ggtgcctatt ggcgatgca cctgcaagcc tggctatgag | 780 |
| cctgagaaca cgtggcatg caaggcttgc cctgcaggga cattcaaggc cagccaggaa | 840 |
| gctgaaggct gctcccactg ccccctccaac agccgctccc ctgcagaggc gtctcccatc | 900 |
| tgcacctgtc ggaccggtta ttaccgagcg actttgacc ctccagaagt ggcatgcact | 960 |
| agcgtcccat caggtccccg caatgttatc tccatcgtca atgagacgtc catcattctg | 1020 |
| gagtggcacc ctccaaggga cagggtggg cgggatgatg tgacctacaa catcatctgc | 1080 |
| aaaaagtgcc gggcagaccg ccggagctgc tcccgctgtg acgacaatgt ggagtttgtg | 1140 |
| cccaggcagc tgggcctgac ggagtgccgc gtctccatca gcagcctgtg ggcccacacc | 1200 |
| ccctacacct ttgacatcca ggccatcaat ggagtctcca gcaagagtcc cttcccccca | 1260 |
| cagcacgtct ctgtcaacat caccacaaac caagccgccc cctccaccgt tcccatcatg | 1320 |
| caccaagtca gtgccactat gaggagcatc accttgtcat ggccacagcc ggagcagccc | 1380 |
| aatggcatca tcctggacta tgagatccgg tactatgaga aggaacacaa tgagttcaac | 1440 |
| tcctccatgg ccaggagtca gaccaacaca gcaaggattg atgggctgcg gcctggcatg | 1500 |
| gtatatgtgg tacaggtgcg tgcccgcact gttgctggct acggcaagtt cagtggcaag | 1560 |
| atgtgcttcc agactctgac tgacgatgat tacaagtcag agctgaggga gcagctgccc | 1620 |
| ctgattgctg gctcggcagc ggccggggtc gtgttcgttg tgtccttggt ggccatctct | 1680 |
| atcgtctgta gcaggaaacg ggcttatagc aaagaggctg tgtacagcga taagctccag | 1740 |
| cattacagca caggccgagg ctccccaggg atgaagatct acattgaccc cttcacttat | 1800 |
| gaggatccca acgaagctgt ccgggagttt gccaaggaga ttgatgtatc ttttgtgaaa | 1860 |

| | |
|---|---|
| attgaagagg tcatcggagc aggggagttt ggagaagtgt acaaggggcg tttgaaactg | 1920 |
| ccaggcaaga gggaaatcta cgtggccatc aagaccctga aggcagggta ctcggagaag | 1980 |
| cagcgtcggg actttctgag tgaggcgagc atcatgggcc agttcgacca tcctaacatc | 2040 |
| attcgcctgg agggtgtggt caccaagagt cggcctgtca tgatcatcac agagttcatg | 2100 |
| gagaatggtg cattggattc tttcctcagg caaaatgacg ggcagttcac cgtgatccag | 2160 |
| cttgtgggta tgctcagggg catcgctgct ggcatgaagt acctggctga gatgaattat | 2220 |
| gtgcatcggg acctggctgc taggaacatt ctggtcaaca gtaacctggt gtgcaaggtg | 2280 |
| tccgactttg gcctctcccg ctacctccag gatgacacct cagatcccac ctacaccagc | 2340 |
| tccttgggag ggaagatccc tgtgagatgg acagctccag aggccatcgc ctaccgcaag | 2400 |
| ttcacttcag ccagcgacgt ttggagctat gggatcgtca tgtgggaagt catgtcattt | 2460 |
| ggagagagac cctattggga tatgtccaac caagatgtca tcaatgccat cgagcaggac | 2520 |
| taccggctgc cccacccat ggactgtcca gctgctctac accagctcat gctggactgt | 2580 |
| tggcagaagg accggaacag ccggccccgg tttgcggaga ttgtcaacac cctagataag | 2640 |
| atgatccgga cccggcaag tctcaagact gtggcaacca tcaccgccgt gccttcccag | 2700 |
| cccctgctcg accgctccat cccagacttc acggccttta ccaccgtgga tgactggctc | 2760 |
| agcgccatca aatggtcca gtacagggac agcttcctca ctgctggctt cacctcccctc | 2820 |
| cagctggtca cccagatgac atcagaagac ctcctgagaa taggcatcac cttggcaggc | 2880 |
| catcagaaga agatcctgaa cagcattcat tctatgaggg tccagataag tcagtcacca | 2940 |
| acggcaatgg catga | 2955 |

<210> SEQ ID NO 22
<211> LENGTH: 3168
<212> TYPE: DNA
<213> ORGANISM: Homo sapiens

<400> SEQUENCE: 22

| | |
|---|---|
| atggctctgc ggaggctggg ggccgcgctg ctgctgctgc cgctgctcgc cgccgtggaa | 60 |
| gaaacgctaa tggactccac tacagcgact gctgagctgg gctggatggt gcatcctcca | 120 |
| tcagggtggg aagaggtgag tggctacgat gagaacatga acacgatccg cacgtaccag | 180 |
| gtgtgcaacg tgtttgagtc aagccagaac aactggctac ggaccaagtt tatccggcgc | 240 |
| cgtggcgccc accgcatcca cgtggagatg aagttttcgg tcgtgactg cagcagcatc | 300 |
| cccagcgtgc ctggctcctg caaggagacc ttcaacctct attactatga ggctgacttt | 360 |
| gactcggcca ccaagacctt ccccaactgg atgagaatc catgggtgaa ggtggatacc | 420 |
| attgcagccg acgagagctt ctcccaggtg acctgggtg ccgcgtcat gaaaatcaac | 480 |
| accgaggtgc ggagcttcgg acctgtgtcc cgcagcggct tctacctggc cttccaggac | 540 |
| tatgcgggct gcatgtccct catcgccgtg cgtgtcttct accgcaagtg ccccgcatc | 600 |
| atccagaatg cgccatctt ccaggaaacc ctgtcggggg ctgagagcac atcgctggtg | 660 |
| gctgcccggg gcagctgcat cgccaatgcg aagaggtgg atgtacccat caagctctac | 720 |
| tgtaacgggg acggcgagtg gctggtgccc atcgggcgct gcatgtgcaa agcaggcttc | 780 |
| gaggccgttg agaatggcac cgtctgccga ggttgtccat ctgggacttt caaggccaac | 840 |
| caaggggatg aggcctgtac ccactgtccc atcaacagcc ggaccacttc tgaaggggcc | 900 |
| accaactgtg tctgccgcaa tggctactac agagcagacc tggaccccct ggacatgccc | 960 |
| tgcacaacca tccctcgc gccccaggct gtgatttcca gtgtcaatga gacctcctc | 1020 |

```
atgctggagt ggacccctcc ccgcgactcc ggaggccgag aggacctcgt ctacaacatc      1080
atctgcaaga gctgtggctc gggccggggt gcctgcaccc gctgcgggga caatgtacag      1140
tacgcaccac gccagctagg cctgaccgag ccacgcattt acatcagtga cctgctggcc      1200
cacacccagt acaccttcga gatccaggct gtgaacggcg ttactgacca gagccccttc      1260
tcgcctcagt tcgcctctgt gaacatcacc accaaccagg cagctccatc ggcagtgtcc      1320
atcatgcatc aggtgagccg caccgtggac agcattaccc tgtcgtggtc ccagccagac      1380
cagcccaatg gcgtgatcct ggactatgag ctgcagtact atgagaagga gctcagtgag      1440
tacaacgcca cagccataaa aagccccacc aacacggtca ccgtgcaggg cctcaaagcc      1500
ggcgccatct atgtcttcca ggtgcgggca cgcaccgtgg caggctacgg cgcctacagc      1560
ggcaagatgt acttccagac catgacagaa gccgagtacc agacaagcat ccaggagaag      1620
ttgccactca tcatcggctc ctcggccgct ggcctggtct tcctcattgc tgtggttgtc      1680
atcgccatcg tgtgtaacag acgggggttt gagcgtgctg actcggagta cacggacaag      1740
ctgcaacact acaccagtgg ccacatgacc ccaggcatga gatctacat cgatcctttc       1800
acctacgagg accccaacga ggcagtgcgg gagtttgcca aggaaattga catctcctgt      1860
gtcaaaattg agcaggtgat cggagcaggg gagtttggcg aggtctgcag tggccacctg      1920
aagctgccag gcaagagaga gatctttgtg gccatcaaga cgctcaagtc gggctacacg      1980
gagaagcagc gccgggactt cctgagcgaa gcctccatca tgggccagtt cgaccatccc      2040
aacgtcatcc acctggaggg tgtcgtgacc aagagcacac tgtgatgat  catcaccgag      2100
ttcatggaga atggctccct ggactccttt ctccggcaaa acgatgggca gttcacagtc      2160
atccagctgg tgggcatgct tcggggcatc gcagctggca tgaagtacct ggcagacatg      2220
aactatgttc accgtgacct ggctgcccgc aacatcctcg tcaacagcaa cctggtctgc      2280
aaggtgtcgg actttgggct ctcacgcttt ctagaggacg ataccctcaga ccccacctac      2340
accagtgccc tgggcggaaa gatccccatc cgctggacag ccccggaagc catccagtac      2400
cggaagttca cctcggccag tgatgtgtgg agctacggca ttgtcatgtg ggaggtgatg      2460
tcctatgggg agcggcccta ctgggacatg accaaccagg atgtaatcaa tgccattgag      2520
caggactatc ggctgccacc gcccatggac tgcccgagcg ccctgcacca actcatgctg      2580
gactgttggc agaaggaccg caaccaccgg cccaagttcg ccaaattgt caacacgcta       2640
gacaagatga tccgcaatcc caacagcctc aaagccatgg cgcccctctc ctctggcatc      2700
aacctgccgc tgctggaccg cacgatcccc gactacacca gctttaacac ggtggacgag      2760
tggctggagg ccatcaagat ggggcagtac aaggagagct cgccaatgc cggcttcacc       2820
tcctttgacg tcgtgtctca gatgatgatg gaggacattc tccgggttgg ggtcactttg      2880
gctggccacc agaaaaaaat cctgaacagt atccaggtga tgcgggcgca gatgaaccag      2940
attcagtctg tggagggcca gccactcgcc aggaggccac gggccacggg aagaaccaag      3000
cggtgccagc cacgagacgt caccaagaaa acatgcaact caaacgacgg aaaaaaaaag      3060
ggaatgggaa aaagaaaac agatcctggg aggggcggg aaatacaagg aatatttttt        3120
aaagaggatt ctcataagga aagcaatgac tgttcttgcg ggggataa                   3168
```

<210> SEQ ID NO 23
<211> LENGTH: 2997
<212> TYPE: DNA
<213> ORGANISM: Homo sapiens

<400> SEQUENCE: 23

```
atggccagag cccgcccgcc gccgccgccg tcgccgccgc cggggcttct gccgctgctc     60
cctccgctgc tgctgctgcc gctgctgctg ctcccgccg gctgccgggc gctggaagag    120
accctcatgg acacaaaatg ggtaacatct gagttggcgt ggacatctca tccagaaagt    180
gggtgggaag aggtgagtgg ctacgatgag ccatgaatc ccatccgcac ataccaggtg    240
tgtaatgtgc gcgagtcaag ccagaacaac tggcttcgca cggggttcat ctggcggcgg    300
gatgtgcagc gggtctacgt ggagctcaag ttcactgtgc gtgactgcaa cagcatcccc    360
aacatccccg gctcctgcaa ggagaccttc aacctcttct actacgaggc tgacagcgat    420
gtggcctcag cctcctcccc cttctggatg gagaacccct acgtgaaagt ggacaccatt    480
gcacccgatg agagcttctc gcggctggat gccggccgtg tcaacaccaa ggtgcgcagc    540
tttgggccac tttccaaggc tggcttctac ctggccttcc aggaccaggg cgcctgcatg    600
tcgctcatct ccgtgcgcgc cttctacaag aagtgtgcat ccaccaccgc aggcttcgca    660
ctcttccccg agaccctcac tggggcggag cccacctcgc tggtcattgc tcctggcacc    720
tgcatcccta cgccgtggga ggtgtcggtg ccactcaagc tctactgcaa cggcgatggg    780
gagtggatgg tgcctgtggg tgcctgcacc tgtgccaccg ccatgagcc agctgccaag    840
gagtcccagt gccgccctg tcccctggg agctacaagg cgaagcaggg agaggggccc    900
tgcctcccat gtcccccaa cagccgtacc acctcccag ccgccagcat ctgcacctgc    960
cacaataact tctaccgtgc agactcggac tctgcggaca gtgcctgtac caccgtgcca   1020
tctccacccc gaggtgtgat ctccaatgtg aatgaaacct cactgatcct cgagtggagt   1080
gagccccggg acctgggtgt ccgggatgac ctcctgtaca atgtcatctg caagaagtgc   1140
catggggctg gaggggcctc agcctgctca cgctgtgatg acaacgtgga gtttgtgcct   1200
cggcagctgg gcctgtcgga gccccgggtc cacaccagcc atctgctggc ccacacgcgc   1260
tacacctttg aggtgcaggc ggtcaacggt gtctcgggca agagccctct gccgcctcgt   1320
tatgcggccg tgaatatcac cacaaaaccag gctgccccgt ctgaagtgcc cacactacgc   1380
ctgcacagca gctcaggcag cagcctcacc ctatcctggg cacccccaga gcggcccaac   1440
ggagtcatcc tggactacga gatgaagtac tttgagaaga gcgagggcat cgcctccaca   1500
gtgaccagcc agatgaactc cgtgcagctg gacgggcttc ggcctgacgc ccgctatgtg   1560
gtccaggtcc gtgcccgcac agtagctggc tatgggcagt acagccgccc tgccgagttt   1620
gagaccacaa gtgagagagg ctctggggcc cagcagctcc aggagcagct tcccctcatc   1680
gtgggctccg ctacagctgg gcttgtcttc gtggtggctg tcgtggtcat cgctatcgtc   1740
tgcctcagga agcagcgaca cggctctgat tcggagtaca cggagaagct gcagcagtac   1800
attgctcctg gaatgaaggt ttatattgac ccttttacct acgaggaccc taatgaggct   1860
gttcgggagt ttgccaagga gatcgacgtg tcctgcgtca agatcgagga ggtgatcgga   1920
gctggggaat tggggaagt gtgccgtggt cgactgaaac agcctggccg ccgagaggtg   1980
tttgtggcca tcaagacgct gaaggtgggc tacaccgaga ggcagcggcg ggacttccta   2040
agcgaggcct ccatcatggg tcagtttgat caccccaata taatccggct cgagggcgtg   2100
gtcaccaaaa gtcggccagt tatgatcctc actgagttca tggaaaactg cgccctggac   2160
tccttcctcc ggctcaacga tgggcagttc acggtcatcc agctggtggg catgttgcgg   2220
ggcattgctg ccggcatgaa gtacctgtcc gagatgaact atgtgcaccg cgacctggct   2280
gctcgcaaca tccttgtcaa cagcaacctg gtctgcaaag tctcagactt tggcctctcc   2340
```

-continued

| | |
|---|---|
| cgcttcctgg aggatgaccc ctccgatcct acctacacca gttccctggg cgggaagatc | 2400 |
| cccatccgct ggactgcccc agaggccata gcctatcgga agttcacttc tgctagtgat | 2460 |
| gtctggagct acggaattgt catgtgggag gtcatgagct atggagagcg accctactgg | 2520 |
| gacatgagca accaggatgt catcaatgcc gtggagcagg attaccggct gccaccaccc | 2580 |
| atggactgtc ccacagcact gcaccagctc atgctggact gctgggtgcg ggaccggaac | 2640 |
| ctcaggccca aattctccca gattgtcaat accctggaca agctcatccg caatgctgcc | 2700 |
| agcctcaagg tcattgccag cgctcagtct ggcatgtcac agcccctcct ggaccgcacg | 2760 |
| gtcccagatt acacaacctt cacgacagtt ggtgattggc tggatgccat caagatgggg | 2820 |
| cggtacaagg agagcttcgt cagtgcgggg tttgcatctt ttgacctggt ggcccagatg | 2880 |
| acggcagaag acctgctccg tattggggtc accctggccg gccaccagaa gaagatcctg | 2940 |
| agcagtatcc aggacatgcg gctgcagatg aaccagacgc tgcctgtgca ggtctga | 2997 |

```
<210> SEQ ID NO 24
<211> LENGTH: 2964
<212> TYPE: DNA
<213> ORGANISM: Homo sapiens

<400> SEQUENCE: 24
```

| | |
|---|---|
| atggagctcc gggtgctgct ctgctgggct tcgttggccg cagctttgga agagaccctg | 60 |
| ctgaacacaa aattggaaac tgctgatctg aagtgggtga cattccctca ggtggacggg | 120 |
| cagtgggagg aactgagcgg cctggatgag gaacagcaca gcgtgcgcac ctacgaagtg | 180 |
| tgtgaagtgc agcgtgcccc gggccaggcc cactggcttc gcacaggttg gtcccacgg | 240 |
| cggggcgccg tccacgtgta cgccacgctg cgcttcacca tgctcgagtg cctgtccctg | 300 |
| cctcgggctg ggcgctcctg caaggagacc ttcaccgtct tctactatga gagcgatgcg | 360 |
| gacacggcca cggccctcac gccagcctgg atggagaacc cctacatcaa ggtggacacg | 420 |
| gtggccgcgg agcatctcac ccggaagcgc cctggggccg aggccaccgg aaggtgaat | 480 |
| gtcaagacgc tgcgtctggg accgctcagc aaggctggct tctacctggc cttccaggac | 540 |
| cagggtgcct gcatggccct gctatccctg cacctcttct acaaaaagtg cgcccagctg | 600 |
| actgtgaacc tgactcgatt cccggagact gtgcctcggg agctggttgt gcccgtggcc | 660 |
| ggtagctgcg tggtggatgc cgtccccgcc cctggcccca gcccagcct ctactgccgt | 720 |
| gaggatggcg agtgggccga acagccggtc acgggctgca gctgtgctcc ggggttcgag | 780 |
| gcagctgagg ggaacaccaa gtgccgagcc tgtgcccagg caccttcaa gcccctgtca | 840 |
| ggagaagggt cctgccagcc atgcccagcc aatagccact ctaacaccat ggatctgcc | 900 |
| gtctgccagt gccgcgtcgg ggacttccgg gcacgcacag accccgggg tgcaccctgc | 960 |
| accaccctc cttcggctcc gcggagcgtg gtttcccgcc tgaacggctc ctccctgcac | 1020 |
| ctggaatgga gtgccccct ggagtctggt ggccgagagg acctcaccta cgccctccgc | 1080 |
| tgccgggagt gccgacccgg aggctcctgt gcgccctgcg ggggagacct gacttttgac | 1140 |
| cccggccccc gggacctggt ggagccctgg gtggtggttc gagggctacg tccggacttc | 1200 |
| acctatacct ttgaggtcac tgcattgaac gggtatcct cctagccac ggggcccgtc | 1260 |
| ccatttgagc ctgtcaatgt caccactgac cgagaggtac ctcctgcagt gtctgacatc | 1320 |
| cgggtgacgc ggtcctcacc cagcagcttg agcctggcct ggctgttcc ccgggcaccc | 1380 |
| agtggggcgt ggctggacta cgaggtcaaa taccatgaga agggcgccga gggtcccagc | 1440 |

-continued

```
agcgtgcggt tcctgaagac gtcagaaaac cgggcagagc tgcggggggct gaagcgggga    1500 gccagctacc tggtgcaggt acgggcgcgc tctgaggccg gctacgggcc cttcggccag    1560
gaacatcaca gccagaccca actggatgag agcgagggct ggcggagca gctggccctg    1620 attgcgggca cggcagtcgt gggtgtggtc ctggtcctgg tggtcattgt ggtcgcagtt    1680
ctctgcctca ggaagcagag caatgggaga gaagcagaat attcggacaa acacggacag    1740
tatctcatcg gacatggtac taaggtctac atcgacccct tcacttatga agaccctaat    1800
gaggctgtga gggaatttgc aaaagagatc gatgtctcct acgtcaagat tgaagaggtg    1860
attggtgcag gtgagtttgg cgaggtgtgc cgggggcggc tcaaggcccc agggaagaag    1920
gagagctgtg tggcaatcaa gaccctgaag ggtggctaca cggagcggca gcggcgtgag    1980
tttctgagcg aggcctccat catgggccag ttcgagcacc ccaatatcat ccgcctggag    2040
ggcgtggtca ccaacagcat gcccgtcatg attctcacag agttcatgga aacggcgcc    2100 ctggactcct tcctgcggct aaacgacgga cagttcacag tcatccagct cgtgggcatg    2160
ctgcggggca tcgcctcggg catgcggtac cttgccgaga tgagctacgt ccaccgagac    2220
ctggctgctc gcaacatcct agtcaacagc aacctcgtct gcaaagtgtc tgactttggc    2280 cttttcccgat tcctggagga gaactcttcc gatcccacct acacgagctc cctgggagga    2340
aagattccca tccgatggac tgccccggag gccattgcct tccggaagtt cacttccgcc    2400
agtgatgcct ggagttacgg gattgtgatg tgggaggtga tgtcatttgg ggagaggccg    2460
tactgggaca tgagcaatca ggacgtgatc aatgccattg aacaggacta ccggctgccc    2520
ccgcccccag actgtcccac ctccctccac cagctcatgc tggactgttg gcagaaagac    2580
cggaatgccc ggccccgctt ccccaggtg gtcagcgccc tggacaagat gatccggaac    2640
cccgccagcc tcaaaatcgt ggcccgggag aatgcggggg cctcacaccc tctcctggac    2700
cagcggcagc tcactactc agcttttggc tctgtgggcg agtggcttcg ggccatcaaa    2760
atgggaagat acgaagcccg tttcgcagcc gctggctttg gctccttcga gctggtcagc    2820
cagatctctg ctgaggacct gctccgaatc ggagtcactc tggcgggaca ccagaagaaa    2880
atcttggcca gtgtccagca catgaagtcc caggccaagc cgggaacccc gggtgggaca    2940
ggaggaccgg ccccgcagta ctga                                          2964
```

<210> SEQ ID NO 25
<211> LENGTH: 1041
<212> TYPE: DNA
<213> ORGANISM: Homo sapiens
<300> PUBLICATION INFORMATION:
<302> TITLE: ephrin-B1
<310> PATENT DOCUMENT NUMBER: NM004429

<400> SEQUENCE: 25

```
atggctcggc ctgggcagcg ttggctcggc aagtggcttg tggcgatggt cgtgtgggcg      60
ctgtgccggc tcgccacacc gctggccaag aacctggagc ccgtatcctg gagctccctc     120
aaccccaagt tcctgagtgg aaggggcttg tgatctatc cgaaaattgg agacaagctg     180
gacatcatct gccccgagc agaagcaggg cggccctatg agtactacaa gctgtacctg     240
gtgcggcctg agcaggcagc tgcctgtagc acagttctcg accccaacgt gttggtcacc     300
tgcaataggc cagagcagga aatacgcttt accatcaagt tccaggagtt cagccccaac     360
tacatgggcc tggagttcaa gaagcaccat gattactaca ttacctcaac atccaatgga     420
agcctggagg ggctggaaaa ccgggagggc ggtgtgtgcc gcacacgcac catgaagatc     480
```

```
atcatgaagg ttgggcaaga tcccaatgct gtgacgcctg agcagctgac taccagcagg      540
cccagcaagg aggcagacaa cactgtcaag atggccacac aggcccctgg tagtcggggc      600
tccctgggtg actctgatgg caagcatgag actgtgaacc aggaagagaa gagtggccca      660
ggtgcaagtg ggggcagcag cggggaccct gatggcttct tcaactccaa ggtggcattg      720
ttcgcggctg tcggtgccgg ttgcgtcatc ttcctgctca tcatcatctt cctgacggtc      780
ctactactga agctacgcaa gcggcaccgc aagcacacac agcagcgggc ggctgccctc      840
tcgctcagta ccctggccag tcccaagggg ggcagtggca cagcgggcac cgagcccagc      900
gacatcatca ttcccttacg gactacagag aacaactact gccccactg tgagaaggtg       960 agtggggact acgggcaccc tgtctacatc gtccaagaga tgccgcccca gagcccggcg     1020
aacatctact acaaggtctg a                                               1041

<210> SEQ ID NO 26
<211> LENGTH: 1002
<212> TYPE: DNA
<213> ORGANISM: Homo sapiens
<300> PUBLICATION INFORMATION:

<400> SEQUENCE: 26
atggctgtga aagggactc cgtgtggaag tactgctggg gtgttttgat ggttttatgc        60
agaactgcga tttccaaatc gatagtttta gagcctatct attggaattc ctcgaactcc      120
aaatttctac ctggacaagg actggtacta tacccacaga taggagacaa attggatatt      180
atttgcccca aagtggactc taaaactgtt ggccagtatg aatattataa agtttatatg      240
gttgataaag accaagcaga cagatgcact attaagaagg aaaatacccc tctcctcaac      300
tgtgccaaac cagaccaaga tatcaaattc accatccaagt ttcaagaatt cagccctaac    360
ctctggggtc tagaatttca gaagaacaaa gattattaca ttatatctac atcaaatggg      420 tcttttggagg gcctggataa ccaggaggga ggggtgtgcc agacaagagc catgaagatc      480
ctcatgaaag ttggacaaga tgcaagttct gctggatcaa ccaggaataa agatccaaca      540
agacgtccag aactagaagc tggtacaaat ggaagaagtt cgacaacaag tcccttgta    600 aaaccaaatc caggttctag cacagacggc aacagcgccg acattcgggg aacaacatc      660 ctcggttccg aagtggcctt atttgcaggg attgcttcag gatgcatcat cttcatcgtc      720
atcatcatca cgctggtggt cctcttgctg aagtaccgga ggagacacag gaagcactcg      780
ccgcagcaca cgaccacgct gtcgctcagc acactggcca cacccaagcg cagcggcaac      840
aacaacggct cagagcccag tgacattatc atcccgctaa ggactgcgga cagcgtcttc      900
tgccctcact acgagaaggt cagcggcgac tacgggcacc cggtgtacat cgtccaggag      960
atgcccccgc agagcccggc gaacatttac tacaaggtct ga                        1002

<210> SEQ ID NO 27
<211> LENGTH: 1023
<212> TYPE: DNA
<213> ORGANISM: Homo sapiens

<400> SEQUENCE: 27
atggggcccc ccattctggg gccggggggc gtgcgagtcg gggccctgct gctgctgggg       60
gttttggggc tggtgtctgg gctcagcctg gagcctgtct actggaactc ggcgaataag      120
aggttccagg cagagggtgg ttatgtgctg taccctcaga tcggggaccg gctagacctg      180
ctctgccccc gggcccggcc tcctggccct cactcctctc ctaattatga gttctacaag      240
```

```
ctgtacctgg taggggggtgc tcagggccgg cgctgtgagg cacccccctgc cccaaacctc     300
cttctcactt gtgatcgccc agacctggat ctccgcttca ccatcaagtt ccaggagtat     360
agccctaatc tctggggcca cgagttccgc tcgcaccacg attactacat cattgccaca     420
tcggatggga cccgggaggg cctggagagc ctgcaggag gtgtgtgcct aaccagaggc     480
atgaaggtgc ttctccgagt gggacaaagt ccccgaggag gggctgtccc ccgaaaacct     540
gtgtctgaaa tgcccatgga aagagaccga ggggcagccc acagcctgga gcctgggaag     600
gagaacctgc caggtgaccc caccagcaat gcaacctccc ggggtgctga aggcccctg     660
ccccctccca gcatgcctgc agtggctggg gcagcagggg ggctggcgct gctcttgctg     720
ggcgtggcag gggctggggg tgccatgtgt tggcggagac ggcgggccaa gccttcggag     780
agtcgccacc ctggtcctgg ctccttcggg aggggagggt ctctgggcct ggggggtgga     840
ggtgggatgg gacctcggga ggctgagcct ggggagctag ggatagctct gcggggtggc     900
ggggctgcag atccccccctt ctgccccccac tatgagaagg tgagtggtga ctatgggcat     960
cctgtgtata tcgtgcagga tgggcccccc cagagccctc caaacatcta ctacaaggta     1020
tga                                                                  1023

<210> SEQ ID NO 28
<211> LENGTH: 3399
<212> TYPE: DNA
<213> ORGANISM: Homo sapiens
<300> PUBLICATION INFORMATION:
<302> TITLE: telomerase reverse transcriptase
<310> PATENT DOCUMENT NUMBER: AF015950

<400> SEQUENCE: 28
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccccctcc ttccgccagg tgtcctgcct gaaggagctg     240
gtggcccgag tgctgcagag gctgtgcgag cgcggcgcga gaacgtgct ggccttcggc     300
ttcgcgctgc tggacgggc ccgcgggggc ccccccgagg ccttcaccac cagcgtgcgc     360
agctacctgc ccaacacggt gaccgacgca ctgcggggga gcggggcgtg ggggctgctg     420
ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcggggggcag tgccagccga agtctgccgt tgcccaagag gcccaggcgt     720
ggcgctgccc ctgagccgga gcggacgccc gttgggcagg gtcctgggc cacccgggc     780
aggacgcgtg gaccgagtga ccgtggtttc tgtgtggtgt cacctgccag acccgccgaa     840
gaagccacct ctttggaggg tgcgctctct ggcacgcgcc actccaccc atccgtgggc     900
cgccagcacc acgcgggccc cccatccaca tcgcggccac cacgtccctg gacacgcct     960
tgtccccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactccccg caggttgccc    1140
cgcctgcccc agcgctactg gcaaatgcgg cccctgtttt tggagctgct tgggaaccac    1200
```

```
gcgcagtgcc cctacggggt gctcctcaag acgcactgcc cgctgcgagc tgcggtcacc   1260
ccagcagccg gtgtctgtgc ccgggagaag ccccagggct ctgtggcggc ccccgaggag   1320
gaggacacag accccgtcg cctggtgcag ctgctccgcc agcacagcag ccctggcag    1380 gtgtacggct tcgtgcgggc ctgcctgcgc cggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc caggggttgg ctgtgttccg gccgcagagc accgtctgcg tgaggagatc   1620
ctggccaagt tcctgcactg gctgatgagt gtgtacgtcg tcgagctgct caggtctttc   1680 tttatgtca cggagaccac gtttcaaaag aacaggctct ttttctaccg gaagagtgtc    1740
tggagcaagt tgcaaagcat tggaatcaga cagcacttga agagggtgca gctgcgggag   1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgccccg gcctcctggg cgcctctgtg   2040
ctgggcctgg acgatatcca cagggcctgg cgcaccttcg tgctgcgtgt gcgggcccag   2100
gacccgccgc ctgagctgta cttgtcaag gtggatgtga cgggcgcgta cgacaccatc   2160
ccccaggaca ggctcacgga ggtcatcgcc agcatcatca accccagaa cacgtactgc   2220 gtgcgtcggt atgccgtggt ccagaaggcc gcccatgggc acgtccgcaa ggccttcaag   2280
agccacgtct ctaccttgac agacctccag ccgtacatgc gacagttcgt ggctcacctg   2340
caggagacca gcccgctgag gatgccgtc gtcatcgagc agagctcctc cctgaatgag   2400
gccagcagtg gcctcttcga cgtcttccta cgcttcatgt gccaccacgc cgtgcgcatc   2460
aggggcaagt cctacgtcca gtgccagggg atcccgcagg gctccatcct ctccacgctg   2520
ctctgcagcc tgtgctacgg cgacatggag aacaagctgt ttgcggggat tcggcgggac   2580
gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attcccctgg tgcggcctgc tgctggatac ccggaccctg   2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgttcct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca ttttcctgc gcgtcatctc tgacacggcc   3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag acagcccag    3300 acgcagctga gtcggaagct cccggggacg acgctgactg ccctggaggc cgcagccaac   3360
ccggcactgc cctcagactt caagaccatc ctggactga                          3399
```

<210> SEQ ID NO 29
<211> LENGTH: 567
<212> TYPE: DNA
<213> ORGANISM: Homo sapiens

```
<300> PUBLICATION INFORMATION:
<302> TITLE: K-ras
<310> PATENT DOCUMENT NUMBER: M54968

<400> SEQUENCE: 29
atgactgaat ataaacttgt ggtagttgga gcttgtggcg taggcaagag tgccttgacg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaacataa agaaaagatg agcaaagatg gtaaaagaa gaaaagaag    540 tcaaagacaa agtgtgtaat tatgtaa                                        567

<210> SEQ ID NO 30
<211> LENGTH: 3840
<212> TYPE: DNA
<213> ORGANISM: Homo sapiens
<300> PUBLICATION INFORMATION:
<302> TITLE: mdr-1
<310> PATENT DOCUMENT NUMBER: AF016535

<400> SEQUENCE: 30
atggatcttg aagggaccg caatggagga gcaaagaaga agaacttttt taaactgaac     60
aataaaagtg aaaagataa gaggaaaag aaaccaactg tcagtgtatt ttcaatgttt    120
cgctattcaa attggcttga caagttgtat atggtggtgg gaactttggc tgccatcatc    180 catgggctg gacttcctct catgatgctg gtgtttggag aaatgacaga tatctttgca    240
aatgcaggaa atttagaaga tctgatgtca aacatcacta atagaagtga tatcaatgat    300
acagggttct tcatgaatct ggaggaagac atgaccaggt atgcctatta ttacagtgga    360
attggtgctg gggtgctggt tgctgcttac attcaggtttc attttggtg cctggcagct    420 ggaagacaaa tacacaaaat tagaaaacag ttttttcatg ctataatgcg acaggagata    480
ggctggtttg atgtgcacga tgttggggag cttaacaccc gacttacaga tgatgtctcc    540
aagattaatg aaggaattgg tgacaaaatt ggaatgttct tcagtcaat ggcaacattt    600 ttcactgggt ttatagtagg atttacacgt ggttggaagc taaccttgt gattttggcc    660 atcagtcctg ttcttggact gtcagctgct gtctgggcaa agatactatc ttcattact    720 gataaagaac tcttagcgta tgcaaaagct ggagcagtag ctgaagaggt cttggcagca    780
attagaactg tgattgcatt tggaggacaa aagaaagaac ttgaaggta caacaaaaat    840 ttagaagaag ctaaaagaat tgggataaag aaagctatta cagccaatat ttctataggt    900
gctgctttcc tgctgatcta tgcatcttat gctctggcct tctggtatgg gaccaccttg    960
gtcctctcag gggaatattc tattggacaa gtactcactg tatttttctgt attaattggg   1020 gcttttagtg ttggacaggc atctccaagc attgaagcat tgcaaatgc aagaggagca   1080 gcttatgaaa tcttcaagat aattgataat aagccaagta ttgacagcta ttcgaagagt   1140
gggcacaaac cagataatat taagggaaat ttggaattca gaaatgttca cttcagttac   1200
ccatctcgaa aagaagttaa gatcttgaag ggtctgaacc tgaaggtgca gagtgggcag   1260
```

```
acggtggccc tggttggaaa cagtggctgt gggaagagca caacagtcca gctgatgcag    1320
aggctctatg accccacaga ggggatggtc agtgttgatg acaggatat taggaccata     1380 aatgtaaggt ttctacggga aatcattggt gtggtgagtc aggaacctgt attgtttgcc    1440
accacgatag ctgaaaacat tcgctatggc cgtgaaaatg tcaccatgga tgagattgag   1500
aaagctgtca aggaagccaa tgcctatgac tttatcatga aactgcctca taaatttgac   1560
accctggttg gagagagagg ggcccagttg agtggtgggc agaagcagag gatcgccatt   1620
gcacgtgccc tggttcgcaa ccccaagatc ctcctgctgg atgaggccac gtcagccttg   1680
gacacagaaa gcgaagcagt ggttcaggtg gctctgata aggccagaaa aggtcggacc     1740
accattgtga tagctcatcg tttgtctaca gttcgtaatg ctgacgtcat cgctggtttc   1800
gatgatggag tcattgtgga gaaaggaaat catgatgaac tcatgaaaga gaaaggcatt  1860
tacttcaaac ttgtcacaat gcagacagca ggaaatgaag ttgaattaga aaatgcagct  1920
gatgaatcca aaagtgaaat tgatgccttg gaaatgtctt caaatgattc aagatccagt  1980
ctaataagaa aaagatcaac tcgtaggagt gtccgtggat cacaagccca agacagaaag  2040
cttagtacca aagaggctct ggatgaaagt atacctccag tttccttttg gaggattatg   2100
aagctaaatt taactgaatg gccttatttt gttgttggtg tattttgtgc cattataaat  2160
ggaggcctgc aaccagcatt tgcaataata ttttcaaaga ttataggggt tttacaaga   2220 attgatgatc ctgaaacaaa acgacagaat agtaacttgt tttcactatt gtttctagcc  2280
cttggaatta tttctttat tacatttttc cttcagggtt tcacatttgg caaagctgga  2340
gagatcctca ccaagcggct ccgatacatg gttttccgat ccatgctcag acaggatgtg  2400
agttggtttg atgaccctaa aaacaccact ggagcattga ctaccaggct cgccaatgat  2460
gctgctcaag ttaaagggc tataggttcc aggcttgctg taattaccca gaatatagca   2520
aatcttggga caggaataat tatatccttc atctatggtt ggcaactaac actgttactc  2580
ttagcaattg tacccatcat tgcaatagca ggagttgttg aaatgaaaat gttgtctgga  2640
caagcactga aagataagaa agaactagaa ggtgctggga agatcgctac tgaagcaata  2700
gaaaacttcc gaaccgttgt ttctttgact caggagcaga gtttgaaca tatgtatgct    2760 cagagtttgc aggtaccata cagaaaactct ttgaggaaag cacacatctt tggaattaca   2820 tttttccttca cccaggcaat gatgtatttt tcctatgctg gatgtttccg gtttggagcc   2880
tacttggtgg cacataaact catgagcttt gaggatgttc tgttagtatt ttcagctgtt   2940
gtctttggtg ccatggccgt ggggcaagtc agttcatttg ctcctgacta tgccaaagcc   3000
aaaatatcag cagcccacat catcatgatc attgaaaaaa ccccttttgat tgacagctac   3060 agcacggaag gcctaatgcc gaacacattg gaaggaaatg tcacatttgg tgaagttgta  3120
ttcaactatc ccacccgacc ggacatccca gtgcttcagg gactgagcct ggaggtgaag   3180
aagggccaga cgctggctct ggtgggcagc agtggctgtg ggaagagcac agtggtccag   3240
ctcctggagc ggttctacga ccccttggca gggaaagtgc tgcttgatgg caaagaaata   3300
aagcgactga atgttcagtg gctccgagca cacctgggca tcgtgtccca ggagcccatc   3360
ctgtttgact gcagcattgc tgagaacatt gcctatggag acaacagccg ggtggtgtca  3420
caggaagaga ttgtgagggc agcaaggag gccaacatac atgccttcat cgagtcactg   3480
cctaataaat atagcactaa agtaggagac aaaggaactc agctctctgg tggccagaaa  3540
caacgcattg ccatagctcg tgcccttgtt agacagcctc atatttttgct tttggatgaa  3600 gccacgtcag ctctggatac agaaaagtgaa aaggttgtcc aagaagccct ggacaaagcc   3660
```

-continued

| | |
|---|---|
| agagaaggcc gcacctgcat tgtgattgct caccgcctgt ccaccatcca gaatgcagac | 3720 |
| ttaatagtgg tgtttcagaa tggcagagtc aaggagcatg gcacgcatca gcagctgctg | 3780 |
| gcacagaaag gcatctattt ttcaatggtc agtgtccagg ctggaacaaa gcgccagtga | 3840 |

<210> SEQ ID NO 31
<211> LENGTH: 1318
<212> TYPE: DNA
<213> ORGANISM: Homo sapiens
<300> PUBLICATION INFORMATION:
<302> TITLE: UPAR (urokinase-type plasminogen activator receptor)
<310> PATENT DOCUMENT NUMBER: XM009232

<400> SEQUENCE: 31

| | |
|---|---|
| atgggtcacc cgccgctgct gccgctgctg ctgctgctcc acacctgcgt cccagcctct | 60 |
| tggggcctgc ggtgcatgca gtgtaagacc aacggggatt gccgtgtgga agagtgcgcc | 120 |
| ctgggacagg acctctgcag gaccacgatc gtgcgcttgt gggaagaagg agaagagctg | 180 |
| gagctggtgg agaaaagctg tacccactca gagaagacca caggaccct gagctatcgg | 240 |
| actggcttga agatcaccag ccttaccgag gttgtgtgtg gttagactt gtgcaaccag | 300 |
| ggcaactctg ccgggctgt cacctattcc cgaagccgtt acctcgaatg catttcctgt | 360 |
| ggctcatcag acatgagctg tgagagggc cggcaccaga gcctgcagtg ccgcagccct | 420 |
| gaagaacagt gcctggatgt ggtgacccac tggatccagg aaggtgaaga agggcgtcca | 480 |
| aaggatgacc gccacctccg tggctgtggc taccttcccg gctgcccggg ctccaatggt | 540 |
| ttccacaaca cgacaccctt ccacttcctg aaatgctgca caccaccaa tgcaacgag | 600 |
| ggcccaatcc tggagcttga aaatctgccg cagaatggcc gccagtgtta cagctgcaag | 660 |
| gggaacagca cccatggatg ctcctctgaa gagactttcc tcattgactg ccgaggcccc | 720 |
| atgaatcaat gtctggtagc caccggcact cacgaaccga aaaccaaag ctatatggta | 780 |
| agaggctgtg caaccgcctc aatgtgccaa catgcccacc tgggtgacgc cttcagcatg | 840 |
| aaccacattg atgtctcctg ctgtactaaa agtggctgta accacccaga cctggatgtc | 900 |
| cagtaccgca gtgggctgc tcctcagcct ggccctgccc atctcagcct caccatcacc | 960 |
| ctgctaatga ctgccagact gtggggaggc actctcctct ggacctaaac ctgaaatccc | 1020 |
| cctctctgcc ctggctggat ccgggggacc ccttgccct tccctcggct cccagcccta | 1080 |
| cagacttgct gtgtgacctc aggccagtgt gccgacctct ctgggcctca gttttcccag | 1140 |
| ctatgaaaac agctatctca caaagttgtg tgaagcagaa gagaaaagct ggaggaaggc | 1200 |
| cgtgggccaa tgggagagct cttgttatta ttaatattgt tgccgctgtt gtgttgttgt | 1260 |
| tattaattaa tattcatatt atttatttta tacttacata agatttgt accagtgg | 1318 |

<210> SEQ ID NO 32
<211> LENGTH: 636
<212> TYPE: DNA
<213> ORGANISM: Homo sapiens
<300> PUBLICATION INFORMATION:
<302> TITLE: Bak
<310> PATENT DOCUMENT NUMBER: U16811

<400> SEQUENCE: 32

| | |
|---|---|
| atggcttcgg ggcaaggccc aggtcctccc aggcaggagt gcggagagcc tgccctgccc | 60 |
| tctgcttctg aggagcaggt agcccaggac acagaggagg ttttccgcag ctacgttttt | 120 |
| taccgccatc agcaggaaca ggaggctgaa ggggtggctg cccctgccga cccagagatg | 180 |

```
gtcaccttac ctctgcaacc tagcagcacc atggggcagg tgggacggca gctcgccatc    240
atcggggacg acatcaaccg acgctatgac tcagagttcc agaccatgtt gcagcacctg    300
cagcccacgg cagagaatgc ctatgagtac ttcaccaaga ttgccaccag cctgtttgag    360
agtggcatca attggggccg tgtggtggct cttctgggct tcggctaccg tctggcccta    420
cacgtctacc agcatggcct gactggcttc ctaggccagg tgacccgctt cgtggtcgac    480
ttcatgctgc atcactgcat tgcccggtgg attgcacaga ggggtggctg ggtggcagcc    540
ctgaacttgg gcaatggtcc catcctgaac gtgctggtgg ttctgggtgt ggttctgttg    600
ggccagtttg tggtacgaag attcttcaaa tcatga                              636

<210> SEQ ID NO 33
<211> LENGTH: 579
<212> TYPE: DNA
<213> ORGANISM: Homo sapiens
<300> PUBLICATION INFORMATION:
<302> TITLE: Bax alpha
<310> PATENT DOCUMENT NUMBER: L22473

<400> SEQUENCE: 33
atggacgggt ccggggagca gcccagaggc ggggggccca ccagctctga gcagatcatg     60
aagacagggg ccttttttgct tcagggtttc atccaggatc gagcagggcg aatggggggg   120
gaggcacccg agctggccct ggacccggtg cctcaggatg cgtccaccaa gaagctgagc    180
gagtgtctca gcgcatcgg ggacgaactg gacagtaaca tggagctgca gaggatgatt     240
gccgccgtgg acacagactc cccccgagag gtcttttttcc gagtggcagc tgacatgttt   300
tctgacggca acttcaactg gggccgggtt gtcgccccttt tctactttgc cagcaaactg   360
gtgctcaagg ccctgtgcac caaggtgccg gaactgatca gaaccatcat gggctggaca    420
ttggacttcc tccgggagcg gctgttgggc tggatccaag accagggtgg ttgggacggc    480
ctcctctcct actttgggac gcccacgtgg cagaccgtga ccatctttgt ggcgggagtg    540
ctcaccgcct cgctcaccat ctggaagaag atgggctga                           579

<210> SEQ ID NO 34
<211> LENGTH: 657
<212> TYPE: DNA
<213> ORGANISM: Homo sapiens
<300> PUBLICATION INFORMATION:
<302> TITLE: Bax beta
<310> PATENT DOCUMENT NUMBER: L22474

<400> SEQUENCE: 34
atggacgggt ccggggagca gcccagaggc ggggggccca ccagctctga gcagatcatg     60
aagacagggg ccttttttgct tcagggtttc atccaggatc gagcagggcg aatggggggg   120
gaggcacccg agctggccct ggacccggtg cctcaggatg cgtccaccaa gaagctgagc    180
gagtgtctca gcgcatcgg ggacgaactg gacagtaaca tggagctgca gaggatgatt     240
gccgccgtgg acacagactc cccccgagag gtcttttttcc gagtggcagc tgacatgttt   300
tctgacggca acttcaactg gggccgggtt gtcgccccttt tctactttgc cagcaaactg   360
gtgctcaagg ccctgtgcac caaggtgccg gaactgatca gaaccatcat gggctggaca    420
ttggacttcc tccgggagcg gctgttgggc tggatccaag accagggtgg ttgggtgaga    480
ctcctcaagc ctcctcaccc ccaccaccgc gccctcacca ccgccctgc cccaccgtcc     540 ctgcccccg ccactcctct gggacccctgg gccttctgga gcaggtcaca gtggtgccct    600
ctccccatct tcagatcatc agatgtggtc tataatgcgt tttccttacg tgtctga       657
```

<210> SEQ ID NO 35
<211> LENGTH: 432
<212> TYPE: DNA
<213> ORGANISM: Homo sapiens
<300> PUBLICATION INFORMATION:
<302> TITLE: Bax delta
<310> PATENT DOCUMENT NUMBER: U19599

<400> SEQUENCE: 35

```
atggacgggt ccggggagca gcccagaggc gggggggccca ccagctctga gcagatcatg     60
aagacagggg cccttttgct tcaggggatg attgccgccg tggacacaga ctcccccga     120
gaggtctttt tccgagtggc agctgacatg ttttctgacg gcaacttcaa ctggggccgg     180
gttgtcgccc ttttctactt tgccagcaaa ctggtgctca aggccctgtg caccaaggtg     240
ccggaactga tcagaaccat catgggctgg acattggact tcctccggga gcggctgttg     300
ggctggatcc aagaccaggg tggttgggac ggcctcctct cctactttgg gacgcccacg     360
tggcagaccg tgaccatctt tgtggcggga gtgctcaccg cctcgctcac catctggaag     420
aagatgggct ga                                                          432
```

<210> SEQ ID NO 36
<211> LENGTH: 495
<212> TYPE: DNA
<213> ORGANISM: Homo sapiens
<300> PUBLICATION INFORMATION:
<302> TITLE: Bax epsolin
<310> PATENT DOCUMENT NUMBER: AF007826

<400> SEQUENCE: 36

```
atggacgggt ccggggagca gcccagaggc gggggggccca ccagctctga gcagatcatg     60
aagacagggg cccttttgct tcagggtttc atccaggatc gagcagggcg aatggggggg     120
gaggcacccg agctggccct ggacccggtg cctcaggatg cgtccaccaa gaagctgagc     180
gagtgtctca gcgcatcgg ggacgaactg acagtaaca tggagctgca gaggatgatt     240
gccgccgtgg acacagactc ccccgagag gtcttttttcc gagtggcagc tgacatgttt     300
tctgacggca acttcaactg gggccgggtt gtcgcccttt tctactttgc cagcaaactg     360
gtgctcaagg ctggcgtgaa atggcgtgat ctgggctcac tgcaacctct gcctcctggg     420
ttcaagcgat tcacctgcct cagcatccca aggagctggg attacaggcc ctgtgcacca     480
aggtgccgga actga                                                       495
```

<210> SEQ ID NO 37
<211> LENGTH: 582
<212> TYPE: DNA
<213> ORGANISM: Homo sapiens
<300> PUBLICATION INFORMATION:
<302> TITLE: bcl-w
<310> PATENT DOCUMENT NUMBER: U59747

<400> SEQUENCE: 37

```
atggcgaccc cagcctcggc cccagacaca cgggctctgg tggcagactt tgtaggttat     60
aagctgaggc agaagggtta tgtctgtgga gctggccccg gggagggccc agcagctgac     120
ccgctgcacc aagccatgcg ggcagctgga gatgagttcg agaccgctt ccggcgcacc     180
ttctctgatc tggcggctca gctgcatgtg accccaggct cagcccagca acgcttcacc     240
caggtctccg acgaactttt tcaagggggc cccaactggg gccgcttgt agccttcttt     300
gtctttgggg ctgcactgtg tgctgagagt gtcaacaagg agatggaacc actggtggga     360
```

```
caagtgcagg agtggatggt ggcctacctg gagacgcggc tggctgactg gatccacagc      420
agtgggggct gggcggagtt cacagctcta tacggggacg gggccctgga ggaggcgcgg      480
cgtctgcggg aggggaactg ggcatcagtg aggacagtgc tgacggggc cgtggcactg       540 ggggccctgg taactgtagg ggccttttt gctagcaagt ga                         582
```

<210> SEQ ID NO 38
<211> LENGTH: 2481
<212> TYPE: DNA
<213> ORGANISM: Homo sapiens
<300> PUBLICATION INFORMATION:
<302> TITLE: HIF-alpha
<310> PATENT DOCUMENT NUMBER: U22431

<400> SEQUENCE: 38

```
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca tgaattgc ttttatttga aagccttgga tggttttgtt      300
atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca acagtaacca acctcagtgt gggtataaga accacctat gacctgcttg     660 gtgctgattt gtgaacccat tcctcaccca tcaaatattg aaattccttt agatagcaag     720
actttcctca gtcgacacag cctggatatg aaattttctt attgtgatga agaattacc     780 gaattgatgg gatatgagcc agaagaactt ttaggccgct caatttatga atattatcat     840
gctttggact ctgatcatct gaccaaaact catcatgata tgtttactaa aggacaagtc     900
accacaggac agtacaggat gcttgccaaa agaggtggat atgtctgggt tgaaactcaa     960
gcaactgtca tatataacac caagaattct caaccacagt gcattgtatg tgtgaattac    1020
gttgtgagtg gtattattca gcacgacttg atttttctccc ttcaacaaac agaatgtgtc    1080
cttaaaccgg ttgaatcttc agatatgaaa atgactcagc tattccacca agttgaatca    1140
gaagatacaa gtagcctctt tgacaaactt aagaaggaac ctgatgcttt aactttgctg    1200
gccccagccg ctggagacac aatcatatct ttagattttg gcagcaacga cacagaaact    1260
gatgaccagc aacttgagga agtaccatta tataatgatg taatgctccc ctcacccaac    1320
gaaaaattac agaatataaa tttggcaatg tctccattac ccaccgctga acgccaaag    1380 ccacttcgaa gtagtgctga ccctgcactc aatcaagaag ttgcattaaa attagaacca    1440
aatccagagt cactggaact ttcttttacc atgccccaga ttcaggatca gacacctagt    1500
ccttccgatg gaagcactag acaaagttca cctgagccta atagtccag tgaatattgt    1560 ttttatgtgg atagtgatat ggtcaatgaa ttcaagttgg aattggtaga aaacttttt    1620 gctgaagaca cagaagcaaa gaacccattt tctactcagg acacagattt agacttggag    1680
atgttagctc cctatatccc aatggatgat gacttccagt acgttccttc gatcagttg     1740 tcaccattag aaagcagttc cgcaagccct gaaagcgcaa gtcctcaaag cacagttaca    1800
```

```
gtattccagc agactcaaat acaagaacct actgctaatg ccaccactac cactgccacc    1860
actgatgaat taaaaacagt gacaaaagac cgtatggaag acattaaaat attgattgca    1920
tctccatctc ctaccacat acataaagaa actactagtg ccacatcatc accatataga     1980
gatactcaaa gtcggacagc ctcaccaaac agagcaggaa aaggagtcat agaacagaca    2040 gaaaatctc atccaagaag ccctaacgtg ttatctgtcg cttgagtca aagaactaca     2100 gttcctgagg aagaactaaa tccaaagata ctagctttgc agaatgctca gagaaagcga    2160
aaaatggaac atgatggttc acttttcaa gcagtaggaa ttggaacatt attacagcag     2220
ccagacgatc atgcagctac tacatcactt tcttggaaac gtgtaaaagg atgcaaatct    2280
agtgaacaga atgaatgga gcaaaagaca attattttaa taccctctga tttagcatgt     2340
agactgctgg ggcaatcaat ggatgaaagt ggattaccac agctgaccag ttatgattgt    2400
gaagttaatg ctcctataca aggcagcaga aacctactgc agggtgaaga attactcaga    2460
gctttggatc aagttaactg a                                              2481
```

<210> SEQ ID NO 39
<211> LENGTH: 481
<212> TYPE: DNA
<213> ORGANISM: Homo sapiens
<300> PUBLICATION INFORMATION:
<302> TITLE: ID1
<310> PATENT DOCUMENT NUMBER: X77956

<400> SEQUENCE: 39

```
atgaaagtcg ccagtggcag caccgccacc gccgccgcgg gccccagctg cgcgctgaag    60
gccggcaaga cagcgagcgg tgcgggcgag gtggtgcgct gtctgtctga gcagagcgtg    120
gccatctcgc gctgccgggg cgccggggcg cgcctgcctg ccctgctgga cgagcagcag    180
gtaaacgtgc tgctctacga catgaacggc tgttactcac gcctcaagga gctggtgccc    240
accctgcccc agaaccgcaa ggtgagcaag gtggagattc tccagcacgt catcgactac    300
atcagggacc ttcagttgga gctgaactcg gaatccgaag ttgggacccc cggggggccga   360 gggctgccgg tccgggctcc gctcagcacc ctcaacggcg agatcagcgc cctgacggcc    420
gaggcggcat gcgttcctgc ggacgatcgc atcttgtgtc gctgaatggt gaaaaaaaaa    480
a                                                                    481
```

<210> SEQ ID NO 40
<211> LENGTH: 110
<212> TYPE: DNA
<213> ORGANISM: Homo sapiens
<300> PUBLICATION INFORMATION:
<302> TITLE: ID2B
<310> PATENT DOCUMENT NUMBER: M96843

<400> SEQUENCE: 40

```
tgaaagcctt cagtcccgtg aggtccatta ggaaaaacag cctgttggac caccgcctgg    60
gcatctccca gagcaaaacc ccggtggatg acctgatgag cctgctgtaa                110
```

<210> SEQ ID NO 41
<211> LENGTH: 486
<212> TYPE: DNA
<213> ORGANISM: Homo sapiens
<300> PUBLICATION INFORMATION:
<302> TITLE: ID4
<310> PATENT DOCUMENT NUMBER: Y07958

<400> SEQUENCE: 41

```
atgaaggcgg tgagcccggt gcgcccctcg ggccgcaagg cgccgtcggg ctgcggcggc    60 gggagctgg cgctgcgctg cctggccgag cacggccaca gctgggtgg ctccgcagcc   120 gcggcggcg cggcggcggc agcgcgctgt aaggcggccg aggcggcggc cgacgagccg   180
gcgctgtgcc tgcagtgcga tatgaacgac tgctatagcc gcctgcggag gctggtgccc   240
accatcccgc caacaagaa agtcagcaaa gtggagatcc tgcagcacgt tatcgactac   300
atcctggacc tgcagctggc gctggagacg caccccggcc tgctgaggca gccaccaccg   360
cccgcgccgc cacaccaccc ggccgggacc tgtccagccg cgccgccgcg acccccgctc   420
actgcgctca acaccgaccc ggccggcgcg gtgaacaagc agggcgacag cattctgtgc   480
cgctga                                                              486

<210> SEQ ID NO 42
<211> LENGTH: 462
<212> TYPE: DNA
<213> ORGANISM: Homo sapiens
<300> PUBLICATION INFORMATION:
<302> TITLE: IGF1
<310> PATENT DOCUMENT NUMBER: NM000618

<400> SEQUENCE: 42
atgggaaaaa tcagcagtct tccaacccaa ttatttaagt gctgcttttg tgatttcttg    60
aaggtgaaga tgcacaccat gtcctcctcg catctcttct acctggcgct gtgcctgctc   120
accttcacca gctctgccac ggctggaccg gagacgctct gcggggctga gctggtggat   180
gctcttcagt tcgtgtgtgg agacaggggc ttttatttca caagcccac agggtatggc   240 tccagcagtc ggagggcgcc tcagacaggc atcgtggatg agtgctgctt ccggagctgt   300
gatctaagga ggctggagat gtattgcgca ccctcaagc ctgccaagtc agctcgctct   360
gtccgtgccc agcgccacac cgacatgccc aagacccaga aggaagtaca tttgaagaac   420
gcaagtagag ggagtgcagg aaacaagaac tacaggatgt ag                      462

<210> SEQ ID NO 43
<211> LENGTH: 591
<212> TYPE: DNA
<213> ORGANISM: Homo sapiens
<300> PUBLICATION INFORMATION:
<302> TITLE: PDGFA
<310> PATENT DOCUMENT NUMBER: NM002607

<400> SEQUENCE: 43
atgaggacct ggcttgcct gctgctcctc ggctgcggat acctcgccca tgttctggcc    60
gaggaagccg agatccccg cgaggtgatc gagaggctgg cccgcagtca gatccacagc   120
atccgggacc tccagcgact cctggagata gactccgtag ggagtgagga ttctttggac   180
accagcctga gagctcacgg ggtccacgcc actaagcatg tgcccgagaa gcggcccctg   240
cccattcgga ggaagagaag catcgaggaa gctgtccccg ctgtctgcaa gaccaggacg   300
gtcatttacg agattcctcg gagtcaggtc gaccccacgt ccgccaactt cctgatctgg   360 ccccccgtgcg tggaggtgaa acgctgcacc ggctgctgca cacgagcag tgtcaagtgc   420 cagccctccc cgcgtccacca ccgcagcgtc aaggtggcca aggtggaata cgtcaggaag   480
aagccaaaat taaaagaagt ccaggtgagg ttagaggagc atttggagtg cgcctgcgcg   540
accacaagcc tgaatccgga ttatcgggaa gaggacacgg atgtgaggtg a             591

<210> SEQ ID NO 44
```

-continued

```
<211> LENGTH: 528
<212> TYPE: DNA
<213> ORGANISM: Homo sapiens
<300> PUBLICATION INFORMATION:
<302> TITLE: PDGFRA
<310> PATENT DOCUMENT NUMBER: XM003568

<400> SEQUENCE: 44
atggccaagc ctgaccacgc taccagtgaa gtctacgaga tcatggtgaa atgctggaac      60
agtgagccgg agaagagacc ctccttttac cacctgagtg agattgtgga gaatctgctg     120
cctggacaat ataaaaagag ttatgaaaaa attcacctgg acttcctgaa gagtgaccat     180
cctgctgtgg cacgcatgcg tgtggactca gacaatgcat acattggtgt cacctacaaa     240
aacgaggaag acaagctgaa ggactgggag ggtggtctgg atgagcagag actgagcgct     300
gacagtggct acatcattcc tctgcctgac attgaccctg tccctgagga ggaggacctg     360
ggcaagagga cagacacag ctcgcagacc tctgaagaga gtgccattga cgggttcc      420 agcagttcca ccttcatcaa gagagaggac gagaccattg aagacatcga catgatggat     480
gacatcggca tagactcttc agacctggtg gaagacagct cctgtaa                   528

<210> SEQ ID NO 45
<211> LENGTH: 1911
<212> TYPE: DNA
<213> ORGANISM: Homo sapiens
<300> PUBLICATION INFORMATION:
<302> TITLE: PDGFRB
<310> PATENT DOCUMENT NUMBER: XM003790

<400> SEQUENCE: 45
atgcggcttc cgggtgcgat gccagctctg gccctcaaag gcgagctgct gttgctgtct      60
ctcctgttac ttctggaacc acagatctct caggggcctgg tcgtcacacc cccggggcca    120
gagcttgtcc tcaatgtctc cagcaccttc gttctgacct gctcgggttc agctccggtg    180
gtgtgggaac ggatgtccca ggagccccca caggaaatgg ccaaggccca ggatggcacc    240
ttctccagcg tgctcacact gaccaacctc actgggctag acacgggaga atacttttgc    300
acccacaatg actcccgtgg actggagacc gatgagcgga acggctcta catctttgtg    360 ccagatccca ccgtgggctt cctccctaat gatgccgagg aactattcat ctttctcacg    420
gaaataactg agatcaccat tccatgccga gtaacagacc cacagctggt ggtgacactg    480
cacgagaaga aggggacgt tgcactgcct gtccctatg atcaccaacg tggcttttct    540 ggtatcttg aggacagaag ctacatctgc aaaaccacca ttggggacag ggaggtggat    600
tctgatgcct actatgtcta cagactccag gtgtcatcca tcaacgtctc tgtgaacgca    660
gtgcagactg tggtccgcca gggtgagaac atcacccctca tgtgcattgt gatcgggaat    720
gaggtggtca acttcgagtg gacataccc cgcaaagaaa gtgggcggct ggtggagccg    780
gtgactgact tcctcttgga tatgccttac cacatccgct ccatcctgca catccccagt    840
gccgagttag aagactcggg gacctacacc tgcaatgtga cggagagtgt gaatgaccat    900
caggatgaaa aggccatcaa catcaccgtg gttgagagcg ctacgtgcg gctcctggga    960 gaggtgggca cactacaatt tgctgagctg catcggagcc ggacactgca ggtagtgttc   1020
gaggcctacc caccgcccac tgtcctgtgg ttcaaagaca accgcaccct gggcgactcc   1080
agcgctggcg aaatcgccct gtccacgcgc aacgtgtcgg agaccgggta tgtgtcagag   1140
ctgacactgg ttcgcgtgaa ggtggcagag ctggccact acaccatgcg ggccttccat   1200
gaggatgctg aggtccagct ctccttccag ctacagatca atgtccctgt ccgagtgctg   1260
```

-continued

```
gagctaagtg agagccaccc tgacagtggg gaacagacag tccgctgtcg tggccggggc      1320
atgccccagc cgaacatcat ctggtctgcc tgcagagacc tcaaaaggtg tccacgtgag      1380
ctgccgccca cgctgctggg aacagttcc  gaagaggaga gccagctgga gactaacgtg      1440
acgtactggg aggaggagca ggagtttgag gtggtgagca cactgcgtct gcagcacgtg      1500
gatcggccac tgtcggtgcg ctgcacgctg cgcaacgctg tgggccagga cacgcaggag      1560
gtcatcgtgg tgccacactc cttgcccttt aaggtggtgg tgatctcagc catcctggcc      1620
ctggtggtgc tcaccatcat ctcccttatc atcctcatca tgctttggca gaagaagcca      1680
cgttacgaga tccgatggaa ggtgattgag tctgtgagct ctgacggcca tgagtacatc      1740
tacgtggacc ccatgcagct gcccatgac  tccacgtggg agctgccgcg ggaccagctt      1800
gtgctgggac gcaccctcgg ctctggggcc tttgggcagg tggtggaggc cacggttcat      1860
ggcctgagcc attttcaagc cccaatgaaa gtggccgtca aaatgctta a               1911
```

<210> SEQ ID NO 46
<211> LENGTH: 1176
<212> TYPE: DNA
<213> ORGANISM: Homo sapiens
<300> PUBLICATION INFORMATION:
<302> TITLE: TGFbeta1
<310> PATENT DOCUMENT NUMBER: NM000660

<400> SEQUENCE: 46

```
atgccgccct ccgggctgcg gctgctgccg ctgctgctac cgctgctgtg gctactggtg       60
ctgacgcctg gccgccggc  cgcgggacta tccacctgca agactatcga catggagctg      120
gtgaagcgga agcgcatcga ggccatccgc ggccagatcc tgtccaagct gcggctcgcc      180
agccccccga gccaggggga ggtgccgccc ggcccgctgc ccgaggccgt gctcgccctg      240
tacaacagca cccgcgaccg ggtggccggg gagagtgcag aaccggagcc cgagcctgag      300
gccgactact acgccaagga ggtcacccgc gtgctaatgg tggaaaccca caacgaaatc      360
tatgacaagt tcaagcagag tacacacagc atatatatgt tcttcaacac atcagagctc      420
cgagaagcgg tacctgaacc cgtgttgctc tcccgggcag agctgcgtct gctgaggagg      480
ctcaagttaa aagtggagca gcacgtggag ctgtaccaga atacagcaa  caattcctgg      540 cgatacctca gcaaccggct gctggcaccc agcgactcgc cagagtggtt atcttttgat      600
gtcaccggag ttgtgcggca gtggttgagc cgtggagggg aaattgaggg ctttcgcctt      660
agcgcccact gctcctgtga cagcagggat aacacactgc aagtggacat caacgggttc      720
actaccggcc gccgaggtga cctggccacc attcatggca tgaaccggcc tttcctgctt      780
ctcatggcca ccccgctgga gagggcccag catctgcaaa gctcccggca ccgccgagcc      840
ctggacacca actattgctt cagctccacg gagaagaact gctgcgtgcg gcagctgtac      900
attgacttcc gcaaggacct cggctggaag tggatccacg agcccaaggg ctaccatgcc      960
aacttctgcc tcgggccctg cccctacatt tggagcctgg acacgcagta cagcaaggtc     1020
ctggccctgt acaaccagca taacccgggc gcctcggcgg cgccgtgctg cgtgccgcag     1080
gcgctggagc cgctgcccat cgtgtactac gtgggccgca agcccaaggt ggagcagctg     1140
tccaacatga tcgtgcgctc ctgcaagtgc agctga                               1176
```

<210> SEQ ID NO 47
<211> LENGTH: 1245
<212> TYPE: DNA
<213> ORGANISM: Homo sapiens

```
<300> PUBLICATION INFORMATION:
<302> TITLE: TGFbeta2
<310> PATENT DOCUMENT NUMBER: NM003238

<400> SEQUENCE: 47
atgcactact gtgtgctgag cgcttttctg atcctgcatc tggtcacggt cgcgctcagc      60
ctgtctacct gcagcacact cgatatggac cagttcatgc gcaagaggat cgaggcgatc     120
cgcgggcaga tcctgagcaa gctgaagctc accagtcccc cagaagacta tcctgagccc     180
gaggaagtcc ccccggaggt gatttccatc tacaacagca ccagggactt gctccaggag     240
aaggcgagcc ggagggcggc cgcctgcgag cgcgagagga cgacgaaga gtactacgcc      300 aaggaggttt acaaaataga catgccgccc ttcttccccc tccgaaaatgc atcccgccc    360 actttctaca gacccctactt cagaattgtt cgatttgacg tctcagcaat ggagaagaat     420
gcttccaatt tggtgaaagc agagttcaga gtctttcgtt tgcagaaccc aaaagccaga     480
gtgcctgaac aacggattga gctatatcag attctcaagt ccaaagattt aacatctcca     540
acccagcgct acatcgacag caaagttgtg aaaacaagag cagaaggcga atggctctcc     600
ttcgatgtaa ctgatgctgt tcatgaatgg cttcaccata agacaggaa cctgggattt      660 aaaataagct acactgtcc ctgctgcact tttgtaccat ctaataatta catcatccca     720
aataaaagtg aagaactaga agcaagattt gcaggtattg atggcacctc acatatacc     780 agtggtgatc agaaaactat aaagtccact aggaaaaaaa acagtgggaa gaccccacat     840
ctcctgctaa tgttattgcc ctcctacaga cttgagtcac aacagaccaa ccggcggaag     900
aagcgtgctt tggatgcggc ctattgcttt agaaatgtgc aggataattg ctgcctacgt     960
ccactttaca ttgatttcaa gagggatcta gggtggaaat ggatacacga acccaaaggg    1020
tacaatgcca acttctgtgc tggagcatgc ccgtatttat ggagttcaga cactcagcac    1080
agcagggtcc tgagcttata taataccata aatccagaag catctgcttc tccttgctgc    1140
gtgtcccaag atttagaacc tctaaccatt ctctactaca ttggcaaaac acccaagatt    1200
gaacagcttt ctaatatgat tgtaaagtct tgcaaatgca gctaa                    1245

<210> SEQ ID NO 48
<211> LENGTH: 1239
<212> TYPE: DNA
<213> ORGANISM: Homo sapiens
<300> PUBLICATION INFORMATION:
<302> TITLE: TGFbeta3
<310> PATENT DOCUMENT NUMBER: XM007417

<400> SEQUENCE: 48
atgaagatgc acttgcaaag ggctctggtg gtcctggccc tgctgaactt tgccacggtc      60
agcctctctc tgtccacttg caccaccttg gacttcggcc acatcaagaa gaagagggtg     120
gaagccatta ggggacagat cttgagcaag ctcaggctca ccagcccccc tgagccaacg     180
gtgatgaccc acgtccccta tcaggtcctg gcccttttaca cagcacccg ggagctgctg     240 gaggagatgc atgggggagag ggaggaaggc tgcacccagg aaaacaccga gtcggaatac     300
tatgccaaag aaatccataa attcgacatg atccaggggc tggcggagca acgaactg      360 gctgtctgcc ctaaaggaat tacctccaag gttttccgct tcaatgtgtc ctcagtggag     420
aaaaatagaa ccaacctatt ccgagcagaa ttccgggtct tgcgggtgcc caaccccagc     480
tctaagcgga atgagcagag gatcgagctc ttccagatcc ttcggccaga tgagcacatt     540
gccaaacagc gctatatcgg tggcaagaat ctgcccacac ggggcactgc cgagtggctg     600
```

```
tcctttgatg tcactgacac tgtgcgtgag tggctgttga gaagagagtc caacttaggt    660
ctagaaatca gcattcactg tccatgtcac acctttcagc ccaatggaga tatcctggaa    720
aacattcacg aggtgatgga aatcaaattc aaaggcgtgg acaatgagga tgaccatggc    780
cgtggagatc tggggcgcct caagaagcag aaggatcacc acaaccctca tctaatcctc    840
atgatgattc ccccacaccg gctcgacaac ccgggccagg ggggtcagag gaagaagcgg    900
gctttggaca ccaattactg cttccgcaac ttggaggaga actgctgtgt gcgcccctc     960 tacattgact tccgacagga tctgggctgg aagtgggtcc atgaacctaa gggctactat   1020
gccaacttct gctcaggccc ttgcccatac ctccgcagtg cagacacaac ccacagcacg   1080
gtgctgggac tgtacaacac tctgaaccct gaagcatctg cctcgccttg ctgcgtgccc   1140
caggacctgg agccctgac catcctgtac tatgttggga ggaccccaa agtggagcag    1200 ctctccaaca tggtggtgaa gtcttgtaaa tgtagctga                         1239
```

<210> SEQ ID NO 49
<211> LENGTH: 1704
<212> TYPE: DNA
<213> ORGANISM: Homo sapiens
<300> PUBLICATION INFORMATION:
<302> TITLE: TGFbetaR2
<310> PATENT DOCUMENT NUMBER: XM003094

<400> SEQUENCE: 49

```
atgggtcggg ggctgctcag gggcctgtgg ccgctgcaca tcgtcctgtg gacgcgtatc     60
gccagcacga tcccaccgca cgttcagaag tcggttaata cgacatgat agtcactgac    120 aacaacggtg cagtcaagtt tccacaactg tgtaaatttt gtgatgtgag attttccacc   180
tgtgacaacc agaaatcctg catgagcaac tgcagcatca cctccatctg tgagaagcca   240
caggaagtct gtgtggctgt atggagaaag aatgacgaga acataacact agagacagtt   300
tgccatgacc ccaagctccc ctaccatgac tttattctgg aagatgctgc ttctccaaag   360
tgcattatga aggaaaaaaa aaagcctggt gagactttct tcatgtgttc ctgtagctct   420
gatgagtgca atgacaacat catcttctca gaagaatata acaccagcaa tcctgacttg   480
ttgctagtca tatttcaagt gacaggcatc agcctcctgc caccactggg agttgccata   540
tctgtcatca tcatcttcta ctgctaccgc gttaaccggc agcagaagct gagttcaacc   600
tgggaaaccg gcaagacgcg gaagctcatg gagttcagcg agcactgtgc catcatcctg   660
gaagatgacc gctctgacat cagctccacg tgtgccaaca acatcaacca caacacagag   720
ctgctgccca ttgagctgga caccctggtg gggaaggtc gctttgctga ggtctataag    780
gccaagctga gcagaacac ttcagagcag tttgagacag tggcagtcaa gatctttccc   840
tatgaggagt atgcctcttg gaagacagag aaggacatct tctcagacat caatctgaag   900
catgagaaca tactccagtt cctgacggct gaggagcgga gacggagtt ggggaaacaa    960 tactggctga tcaccgcctt ccacgccaag ggcaacctac aggagtacct gacgcggcat   1020
gtcatcagct gggaggacct gcgcaagctg ggcagctccc tcgcccgggg gattgctcac   1080
ctccacagtg atcacactcc atgtgggagg cccaagatgc ccatcgtgca cagggacctc   1140
aagagctcca atatcctcgt gaagaacgac ctaacctgct gcctgtgtga ctttgggctt   1200
tccctgcgtc tggaccctac tctgtctgtg gatgacctgg ctaacagtgg gcaggtggga   1260
actgcaagat acatggctcc agaagtccta gaatccagga tgaatttgga gaatgttgag   1320
tccttcaagc agaccgatgt ctactccatg gctctggtgc tctgggaaat gacatctcgc   1380
```

| | |
|---|---|
| tgtaatgcag tgggagaagt aaaagattat gagcctccat ttggttccaa ggtgcgggag | 1440 |
| caccccctgtg tcgaaagcat gaaggacaac gtgttgagag atcgagggcg accagaaatt | 1500 |
| cccagcttct ggctcaacca ccagggcatc cagatggtgt gtgagacgtt gactgagtgc | 1560 |
| tgggaccacg acccagaggc ccgtctcaca gcccagtgtg tggcagaacg cttcagtgag | 1620 |
| ctggagcatc tggacaggct ctcggggagg agctgctcgg aggagaagat tcctgaagac | 1680 |
| ggctccctaa acactaccaa atag | 1704 |

<210> SEQ ID NO 50
<211> LENGTH: 609
<212> TYPE: DNA
<213> ORGANISM: Homo sapiens
<300> PUBLICATION INFORMATION:
<302> TITLE: TGFbeta3
<310> PATENT DOCUMENT NUMBER: XM001924

<400> SEQUENCE: 50

| | |
|---|---|
| atgtctcatt acaccattat tgagaatatt tgtcctaaag atgaatctgt gaaattctac | 60 |
| agtcccaaga gagtgcactt tcctatcccg caagctgaca tggataagaa gcgattcagc | 120 |
| tttgtcttca agcctgtctt caacacctca ctgctctttc tacagtgtga gctgacgctg | 180 |
| tgtacgaaga tggagaagca cccccagaag ttgcctaagt gtgtgcctcc tgacgaagcc | 240 |
| tgcacctcgc tggacgcctc gataatctgg gccatgatgc agaataagaa gacgttcact | 300 |
| aagcccttg ctgtgatcca ccatgaagca gaatctaaag aaaaaggtcc aagcatgaag | 360 |
| gaaccaaatc caatttctcc accaattttc catggtctgg acaccctaac cgtgatgggc | 420 |
| attgcgtttg cagcctttgt gatcggagca ctcctgacgg gggccttgtg gtacatctat | 480 |
| tctcacacag gggagacagc aggaaggcag caagtcccca cctcccccgcc agcctcggaa | 540 |
| aacagcagtg ctgcccacag catcggcagc acgcagagca cgccttgctc cagcagcagc | 600 |
| acggcctag | 609 |

<210> SEQ ID NO 51
<211> LENGTH: 3633
<212> TYPE: DNA
<213> ORGANISM: Homo sapiens
<300> PUBLICATION INFORMATION:
<302> TITLE: EGFR
<310> PATENT DOCUMENT NUMBER: X00588

<400> SEQUENCE: 51

| | |
|---|---|
| atgcgaccct ccgggacggc cggggcagcg ctcctggcgc tgctggctgc gctctgcccg | 60 |
| gcgagtcggg ctctggagga aaagaaagtt tgccaaggca cgagtaacaa gctcacgcag | 120 |
| ttgggcactt ttgaagatca ttttctcagc ctccagagga tgttcaataa ctgtgaggtg | 180 |
| gtccttggga atttggaaat tacctatgtg cagaggaatt atgatctttc cttcttaaag | 240 |
| accatccagg aggtggctgg ttatgtcctc attgccctca acacagtgga gcgaattcct | 300 |
| ttggaaaaacc tgcagatcat cagaggaaat atgtactacg aaaattccta tgccttagca | 360 |
| gtcttatcta actatgatgc aaataaaacc ggactgaagg agctgcccat gagaaattta | 420 |
| caggaaatcc tgcatggcgc cgtgcggttc agcaacaacc ctgccctgtg caacgtggag | 480 |
| agcatccagt ggcgggacat agtcagcagt gactttctca gcaacatgtc gatggacttc | 540 |
| cagaaccacc tgggcagctg ccaaaagtgt gatccaagct gtcccaatgg gagctgctgg | 600 |
| ggtgcaggag aggagaactg ccagaaactg accaaaatca tctgtgccca gcagtgctcc | 660 |
| gggcgctgcc gtggcaagtc ccccagtgac tgctgccaca accagtgtgc tgcaggctgc | 720 |

```
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca cacccctggt ctggaagtac gcagacgccg gccatgtgtg ccacctgtgc   1860
catccaaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta aagggactct ggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag accccagcg ctaccttgtc   2940
attcagggggg atgaaagaat gcatttgcca agtcctacag actccaactt ctaccgtgcc   3000
ctgatggatg aagaagacat ggacgacgtg gtggatgccg acgagtacct catcccacag   3060
```

| | | | |
|---|---|---|---|
| cagggcttct | tcagcagccc | ctccacgtca | cggactcccc tcctgagctc tctgagtgca | 3120 |
| accagcaaca | attccaccgt | ggcttgcatt | gatagaaatg ggctgcaaag ctgtcccatc | 3180 |
| aaggaagaca | gcttcttgca | gcgatacagc | tcagaccccca caggcgcctt gactgaggac | 3240 |
| agcatagacg | acaccttcct | cccagtgcct | gaatacataa accagtccgt tcccaaaagg | 3300 |
| cccgctggct | ctgtgcagaa | tcctgtctat | cacaatcagc ctctgaaccc cgcgcccagc | 3360 |
| agagacccac | actaccagga | ccccacagc | actgcagtgg gcaaccccga gtatctcaac | 3420 |
| actgtccagc | ccacctgtgt | caacagcaca | ttcgacagcc ctgcccactg ggcccagaaa | 3480 |
| ggcagccacc | aaattagcct | ggacaaccct | gactaccagc aggacttctt tcccaaggaa | 3540 |
| gccaagccaa | atggcatctt | taagggctcc | acagctgaaa atgcagaata cctaagggtc | 3600 |
| gcgccacaaa | gcagtgaatt | tattggagca | tga | 3633 |

<210> SEQ ID NO 52
<211> LENGTH: 3768
<212> TYPE: DNA
<213> ORGANISM: Homo sapiens
<300> PUBLICATION INFORMATION:
<302> TITLE: ERBB2
<310> PATENT DOCUMENT NUMBER: NM004448

<400> SEQUENCE: 52

| | | | |
|---|---|---|---|
| atggagctgg | cggccttgtg | ccgctggggg | ctcctcctcg ccctcttgcc ccccggagcc | 60 |
| gcgagcaccc | aagtgtgcac | cggcacagac | atgaagctgc ggctccctgc cagtcccgag | 120 |
| acccacctgg | acatgctccg | ccacctctac | cagggctgcc aggtggtgca gggaaacctg | 180 |
| gaactcacct | acctgcccac | caatgccagc | ctgtccttcc tgcaggatat ccaggaggtg | 240 |
| cagggctacg | tgctcatcgc | tcacaaccaa | gtgaggcagg tcccactgca gaggctgcgg | 300 |
| attgtgcgag | gcacccagct | ctttgaggac | aactatgccc tggccgtgct agacaatgga | 360 |
| gacccgctga | acaataccac | ccctgtcaca | ggggcctccc caggaggcct gcgggagctg | 420 |
| cagcttcgaa | gcctcacaga | gatcttgaaa | ggaggggtct tgatccagcg gaaccccccag | 480 |
| ctctgctacc | aggacacgat | tttgtggaag | gacatcttcc acaagaacaa ccagctggct | 540 |
| ctcacactga | tagacaccaa | ccgctctcgg | gcctgccacc cctgttctcc gatgtgtaag | 600 |
| ggctcccgct | gctggggaga | gagttctgag | gattgtcaga gcctgacgcg cactgtctgt | 660 |
| gccggtggct | gtgcccgctg | caaggggcca | ctgcccactg actgctgcca tgagcagtgt | 720 |
| gctgccggct | gcacgggccc | caagcactct | gactgcctgg cctgcctcca cttcaaccac | 780 |
| agtggcatct | gtgagctgca | ctgcccagcc | ctggtcacct acaacacaga cacgtttgag | 840 |
| tccatgccca | atcccgaggg | ccggtataca | ttcggcgcca gctgtgtgac tgcctgtccc | 900 |
| tacaactacc | tttctacgga | cgtgggatcc | tgcaccctcg tctgccccct gcacaaccaa | 960 |
| gaggtgacag | cagaggatgg | aacacagcgg | tgtgagaagt gcagcaagcc ctgtgcccga | 1020 |
| gtgtgctatg | gtctgggcat | ggagcacttg | cgagaggtga gggcagttac cagtgccaat | 1080 |
| atccaggagt | ttgctggctg | caagaagatc | tttgggagcc tggcatttct gccggagagc | 1140 |
| tttgatgggg | acccagcctc | caacactgcc | ccgctccagc cagagcagct ccaagtgttt | 1200 |
| gagactctgg | aagagatcac | aggttaccta | tacatctcag catggccgga cagcctgcct | 1260 |
| gacctcagcg | tcttccagaa | cctgcaagta | atccgggac gaattctgca caatggcgcc | 1320 |
| tactcgctga | ccctgcaagg | gctgggcatc | agctggctgg ggctgcgctc actgagggaa | 1380 |
| ctgggcagtg | gactggccct | catccaccat | aacacccacc tctgcttcgt gcacacggtg | 1440 |

```
ccctgggacc agctctttcg aacccgcac caagctctgc tccacactgc caaccggcca    1500
gaggacgagt gtgtgggcga gggcctggcc tgccaccagc tgtgcgcccg agggcactgc    1560
tggggtccag ggcccaccca gtgtgtcaac tgcagccagt tccttcgggg ccaggagtgc    1620
gtggaggaat gccgagtact gcaggggctc cccagggagt atgtgaatgc caggcactgt    1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
ggctgccccg ccgagcagag agccagccct ctgacgtcca tcgtctctgc ggtggttggc    1980
attctgctgg tcgtggtctt gggggtggtc tttgggatcc tcatcaagcg acggcagcag    2040
aagatccgga agtacacgat gcggagactg ctgcaggaaa cggagctggt ggagccgctg    2100
acacctagcg gagcgatgcc caaccaggcg cagatgcgga tcctgaaaga gacggagctg    2160
aggaaggtga aggtgcttgg atctggcgct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400
atgcccctatg gctgcctctt agaccatgtc cgggaaaacc gcggacgcct gggctcccag    2460
gacctgctga actggtgtat gcagattgcc aaggggatga gctacctgga ggatgtgcgg    2520
ctcgtacaca gggacttggc cgctcggaac gtgctggtca agagtcccaa ccatgtcaaa    2580
attacagact tcgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccgggag atccctgacc tgctggaaaa ggggagcgg    2820
ctgccccagc cccccatctg caccattgat gtctacatga tcatggtcaa atgttggatg    2880
attgactctg aatgtcggcc aagattccgg gagttggtgt ctgaattctc ccgcatggcc    2940
agggaccccc agcgctttgt ggtcatccag aatgaggact ggggcccagc cagtcccttg    3000
gacagcacct tctaccgctc actgctggag gacgatgaca tggggacct ggtggatgct    3060
gaggagtatc tggtaccccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggacccac agtacccctg    3360
ccctctgaga ctgatggcta cgttgccccc ctgacctgca gccccagcc tgaatatgtg    3420
aaccagccag atgttcggcc ccagccccct tcgcccgag agggccctct gcctgctgcc    3480
cgacctgctg gtgccactct ggaaagggcc aagactctct ccccagggaa gaatggggtc    3540
gtcaaagacg tttttgcctt tggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg gggctccac ccagcacctt caagggaca    3720
cctacggcag agaacccaga gtacctgggt ctggacgtgc cagtgtga            3768
```

<210> SEQ ID NO 53
<211> LENGTH: 1986
<212> TYPE: DNA
<213> ORGANISM: Homo sapiens
<300> PUBLICATION INFORMATION:
<302> TITLE: ERBB3
<310> PATENT DOCUMENT NUMBER: XM006723

<400> SEQUENCE: 53

| | | | | | |
|---|---|---|---|---|---|
| atgcacaact | tcagtgtttt | ttccaatttg | acaaccattg | gaggcagaag | cctctacaac | 60 |
| cggggcttct | cattgttgat | catgaagaac | ttgaatgtca | catctctggg | cttccgatcc | 120 |
| ctgaaggaaa | ttagtgctgg | gcgtatctat | ataagtgcca | ataggcagct | ctgctaccac | 180 |
| cactctttga | actggaccaa | ggtgcttcgg | gggcctacgg | aagagcgact | agacatcaag | 240 |
| cataatcggc | cgcgcagaga | ctgcgtggca | gagggcaaag | tgtgtgaccc | actgtgctcc | 300 |
| tctgggggat | gctggggccc | aggccctggt | cagtgcttgt | cctgtcgaaa | ttatagccga | 360 |
| ggaggtgtct | gtgtgaccca | ctgcaacttt | ctgaatgggg | agcctcgaga | atttgcccat | 420 |
| gaggccgaat | gcttctcctg | ccacccggaa | tgccaaccca | tggagggcac | tgccacatgc | 480 |
| aatggctcgg | gctctgatac | ttgtgctcaa | tgtgcccatt | tcgagatgg | cccccactgt | 540 |
| gtgagcagct | gcccccatgg | agtcctaggt | gccaagggcc | aatctacaa | gtacccagat | 600 |
| gttcagaatg | aatgtcggcc | ctgccatgag | aactgcaccc | aggggtgtaa | aggaccagag | 660 |
| cttcaagact | gtttaggaca | aacactggtg | ctgatcggca | aaacccatct | gacaatggct | 720 |
| ttgacagtga | tagcaggatt | ggtagtgatt | ttcatgatgc | tgggcggcac | ttttctctac | 780 |
| tggcgtgggc | gccggattca | gaataaaagg | gctatgaggc | gatacttgga | acggggtgag | 840 |
| agcatagagc | tctggaccc | cagtgagaag | gctaacaaag | tcttggccag | aatcttcaaa | 900 |
| gagacagagc | taaggaagct | taaagtgctt | ggctcgggtg | tctttggaac | tgtgcacaaa | 960 |
| ggagtgtgga | tccctgaggg | tgaatcaatc | aagattccag | tctgcattaa | agtcattgag | 1020 |
| gacaagagtg | gacggcagag | ttttcaagct | gtgacagatc | atatgctggc | cattggcagc | 1080 |
| ctggaccatg | cccacattgt | aaggctgctg | ggactatgcc | agggtcatc | tctgcagctt | 1140 |
| gtcactcaat | atttgcctct | gggttctctg | ctggatcatg | tgagacaaca | ccggggggca | 1200 |
| ctggggccac | agctgctgct | caactgggga | gtacaaattg | ccaagggaat | gtactacctt | 1260 |
| gaggaacatg | gtatggtgca | tagaaacctg | gctgcccgaa | acgtgctact | caagtcaccc | 1320 |
| agtcaggttc | aggtggcaga | ttttggtgtg | gctgacctgc | tgcctcctga | tgataagcag | 1380 |
| ctgctataca | gtgaggccaa | gactccaatt | aagtggatgg | cccttgagag | tatccacttt | 1440 |
| gggaaataca | cacaccagag | tgatgtctgg | agctatggtg | tgacagtttg | ggagttgatg | 1500 |
| accttcgggg | cagagcccta | tgcagggcta | cgattggctg | aagtaccaga | cctgctagag | 1560 |
| aagggggagc | ggttggcaca | gccccagatc | tgcacaattg | atgtctacat | ggtgatggtc | 1620 |
| aagtgttgga | tgattgatga | aacattcgc | ccaaccttta | agaactagc | caatgagttc | 1680 |
| accaggatgg | cccgagaccc | accacggtat | ctggtcataa | agagagagag | tgggcctgga | 1740 |
| atagccctg | ggccagagcc | ccatggtctg | acaaacaaga | agctagagga | agtagagctg | 1800 |
| gagccagaac | tagacctaga | cctagacttg | gaagcagagg | aggacaacct | ggcaaccacc | 1860 |
| acactgggct | ccgccctcag | cctaccagtt | ggaaacactta | atcggccacg | tgggagccag | 1920 |
| agccttttaa | gtccatcatc | tggatacatg | cccatgaacc | aggtaatct | tggggttctt | 1980 |
| ccttag | | | | | | 1986 |

<210> SEQ ID NO 54
<211> LENGTH: 1437
<212> TYPE: DNA
<213> ORGANISM: Homo sapiens
<300> PUBLICATION INFORMATION:
<302> TITLE: ERBB4
<310> PATENT DOCUMENT NUMBER: XM002260

<400> SEQUENCE: 54

```
atgatgtacc tggaagaaag acgactcgtt catcgggatt tggcagcccg taatgtctta      60
gtgaaatctc caaccatgt gaaaatcaca gattttgggc tagccagact cttggaagga     120
gatgaaaaag agtacaatgc tgatggagga aagatgccaa ttaaatggat ggctctggag    180
tgtatacatt acaggaaatt cacccatcag agtgacgttt ggagctatgg agttactata    240
tgggaactga tgacctttgg aggaaaaccc tatgatggaa ttccaacgcg agaaatccct    300
gatttattag agaaaggaga acgtttgcct cagcctccca tctgcactat tgacgtttac    360
atggtcatgg tcaaatgttg gatgattgat gctgacagta gacctaaatt taaggaactg    420
gctgctgagt tttcaaggat ggctcgagac cctcaaagat acctagttat tcagggtgat    480
gatcgtatga gcttcccag tccaaatgac agcaagttct ttcagaatct cttggatgaa    540
gaggatttgg aagatatgat ggatgctgag gagtacttgg tccctcaggc tttcaacatc    600
ccacctccca tctatacttc cagagcaaga attgactcga ataggagtga aattggacac    660
agccctcctc ctgcctacac ccccatgtca ggaaaccagt ttgtataccg agatggaggt    720
tttgctgctg aacaaggagt gtctgtgccc tacagagccc caactagcac aattccagaa    780
gctcctgtgg cacagggtgc tactgctgag atttttgatg actcctgctg taatggcacc    840
ctacgcaagc cagtggcacc ccatgtccaa gaggacagta gcacccagag gtacagtgct    900
gaccccaccg tgtttgcccc agaacggagc ccacgaggag agctggatga ggaaggttac    960
atgactccta tgcgagacaa acccaaacaa gaatacctga tccagtggga ggagaaccct   1020
tttgtttctc ggagaaaaaa tggagacctt caagcattgg ataatcccga atatcacaat   1080
gcatccaatg tcccaccaa ggccaggat gagtatgtga tgagccact gtacctcaac   1140
acctttgcca acaccttggg aaaagctgag tacctgaaga caacatact gtcaatgcca   1200
gagaaggcca agaaagcgtt tgacaaccct gactactgga ccacagcct gccacctcgg   1260
agcacccttc agcacccaga ctacctgcag gagtacagca caaatatttt ttataaacag   1320
aatgggcgga tccggcctat tgtggcagag aatcctgaat acctctctga gttctccctg   1380
aagccaggca ctgtgctgcc gcctccacct tacagacacc ggaatactgt ggtgtaa     1437
```

<210> SEQ ID NO 55
<211> LENGTH: 627
<212> TYPE: DNA
<213> ORGANISM: Homo sapiens
<300> PUBLICATION INFORMATION:
<302> TITLE: FGF10
<310> PATENT DOCUMENT NUMBER: NM004465

<400> SEQUENCE: 55

```
atgtggaaat ggatactgac acattgtgcc tcagcctttc cccacctgcc cggctgctgc      60
tgctgctgct ttttgttgct gttcttggtg tcttccgtcc ctgtcacctg ccaagccctt    120
ggtcaggaca tggtgtcacc agaggccacc aactcttctt cctcctcctt ctcctctcct    180
tccagcgcgg gaaggcatgt gcggagctac aatcacttc aaggagatgt ccgctggaga   240
aagctattct cttcaccaa gtactttctc aagattgaga gaacgggaa ggtcagcggg   300
```

| | |
|---|---|
| accaagaagg agaactgccc gtacagcatc ctggagataa catcagtaga aatcggagtt | 360 |
| gttgccgtca aagccattaa cagcaactat tacttagcca tgaacaagaa ggggaaactc | 420 |
| tatggctcaa aagaatttaa caatgactgt aagctgaagg agaggataga ggaaaatgga | 480 |
| tacaatacct atgcatcatt taactggcag cataatggga ggcaaatgta tgtggcattg | 540 |
| aatggaaaag gagctccaag gagaggacag aaaacacgaa ggaaaaacac ctctgctcac | 600 |
| tttcttccaa tggtggtaca ctcatag | 627 |

<210> SEQ ID NO 56
<211> LENGTH: 679
<212> TYPE: DNA
<213> ORGANISM: Homo sapiens
<300> PUBLICATION INFORMATION:
<302> TITLE: FGF11
<310> PATENT DOCUMENT NUMBER: XM008660

<400> SEQUENCE: 56

| | |
|---|---|
| aatggcggcg ctggccagta gcctgatccg gcagaagcgg gaggtccgcg agcccggggg | 60 |
| cagccggccg tgtcggcgc agcggcgcgt gtgtccccgc ggcaccaagt ccctttgcca | 120 |
| gaagcagctc ctcatcctgc tgtccaaggt gcgactgtgc gggggcggc ccgcgcggcc | 180 |
| ggaccgcggc ccggagcctc agctcaaagg catcgtcacc aaactgttct gccgccaggg | 240 |
| tttctacctc caggcgaatc ccgacggaag catccagggc accccagagg ataccagctc | 300 |
| cttcacccac ttcaacctga tccctgtggg cctccgtgtg gtcaccatcc agagcgccaa | 360 |
| gctgggtcac tacatggcca tgaatgctga gggactgctc tacagttcgc gcatttcac | 420 |
| agctgagtgt cgctttaagg agtgtgtctt tgagaattac tacgtcctgt acgcctctgc | 480 |
| tctctaccgc cagcgtcgtt ctggccgggc ctggtacctc ggcctggaca aggagggcca | 540 |
| ggtcatgaag ggaaaccgag ttaagaagac caaggcagct gcccactttc tgcccaagct | 600 |
| cctggaggtg gccatgtacc aggagccttc tctccacagt gtccccgagg cctccccttc | 660 |
| cagtccccct gccccctga | 679 |

<210> SEQ ID NO 57
<211> LENGTH: 732
<212> TYPE: DNA
<213> ORGANISM: Homo sapiens
<300> PUBLICATION INFORMATION:
<302> TITLE: FGF12
<310> PATENT DOCUMENT NUMBER: NM021032

<400> SEQUENCE: 57

| | |
|---|---|
| atggctgcgg cgatagccag ctccttgatc cggcagaagc ggcaggcgag ggagtccaac | 60 |
| agcgaccgag tgtcggcctc caagcgccgc tccagcccca gcaaagacgg gcgctccctg | 120 |
| tgcgagaggc acgtcctcgg ggtgttcagc aaagtgcgct tctgcagcgg ccgcaagagg | 180 |
| ccggtgagc ggagaccaga accccagctc aaagggattg tgacaaggtt attcagccag | 240 |
| cagggatact tcctgcagat gcacccagat ggtaccattg atgggaccaa ggacgaaaac | 300 |
| agcgactaca ctctcttcaa tctaattccc gtgggcctgc gtgtagtggc catccaagga | 360 |
| gtgaaggcta gcctctatgt ggccatgaat ggtgaaggct atctctacag ttcagatgtt | 420 |
| ttcactccag aatgcaaatt caaggaatct gtgtttgaaa actactatgt gatctattct | 480 |
| tccacactgt accgccagca agaatcaggc cgagcttggt ttctgggact caataagaa | 540 |
| ggtcaaatta tgaaggggaa cagagtgaag aaaaccaagc cctcatcaca tttttgtaccg | 600 |
| aaacctattg aagtgtgtat gtacagagaa ccatcgctac atgaaattgg agaaaaacaa | 660 |

```
gggcgttcaa ggaaaagttc tggaacacca accatgaatg gaggcaaagt tgtgaatcaa    720
gattcaacat ag                                                        732

<210> SEQ ID NO 58
<211> LENGTH: 738
<212> TYPE: DNA
<213> ORGANISM: Homo sapiens
<300> PUBLICATION INFORMATION:
<302> TITLE: FGF13
<310> PATENT DOCUMENT NUMBER: XM010269

<400> SEQUENCE: 58
atggcggcgg ctatcgccag ctcgctcatc cgtcagaaga ggcaagcccg cgagcgcgag     60
aaatccaacg cctgcaagtg tgtcagcagc cccagcaaag caagaccag ctgcgacaaa    120 aacaagttaa atgtcttttc ccgggtcaaa ctcttcggct ccaagaagag cgcagaaga    180 agaccagagc ctcagcttaa gggtatagtt accaagctat acagccgaca aggctaccac    240
ttgcagctgc aggcggatgg aaccattgat ggcaccaaag atgaggacag cacttacact    300
ctgtttaacc tcatccctgt gggtctgcga gtggtggcta tccaaggagt tcaaaccaag    360
ctgtacttgg caatgaacag tgagggatac ttgtacacct cggaactttt cacacctgag    420
tgcaaattca agaatcagt gtttgaaaat tattatgtga catattcatc aatgatatac    480
cgtcagcagc agtcaggccg agggtggtat ctgggtctga caaagaagg agagatcatg    540 aaaggcaacc atgtgaagaa gaacaagcct gcagctcatt ttctgcctaa ccactgaaa    600 gtggccatgt acaaggagcc atcactgcac gatctcacgg agttctcccg atctggaagc    660
gggaccccaa ccaagagcag aagtgtctct ggcgtgctga acggaggcaa atccatgagc    720
cacaatgaat caacgtag                                                  738

<210> SEQ ID NO 59
<211> LENGTH: 624
<212> TYPE: DNA
<213> ORGANISM: Homo sapiens
<300> PUBLICATION INFORMATION:
<302> TITLE: FGF16
<310> PATENT DOCUMENT NUMBER: NM003868

<400> SEQUENCE: 59
atggcagagg tgggggcgt cttcgcctcc ttggactggg atctacacgg cttctcctcg     60
tctctgggga acgtgccctt agctgactcc ccaggtttcc tgaacgagcg cctgggccaa    120 atcgaggga agctgcagcg tggctcaccc acagacttcg cccacctgaa ggggatcctg    180
cggcgccgcc agctctactg ccgcaccggc ttccacctgg agatcttccc caacggcacg    240
gtgcacggga cccgccacga ccacagccgc ttcggaatcc tggagtttat cagcctggct    300
gtggggctga tcagcatccg gggagtggac tctggcctgt acctaggaat gaatgagcga    360
ggagaactct atgggtcgaa gaaactcaca cgtgaatgtg ttttccggga acagtttgaa    420
gaaaactggt acaacaccta tgcctcaacc ttgtacaaac attcggactc agagagacag    480
tattacgtgg ccctgaacaa agatggctca ccccgggagg atacaggac taaacgacac    540 cagaaattca ctcactttt acccaggcct gtagatcctt ctaagttgcc ctccatgtcc    600
agagacctct ttcactatag gtaa                                           624

<210> SEQ ID NO 60
<211> LENGTH: 651
<212> TYPE: DNA
```

<213> ORGANISM: Homo sapiens
<300> PUBLICATION INFORMATION:
<302> TITLE: FGF17
<310> PATENT DOCUMENT NUMBER: XM005316

<400> SEQUENCE: 60

| | |
|---|---|
| atgggagccg cccgcctgct gcccaacctc actctgtgct tacagctgct gattctctgc | 60 |
| tgtcaaactc aggggagaa tcacccgtct cctaatttta accagtacgt gagggaccag | 120 |
| ggcgccatga ccgaccagct gagcaggcgg cagatccgcg agtaccaact ctacagcagg | 180 |
| accagtggca agcacgtgca ggtcaccggg cgtcgcatct ccgccaccgc cgaggacggc | 240 |
| aacaagtttg ccaagctcat agtggagacg gacacgtttg gcagccgggt tcgcatcaaa | 300 |
| ggggctgaga gtgagaagta catctgtatg aacaagaggg gcaagctcat cgggaagccc | 360 |
| agcgggaaga gcaaagactg cgtgttcacg gagatcgtgc tggagaacaa ctatacggcc | 420 |
| ttccagaacg cccggcacga gggctggttc atggccttca gcggcagggg cggcccgc | 480 |
| caggcttccc gcagccgcca gaaccagcgc gaggcccact tcatcaagcg cctctaccaa | 540 |
| ggccagctgc ccttccccaa ccacgccgag aagcagaagc agttcgagtt tgtgggctcc | 600 |
| gcccccaccc gccggaccaa gcgcacacgg cggccccagc ccctcacgta g | 651 |

<210> SEQ ID NO 61
<211> LENGTH: 624
<212> TYPE: DNA
<213> ORGANISM: Homo sapiens
<300> PUBLICATION INFORMATION:
<302> TITLE: FGF18
<310> PATENT DOCUMENT NUMBER: AF075292

<400> SEQUENCE: 61

| | |
|---|---|
| atgtattcag cgccctccgc ctgcacttgc ctgtgtttac acttcctgct gctgtgcttc | 60 |
| caggtacagg tgctggttgc cgaggagaac gtggacttcc gcatccacgt ggagaaccag | 120 |
| acgcgggctc gggacgatgt gagccgtaag cagctgcggc tgtaccagct ctacagccgg | 180 |
| accagtggga aacacatcca ggtcctgggc cgcaggatca gtgcccgcgg cgaggatggg | 240 |
| gacaagtatg cccagctcct agtggagaca gacaccttcg gtagtcaagt ccggatcaag | 300 |
| ggcaaggaga cggaattcta cctgtgcatg aaccgcaaag gcaagctcgt ggggaagccc | 360 |
| gatggcacca gcaaggagtg tgtgttcatc gagaaggttc tggagaacaa ctacacggcc | 420 |
| ctgatgtcgg ctaagtactc cggctggtac gtgggcttca ccaagaaggg gcggccgcgg | 480 |
| aagggcccca agacccggga gaaccagcag acgtgcatt tcatgaagcg ctaccccaag | 540 |
| gggcagccgg agcttcagaa gcccttcaag tacacgacgg tgaccaagag gtcccgtcgg | 600 |
| atccggccca cacaccctgc ctag | 624 |

<210> SEQ ID NO 62
<211> LENGTH: 651
<212> TYPE: DNA
<213> ORGANISM: Homo sapiens
<300> PUBLICATION INFORMATION:
<302> TITLE: FGF19
<310> PATENT DOCUMENT NUMBER: AF110400

<400> SEQUENCE: 62

| | |
|---|---|
| atgcggagcg ggtgtgtggt ggtccacgta tggatcctgg ccggcctctg gctggccgtg | 60 |
| gccgggcgcc cctcgccctt ctcggacgcg ggccccacg tgcactacgg ctggggcgac | 120 |
| cccatccgcc tgcggcacct gtacacctcc ggcccccacg gctctccag ctgcttcctg | 180 |

-continued

```
cgcatccgtg ccgacggcgt cgtggactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga gaagcaccgc    420
ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg ccctggaga ccgacagcat ggacccattt    600
gggcttgtca ccggactgga ggccgtgagg agtcccagct tgagaagta a              651
```

<210> SEQ ID NO 63
<211> LENGTH: 468
<212> TYPE: DNA
<213> ORGANISM: Homo sapiens

<400> SEQUENCE: 63

```
atggctgaag ggaaatcac caccttcaca gccctgaccg agaagtttaa tctgcctcca    60
gggaattaca agaagcccaa actcctctac tgtagcaacg gggccacttc cctgaggatc    120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468
```

<210> SEQ ID NO 64
<211> LENGTH: 636
<212> TYPE: DNA
<213> ORGANISM: Homo sapiens
<300> PUBLICATION INFORMATION:
<302> TITLE: FGF20
<310> PATENT DOCUMENT NUMBER: NM019851

<400> SEQUENCE: 64

```
atggctccct tagccgaagt cggggggcttt ctgggcggcc tggagggctt gggccagcag    60
gtgggttcgc atttcctgtt gcctcctgcc ggggagcggc cgccgctgct gggcgagcgc    120
aggagcgcgg cggagcggag cgcccgcggc gggccggggg ctgcgcagct ggcgcacctg    180
cacggcatcc tgcgccgccg gcagctctat tgccgcaccg gcttccacct gcagatcctg    240
cccgacggca gcgtgcaggg cacccggcag gaccacagcc tcttcggtat cttggaattc    300
atcagtgtgg cagtgggact ggtcagtatt agaggtgtgg acagtggtct ctatcttgga    360
atgaatgaca aggagaact ctatggatca gagaaactta cttccgaatg catctttagg    420
gagcagtttg aagagaactg gtataacacc tattcatcta acatatataa acatggagac    480
actggccgca ggtattttgt ggcacttaac aaagacggaa ctccaagaga tggcgccagg    540
tccaagaggc atcagaaatt tacacatttc ttacctagac cagtggatcc agaaagagtt    600
ccagaattgt acaaggacct actgatgtac acttga                              636
```

<210> SEQ ID NO 65
<211> LENGTH: 630
<212> TYPE: DNA
<213> ORGANISM: Homo sapiens
<300> PUBLICATION INFORMATION:

```
<302> TITLE: FGF21
<310> PATENT DOCUMENT NUMBER: XM009100

<400> SEQUENCE: 65
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc gaaagtctc     240 ctgcagctga aagccttgaa gccgggagtt attcaaatct tgggagtcaa gacatccagg     300
ttcctgtgcc agcggccaga tgggccctg tatggatcgc tccactttga ccctgaggcc      360
tgcagcttcc gggagctgct tcttgaggac ggatacaatg tttaccagtc cgaagcccac     420
ggcctcccgc tgcacctgcc agggaacaag tccccacacc gggaccctgc accccgagga     480
ccagctcgct tcctgccact accaggcctg cccccgcac tccggagcc acccggaatc       540 ctggccccc agccccccga tgtgggctcc tcggaccctc tgagcatggt gggaccttcc     600
cagggccgaa gccccagcta cgcttcctga                                    630

<210> SEQ ID NO 66
<211> LENGTH: 513
<212> TYPE: DNA
<213> ORGANISM: Homo sapiens
<300> PUBLICATION INFORMATION:
<302> TITLE: FGF22
<310> PATENT DOCUMENT NUMBER: XM009271

<400> SEQUENCE: 66
atgcgccgcc gcctgtggct gggcctggcc tggctgctgc tggcgcgggc gccggacgcc      60
gcgggaaccc cgagcgcgtc gcggggaccg cgcagctacc cgcacctgga gggcgacgtg     120
cgctggcggc gcctcttctc ctccactcac ttcttcctgc gcgtggatcc cggcggccgc     180
gtgcagggca cccgctggcg ccacggccag gacagcatcc tggagatccg ctctgtacac     240
gtgggcgtcg tggtcatcaa agcagtgtcc tcaggcttct acgtggccat gaaccgccgg     300
ggccgcctct acgggtcgcg actctacacc gtggactgca ggttccggga gcgcatcgaa     360
gagaacggcc acaacaccta cgcctcacag cgctggcgcc gccgcggcca gcccatgttc     420
ctggcgctgg acaggagggg ggggcccgg ccaggcggcc ggacgcggcg gtaccacctg     480
tccgcccact cctgcccgt cctggtctcc tga                                  513

<210> SEQ ID NO 67
<211> LENGTH: 621
<212> TYPE: DNA
<213> ORGANISM: Homo sapiens
<300> PUBLICATION INFORMATION:
<302> TITLE: FGF4
<310> PATENT DOCUMENT NUMBER: NM002007

<400> SEQUENCE: 67
atgtcggggc ccgggacggc cgcggtagcg ctgctcccgg cggtcctgct ggccttgctg      60
gcgccctggg cggccgagg gggcgccgcc gcacccactg cacccaacgg cacgctggag     120
gccgagctgg agcgccgctg ggagagcctg gtggcgctct cgttggcgcg cctgccggtg     180
gcagcgcagc ccaaggaggc ggccgtccag agcggcgccg cgactacct gctgggcatc     240 aagcggctgc ggcggctcta ctgcaacgtg ggcatcggct tccacctcca ggcgctcccc     300
gacggccgca tcgcggcgcg cacgcggac acccgcgaca gctgctgga gctctcgccc     360
```

```
gtggagcggg gcgtggtgag catcttcggc gtggccagcc ggttcttcgt ggccatgagc      420
agcaagggca agctctatgg ctcgcccttc ttcaccgatg agtgcacgtt caaggagatt      480
ctccttccca acaactacaa cgcctacgag tcctacaagt accccggcat gttcatcgcc      540
ctgagcaaga atgggaagac caagaagggg aaccgagtgt cgcccaccat gaaggtcacc      600
cacttcctcc ccaggctgtg a                                                621

<210> SEQ ID NO 68
<211> LENGTH: 597
<212> TYPE: DNA
<213> ORGANISM: Homo sapiens
<300> PUBLICATION INFORMATION:
<302> TITLE: FGF6
<310> PATENT DOCUMENT NUMBER: NM020996

<400> SEQUENCE: 68
atgtcccggg gagcaggacg tctgcagggc acgctgtggg ctctcgtctt cctaggcatc       60
ctagtgggca tggtggtgcc ctcgcctgca ggcacccgtg ccaacaacac gctgctggac      120 tcgagggget ggggcaccct gctgtccagg tctcgcgcgg ggctagctgg agagattgcc      180
ggggtgaact gggaaagtgg ctatttggtg gggatcaagc ggcagcggag gctctactgc      240
aacgtgggca tcggctttca cctccaggtg ctccccgacg gccggatcag cgggacccac      300
gaggagaacc cctacagcct gctggaaatt tccactgtgg agcgaggcgt ggtgagtctc      360
tttggagtga aagtgccct cttcgttgcc atgaacagta aggaagatt gtacgcaacg       420 cccagcttcc aagaagaatg caagttcaga gaaaccctcc tgcccaacaa ttacaatgcc      480
tacgagtcag acttgtacca agggacctac attgccctga gcaaatacgg acgggtaaag      540
cggggcagca ggtgtccccc gatcatgact gtcactcatt ccttcccag gatctaa        597

<210> SEQ ID NO 69
<211> LENGTH: 150
<212> TYPE: DNA
<213> ORGANISM: Homo sapiens
<300> PUBLICATION INFORMATION:
<302> TITLE: FGF7
<310> PATENT DOCUMENT NUMBER: XM007559

<400> SEQUENCE: 69
atgtcttggc aatgcacttc atacacaatg actaatctat actgtgatga tttgactcaa       60
aaggagaaaa gaaattatgt agttttcaat tctgattcct attcaccttt tgtttatgaa      120
tggaaagctt tgtgcaaaat atacatataa                                       150

<210> SEQ ID NO 70
<211> LENGTH: 628
<212> TYPE: DNA
<213> ORGANISM: Homo sapiens
<300> PUBLICATION INFORMATION:
<302> TITLE: FGF9
<310> PATENT DOCUMENT NUMBER: XM007105

<400> SEQUENCE: 70
gatggctccc ttaggtgaag ttgggaacta tttcggtgtg caggatgcgg taccgtttgg       60
gaatgtgccc gtgttgccgg tggacagccc ggttttgtta agtgaccacc tgggtcagtc      120
cgaagcaggg gggctcccca ggggacccgc agtcacggac ttggatcatt taagggggat      180
tctcaggcgg aggcagctat actgcaggac tggatttcac ttagaaatct tccccaatgg      240
tactatccag ggaaccagga aagaccacag ccgatttggc attctggaat ttatcagtat      300
```

| | |
|---|---|
| agcagtgggc ctggtcagca ttcgaggcgt ggacagtgga ctctacctcg ggatgaatga | 360 |
| gaaggggag ctgtatggat cagaaaaact aacccaagag tgtgtattca gagaacagtt | 420 |
| cgaagaaaac tggtataata cgtactcatc aaacctatat aagcacgtgg acactggaag | 480 |
| gcgatactat gttgcattaa ataaagatgg gaccccgaga aagggacta ggactaaacg | 540 |
| gcaccagaaa ttcacacatt ttttacctag accagtggac cccgacaaag tacctgaact | 600 |
| gtataaggat attctaagcc aaagttga | 628 |

<210> SEQ ID NO 71
<211> LENGTH: 2469
<212> TYPE: DNA
<213> ORGANISM: Homo sapiens
<300> PUBLICATION INFORMATION:
<302> TITLE: FGFR1
<310> PATENT DOCUMENT NUMBER: NM000604

<400> SEQUENCE: 71

| | |
|---|---|
| atgtggagct ggaagtgcct cctcttctgg gctgtgctgg tcacagccac actctgcacc | 60 |
| gctaggccgt ccccgacctt gcctgaacaa gcccagccct ggggagcccc tgtggaagtg | 120 |
| gagtccttcc tggtccaccc cggtgacctg ctgcagcttc gctgtcggct gcgggacgat | 180 |
| gtgcagagca tcaactggct gcgggacggg gtgcagctgg cggaaagcaa ccgcacccgc | 240 |
| atcacagggg aggaggtgga ggtgcaggac tccgtgcccg cagactccgg cctctatgct | 300 |
| tgcgtaacca gcagcccctc gggcagtgac accacctact ctccgtcaa tgtttcagat | 360 |
| gctctcccct cctcggagga tgatgatgat gatgatgact cctcttcaga ggagaaagaa | 420 |
| acagataaca ccaaaccaaa ccgtatgccc gtagctccat attggacatc cccagaaaag | 480 |
| atggaaaaga aattgcatgc agtgccggct gccaagacag tgaagttcaa atgcccttcc | 540 |
| agtgggaccc caaaccccac actgcgctgg ttgaaaaatg gcaaagaatt caaacctgac | 600 |
| cacagaattg gaggctacaa ggtccgttat gccacctgga gcatcataat ggactctgtg | 660 |
| gtgccctctg acaagggcaa ctacacctgc attgtggaga tgagtacgg cagcatcaac | 720 |
| cacacatacc agctggatgt cgtggagcgg tcccctcacc ggcccatcct gcaagcaggg | 780 |
| ttgcccgcca caaaacagt ggccctgggt agcaacgtgg agttcatgtg taaggtgtac | 840 |
| agtgacccgc agccgcacat ccagtggcta aagcacatcg aggtgaatgg gagcaagatt | 900 |
| ggcccagaca acctgcctta tgtccagatc ttgaagactg ctggagttaa taccaccgac | 960 |
| aaagagatga ggtgcttca cttaagaaat gtctccttg aggacgcagg ggagtatacg | 1020 |
| tgcttggcgg gtaactctat cggactctcc catcactctg catggttgac cgttctggaa | 1080 |
| gccctggaag agaggccggc agtgatgacc tcgcccctgt acctggagat catcatctat | 1140 |
| tgcacagggg ccttcctcat ctcctgcatg gtggggtcgg tcatcgtcta caagatgaag | 1200 |
| agtggtacca agaagagtga cttccacagc cagatggctg tgcacaagct ggccaagagc | 1260 |
| atccctctgc gcagacaggt aacagtgtct gctgactcca gtgcatccat gaactctggg | 1320 |
| gttcttctgg ttcggccatc acggctctcc tccagtggga ctcccatgct agcaggggtc | 1380 |
| tctgagtatg agcttcccga agaccctcgc tgggagctgc ctcgggacag actggtctta | 1440 |
| ggcaaacccc tggagagggg ctgctttggc caggtggtgt tggcagaggc tatcgggctg | 1500 |
| gacaaggaca aacccaaccg tgtgaccaaa gtggctgtga agatgttgaa gtcggacgca | 1560 |
| acagagaaag acttgtcaga cctgatctca gaaatggaga tgatgaagat gatcgggaag | 1620 |
| cataagaata tcatcaacct gctggggcc tgcacgcagg atggtccctt gtatgtcatc | 1680 |

```
gtggagtatg cctccaaggg caacctgcgg gagtacctgc aggcccggag gcccccaggg     1740
ctggaatact gctacaaccc cagccacaac ccagaggagc agctctcctc caaggacctg     1800
gtgtcctgcg cctaccaggt ggcccgaggc atggagtatc tggcctccaa gaagtgcata     1860
caccgagacc tggcagccag gaatgtcctg gtgacagagg acaatgtgat gaagatagca     1920
gactttggcc tcgcacggga cattcaccac atcgactact ataaaaagac aaccaacggc     1980
cgactgcctg tgaagtggat ggcacccgag gcattatttg accggatcta cacccaccag     2040
agtgatgtgt ggtctttcgg ggtgctcctg tgggagatct tcactctggg cggctcccca     2100
taccccggtg tgcctgtgga ggaacttttc aagctgctga ggagggtca ccgcatggac      2160 aagcccagta actgcaccaa cgagctgtac atgatgatgc gggactgctg gcatgcagtg     2220
ccctcacaga gacccacctt caagcagctg gtggaagacc tggaccgcat cgtggccttg     2280
acctccaacc aggagtacct ggacctgtcc atgcccctgg accagtactc ccccagcttt     2340
cccgacaccc ggagctctac gtgctcctca ggggaggatt ccgtcttctc tcatgagccg     2400
ctgcccgagg agccctgcct gccccgacac ccagcccagc ttgccaatgg cggactcaaa     2460
cgccgctga                                                            2469

<210> SEQ ID NO 72
<211> LENGTH: 2409
<212> TYPE: DNA
<213> ORGANISM: Homo sapiens
<300> PUBLICATION INFORMATION:
<302> TITLE: FGFR4
<310> PATENT DOCUMENT NUMBER: XM003910

<400> SEQUENCE: 72
atgcggctgc tgctggccct gttgggggtc ctgctgagtg tgcctgggcc tccagtcttg       60
tccctggagg cctctgagga agtggagctt gagccctgcc tggctcccag cctggagcag      120
caagagcagg agctgacagt agcccttggg cagcctgtgc ggctgtgctg tgggcgggct      180
gagcgtggtg gccactggta caaggagggc agtcgcctgg cacctgctgg ccgtgtacgg      240
ggctggaggg gccgcctaga gattgccagc ttcctacctg aggatgctgg ccgctacctc      300
tgcctggcac gaggctccat gatcgtcctg cagaatctca ccttgattac aggtgactcc      360
ttgacctcca gcaacgatga tgaggacccc aagtcccata gggacctctc gaataggcac      420
agttaccccc agcaagcacc ctactggaca caccccagc gcatggagaa gaaactgcat      480
gcagtacctg cggggaacac cgtcaagttc cgctgtccag ctgcaggcaa ccccacgccc      540
accatccgct ggcttaagga tggacaggcc tttcatgggg agaaccgcat tggaggcatt      600
cggctgcgcc atcagcactg gagtctcgtg atggagagcg tggtgccctc ggaccgcggc      660
acatacacct gcctggtaga aacgctgtgt ggcagcatcc gttataacta cctgctagat      720
gtgctggagc ggtccccgca ccggcccatc ctgcaggccg gctccggc caacaccaca      780 gccgtggtgg cagcgacgt ggagctgctg tgcaaggtgt acagcgatgc ccagccccac      840
atccagtggc tgaagcacat cgtcatcaac ggcagcagct tcggagccga cggtttcccc      900
tatgtgcaag tcctaaagac tgcagacatc aatagctcag aggtggaggt cctgtacctg      960
cggaacgtgt cagccgagga cgcaggcgag tacacctgcc tcgcaggcaa ttccatcggc     1020
ctctcctacc agtctgcctg gctcacggtg ctgccagagg aggacccac atggaccgca     1080 gcagcgcccg aggccaggta tacgacatc atcctgtacg cgtcgggctc cctggccttg     1140
gctgtgctcc tgctgctggc caggctgtat cgagggcagg cgctccacgg ccggcacccc     1200
```

```
cgcccgcccg ccactgtgca gaagctctcc cgcttccctc tggcccgaca gttctccctg     1260
gagtcaggct cttccggcaa gtcaagctca tccctggtac gaggcgtgcg tctctcctcc     1320
agcggccccg ccttgctcgc cggcctcgtg agtctagatc tacctctcga cccactatgg     1380
gagttccccc gggacaggct ggtgcttggg aagcccctag gcgagggctg ctttggccag     1440
gtagtacgtg cagaggcctt tggcatggac cctgcccggc ctgaccaagc cagcactgtg     1500
gccgtcaaga tgctcaaaga caacgcctct gacaaggacc tggccgacct ggtctcggag     1560
atggaggtga tgaagctgat cggccgacac aagaacatca tcaacctgct tggtgtctgc     1620
acccaggaag ggcccctgta cgtgatcgtg gagtgcgccg ccaagggaaa cctgcgggag     1680
ttcctgcggg cccggcgccc ccaggccccc gacctcagcc ccgacggtcc tcggagcagt     1740
gaggggccgc tctccttccc agtcctggtc tcctgcgcct accaggtggc ccgaggcatg     1800
cagtatctgg agtcccggaa gtgtatccac cgggacctgg ctgcccgcaa tgtgctggtg     1860
actgaggaca atgtgatgaa gattgctgac tttgggctgg cccgcggcgt ccaccacatt     1920
gactactata agaaaaccag caacggccgc ctgcctgtga gtggatggc gcccgaggcc     1980 ttgtttgacc gggtgtacac acaccagagt gacgtgtggt cttttgggat cctgctatgg     2040
gagatcttca ccctcggggg ctccccgtat cctggcatcc cggtggagga gctgttctcg     2100
ctgctgcggg agggacatcg gatggaccga ccccacact gcccccaga gctgtacggg     2160 ctgatgcgtg agtgctggca cgcagcgccc tcccagaggc ctaccttcaa gcagctggtg     2220
gaggcgctgg acaaggtcct gctggccgtc tctgaggagt acctcgacct ccgcctgacc     2280
ttcggaccct attccccctc tggtggggac gccagcagca cctgctcctc cagcgattct     2340
gtcttcagcc acgaccccct gccattggga tccagctcct tccccttcgg gtctggggtg     2400
cagacatga                                                             2409

<210> SEQ ID NO 73
<211> LENGTH: 1695
<212> TYPE: DNA
<213> ORGANISM: Homo sapiens
<300> PUBLICATION INFORMATION:
<302> TITLE: MT2MMP
<310> PATENT DOCUMENT NUMBER: D86331

<400> SEQUENCE: 73
atgaagcggc cccgctgtgg ggtgccagac cagttcgggg tacgagtgaa agccaacctg       60
cggcggcgtc ggaagcgcta cgccctcacc gggaggaagt ggaacaacca ccatctgacc      120
tttagcatcc agaactacac ggagaagttg ggctggtacc actcgatgga ggcggtgcgc      180
agggccttcc gcgtgtggga gcaggccacg cccctggtct tccaggaggt gcccatgag      240 gacatccggc tgcggcgaca gaaggaggcc gacatcatgg tactctttgc ctctggcttc      300
cacggcgaca gctcgccgtt tgatggcacc ggtggctttc tggcccacgc ctatttccct      360
ggccccggcc taggcgggga cacccatttt gacgcagatg agccctggac cttctccagc      420
actgacctgc atgaaacaa cctcttcctg gtggcagtgc atgagctggg ccacgcgctg      480
gggctggagc actccagcaa ccccaatgcc atcatggcgc cgttctacca gtggaaggac      540
gttgacaact tcaagctgcc cgaggacgat ctcgtggca tccagcagct ctacggtacc      600
ccagacggtc agccacagcc tacccagcct ctccccactg tgacgccacg gcggccaggc      660
cggcctgacc accggccgcc ccggcctccc agccaccac cccaggtgg aagccagag      720 cggcccccaa agccgggccc cccagtccag ccccgagcca cagagcggcc cgaccagtat      780
```

```
ggccccaaca tctgcgacgg ggactttgac acagtggcca tgcttcgcgg ggagatgttc    840
gtgttcaagg gccgctggtt ctggcgagtc cggcacaacc gcgtcctgga caactatccc    900
atgcccatcg gcacttctg gcgtggtctg cccggtgaca tcagtgctgc ctacgagcgc    960
caagacggtc gttttgtctt tttcaaggt gaccgctact ggctctttcg agaagcgaac   1020
ctggagcccg gctacccaca gccgctgacc agctatggcc tgggcatccc ctatgaccgc   1080
attgacacgg ccatctggtg ggagcccaca ggccacacct tcttcttcca agaggacagg   1140
tactggcgct tcaacgagga gacacagcgt ggagaccctg ggtaccccaa gcccatcagt   1200
gtctggcagg ggatccctgc ctcccctaaa ggggccttcc tgagcaatga cgcagcctac   1260
acctacttct acaagggcac caaatactgg aaattcgaca tgagcgcct gcggatggag   1320 cccggctacc ccaagtccat cctgcgggac ttcatgggct gccaggagca cgtggagcca   1380
ggcccccgat ggcccgacgt ggcccggccg cccttcaacc ccacgggggg tgcagagccc   1440
ggggcggaca cgcagagggg cgacgtgggg gatgggggatg gggactttgg ggccgggggtc   1500 aacaaggaca gggggcagccg cgtggtggtg cagatggagg aggtggcacg gacggtgaac   1560
gtggtgatgg tgctggtgcc actgctgctg ctgctctgcg tcctgggcct cacctacgcg   1620
ctggtgcaga tgcagcgcaa gggtgcgcca cgtgtcctgc tttactgcaa gcgctcgctg   1680
caggagtggg tctga                                                    1695
```

```
<210> SEQ ID NO 74
<211> LENGTH: 1824
<212> TYPE: DNA
<213> ORGANISM: Homo sapiens
<300> PUBLICATION INFORMATION:
<302> TITLE: MT3MMP
<310> PATENT DOCUMENT NUMBER: D85511

<400> SEQUENCE: 74
atgatcttac tcacattcag cactggaaga cggttggatt tcgtgcatca ttcgggggtg     60
tttttcttgc aaaccttgct ttggatttta tgtgctacag tctgcggaac ggagcagtat    120
ttcaatgtgg aggtttggtt acaaaagtac ggctaccttc caccgactga ccccagaatg    180
tcagtgctgc gctctgcaga gaccatgcag tctgccctag ctgccatgca gcagttctat    240
ggcattaaca tgacaggaaa agtggacaga aacacaattg actggatgaa gaagcccga    300 tgcggtgtac ctgaccagac aagaggtagc tccaaatttc atattcgtcg aaagcgatat    360
gcattgacag acagaaatg gcagcacaag cacatcactt acagtataaaa gaacgtaact    420 ccaaaagtag gagaccctga gactcgtaaa gctattcgcc gtgcctttga tgtgtggcag    480
aatgtaactc ctctgacatt tgaagaagtt ccctacagtg aattagaaaa tggcaaacgt    540
gatgtggata taaccattat ttttgcatct ggtttccatg gggacagctc tccctttgat    600
ggagagggag gattttttggc acatgcctac ttccctggac caggaattgg aggagatacc    660
cattttgact cagatgagcc atggacacta ggaaatccta atcatgatgg aaatgactta    720
tttcttgtag cagtccatga actgggacat gctctgggat tgagcattc caatgacccc    780 actgccatca tggctccatt ttaccagtac atggaaacag acaacttcaa actacctaat    840
gatgatttac agggcatcca gaagatatat ggtccacctg caagattcc tccacctaca    900 agacctctac cgacagtgcc cccacacccgc tctattcctc cggctgaccc aaggaaaaat   960
gacaggccaa aacctcctcg gcctccaacc ggcagaccct cctatcccgg agccaaaccc   1020
aacatctgtg atgggaactt taacactcta gctattcttc gtcgtgagat gtttgttttc   1080
```

| | |
|---|---|
| aaggaccagt ggttttggcg agtgagaaac aacagggtga tggatggata cccaatgcaa | 1140 |
| attacttact tctggcgggg cttgcctcct agtatcgatg cagtttatga aaatagcgac | 1200 |
| gggaattttg tgttctttaa aggtaacaaa tattgggtgt tcaaggatac aactcttcaa | 1260 |
| cctggttacc ctcatgactt gataacccTt ggaagtggaa ttccccctca tggtattgat | 1320 |
| tcagccattt ggtgggagga cgtcgggaaa acctatttct tcaagggaga cagatattgg | 1380 |
| agatatagtg aagaaatgaa aacaatggac cctggctatc ccaagccaat cacagtctgg | 1440 |
| aaagggatcc ctgaatctcc tcagggagca tttgtacaca agaaaatgg ctttacgtat | 1500 |
| ttctacaaag gaaggagta ttggaaattc aacaaccaga tactcaaggt agaacctgga | 1560 |
| tatccaagat ccatcctcaa ggattttatg ggctgtgatg gaccaacaga cagagttaaa | 1620 |
| gaaggacaca gcccaccaga tgatgtagac attgtcatca aactggacaa cacagccagc | 1680 |
| actgtgaaag ccatagctat tgtcattccc tgcatcttgg ccttatgcct ccttgtattg | 1740 |
| gtttacactg tgttccagtt caagaggaaa ggaacacccc gccacatact gtactgtaaa | 1800 |
| cgctctatgc aagagtgggt gtga | 1824 |

```
<210> SEQ ID NO 75
<211> LENGTH: 1818
<212> TYPE: DNA
<213> ORGANISM: Homo sapiens
<300> PUBLICATION INFORMATION:
<302> TITLE: MT4MMP
<310> PATENT DOCUMENT NUMBER: AB021225

<400> SEQUENCE: 75
```

| | |
|---|---|
| atgcggcgcc gcgcagcccg gggacccggc ccgccgcccc cagggcccgg actctcgcgg | 60 |
| ctgccgctgc tgccgctgcc gctgctgctg ctgctggcgc tggggacccg cgggggctgc | 120 |
| gccgcgccgg aacccgcgcg gcgcgccgag gacctcagcc tgggagtgga gtggctaagc | 180 |
| aggttcggtt acctgccccc ggctgacccc acaacagggc agctgcagac gcaagaggag | 240 |
| ctgtctaagg ccatcacagc catgcagcag tttggtggcc tggaggccac cggcatcctg | 300 |
| gacgaggcca cctggccct gatgaaaacc ccacgctgct ccctgccaga cctccctgtc | 360 |
| ctgacccagg ctcgcaggag acgccaggct ccagccccca ccaagtggaa caagaggaac | 420 |
| ctgtcgtgga gggtccggac gttcccacg gactcaccac tggggcacga cacggtgcgt | 480 |
| gcactcatgt actacgccct caaggtctgg agcgacattg cgccctgaa cttccacgag | 540 |
| gtggcgggca gcaccgccga catccagatc gacttctcca aggccgacca taacgacggc | 600 |
| tacccccttcg acgccggcg gcaccgtgcc cacgccttct tccccggcca ccaccacacc | 660 |
| gccgggtaca cccactttaa cgatgacgag gcctggacct tccgctcctc ggatgcccac | 720 |
| gggatggacc tgtttgcagt ggctgtccac gagtttggcc acgccattgg gttaagccat | 780 |
| gtggccgctg cacactccat catgcggccg tactaccagg gccggtggg tgacccgctg | 840 |
| cgctacgggc tcccctacga ggacaaggtg cgcgtctggc agctgtacgg tgtgcgggag | 900 |
| tctgtgtctc ccacgcgca gcccgaggag cctcccctgc tgccggagcc cccagacaac | 960 |
| cggtccagcg ccccgcccag gaaggacgtg ccccacagat gcagcactca ctttgacgcg | 1020 |
| gtggcccaga tccggggtga agcttttcttc ttcaaaggca gtacttctg gcggctgacg | 1080 |
| cgggaccggc acctggtgtc cctgcagccg gcacagatgc accgcttctg gcggggcctg | 1140 |
| ccgctgcacc tggacagcgt ggacgccgtg tacgagcgca ccagcgacca caagatcgtc | 1200 |
| ttctttaaag gagacaggta ctgggtgttc aaggacaata cgtagagga aggatacccg | 1260 |

```
cgccccgtct ccgacttcag cctcccgcct ggcggcatcg acgctgcctt ctcctgggcc    1320
cacaatgaca ggacttattt ctttaaggac cagctgtact ggcgctacga tgaccacacg    1380
aggcacatgg accccggcta ccccgcccag agcccctgt ggaggggtgt cccagcacg      1440 ctggacgacg ccatgcgctg gtccgacggt gcctcctact tcttccgtgg ccaggagtac    1500
tggaaagtgc tggatggcga gctggaggtg cacccgggt acccacagtc cacggcccgg     1560
gactggctgg tgtgtggaga ctcacaggcc gatggatctg tggctgcggg cgtggacgcg    1620
gcagaggggc ccgcgcccc tccaggacaa catgaccaga gccgctcgga ggacggttac     1680
gaggtctgct catgcacctc tggggcatcc tctccccgg ggccccagg cccactggtg       1740 gctgccacca tgctgctgct gctgccgcca ctgtcaccag gcgccctgtg gacagcggcc    1800
caggccctga cgctatga                                                   1818

<210> SEQ ID NO 76
<211> LENGTH: 1938
<212> TYPE: DNA
<213> ORGANISM: Homo sapiens
<300> PUBLICATION INFORMATION:
<302> TITLE: MT5MMP
<310> PATENT DOCUMENT NUMBER: AB021227

<400> SEQUENCE: 76
atgccgagga gccggggcgg ccgcgccgcg ccggggccgc cgccgccgcc gccgccgccg     60
ggccaggccc cgcgctggag ccgctggcgg gtccctgggc ggctgctgct gctgctgctg    120
cccgcgctct gctgcctccc gggcgccgcg cgggcggcgg cggcggcggc gggggcaggg    180
aaccgggcag cggtggcggt ggcggtggcg cgggcggacg aggcggaggc gcccttcgcc    240
gggcagaact ggttaaagtc ctatggctat ctgcttccct atgactcacg ggcatctgcg    300
ctgcactcag cgaaggcctt gcagtcggca gtctccacta tgcagcagtt ttacgggatc    360
ccggtcaccg tgtgttgga tcagacaacg atcgagtgga tgaagaaacc ccgatgtggt    420
gtccctgatc acccccactt aagccgtagg cggagaaaca agcgctatgc cctgactgga    480
cagaagtgga ggcaaaaaca catcacctac agcattcaca actataccc aaaagtgggt     540 gagctagaca cgcggaaagc tattcgccag gctttcgatg tgtggcagaa ggtgaccccca   600 ctgaccttg aagaggtgcc ataccatgag atcaaaagtg accggaagga ggcagacatc     660
atgatctttt ttgcttctgg tttccatggc acagctccc catttgatgg agaagggga     720 ttcctggccc atgcctactt ccctggccca gggattggag agacacca ctttgactcc      780 gatgagccat ggacgctagg aaacgccaac catgacggga acgacctctt cctggtggct    840
gtgcatgagc tgggccacgc gctgggactg agcactcca gcgaccccag cgccatcatg     900
gcgcccttct accagtacat ggagacgcac aacttcaagc tgccccagga cgatctccag    960
ggcatccaga gatctatgg accccagcc gagcctctgg agcccacaag gccactccct     1020
acactccccg tccgcaggat ccactcacca tcggagagga acacgagcg ccagcccagg    1080 cccctcggc cgcccctcgg ggaccggcca tccacaccag gcaccaaacc caacatctgt   1140
gacggcaact tcaacacagt ggccctcttc cggggcgaga tgtttgtctt taaggatcgc    1200
tggttctggc gtctgcgcaa taaccgagtc caggagggct acccccatgca gatcgagcag   1260 ttctggaagg gcctgcctgc ccgcatcgac gcagcctatg aaagggccga tgggagattt    1320
gtcttcttca aggtgacaa gtattgggtg tttaaggagg tgacggtgga gcctgggtac     1380
ccccacagcc tgggggagct gggcagctgt ttgccccgtg aaggcattga cacagctctg    1440
```

-continued

| cgctgggaac ctgtgggcaa gacctacttt ttcaaaggcg agcggtactg gcgctacagc | 1500 |
| gaggagcggc gggccacgga ccctggctac cctaagccca tcaccgtgtg aagggcatc | 1560 |
| ccacaggctc cccaaggagc cttcatcagc aaggaaggat attacaccta tttctacaag | 1620 |
| ggccgggact actggaagtt tgacaaccag aaactgagcg tggagccagg ctacccgcgc | 1680 |
| aacatcctgc gtgactggat gggctgcaac cagaaggagg tggagcggcg aaggagcgg | 1740 |
| cggctgcccc aggacgacgt ggacatcatg gtgaccatca cgatgtgcc gggctccgtg | 1800 |
| aacgccgtgg ccgtggtcat cccctgcatc ctgtccctct gcatcctggt gctggtctac | 1860 |
| accatcttcc agttcaagaa caagacaggc cctcagcctg tcacctacta taagcggcca | 1920 |
| gtccaggaat gggtgtga | 1938 |

```
<210> SEQ ID NO 77
<211> LENGTH: 1689
<212> TYPE: DNA
<213> ORGANISM: Homo sapiens
<300> PUBLICATION INFORMATION:
<302> TITLE: MT6MMP
<310> PATENT DOCUMENT NUMBER: AJ27137

<400> SEQUENCE: 77
```

| atgcggctgc ggctccggct tctggcgctg ctgcttctgc tgctggcacc gcccgcgcgc | 60 |
| gccccgaagc cctcggcgca ggacgtgagc ctgggcgtgg actggctgac tcgctatggt | 120 |
| tacctgccgc caccccaccc tgcccaggcc cagctgcaga gccctgagaa gttgcgcgat | 180 |
| gccatcaaag tcatgcagag gttcgcgggg ctgccggaga ccggccgcat ggacccaggg | 240 |
| acagtggcca ccatgcgtaa gccccgctgc tccctgcctg acgtgctggg ggtggcgggg | 300 |
| ctggtcaggc ggcgtcgccg gtacgctctg agcggcagcg tgtggaagaa gcgaaccctg | 360 |
| acatggaggg tacgttcctt cccccagagc tcccagctga gccaggagac cgtgcgggtc | 420 |
| ctcatgagct atgccctgat ggcctggggc atggagtcag gcctcacatt tcatgaggtg | 480 |
| gattcccccc agggccagga gcccgacatc ctcatcgact ttgcccgcgc cttccaccag | 540 |
| gacagctacc cctttgacgg gttggggggc accctagccc atgccttctt ccctggggag | 600 |
| cacccccatct ccggggacac tcactttgac gatgaggaga cctggacttt tgggtcaaaa | 660 |
| gacgcgagg ggaccgacct gtttgccgtg gctgtccatg agtttggcca cgccctgggc | 720 |
| ctgggccact cctcagcccc caactccatt atgaggccct ctaccaggg tccggtgggc | 780 |
| gaccctgaca gtaccgcct gtctcaggat gaccgcgatg gcctgcagca actctatggg | 840 |
| aaggcgcccc aaaccccata tgacaagccc acaaggaaac ccctggctcc tccgcccag | 900 |
| cccccggcct cgcccacaca cagcccatcc ttccccatcc ctgatcgatg tgagggcaat | 960 |
| tttgacgcca tcgccaacat ccgaggggaa actttcttct tcaaaggccc ctggttctgg | 1020 |
| cgcctccagc cctccggaca gctggtgtcc ccgcgacccg cacggctgca ccgcttctgg | 1080 |
| gaggggctgc ccgcccaggt gagggtggtg caggccgcct atgctcggca ccgagacggc | 1140 |
| cgaatcctcc tctttagcgg gccccagttc tgggtgttcc aggaccggca gctggagggc | 1200 |
| ggggcgcggc cgctcacgga gctggggctg ccccgggag aggaggtgga cgccgtgttc | 1260 |
| tcgtggccac agaacgggaa gacctacctg gtccgcggcc ggcagtactg gcgctacgac | 1320 |
| gaggcggcgg cgcgcccgga cccggctac cctcgcgacc tgagcctctg ggaaggcgcg | 1380 |
| cccccctccc ctgacgatgt caccgtcagc aacgcaggtg acacctactt cttcaagggc | 1440 |
| gcccactact ggcgcttccc caagaacagc atcaagaccg agccggacgc ccccagccc | 1500 |

| | |
|---|---|
| atgggccca actggctgga ctgccccgcc ccgagctctg gtccccgcgc ccccaggccc | 1560 |
| cccaaagcga cccccgtgtc cgaaacctgc gattgtcagt gcgagctcaa ccaggccgca | 1620 |
| ggacgttggc ctgctcccat cccgctgctc ctcttgcccc tgctggtggg gggtgtagcc | 1680 |
| tcccgctga | 1689 |

<210> SEQ ID NO 78
<211> LENGTH: 1749
<212> TYPE: DNA
<213> ORGANISM: Homo sapiens
<300> PUBLICATION INFORMATION:
<302> TITLE: MTMMP
<310> PATENT DOCUMENT NUMBER: X90925

<400> SEQUENCE: 78

| | |
|---|---|
| atgtctcccg ccccaagacc ctcccgttgt ctcctgctcc ccctgctcac gctcggcacc | 60 |
| gcgctcgcct ccctcggctc ggcccaaagc agcagcttca gccccgaagc ctggctacag | 120 |
| caatatggct acctgcctcc cggggaccta cgtacccaca cacagcgctc accccagtca | 180 |
| ctctcagcgg ccatcgctgc catgcagaag ttttacggct tgcaagtaac aggcaaagct | 240 |
| gatgcagaca ccatgaaggc catgaggcgc ccccgatgtg gtgttccaga caagtttggg | 300 |
| gctgagatca aggccaatgt tcgaaggaag cgctacgcca tccagggtct caaatggcaa | 360 |
| cataatgaaa tcactttctg catccagaat tacaccccca aggtgggcga gtatgccaca | 420 |
| tacgaggcca ttcgcaaggc gttccgcgtg tgggagagtg ccacaccact gcgcttccgc | 480 |
| gaggtgccct atgcctacat ccgtgagggc catgagaagc aggccgacat catgatcttc | 540 |
| tttgccgagg gcttccatgg cgacagcacg cccttcgatg gtgagggcgg cttcctggcc | 600 |
| catgcctact cccagggccc caacattgga ggagacaccc actttgactc tgccgagcct | 660 |
| tggactgtca ggaatgagga tctgaatgga aatgacatct tcctggtggc tgtgcacgag | 720 |
| ctgggccatg ccctggggct cgagcattcc agtgaccccct cggccatcat ggcacccttt | 780 |
| taccagtgga tggacacgga gaattttgtg ctgcccgatg atgaccgccg gggcatccag | 840 |
| caactttatg ggggtgagtc agggttcccc accaagatgc cccctcaacc caggactacc | 900 |
| tcccggcctt ctgttcctga taaacccaaa aaccccacct atgggcccaa catctgtgac | 960 |
| gggaactttg acaccgtggc catgctccga ggggagatgt ttgtcttcaa ggagcgctgg | 1020 |
| ttctggcggg tgaggaataa ccaagtgatg gatggatacc caatgcccat tggccagttc | 1080 |
| tggcggggcc tgcctgcgtc catcaacact gcctacgaga ggaaggatgg caaattcgtc | 1140 |
| ttcttcaaag gagacaagca ttgggtgttt gatgaggcgt ccctggaacc tggctacccc | 1200 |
| aagcacatta ggagctgggc cgagggctgc ctaccgaca agattgatgc tgctctcttc | 1260 |
| tggatgccca atggaaagac ctacttcttc cgtggaaaca agtactaccg tttcaacgaa | 1320 |
| gagctcaggg cagtggatag cgagtacccc aagaacatca agtctggga agggatccct | 1380 |
| gagtctccca gagggtcatt catgggcagc gatgaagtct tcacttactt ctacaagggg | 1440 |
| aacaaatact ggaaattcaa caaccagaag ctgaaggtag aaccgggcta ccccaagcca | 1500 |
| gccctgaggg actggatggg ctgcccatcg ggaggccggc cggatgaggg gactgaggag | 1560 |
| gagacgagg tgatcatcat tgaggtggac gaggagggcg gcggggcggt gagcgcggct | 1620 |
| gccgtggtgc tgcccgtgct gctgctgctc ctggtgctgg cggtgggcct tgcagtcttc | 1680 |
| ttcttcagac gccatgggac ccccaggcga ctgctctact gccagcgttc cctgctggac | 1740 |
| aaggtctga | 1749 |

-continued

```
<210> SEQ ID NO 79
<211> LENGTH: 744
<212> TYPE: DNA
<213> ORGANISM: Homo sapiens
<300> PUBLICATION INFORMATION:
<302> TITLE: FGF1
<310> PATENT DOCUMENT NUMBER: XM003647

<400> SEQUENCE: 79
atggccgcgg ccatcgctag cggcttgatc cgccagaagc ggcaggcgcg ggagcagcac      60
tgggaccggc cgtctgccag caggaggcgg agcagcccca gcaagaaccg cgggctctgc     120
aacggcaacc tggtggatat cttctccaaa gtgcgcatct tcggcctcaa gaagcgcagg     180
ttgcggcgcc aagatcccca gctcaagggt atagtgacca ggttatattg caggcaaggc     240
tactacttgc aaatgcaccc cgatggagct ctcgatggaa ccaaggatga cagcactaat     300
tctacactct tcaacctcat accagtggga ctacgtgttg ttgccatcca gggagtgaaa     360
acagggttgt atatagccat gaatggagaa ggttacctct acccatcaga acttttttacc    420 cctgaatgca gtttaaaaga atctgttttt gaaaattatt atgtaatcta ctcatccatg     480
ttgtacagac aacaggaatc tggtagagcc tggttttttgg gattaaataa ggaagggcaa    540
gctatgaaag ggaacagagt aaagaaaacc aaaccagcag ctcatttcct acccaagcca    600
ttggaagttg ccatgtaccg agaaccatct ttgcatgatg ttgggaaaac ggtcccgaag     660
cctggggtga cgccaagtaa aagcacaagt gcgtctgcaa taatgaatgg aggcaaaccca    720 gtcaacaaga gtaagacaac atag                                            744

<210> SEQ ID NO 80
<211> LENGTH: 468
<212> TYPE: DNA
<213> ORGANISM: Homo sapiens
<300> PUBLICATION INFORMATION:
<302> TITLE: FGF2
<310> PATENT DOCUMENT NUMBER: NM002006

<400> SEQUENCE: 80
atggcagccg ggagcatcac cacgctgccc gccttgcccg aggatggcgg cagcggcgcc      60
ttcccgcccg ccacttcaa ggaccccaag cggctgtact gcaaaaacgg ggcttcttc      120 ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt tgaacgatt ggaatctaat aactacaata cttaccggtc aaggaaatac     360
accagttggt atgtggcact gaaacgaact gggcagtata acttggatc caaaacagga     420 cctgggcaga aagctatact tttttcttcca atgtctgcta agagctga                 468

<210> SEQ ID NO 81
<211> LENGTH: 756
<212> TYPE: DNA
<213> ORGANISM: Homo sapiens
<300> PUBLICATION INFORMATION:
<302> TITLE: FGF23
<310> PATENT DOCUMENT NUMBER: NM020638

<400> SEQUENCE: 81
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
```

```
cacctgtaca cagccacagc caggaacagc taccacctgc agatccacaa gaatggccat    180
gtggatggcg caccccatca gaccatctac agtgccctga tgatcagatc agaggatgct    240
ggctttgtgg tgattacagg tgtgatgagc agaagatacc tctgcatgga tttcagaggc    300 aacattttg gatcacacta tttcgacccg gagaactgca ggttccaaca ccagacgctg    360
gaaaacgggt acgacgtcta ccactctcct cagtatcact tcctggtcag tctgggccgg    420
gcgaagagag ccttcctgcc aggcatgaac ccaccccgt actcccagtt cctgtcccgg    480
aggaacgaga tcccctaat tcacttcaac accccatac cacggcggca cccggagc      540 gccgaggacg actcggagcg ggacccctg aacgtgctga gccccggc ccggatgacc      600 ccggccccgg cctcctgttc acaggagctc ccgagcgccg aggacaacag cccgatggcc    660
agtgacccat taggggtggt cagggccggt cgagtgaaca cgcacgctgg gggaacgggc    720
ccggaaggct gccgccccatt cgccaagttc atctag                              756

<210> SEQ ID NO 82
<211> LENGTH: 720
<212> TYPE: DNA
<213> ORGANISM: Homo sapiens
<300> PUBLICATION INFORMATION:
<302> TITLE: FGF3
<310> PATENT DOCUMENT NUMBER: NM005247

<400> SEQUENCE: 82
atgggcctaa tctggctgct actgctcagc ctgctggagc ccggctggcc cgcagcgggc    60
cctggggcgc ggttgcggcg cgatgcgggc ggccgtggcg cgtctacga gcaccttggc    120 ggggcgcccc ggcgccgcaa gctctactgc gccacgaagt accacctcca gctgcacccg    180
agcggccgcg tcaacggcag cctggagaac agcgcctaca gtattttgga gataacggca    240
gtggaggtgg gcattgtggc catcagggt ctcttctccg gcggtacct ggccatgaac     300 aagagggac gactctatgc ttcggagcac tacagcgccg agtgcgagtt tgtggagcgg    360
atccacgagc tgggctataa tacgtatgcc tcccggctgt accggacggt gtctagtacg    420
cctggggccc gccggcagcc cagcgccgag agactgtggt acgtgtctgt gaacggcaag    480
ggccggcccc gcaggggctt caagacccgc cgcacacaga gtcctccct gttcctgccc    540 cgcgtgctgg accacaggga ccacgagatg gtgcggcagc tacagagtgg gctgcccaga    600 cccctggta aggggtcca gccccgacgg cggcggcaga agcagagccc ggataacctg    660
gagccctctc acgttcaggc ttcgagactg ggctcccagc tggaggccag tgcgcactag    720

<210> SEQ ID NO 83
<211> LENGTH: 807
<212> TYPE: DNA
<213> ORGANISM: Homo sapiens
<300> PUBLICATION INFORMATION:
<302> TITLE: FGF5
<310> PATENT DOCUMENT NUMBER: NM004464

<400> SEQUENCE: 83
atgagcttgt ccttcctcct cctcctcttc ttcagccacc tgatcctcag cgcctgggct    60
cacgggagag agcgtctcgc ccccaaaggg caacccggac ccgctgccac tgataggaac    120
cctataggct ccagcagcag acagagcagc agtagcgcta tgtcttcctc ttctgcctcc    180
tcctcccccg cagcttctct gggcagccaa ggaagtggct tggagcagag cagtttccag    240 tggagccccat cggggcgccg gaccggcagc ctctactgca gagtgggcat cggtttccat    300
ctgcagatct acccggatgg caaagtcaat ggatcccacg aagccaatat gttaagtgtt    360
```

-continued

```
ttggaaatat tgctgtgtc tcagggatt gtaggaatac gaggagtttt cagcaacaaa      420
tttttagcga tgtcaaaaaa aggaaaactc catgcaagtg ccaagttcac agatgactgc      480
aagttcaggg agcgttttca agaaaatagc tataatacct atgcctcagc aatacataga      540
actgaaaaaa cagggcggga gtggtatgtt gccctgaata aagaggaaa agccaaacga       600 gggtgcagcc cccgggttaa accccagcat atctctaccc attttcttcc aagattcaag      660
cagtcggagc agccagaact ttctttcacg gttactgttc ctgaaaagaa aaatccacct      720
agccctatca agtcaaagat tccccttcct gcacctcgga aaaataccaa ctcagtgaaa      780
tacagactca agtttcgctt tggataa                                          807
```

<210> SEQ ID NO 84
<211> LENGTH: 649
<212> TYPE: DNA
<213> ORGANISM: Homo sapiens
<300> PUBLICATION INFORMATION:
<302> TITLE: FGF8
<310> PATENT DOCUMENT NUMBER: NM006119

<400> SEQUENCE: 84

```
atgggcagcc cccgctccgc gctgagctgc ctgctgttgc acttgctggt cctctgcctc       60
caagcccagg taactgttca gtcctcacct aattttacac agcatgtgag ggagcagagc      120
ctggtgacgg atcagctcag ccgccgcctc atccggacct accaactcta cagccgcacc      180
agcgggaagc acgtgcaggt cctggccaac aagcgcatca cgccatggc agaggacggc      240 gacccctccg caaagctcat cgtggagacg gacacctttg aagcagagt tcgagtccga      300 ggagccgaga cgggcctcta catctgcatg aacaagaagg ggaagctgat cgccaagagc      360
aacggcaaag gcaaggactg cgtcttcacg gagattgtgc tggagaacaa ctacacagcg      420
ctgcagaatg ccaagtacga gggctggtac atggccttca cccgcaaggg ccggcccccgc     480 aagggctcca agacgcggca gcaccagcgt gaggtccact tcatgaagcg gctgccccgg      540
ggccaccaca ccaccgagca gagcctgcgc ttcgagttcc tcaactaccc gcccttcacg      600
cgcagcctgc gcggcagcca gaggacttgg gccccggaac ccgatagg                   649
```

<210> SEQ ID NO 85
<211> LENGTH: 2466
<212> TYPE: DNA
<213> ORGANISM: Homo sapiens
<300> PUBLICATION INFORMATION:
<302> TITLE: FGFR2
<310> PATENT DOCUMENT NUMBER: NM000141

<400> SEQUENCE: 85

```
atggtcagct ggggtcgttt catctgcctg gtcgtggtca ccatggcaac cttgtccctg       60
gcccggccct ccttcagttt agttgaggat accacattag agccagaaga gccaccaacc      120
aaataccaaa tctctcaacc agaagtgtac gtggctgcgc caggggagtc gctagaggtg      180
cgctgcctgt tgaaagatgc cgccgtgatc agttggacta aggatgggt gcacttgggg      240 cccaacaata ggacagtgct tattggggag tacttgcaga taaagggcgc cacgcctaga      300
gactccggcc tctatgcttg tactgccagt aggactgtag acagtgaaac ttggtacttc      360
atggtgaatg tcacagatgc catctcatcc ggagatgatg aggatgacac cgatggtgcg      420
gaagattttg tcagtgagaa cagtaacaac aagagagcac catactggac caacacagaa      480
aagatggaaa agcggctcca tgctgtgcct gcggccaaca ctgtcaagtt tcgctgccca      540
```

```
gccgggggga acccaatgcc aaccatgcgg tggctgaaaa acgggaagga gtttaagcag      600
gagcatcgca ttggaggcta caaggtacga aaccagcact ggagcctcat tatggaaagt      660
gtggtcccat ctgacaaggg aaattatacc tgtgtggtgg agaatgaata cgggtccatc      720
aatcacacgt accacctgga tgttgtggag cgatcgcctc accggcccat cctccaagcc      780
ggactgccgg caaatgcctc acagtggtc ggaggagacg tagagtttgt ctgcaaggtt       840
tacagtgatg cccagcccca catccagtgg atcaagcacg tggaaaagaa cggcagtaaa      900
tacgggcccg acgggctgcc ctacctcaag gttctcaagg ccgccggtgt taacaccacg      960
gacaaagaga ttgaggttct ctatattcgg aatgtaactt ttgaggacgc tggggaatat     1020
acgtgcttgg cgggtaattc tattgggata tcctttcact ctgcatggtt gacagttctg     1080
ccagcgcctg aagagaaaa ggagattaca gcttccccag actacctgga gatagccatt      1140
tactgcatag gggtcttctt aatcgcctgt atggtggtaa cagtcatcct gtgccgaatg     1200
aagaacacga ccaagaagcc agacttcagc agccagccgg ctgtgcacaa gctgaccaaa     1260
cgtatccccc tgcggagaca ggtaacagtt tcggctgagt ccagctcctc catgaactcc     1320
aacacccccg tggtgaggat aacaacacgc ctctcttcaa cggcagacac ccccatgctg     1380 gcagggtct ccgagtatga acttccagag gacccaaaat gggagtttcc aagagataag      1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
ccacccggga tggagtactc ctatgacatt aaccgtgttc ctgaggagca gatgaccttc     1800
aaggacttgg tgtcatgcac ctaccagctg gccagaggca tggagtactt ggcttcccaa     1860
aaatgtattc atcgagattt agcagccaga aatgttttgg taacagaaaa caatgtgatg     1920
aaaatagcag actttggact cgccagagat atcaacaata tagactatta caaaaagacc     1980
accaatgggc ggcttccagt caagtggatg gctccagaag ccctgtttga tagagtatac     2040
actcatcaga gtgatgtctg gtccttcggg gtgttaatgt gggagatctt cactttaggg     2100
ggctcgccct acccagggat tcccgtggag gaactttta agctgctgaa ggaaggacac     2160
agaatggata gccagccaa ctgcaccaac gaactgtaca tgatgatgag ggactgttgg     2220
catgcagtgc cctcccagag accaacgttc aagcagttgg tagaagactt ggatcgaatt     2280
ctcactctca caaccaatga ggaatacttg gacctcagcc aacctctcga acagtattca     2340
cctagttacc ctgacacaag aagttcttgt tcttcaggag atgattctgt tttttctcca     2400
gaccccatgc cttacgaacc atgccttcct cagtatccac acataaacgg cagtgttaaa     2460
acatga                                                                2466

<210> SEQ ID NO 86
<211> LENGTH: 2421
<212> TYPE: DNA
<213> ORGANISM: Homo sapiens
<300> PUBLICATION INFORMATION:
<302> TITLE: FGFR3
<310> PATENT DOCUMENT NUMBER: NM000142

<400> SEQUENCE: 86
atgggcgccc ctgcctgcgc cctcgcgctc tgcgtggccg tggccatcgt ggccggcgcc      60
```

-continued

| | |
|---|---|
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtcccccgc ccgggggtgg tcccatgggg cccactgtct gggtcaagga tggcacaggg | 240 |
| ctggtgccct cggagcgtgt cctggtgggg ccccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga cgctccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga acggcagcaa ggtgggcccg | 900 |
| gacggcacac cctacgttac cgtgctcaag acggcgggcg ctaacaccac cgacaaggag | 960 |
| ctagaggttc tctccttgca caacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg gcggctgtga cgctctgccg cctgcgcagc | 1200 |
| ccccccaaga aaggcctggg ctcccccacc gtgcacaaga tctcccgctt cccgctcaag | 1260 |
| cgacaggtgt ccctggagtc caacgcgtcc atgagctcca acacaccact ggtgcgcatc | 1320 |
| gcaaggctgt cctcagggga gggccccacg ctggccaatg tctccgagct cgagctgcct | 1380 |
| gccgacccca atgggagctg tctcgggccc cggctgaccc tgggcaagcc ccttggggag | 1440 |
| ggctgcttcg ccaggtggt catggcggag ccatcggca ttgacaagga ccgggccgcc | 1500 |
| aagcctgtca ccgtagccgt gaagatgctg aaagacgatg ccactgacaa ggacctgtcg | 1560 |
| gacctggtgt ctgagatgga gatgatgaag atgatcggga acacaaaaaa catcatcaac | 1620 |
| ctgctgggcg cctgcacgca gggcgggccc ctgtacgtgc tggtggagta cgcggccaag | 1680 |
| ggtaacctgc gggagtttct gcgggcgcgg cggccccgg gcctggacta ctccttcgac | 1740 |
| acctgcaagc cgcccgagga gcagctcacc ttcaaggacc tggtgtcctg tgcctaccag | 1800 |
| gtggcccggg gcatggagta cttggcctcc agaagtgca tccacaggga cctggctgcc | 1860 |
| cgcaatgtgc tggtgaccga ggacaacgtg atgaagatcg cagacttcgg gctggcccgg | 1920 |
| gacgtgcaca acctcgacta ctacaagaag acaaccaacg gccggctgcc cgtgaagtgg | 1980 |
| atggcgcctg aggccttgtt tgaccgagtc tacactcacc agagtgacgt ctggtccttt | 2040 |
| ggggtcctgc tctgggagat cttcacgctg ggggctccc cgtaccccgg catccctgtg | 2100 |
| gaggagctct tcaagctgct gaaggagggc caccgcatgg acaagcccgc caactgcaca | 2160 |
| cacgacctgt acatgatcat gcgggagtgc tggcatgccg cgccctccca gaggcccacc | 2220 |
| ttcaagcagc tggtggagga cctggaccgt gtccttaccg tgacgtccac cgacgagtac | 2280 |
| ctggacctgt cggcgccttt cgagcagtac tccccgggtg gccaggacac cccagctcc | 2340 |
| agctcctcag gggacgactc cgtgtttgcc cacgacctgc tgcccccggc cccacccagc | 2400 |
| agtgggggct cgcggacgtg a | 2421 |

<210> SEQ ID NO 87
<211> LENGTH: 2102
<212> TYPE: DNA
<213> ORGANISM: Homo sapiens
<300> PUBLICATION INFORMATION:
<302> TITLE: HGF
<310> PATENT DOCUMENT NUMBER: E08541

<400> SEQUENCE: 87

| | | | | | |
|---|---|---|---|---|---|
| atgcagaggg | acaaaggaaa | agaagaaata | caattcatga | attcaaaaaa | tcagcaaaga | 60 |
| ctaccctaat | caaatagat | ccagcactga | agataaaaac | caaaaagtg | aatactgcag | 120 |
| accaatgtgc | taatagatgt | actaggaata | aaggacttcc | attcacttgc | aaggcttttg | 180 |
| tttttgataa | agcaagaaaa | caatgcctct | ggttcccctt | caatagcatg | tcaagtggag | 240 |
| tgaaaaaga | atttggccat | gaatttgacc | tctatgaaaa | caaagactac | attagaaact | 300 |
| gcatcattgg | taaggacgc | agctacaagg | gaacagtatc | tatcactaag | agtggcatca | 360 |
| aatgtcagcc | ctggagttcc | atgataccac | acgaacacag | cttttttgcct | tcgagctatc | 420 |
| ggggtaaaga | cctacaggaa | aactactgtc | gaaatcctcg | aggggaagaa | ggggaccct | 480 |
| ggtgtttcac | aagcaatcca | gaggtacgct | acgaagtctg | tgacattcct | cagtgttcag | 540 |
| aagttgaatg | catgacctgc | aatggggaga | gttatcgagg | tctcatggat | catacagaat | 600 |
| caggcaagat | ttgtcagcgc | tgggatcatc | agacaccaca | ccggcacaaa | ttcttgcctg | 660 |
| aaagatatcc | cgacaaggc | tttgatgata | attattgccg | caatcccgat | ggccagccga | 720 |
| ggccatggtg | ctatactctt | gaccctcaca | cccgctggga | gtactgtgca | attaaaacat | 780 |
| gcgctgacaa | tactatgaat | gacactgatg | ttcctttgga | aacaactgaa | tgcatccaag | 840 |
| gtcaaggaga | aggctacagg | ggcactgtca | ataccatttg | gaatggaatt | ccatgtcagc | 900 |
| gttgggattc | tcagtatcct | cacgagcatg | acatgactcc | tgaaaatttc | aagtgcaagg | 960 |
| acctacgaga | aaattactgc | cgaaatccag | atggggtctga | atcaccctgg | tgttttacca | 1020 |
| ctgatccaaa | catccgagtt | ggctactgct | cccaaattcc | aaactgtgat | atgtcacatg | 1080 |
| gacaagattg | ttatcgtggg | aatggcaaaa | attatatggg | caacttatcc | caaacaagat | 1140 |
| ctggactaac | atgttcaatg | tgggacaaga | acatggaaga | cttacatcgt | catatcttct | 1200 |
| gggaaccaga | tgcaagtaag | ctgaatgaga | attactgccg | aaatccagat | gatgatgctc | 1260 |
| atggaccctg | gtgctacacg | ggaaatccac | tcattccttg | ggattattgc | cctatttctc | 1320 |
| gttgtgaagg | tgataccaca | cctacaatag | tcaatttaga | ccatcccgta | atatcttgtg | 1380 |
| ccaaaaggaa | acaattgcga | gttgtaaatg | ggattccaac | acgaacaaac | ataggatgga | 1440 |
| tggttagttt | gagatacaga | aataaacata | tctgcggagg | atcattgata | aaggagagtt | 1500 |
| gggttcttac | tgcacgacag | tgtttccctt | ctcgagactt | gaaagattat | gaagcttggc | 1560 |
| ttggaattca | tgatgtccac | ggaagaggag | atgagaaatg | caaacaggtt | ctcaatgttt | 1620 |
| cccagctggt | atatggccct | gaaggatcag | atctggtttt | aatgaagctt | gccaggcctg | 1680 |
| ctgtcctgga | tgatttttgtt | agtacgattg | atttacctaa | ttatgatgc | acaattcctg | 1740 |
| aaaagaccag | ttgcagtgtt | tatggctggg | gctacactgg | attgatcaac | tatgatggcc | 1800 |
| tattacgagt | ggcacatctc | tatataatgg | aaatgagaa | atgcagccag | catcatcgag | 1860 |
| ggaaggtgac | tctgaatgag | tctgaaatat | gtgctgggc | tgaaaagatt | ggatcaggac | 1920 |
| catgtgaggg | ggattatggt | ggcccacttg | tttgtgagca | acataaaatg | agaatggttc | 1980 |
| ttggtgtcat | tgttcctggt | cgtggatgtg | ccattccaaa | tcgtcctggt | atttttgtcc | 2040 |

-continued

| | |
|---|---|
| gagtagcata ttatgcaaaa tggatacaca aaattatttt aacatataag gtaccacagt | 2100 |
| ca | 2102 |

<210> SEQ ID NO 88
<211> LENGTH: 360
<212> TYPE: DNA
<213> ORGANISM: Homo sapiens
<300> PUBLICATION INFORMATION:
<302> TITLE: ID3
<310> PATENT DOCUMENT NUMBER: XM001539

<400> SEQUENCE: 88

| | |
|---|---|
| atgaaggcgc tgagcccggt gcgcggctgc tacgaggcgg tgtgctgcct gtcggaacgc | 60 |
| agtctggcca tcgcccgggg ccgagggaag ggcccggcag ctgaggagcc gctgagcttg | 120 |
| ctggacgaca tgaaccactg ctactcccgc ctgcgggaac tggtacccgg agtcccgaga | 180 |
| ggcactcagc ttagccaggt ggaaatccta cagcgcgtca tcgactacat tctcgacctg | 240 |
| caggtagtcc tggccgagcc agcccctgga ccccctgatg gcccccacct tcccatccag | 300 |
| acagccgagc tcactccgga acttgtcatc tccaacgaca aaaggagctt ttgccactga | 360 |

<210> SEQ ID NO 89
<211> LENGTH: 743
<212> TYPE: DNA
<213> ORGANISM: Homo sapiens
<300> PUBLICATION INFORMATION:
<302> TITLE: IGF2
<310> PATENT DOCUMENT NUMBER: NM000612

<400> SEQUENCE: 89

| | |
|---|---|
| atgggaatcc caatggggaa gtcgatgctg gtgcttctca ccttcttggc cttcgcctcg | 60 |
| tgctgcattg ctgcttaccg ccccagtgag accctgtgcg gcggggagct ggtggacacc | 120 |
| ctccagttcg tctgtgggga ccgcggcttc tacttcagca ggcccgcaag ccgtgtgagc | 180 |
| cgtcgcagcc gtggcatcgt tgaggagtgc tgtttccgca gctgtgacct ggccctcctg | 240 |
| gagacgtact gtgctacccc cgccaagtcc gagagggacg tgtcgacccc tcgaccgtg | 300 |
| cttccggaca acttccccag atacccgtg ggcaagttct tccaatatga cacctggaag | 360 |
| cagtccaccc agcgcctgcg caggggcctg cctgccctcc tgcgtgcccg ccggggtcac | 420 |
| gtgctcgcca aggagctcga ggcgttcagg gaggccaaac gtcaccgtcc cctgattgct | 480 |
| ctacccaccc aagaccccgc ccacggggc gccccccag agatggccag caatcggaag | 540 |
| tgagcaaaac tgccgcaagt ctgcagcccg gcgccaccat cctgcagcct cctcctgacc | 600 |
| acggacgttt ccatcaggtt ccatcccgaa aatctctcgg ttccacgtcc ccctgggct | 660 |
| tctcctgacc cagtccccgt gccccgcctc ccgaaacag gctactctcc tcggcccct | 720 |
| ccatcgggct gaggaagcac agc | 743 |

<210> SEQ ID NO 90
<211> LENGTH: 7476
<212> TYPE: DNA
<213> ORGANISM: Homo sapiens
<300> PUBLICATION INFORMATION:
<302> TITLE: IGF2R
<310> PATENT DOCUMENT NUMBER: NM000876

<400> SEQUENCE: 90

| | |
|---|---|
| atggggccg ccgccggccg gagccccac ctggggcccg cgcccgcccg ccgcccgcag | 60 |
| cgctctctgc tcctgctgca gctgctgctg ctcgtcgctg cccgggtc cacgcaggcc | 120 |

```
caggccgccc cgttccccga gctgtgcagt tatacatggg aagctgttga taccaaaaat    180
aatgtacttt ataaaatcaa catctgtgga agtgtggata ttgtccagtg cgggccatca    240
agtgctgttt gtatgcacga cttgaagaca cgcacttatc attcagtggg tgactctgtt    300
ttgagaagtg caaccagatc tctcctggaa ttcaacacaa cagtgagctg tgaccagcaa    360
ggcacaaatc acagagtcca gagcagcatt gccttcctgt gtgggaaaac cctgggaact    420
cctgaatttg taactgcaac agaatgtgtg cactactttg agtggaggac cactgcagcc    480
tgcaagaaag acatatttaa agcaaataag gaggtgccat gctatgtgtt tgatgaagag    540
ttgaggaagc atgatctcaa tcctctgatc aagcttagtg gtgcctactt ggtggatgac    600
tccgatccgg acacttctct attcatcaat gtttgtagag acatagacac actacgagac    660
ccaggttcac agctgcgggc ctgtcccccc ggcactgccg cctgcctggt aagaggacac    720
caggcgtttg atgttggcca gccccgggac ggactgaagc tggtgcgcaa ggacaggctt    780
gtcctgagtt acgtgaggga agaggcagga aagctagact tttgtgatgg tcacagccct    840
gcggtgacta ttacatttgt ttgcccgtcg gagcggagag agggcaccat tcccaaactc    900
acagctaaat ccaactgccg ctatgaaatt gagtggatta ctgagtatgc ctgccacaga    960
gattacctgg aaagtaaaac ttgttctctg agcggcgagc agcaggatgt ctccatagac   1020
ctcacaccac ttgcccagag cggaggttca tcctatattt cagatggaaa agaatatttg   1080
ttttatttga atgtctgtgg agaaactgaa atacagttct gtaataaaaa acaagctgca   1140
gtttgccaag tgaaaaagag cgatacctct caagtcaaag cagcaggaag ataccacaat   1200
cagaccctcc gatattcgga tggagacctc accttgatat attttggagg tgatgaatgc   1260
agctcagggt ttcagcggat gagcgtcata aactttgagt gcaataaaac cgcaggtaac   1320
gatgggaaag gaactcctgt attcacaggg gaggttgact gcacctactt cttcacatgg   1380
gacacggaat acgcctgtgt taaggagaag gaagacctcc tctgcggtgc caccgacggg   1440
aagaagcgct atgacctgtc cgcgctggtc cgccatgcag aaccagagca gaattgggaa   1500
gctgtggatg gcagtcagac ggaaacagag aagaagcatt ttttcattaa tatttgtcac   1560
agagtgctgc aggaaggcaa ggcacgaggg tgtcccgagg acgcggcagt gtgtgcagtg   1620
gataaaaatg gaagtaaaaa tctgggaaaa tttatttcct ctcccatgaa agagaaagga   1680
aacattcaac tctcttattc agatggtgat gattgtggtc atggcaagaa aattaaaact   1740
aatatcacac ttgtatgcaa gccaggtgat ctggaaagtg caccagtgtt gagaacttct   1800
ggggaaggcg gttgctttta tgagtttgag tggcgcacag ctgcggcctg tgtgctgtct   1860
aagacagaag gggagaactg cacggtcttt gactcccagg cagggttttc ttttgactta   1920
tcacctctca caaagaaaaa tggtgcctat aaagttgaga caaagaagta tgacttttat   1980
ataaatgtgt gtggcccggt gtctgtgagc ccctgtcagc cagactcagg agcctgccag   2040
gtggcaaaaa gtgatgagaa gacttggaac ttgggtctga gtaatgcgaa gctttcatat   2100
tatgatggga tgatccaact gaactacaga ggcggcacac cctataacaa tgaaagacac   2160
acaccgagag ctacgctcat caccttttcc tgtgatcgag acgcgggagt gggcttccct   2220
gaatatcagg aagaggataa ctccacctac aacttccggt ggtacaccag ctatgcctgc   2280
ccggaggagc ccctggaatg cgtagtgacc gaccccctcca cgctggagca gtacgacctc   2340
tccagtctgg caaatctga aggtggcctt ggaggaaact ggtatgccat ggacaactca   2400
ggggaacatg tcacgtggag gaaatactac attaacgtgt gtcggcctct gaatccagtg   2460
```

-continued

```
ccgggctgca accgatatgc atcggcttgc cagatgaagt atgaaaaaga tcagggctcc    2520
ttcactgaag tggttttccat cagtaacttg ggaatggcaa agaccggccc ggtggttgag   2580
gacagcggca gcctccttct ggaatacgtg aatgggtcgg cctgcaccac cagcgatggc   2640
agacagacca catataccac gaggatccat ctcgtctgct ccaggggcag gctgaacagc   2700
caccccatct tttctctcaa ctgggagtgt gtggtcagtt tcctgtggaa cacagaggct   2760
gcctgtccca ttcagacaac gacggataca gaccaggctt gctctataag ggatcccaac   2820
agtggatttg tgtttaatct taatccgcta aacagttcgc aaggatataa cgtctctggc   2880
attgggaaga tttttatgtt taatgtctgc ggcacaatgc ctgtctgtgg gaccatcctg   2940
ggaaaacctg cttctggctg tgaggcagaa acccaaactg aagagctcaa gaattggaag   3000
ccagcaaggc cagtcggaat tgagaaaagc ctccagctgt ccacagaggg cttcatcact   3060
ctgacctaca aagggcctct ctctgccaaa ggtaccgctg atgcttttat cgtccgcttt   3120
gtttgcaatg atgatgttta ctcagggccc ctcaaattcc tgcatcaaga tatcgactct   3180
gggcaaggga tccgaaacac ttactttgag tttgaaaccg cgttggcctg tgttccttct   3240
ccagtggact gccaagtcac cgacctggct ggaaatgagt acgacctgac tggcctaagc   3300
acagtcagga aaccttggac ggctgttgac acctctgtcg atgggagaaa gaggactttc   3360
tatttgagcg tttgcaatcc tctcccttac attcctggat gccagggcag cgcagtgggg   3420
tcttgcttag tgtcagaagg caatagctgg aatctgggtg tggtgcagat gagtccccaa   3480
gccgcggcga atggatcttt gagcatcatg tatgtcaacg gtgacaagtg tgggaaccag   3540
cgcttctcca ccaggatcac gtttgagtgt gctcagatat cgggctcacc agcatttcag   3600
cttcaggatg gttgtgagta cgtgtttatc tggagaactg tggaagcctg tcccgttgtc   3660
agagtggaag gggacaactg tgaggtgaaa gacccaaggc atggcaactt gtatgacctg   3720
aagcccctgg gcctcaacga caccatcgtg agcgctggcg aatacactta ttacttccgg   3780
gtctgtggga agctttcctc agacgtctgc cccacaagtg acaagtccaa ggtggtctcc   3840
tcatgtcagg aaaagcggga accgcaggga tttcacaaag tggcaggtct cctgactcag   3900
aagctaactt atgaaaatgg cttgttaaaa atgaacttca cggggggga cacttgccat   3960
aaggtttatc agcgctccac agccatcttc ttctactgtg accgcggcac ccagcggcca   4020
gtatttctaa aggagacttc agattgttcc tacttgtttg agtggcgaac gcagtatgcc   4080
tgccccacct tcgatctgac tgaatgttca ttcaaagatg gggctggcaa ctccttcgac   4140
ctctcgtccc tgtcaaggta cagtgacaac tgggaagcca tcactgggac gggggacccg   4200
gagcactacc tcatcaatgt ctgcaagtct ctggcccgc aggctggcac tgagccgtgc   4260
cctccagaag cagccgcgtg tctgctgggt ggctccaagc ccgtgaacct cggcagggta   4320
agggacggac tcagtggag agatggcata attgtcctga atacgttga tggcgactta   4380
tgtcagatg ggattcggaa aaagtcaacc accatccgat tcacctgcag cgagagccaa   4440
gtgaactcca ggcccatgtt catcagcgcc gtggaggact gtgagtacac ctttgcctgg   4500
cccacagcca cagcctgtcc catgaagagc aacgagcatg atgactgcca ggtcaccaac   4560
ccaagcacag gacacctgtt tgatctgagc tccttaagtg cagggcggg attcacagct   4620
gcttacagcg agaaggggtt ggtttacatg agcatctgtg gggagaatga aaactgccct   4680
cctggcgtgg gggcctgctt tggacagacc aggattagcg tgggcaaggc caacaagagg   4740
ctgagatacg tggaccaggt cctgcagctg gtgtacaagg atgggtcccc ttgtccctcc   4800
aaatccggcc tgagctataa gagtgtgatc agtttcgtgt gcaggcctga ggccgggcca   4860
```

```
accaataggc ccatgctcat ctccctggac aagcagacat gcactctctt cttctcctgg   4920
cacacgccgc tggcctgcga gcaagcgacc gaatgttccg tgaggaatgg aagctctatt   4980
gttgacttgt ctcccttat tcatcgcact ggtggttatg aggcttatga tgagagtgag    5040
gatgatgcct ccgataccaa ccctgatttc tacatcaata tttgtcagcc actaaatccc   5100
atgcacgcag tgccctgtcc tgccggagcc gctgtgtgca agttcctat tgatggtccc    5160 cccatagata tcggccgggt agcaggacca ccaatactca atccaatagc aaatgagatt   5220
tacttgaatt ttgaaagcag tactccttgc ttagcggaca agcatttcaa ctacacctcg   5280
ctcatcgcgt ttcactgtaa gagaggtgtg agcatgggaa cgcctaagct gttaaggacc   5340
agcgagtgcg actttgtgtt cgaatgggag actcctgtcg tctgtcctga tgaagtgagg   5400
atggatggct gtaccctgac agatgagcag ctcctctaca gcttcaactt gtccagcctt   5460
tccacgagca cctttaaggt gactcgcgac tcgcgcacct acagcgttgg ggtgtgcacc   5520
tttgcagtcg ggccagaaca aggaggctgt aaggacggag gagtctgtct gctctcaggc   5580 accaagggg catcctttgg acggctgcaa tcaatgaaac tggattacag gcaccaggat   5640
gaagcggtcg tttaagtta cgtgaatggt gatcgttgcc ctccagaaac cgatgacggc   5700
gtcccctgtg tcttcccctt catattcaat gggaagagct acgaggagtg catcatagag   5760
agcagggcga agctgtggtg tagcacaact gcggactaca cagagacca cgagtggggc   5820 ttctgcagac actcaaacag ctaccggaca tccagcatca tatttaagtg tgatgaagat   5880
gaggacattg ggaggccaca agtcttcagt gaagtgcgtg ggtgtgatgt gacatttgag   5940
tggaaaacaa aagttgtctg ccctccaaag aagttggagt gcaaattcgt ccagaaacac   6000
aaaacctacg acctgcggct gctctcctct ctcaccgggt cctggtccct ggtccacaac   6060
ggagtctcgt actatataaa tctgtgccag aaaatatata aagggcccct gggctgctct   6120
gaaagggcca gcatttgcag aaggaccaca actggtgacg tccaggtcct gggactcgtt   6180
cacacgcaga agctgggtgt cataggtgac aaagttgttg tcacgtactc caaaggttat   6240
ccgtgtggtg gaaataagac cgcatcctcc gtgatagaat tgacctgtac aaagacggtg   6300
ggcagacctg cattcaagag gtttgatatc gacagctgca cttactactt cagctgggac   6360
tcccgggctg cctgcgccgt gaagcctcag gaggtgcaga tggtgaatgg gaccatcacc   6420
aaccctataa atggcaagag cttcagcctc ggagatattt attttaagct gttcagagcc   6480
tctggggaca tgaggaccaa tggggacaac tacctgtatg agatccaact ttcctccatc   6540
acaagctcca gaaacccggc gtgctctgga gccaacatat gccaggtgaa gcccaacgat   6600
cagcacttca gtcggaaagt tggaacctct gacaagacca gtactacct tcaagacggc    6660 gatctcgatg tcgtgtttgc ctcttcctct aagtgcggaa aggataagac caagtctgtt   6720
tcttccacca tcttcttcca ctgtgaccct ctggtggagg acgggatccc cgagttcagt   6780
cacgagactg ccgactgcca gtacctcttc tcttggtaca cctcagccgt gtgtcctctg   6840
ggggtgggct ttgacagcga gaatcccggg gacgacgggc agatgcacaa ggggctgtca   6900
gaacggagcc aggcagtcgg cgcggtgctc agcctgctgc tggtggcgct cacctgctgc   6960
ctgctggccc tgttgctcta caagaaggag aggaggaaa cagtgataag taagctgacc   7020
acttgctgta ggagaagttc caacgtgtcc tacaaatact caaaggtgaa taaggaagaa   7080
gagacagatg agaatgaaac agagtggctg atgaagagaga tccagctgcc tcctccacgg   7140
cagggaaagg aagggcagga gaacggccat attaccacca gtcagtgaa agccctcagc   7200
```

-continued

| | |
|---|---|
| tccctgcatg gggatgacca ggacagtgag gatgaggttc tgaccatccc agaggtgaaa | 7260 |
| gttcactcgg gcaggggagc tggggcagag agctcccacc cagtgagaaa cgcacagagc | 7320 |
| aatgcccttc aggagcgtga ggacgatagg gtggggctgg tcaggggtga aaggcgagg | 7380 |
| aaagggaagt ccagctctgc acagcagaag acagtgagcc ccaccaagct ggtgtccttc | 7440 |
| catgacgaca gcgacgagga cctcttacac atctga | 7476 |

<210> SEQ ID NO 91
<211> LENGTH: 4104
<212> TYPE: DNA
<213> ORGANISM: Homo sapiens
<300> PUBLICATION INFORMATION:
<302> TITLE: IGF1R
<310> PATENT DOCUMENT NUMBER: NM000875

<400> SEQUENCE: 91

| | |
|---|---|
| atgaagtctg gctccggagg agggtccccg acctcgctgt gggggctcct gtttctctcc | 60 |
| gccgcgctct cgctctggcc gacgagtgga gaaatctgcg ggccaggcat cgacatccgc | 120 |
| aacgactatc agcagctgaa gcgcctggag aactgcacgg tgatcgaggg ctacctccac | 180 |
| atcctgctca tctccaaggc cgaggactac cgcagctacc gcttccccaa gctcacggtc | 240 |
| attaccgagt acttgctgct gttccgagtg gctggcctcg agagcctcgg agacctcttc | 300 |
| cccaacctca cggtcatccg cggctggaaa ctcttctaca actacgccct ggtcatcttc | 360 |
| gagatgacca atctcaagga tattgggctt tacaacctga ggaacattac tcgggggggcc | 420 |
| atcaggattg agaaaaatgc tgacctctgt tacctctcca ctgtggactg gtccctgatc | 480 |
| ctggatgcgg tgtccaataa ctacattgtg gggaataagc ccccaaagga atgtggggac | 540 |
| ctgtgtccag ggaccatgga ggagaagccg atgtgtgaga gaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccacccg agtgcctggg cagctgcagc | 720 |
| gcgcctgaca acgacacggc ctgtgtagct tgccgccact actactatgc cggtgtctgt | 780 |
| gtgcctgcct gcccgcccaa cacctacagg tttgagggct ggcgctgtgt ggaccgtgac | 840 |
| ttctgcgcca acatcctcag cgccgagagc agcgactccg aggggtttgt gatccacgac | 900 |
| ggcgagtgca tgcaggagtg cccctcgggc ttcatccgca acggcagcca gagcatgtac | 960 |
| tgcatccctt gtgaaggtcc ttgcccgaag gtctgtgagg aagaaagaa aacaaagacc | 1020 |
| attgattctg ttacttctgc tcagatgctc caaggatgca ccatcttcaa gggcaatttg | 1080 |
| ctcattaaca tccgacgggg gaataacatt gcttcagagc tggagaactt catggggctc | 1140 |
| atcgaggtgg tgacgggcta cgtgaagatc cgccattctc atgccttggt ctccttgtcc | 1200 |
| ttcctaaaaa accttcgcct catcctagga gaggagcagc tagaagggaa ttactccttc | 1260 |
| tacgtcctcg acaaccagaa cttgcagcaa ctgtgggact gggaccaccg caacctgacc | 1320 |
| atcaaagcag ggaaaatgta ctttgctttc aatcccaaat tatgtgtttc gaaatttac | 1380 |
| cgcatggagg aagtgacggg gactaaaggg cgccaaagca agggggacat aaacaccagg | 1440 |
| aacaacgggg agagagcctc ctgtgaaagt gacgtcctgc atttcacctc caccaccacg | 1500 |
| tcgaagaatc gcatcatcat aacctggcac cggtaccggc ccctgactac cagggatctc | 1560 |
| atcagcttca ccgttacta caaggaagca cccttttaaga atgtcacaga gtatgatggg | 1620 |
| caggatgcct gcggctccaa cagctggaac atggtggacg tggacctccc gcccaacaag | 1680 |
| gacgtggagc ccggcatctt actacatggg ctgaagcct ggactcagta cgccgtttac | 1740 |

```
gtcaaggctg tgaccctcac catggtggag aacgaccata tccgtgggc caagagtgag    1800 atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggccttttcac attgtaccgc    2400 atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catcttttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga agatcacc     3000 atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaga ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga atggagaat    3300 aatccagtcc tagcacctcc aagcctgagc aagatgattc agatggccgg agagattgca    3360
gacggcatgg catacctcaa cgccaataag ttcgtccaca gagaccttgc tgcccggaat    3420
tgcatggtag ccgaagattt cacagtcaaa atcggagatt ttggtatgac gcagagatatc    3480 tatgagacag actattaccg gaaaggaggc aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
ctgtttgaac tgatgcgcat gtgctggcag tataaccca agatgaggcc ttccttcctg    3780
gagatcatca gcagcatcaa agaggagatg gagcctggct ccgggaggt ctccttctac    3840 tacagcgagg agaacaagct gcccgagccg gaggagctgg acctggagcc agagaacatg    3900
gagagcgtcc cctgaccc ctcggcctcc tcgtcctccc tgccactgcc cgacagacac    3960
tcaggacaca aggccgagaa cggcccggc cctggggtgc tggtcctccg cgccagcttc    4020
gacgagagac agccttacgc ccacatgaac ggggccgca agaacgagcg ggccttgccg    4080
ctgccccagt cttcgacctg ctga                                         4104
```

<210> SEQ ID NO 92
<211> LENGTH: 726
<212> TYPE: DNA
<213> ORGANISM: Homo sapiens
<300> PUBLICATION INFORMATION:
<302> TITLE: PDGFB
<310> PATENT DOCUMENT NUMBER: NM002608

<400> SEQUENCE: 92

| | | | | | |
|---|---|---|---|---|---|
| atgaatcgct | gctgggcgct | cttcctgtct | ctctgctgct | acctgcgtct | ggtcagcgcc | 60 |
| gagggggacc | ccattcccga | ggagctttat | gagatgctga | gtgaccactc | gatccgctcc | 120 |
| tttgatgatc | tccaacgcct | gctgcacgga | gaccccggag | aggaagatgg | ggccgagttg | 180 |
| gacctgaaca | tgacccgctc | ccactctgga | ggcgagctgg | agagcttggc | tcgtggaaga | 240 |
| aggagcctgg | gttccctgac | cattgctgag | ccggccatga | tcgccgagtg | caagacgcgc | 300 |
| accgaggtgt | tcgagatctc | ccggcgcctc | atagaccgca | ccaacgccaa | cttcctggtg | 360 |
| tggccgccct | gtgtggaggt | gcagcgctgc | tccggctgct | gcaacaaccg | caacgtgcag | 420 |
| tgccgcccca | cccaggtgca | gctgcgacct | gtccaggtga | aaagatcga | gattgtgcgg | 480 |
| aagaagccaa | tctttaagaa | ggccacggtg | acgctggaag | accacctggc | atgcaagtgt | 540 |
| gagacagtgg | cagctgcacg | gcctgtgacc | cgaagcccgg | ggggttccca | ggagcagcga | 600 |
| gccaaaacgc | cccaaactcg | ggtgaccatt | cggacggtgc | gagtccgccg | gccccccaag | 660 |
| ggcaagcacc | ggaaattcaa | gcacacgcat | gacaagacgg | cactgaagga | gacccttgga | 720 |
| gcctag | | | | | | 726 |

<210> SEQ ID NO 93
<211> LENGTH: 1512
<212> TYPE: DNA
<213> ORGANISM: Homo sapiens
<300> PUBLICATION INFORMATION:
<302> TITLE: TGFbetaR1
<310> PATENT DOCUMENT NUMBER: NM004612

<400> SEQUENCE: 93

| | | | | | |
|---|---|---|---|---|---|
| atggaggcgg | cggtcgctgc | tccgcgtccc | cggctgctcc | tcctcgtgct | ggcggcggcg | 60 |
| gcggcggcgc | cggcggcgct | gctcccgggg | gcgacggcgt | acagtgtttt | ctgccacctc | 120 |
| tgtacaaaag | acaattttac | ttgtgtgaca | gatgggctct | gctttgtctc | tgtcacagag | 180 |
| accacagaca | agttatacaa | caacagcatg | tgtatagctg | aaattgactt | aattcctcga | 240 |
| gataggccgt | ttgtatgtgc | accctcttca | aaaactgggt | ctgtgactac | aacatattgc | 300 |
| tgcaatcagg | accattgcaa | taaaatagaa | cttccaacta | ctgtaaagtc | atcacctggc | 360 |
| cttggtcctg | tggaactggc | agctgtcatt | gctggaccag | tgtgcttcgt | ctgcatctca | 420 |
| ctcatgttga | tggtctatat | ctgccacaac | cgcactgtca | ttcaccatcg | agtgccaaat | 480 |
| gaagaggacc | cttcattaga | tcgccctttt | atttcagagg | gtactacgtt | gaaagactta | 540 |
| atttatgata | tgacaacgtc | aggttctggc | tcaggtttac | cattgcttgt | tcagagaaca | 600 |
| attgcgagaa | ctattgtgtt | acaagaaagc | attggcaaag | gtcgatttgg | agaagtttgg | 660 |
| agaggaaagt | ggcggggaga | agaagttgct | gttaagatat | ctcctctag | agaagaacgt | 720 |
| tcgtggttcc | gtgaggcaga | gatttatcaa | actgtaatgt | tacgtcatga | aaacatcctg | 780 |
| ggatttatag | cagcagacaa | taaagacaat | ggtacttgga | ctcagctctg | gttggtgtca | 840 |
| gattatcatg | agcatggatc | ccttttgat | tacttaaaca | gatacacagt | tactgtggaa | 900 |

-continued

| | |
|---|---|
| ggaatgataa aacttgctct gtccacggcg agcggtcttg cccatcttca catggagatt | 960 |
| gttggtaccc aaggaaagcc agccattgct catagagatt tgaaatcaaa gaatatcttg | 1020 |
| gtaaagaaga atggaacttg ctgtattgca gacttaggac tggcagtaag acatgattca | 1080 |
| gccacagata ccattgatat tgctccaaac cacagagtgg gaacaaaaag gtacatggcc | 1140 |
| cctgaagttc tcgatgattc cataaatatg aaacattttg aatccttcaa acgtgctgac | 1200 |
| atctatgcaa tgggcttagt attctgggaa attgctcgac gatgttccat ggtggaatt | 1260 |
| catgaagatt accaactgcc ttattatgat cttgtacctt ctgacccatc agttgaagaa | 1320 |
| atgagaaaag ttgtttgtga acagaagtta aggccaaata tcccaaacag atggcagagc | 1380 |
| tgtgaagcct tgagagtaat ggctaaaatt atgagagaat gttggtatgc caatggagca | 1440 |
| gctaggctta cagcattgcg gattaagaaa acattatcgc aactcagtca acaggaaggc | 1500 |
| atcaaaatgt aa | 1512 |

<210> SEQ ID NO 94
<211> LENGTH: 4044
<212> TYPE: DNA
<213> ORGANISM: Homo sapiens
<300> PUBLICATION INFORMATION:
<302> TITLE: Flk1
<310> PATENT DOCUMENT NUMBER: AF035121

<400> SEQUENCE: 94

| | |
|---|---|
| atgcagagca aggtgctgct ggccgtcgcc ctgtggctct gcgtggagac ccgggccgcc | 60 |
| tctgtgggtt tgcctagtgt ttctcttgat ctgcccaggc tcagcataca aaagacata | 120 |
| cttacaatta aggctaatac aactcttcaa attacttgca ggggacagag ggacttggac | 180 |
| tggctttggc ccaataatca gagtggcagt gagcaagggt ggaggtgact gagtgcagc | 240 |
| gatggcctct tctgtaagac actcacaatt ccaaaagtga tcggaaatga cactggagcc | 300 |
| tacaagtgct ctaccgggga aactgacttg gcctcggtc tttatgtcta tgttcaagat | 360 |
| tacagatctc catttattgc ttctgttagt gaccaacatg gagtcgtgta cattactgag | 420 |
| aacaaaaaca aaactgtggt gattccatgt ctcgggtcca tttcaaatct caacgtgtca | 480 |
| ctttgtgcaa gatacccaga aaagagattt gttcctgatg gtaacagaat tcctgggac | 540 |
| agcaagaagg gctttactat tcccagctac atgatcagct atgctggcat ggtcttctgt | 600 |
| gaagcaaaaa ttaatgatga agttaccag tctattatgt acatagttgt cgttgtaggg | 660 |
| tataggattt atgatgtggt tctgagtccg tctcatggaa ttgaactatc tgttggagaa | 720 |
| aagcttgtct taaattgtac agcaagaact gaactaaatg tggggattga cttcaactgg | 780 |
| gaataccctt cttcgaagca tcagcataag aaacttgtaa accgagacct aaaaacccag | 840 |
| tctgggagtg agatgaagaa atttttgagc accttaacta tagatggtgt aacccggagt | 900 |
| gaccaaggat tgtacacctg tgcagcatcc agtgggctga tgaccaagaa gaacagcaca | 960 |
| tttgtcaggg tccatgaaaa accttttgtt gcttttggaa gtggcatgga atctctggtg | 1020 |
| gaagccacgg tgggggagcg tgtcagaatc cctgcgaagt accttggtta cccaccccca | 1080 |
| gaaataaaat ggtataaaaa tggaatacc cttgagtcca atcacacaat taaagcgggg | 1140 |
| catgtactga cgattatgga agtgagtgaa agagacacag gaaattacac tgtcatcctt | 1200 |
| accaatccca tttcaaagga gaagcagagc catgtggtct ctctggttgt gtatgtccca | 1260 |
| ccccagattg gtgagaaatc tctaatctct cctgtggatt cctaccagta cggcaccact | 1320 |
| caaacgctga catgtacggt ctatgccatt cctcccccgc atcacatcca ctggtattgg | 1380 |

```
cagttggagg aagagtgcgc caacgagccc agccaagctg tctcagtgac aaacccatac    1440
ccttgtgaag aatggagaag tgtggaggac ttccagggag gaaataaaat tgaagttaat    1500
aaaaatcaat ttgctctaat tgaaggaaaa acaaaactg taagtaccct tgttatccaa     1560
gcggcaaatg tgtcagcttt gtacaaatgt gaagcggtca acaaagtcgg gagaggagag    1620
agggtgatct ccttccacgt gaccaggggt cctgaaatta ctttgcaacc tgacatgcag    1680
cccactgagc aggagagcgt gtcttttgtgg tgcactgcag acagatctac gtttgagaac   1740
ctcacatggt acaagcttgg cccacagcct ctgccaatcc atgtgggaga gttgcccaca    1800
cctgtttgca agaacttgga tactcttttgg aaattgaatg ccaccatgtt ctctaatagc   1860
acaaatgaca ttttgatcat ggagcttaag aatgcatcct tgcaggacca aggagactat    1920
gtctgccttg ctcaagacag gaagaccaag aaaagacatt gcgtggtcag gcagctcaca    1980
gtcctagagc gtgtggcacc cacgatcaca ggaaacctgg agaatcagac gacaagtatt    2040
ggggaaagca tcgaagtctc atgcacggca tctgggaatc cccctccaca gatcatgtgg    2100
tttaaagata atgagaccct tgtagaagac tcaggcattg tattgaagga tgggaaccgg    2160
aacctcacta tccgcagagt gaggaaggag gacgaaggcc tctacacctg ccaggcatgc    2220
agtgttcttg gctgtgcaaa agtggaggca ttttcataa tagaaggtgc ccaggaaaag     2280
acgaacttgg aaatcattat tctagtaggc acggcggtga ttgccatgtt cttctggcta    2340
cttcttgtca tcatcctacg gaccgttaag cgggccaatg gaggggaact gaagacaggc    2400
tacttgtcca tcgtcatgga tccagatgaa ctcccattgg atgaacattg tgaacgactg    2460
ccttatgatg ccagcaaatg ggaattcccc agagaccggc tgaagctagg taagcctctt    2520
ggccgtggtg ccttttggcca agtgattgaa gcagatgcct ttggaattga caagacagca    2580
acttgcagga cagtagcagt caaaatgttg aagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820
aaaggggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatgcccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta aatgagggc ccctgattat actacaccag aaatgtacca gaccatgctg    3420
gactgctggc acgggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgttttcc   3600
tgtatggagg aggaggaagt atgtgacccc aaattccatt atgacaacac agcaggaatc    3660
agtcagtatc tgcagaacag taagcgaaag agccggcctg tgagtgtaaa acatttgaa     3720
gatatcccgt tagaagaacc agaagtaaaa gtaatcccag atgacaacca gacggacagt    3780
```

-continued

| | |
|---|---:|
| ggtatggttc ttgcctcaga agagctgaaa actttggaag acagaaccaa attatctcca | 3840 |
| tcttttggtg gaatggtgcc cagcaaaagc agggagtctg tggcatctga aggctcaaac | 3900 |
| cagacaagcg gctaccagtc cggatatcac tccgatgaca cagacaccac cgtgtactcc | 3960 |
| agtgaggaag cagaactttt aaagctgata gagattggag tgcaaaccgg tagcacagcc | 4020 |
| cagattctcc agcctgactc gggg | 4044 |

```
<210> SEQ ID NO 95
<211> LENGTH: 4017
<212> TYPE: DNA
<213> ORGANISM: Homo sapiens
<300> PUBLICATION INFORMATION:
<302> TITLE: Flt1
<310> PATENT DOCUMENT NUMBER: AF063657

<400> SEQUENCE: 95
```

| | |
|---|---:|
| atggtcagct actgggacac cggggtcctg ctgtgcgcgc tgctcagctg tctgcttctc | 60 |
| acaggatcta gttcaggttc aaaattaaaa gatcctgaac tgagtttaaa aggcacccag | 120 |
| cacatcatgc aagcaggcca gacactgcat ctccaatgca ggggggaagc agcccataaa | 180 |
| tggtctttgc ctgaaatggt gagtaaggaa agcgaaaggc tgagcataac taaatctgcc | 240 |
| tgtggaagaa atggcaaaca attctgcagt acttttaacct tgaacacagc tcaagcaaac | 300 |
| cacactggct tctacagctg caaatatcta gctgtaccta cttcaaagaa gaaggaaaca | 360 |
| gaatctgcaa tctatatatt tattagtgat acaggtagac ctttcgtaga gatgtacagt | 420 |
| gaaatccccg aaattataca catgactgaa ggaagggagc tcgtcattcc ctgccggptt | 480 |
| acgtcaccta acatcactgt tactttaaaa aagtttccac ttgacacttt gatccctgat | 540 |
| ggaaaacgca taatctggga cagtagaaag ggcttcatca tatcaaatgc aacgtacaaa | 600 |
| gaaatagggc ttctgacctg tgaagcaaca gtcaatgggc atttgtataa gacaaactat | 660 |
| ctcacacatc gacaaaccaa taccatcata gatgtccaaa taagcacacc acgcccagtc | 720 |
| aaattactta gaggccatac tcttgtcctc aattgtactg ctaccactcc cttgaacacg | 780 |
| agagttcaaa tgacctggag ttaccctgat gaaaaaaata gagagcttc cgtaaggcga | 840 |
| cgaattgacc aaagcaattc ccatgccaac atattctaca gtgttcttac tattgacaaa | 900 |
| atgcagaaca agacaaagg actttatact tgtcgtgtaa ggagtggacc atcattcaaa | 960 |
| tctgttaaca cctcagtgca tatatatgat aaagcattca tcactgtgaa acatcgaaaa | 1020 |
| cagcaggtgc ttgaaaccgt agctggcaag cggtcttacc ggctctctat gaaagtgaag | 1080 |
| gcatttcct cgccggaagt tgtatggtta aaagatgggt acctgcgac tgagaaatct | 1140 |
| gctcgctatt tgactcgtgg ctactcgtta attatcaagg acgtaactga agaggatgca | 1200 |
| gggaattata caatcttgct gagcataaaa cagtcaaatg tgttaaaaa cctcactgcc | 1260 |
| actctaattg tcaatgtgaa accccagatt tacgaaaagg ccgtgtcatc gtttccagac | 1320 |
| ccggctctct acccactggg cagcagacaa atcctgactt gtaccgcata tggtatccct | 1380 |
| caacctacaa tcagtggtt ctggcacccc tgtaaccata atcattccga agcaaggtgt | 1440 |
| gactttgtt ccaataatga agagtccttt atcctggatg ctgacagcaa catgggaaac | 1500 |
| agaattgaga gcatcactca gcgcatggca ataatagaag gaagaataa gatggctagc | 1560 |
| accttggttt tggctgactc tagaatttct ggaatctaca tttgcatagc ttccaataaa | 1620 |
| gttgggactg tgggaagaaa cataagcttt tatatcacag atgtgccaaa tgggtttcat | 1680 |
| gttaacttgg aaaaaatgcc gacggaagga gaggacctga aactgtcttg cacagttaac | 1740 |

-continued

```
aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagaga tcaggaagca    1980
ccatacctcc tgcgaaacct cagtgatcac acagtggcca tcagcagttc caccacttta    2040
gactgtcatg ctaatggtgt ccccgagcct cagatcactt ggtttaaaaa caaccacaaa    2100
atacaacaag agcctggaat tatttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaaggtcttc ttctgaaata aagactgact acctatcaat tataatggac    2400
ccagatgaag ttcctttgga tgagcagtgt gagcggctcc cttatgatgc cagcaagtgg    2460
gagtttgccc gggagagact taaactgggc aaatcacttg gaagaggggc ttttggaaaa    2520
gtggttcaag catcagcatt tggcattaag aaatcaccta cgtgccggac tgtggctgtg    2580
aaaatgctga agaggggggc cacggccagc gagtacaaag ctctgatgac tgagctaaaa    2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca aacgtgactt attttttctc aacaaggatg cagcactaca catggagcct    2820 aagaagaaa aaatggagcc aggcctggaa caaggcaaga aaccaagact agatagcgtc    2880
accagcagcg aaagctttgc gagctccggc tttcaggaag ataaaagtct gagtgatgtt    2940
gaggaagagg aggattctga cggtttctac aaggagccca tcactatgga agatctgatt    3000
tcttacagtt ttcaagtggc cagaggcatg gagttcctgt cttccagaaa gtgcattcat    3060
cgggacctgg cagcgagaaa cattctttta tctgagaaca acgtggtgaa gatttgtgat    3120
tttggccttg cccgggatat ttataagaac cccgattatg tgagaaaagg agatactcga    3180
cttcctctga aatggatggc tcctgaatct atctttgaca aaatctacag caccaagagc    3240
gacgtgtggt cttacggagt attgctgtgg gaaatcttct ccttaggtgg gtctccatac    3300
ccaggagtac aaatggatga ggacttttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc ccaatcaatg ccatactgac aggaaatagt    3540
gggtttacat actcaactcc tgccttctct gaggacttct tcaaggaaag tatttcagct    3600
ccgaagttta attcaggaag ctctgatgat gtcagatatg taaatgcttt caagttcatg    3660
agcctggaaa gaatcaaaac ctttgaagaa ctttttaccga atgccacctc catgtttgat    3720
gactaccagg gcgacagcag cactctgttg gcctctccca tgctgaagcg cttcacctgg    3780
actgacagca aacccaaggc ctcgctcaag attgacttga gagtaaccag taaaagtaag    3840
gagtcggggc tgtctgatgt cagcaggccc agtttctgcc attccagctg tgggcacgtc    3900
agcgaaggca agcgcaggtt cacctacgac cacgctgagc tggaaaggaa aatcgcgtgc    3960
tgctccccgc ccccagacta caactcggtg gtcctgtact ccaccccacc catctag      4017
```

<210> SEQ ID NO 96

<211> LENGTH: 3897
<212> TYPE: DNA
<213> ORGANISM: Homo sapiens
<300> PUBLICATION INFORMATION:
<302> TITLE: Flt4
<310> PATENT DOCUMENT NUMBER: XM003852

<400> SEQUENCE: 96

| | | | | | |
|---|---|---|---|---|---|
| atgcagcggg | gcgccgcgct | gtgcctgcga | ctgtggctct | gcctgggact | cctggacggc         60 |
| ctggtgagtg | gctactccat | gacccccccg | accttgaaca | tcacggagga | gtcacacgtc        120 |
| atcgacaccg | tgacagcct | gtccatctcc | tgcaggggac | agcacccct | cgagtgggct         180 |
| tggccaggag | ctcaggaggc | gccagccacc | ggagacaagg | acagcgagga | cacgggggtg        240 |
| gtgcgagact | gcgagggcac | agacgccagg | ccctactgca | aggtgttgct | gctgcacgag        300 |
| gtacatgcca | acgacacagg | cagctacgtc | tgctactaca | agtacatcaa | ggcacgcatc        360 |
| gagggcacca | cggccgccag | ctcctacgtg | ttcgtgagag | actttgagca | gccattcatc        420 |
| aacaagcctg | acacgctctt | ggtcaacagg | aaggacgcca | tgtgggtgcc | ctgtctggtg        480 |
| tccatccccg | gcctcaatgt | cacgctgcgc | tcgcaaagct | cggtgctgtg | gccagacggg        540 |
| caggaggtgg | tgtgggatga | ccggcggggc | atgctcgtgt | ccacgccact | gctgcacgat        600 |
| gccctgtacc | tgcagtgcga | gaccacctgg | ggagaccagg | acttcctttc | caacccttc         660 |
| ctggtgcaca | tcacaggcaa | cgagctctat | gacatccagc | tgttgcccag | gaagtcgctg        720 |
| gagctgctgg | tagggagaa | gctggtcctg | aactgcaccg | tgtgggctga | gtttaactca        780 |
| ggtgtcacct | ttgactggga | ctacccaggg | aagcaggcag | agcggggtaa | gtgggtgccc        840 |
| gagcgacgct | cccagcagac | ccacacagaa | ctctccagca | tcctgaccat | ccacaacgtc        900 |
| agccagcacg | acctgggctc | gtatgtgtgc | aaggccaaca | acggcatcca | gcgatttcgg        960 |
| gagagcaccg | aggtcattgt | gcatgaaaat | cccttcatca | gcgtcgagtg | gctcaaagga       1020 |
| cccatcctgg | aggccacggc | aggagacgag | ctggtgaagc | tgcccgtgaa | gctggcagcg       1080 |
| tacccccgc | ccgagttcca | gtggtacaag | gatggaaagg | cactgtccgg | gcgccacagt       1140 |
| ccacatgccc | tggtgctcaa | ggaggtgaca | gaggccagca | caggcaccta | cacctcgcc        1200 |
| ctgtggaact | ccgctgctgg | cctgaggcgc | aacatcagcc | tggagctggt | ggtgaatgtg       1260 |
| ccccccaga | tacatgagaa | ggaggcctcc | tcccccagca | tctactcgcg | tcacagccgc       1320 |
| caggccctca | cctgcacggc | tacggggtg | cccctgcctc | tcagcatcca | gtggcactgg       1380 |
| cggccctgga | caccctgcaa | gatgtttgcc | cagcgtagtc | tccggcggcg | gcagcagcaa       1440 |
| gacctcatgc | cacagtgccg | tgactggagg | gcggtgaccg | cgcaggatgc | cgtgaacccc       1500 |
| atcgagagcc | tggacacctg | gaccgagttt | gtggagggaa | agaataagac | tgtgagcaag       1560 |
| ctggtgatcc | agaatgccaa | cgtgtctgcc | atgtacaagt | gtgtggtctc | caacaaggtg       1620 |
| ggccaggatg | agcggctcat | ctacttctat | gtgaccacca | tccccgacgg | cttcaccatc       1680 |
| gaatccaagc | catccgagga | gctactagag | ggccagccgg | tgctcctgag | ctgccaagcc       1740 |
| gacagctaca | agtacgagca | tctgcgctgg | taccgcctca | acctgtccac | gctgcacgat       1800 |
| gcgcacggga | acccgcttct | gctcgactgc | aagaacgtgc | atctgttcgc | cacccctctg       1860 |
| gccgccagcc | tggaggaggt | ggcacctggg | gcgcgcacg | ccacgctcag | cctgagtatc       1920 |
| ccccgcgtcg | cgcccgagca | cgagggccac | tatgtgtgcg | aagtgcaaga | ccggcgcagc       1980 |
| catgacaagc | actgccacaa | gaagtacctg | tcggtgcagg | ccctggaagc | ccctcggctc       2040 |
| acgcagaact | tgaccgacct | cctggtgaac | gtgagcgact | cgctggagat | gcagtgcttg       2100 |

```
gtggccggag cgcacgcgcc cagcatcgtg tggtacaaag acgagaggct gctggaggaa   2160
aagtctggag tcgacttggc ggactccaac cagaagctga gcatccagcg cgtgcgcgag   2220
gaggatgcgg gacgctatct gtgcagcgtg tgcaacgcca agggctgcgt caactcctcc   2280
gccagcgtgg ccgtggaagg ctccgaggat aagggcagca tggagatcgt gatccttgtc   2340
ggtaccggcg tcatcgctgt cttcttctgg gtcctcctcc tcctcatctt ctgtaacatg   2400
aggaggccgg cccacgcaga catcaagacg ggctacctgt ccatcatcat ggaccccggg   2460
gaggtgcctc tggaggagca atgcgaatac ctgtcctacg atgccagcca gtgggaattc   2520
ccccgagagc ggctgcacct ggggagagtg ctcggctacg cgccttcgg gaaggtggtg    2580 gaagcctccg ctttcggcat ccacaagggc agcagctgtg acaccgtggc cgtgaaaatg   2640
ctgaaagagg cgccacggc cagcgagcag cgcgcgctga tgtcggagct caagatcctc    2700
attcacatcg gcaaccacct caacgtggtc aacctcctcg ggcgtgcac caagccgcag    2760 ggccccctca tggtgatcgt ggagttctgc aagtacggca acctctccaa cttcctgcgc   2820
gccaagcggg acgccttcag ccccctgcgcg agaagtctc ccgagcagcg cggacgcttc    2880
cgcgccatgg tggagctcgc caggctggat cggaggcggc cggggagcag cgacagggtc    2940
ctcttcgcgc ggttctcgaa gaccgagggc ggagcgaggc gggcttctcc agaccaagaa    3000
gctgaggacc tgtggctgag cccgctgacc atggaagatc ttgtctgcta cagcttccag   3060
gtggccagag gatggagtt cctggcttcc cgaaagtgca tccacagaga cctggctgct   3120
cggaacattc tgctgtcgga aagcgacgtg gtgaagatct gtgactttgg ccttgcccgg   3180
gacatctaca agaccccga ctacgtccgc aagggcagtg cccggctgcc cctgaagtgg    3240
atggcccctg aaagcatctt cgacaaggtg tacaccacgc agagtgacgt gtggtccttt   3300
ggggtgcttc tctgggagat cttctctctg ggggcctccc cgtaccctgg ggtgcagatc   3360
aatgaggagt tctgccagcg gctgagagac ggcacaagga tgagggcccc ggagctggcc    3420
actcccgcca tacgccgcat catgctgaac tgctggtccg agaccccaa ggcgagacct    3480 gcattctcgg agctggtgga gatcctgggg gacctgctcc agggcagggg cctgcaagag   3540
gaagaggagg tctgcatggc cccgcgcagc tctcagagct cagaagaggg cagcttctcg   3600
caggtgtcca ccatggccct acacatcgcc caggctgacg ctgaggacag cccgccaagc   3660
ctgcagcgcc acagcctggc cgccaggtat tacaactggg tgtcctttcc cgggtgcctg   3720
gccagagggg ctgagacccg tggttcctcc aggatgaaga catttgagga attccccatg   3780
accccaacga cctacaaagg ctctgtggac aaccagacac acagtgggat ggtgctggcc   3840
tcggaggagt ttgagcagat agagagcagg catagacaag aaagcggctt caggtag      3897
```

<210> SEQ ID NO 97
<211> LENGTH: 4071
<212> TYPE: DNA
<213> ORGANISM: Homo sapiens
<300> PUBLICATION INFORMATION:
<302> TITLE: KDR
<310> PATENT DOCUMENT NUMBER: AF063658

<400> SEQUENCE: 97

```
atggagagca aggtgctgct ggccgtcgcc ctgtggctct gcgtggagac ccgggccgcc    60
tctgtgggtt tgcctagtgt ttctcttgat ctgcccaggc tcagcataca aaaagacata   120
cttacaatta aggctaatac aactcttcaa attacttgca ggggacagag ggacttggac   180 tggcttttggc ccaataatca gagtggcagt gagcaaaggg tggaggtgac tgagtgcagc    240
```

```
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat tcctgggac    540 agcaagaagg gctttactat tcccagctac atgatcagct atgctggcat ggtcttctgt    600
gaagcaaaaa ttaatgatga agttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaatacccct cttcgaagca tcagcataag aaacttgtaa accgagacct aaaaacccag    840
tctgggagtg agatgaagaa attttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgt gggggagcg tgtcagaatc cctgcgaagt accttggtta cccaccccca   1080
gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg tgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtacccct tgttatccaa   1560 gcggcaaatg tgtcagcttt gtacaaatgt gaagcggtca acaaagtcgg gagaggagag   1620
agggtgatct ccttccacgt gaccaggggt cctgaaatta ctttgcaacc tgacatgcag   1680
cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800 cctgttttgca agaacttgga tactctttgg aaattgaatg ccaccatgtt ctctaatagc   1860
acaaatgaca ttttgatcat ggagcttaag aatgcatcct gcaggacca aggagactat   1920 gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata tgagacccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg ccttttggcca agtgattgaa gcagatgcct ttggaattga caagacagca   2580
acttgcagga cagtagcagt caaaatgttg aaagaaggag caacacacag tgagcatcga   2640
```

```
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820 aaagggcac gattccgtca agggaaagac tacgttggag caatccctgt ggatctgaaa     2880
cggcgcttgg acagcatcac cagtagccag agctcagcca gctctggatt tgtgaggag    2940 aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acgggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgttcc    3600 tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagtgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc tcctgtttta a              4071
```

<210> SEQ ID NO 98
<211> LENGTH: 1410
<212> TYPE: DNA
<213> ORGANISM: Homo sapiens
<300> PUBLICATION INFORMATION:
<302> TITLE: MMP1
<310> PATENT DOCUMENT NUMBER: M13509

<400> SEQUENCE: 98

```
atgcacagct ttcctccact gctgctgctg ctgttctggg gtgtggtgtc tcacagcttc     60
ccagcgactc tagaaacaca agagcaagat gtggacttag tccagaaata cctggaaaaa    120
tactacaacc tgaagaatga tgggaggcaa gttgaaaagc ggagaaatag tggcccagtg    180
gttgaaaaat tgaagcaaat gcaggaattc tttgggctga agtgactgg gaaaccagat     240 gctgaaaccc tgaaggtgat gaagcagccc agatgtggag tgcctgatgt ggctcagttt    300
gtcctcactg agggaaaccc tcgctggag caaacacatc tgaggtacag gattgaaaat     360
tacacgccag atttgccaag agcagatgtg accatgcca ttgagaaagc cttccaactc     420
tggagtaatg tcacacctct gacattcacc aaggtctctg agggtcaagc agacatcatg    480 atatctttg tcaggggaga tcatcggac aactctcctt ttgatggacc tggaggaaat      540
cttgctcatg cttttcaacc aggcccaggt attggagggg atgctcattt tgatgaagat    600
```

```
gaaaggtgga ccaacaattt cagagagtac aacttacatc gtgttgcggc tcatgaactc      660
ggccattctc ttggactctc ccattctact gatatcgggg ctttgatgta ccctagctac      720
accttcagtg gtgatgttca gctagctcag gatgacattg atggcatcca agccatatat      780
ggacgttccc aaaatcctgt ccagcccatc ggcccacaaa ccccaaaagc gtgtgacagt      840
aagctaacct tgatgctat aactacgatt cggggagaag tgatgttctt taaagacaga      900
ttctacatgc gcacaaatcc cttctacccg gaagttgagc tcaatttcat ttctgttttc      960
tggccacaac tgccaaatgg gcttgaagct gcttacgaat tgccgacag agatgaagtc     1020 cggttttca agggaataa gtactgggct gttcagggac agaatgtgct acacggatac     1080
cccaaggaca tctacagctc ctttggcttc cctagaactg tgaagcatat cgatgctgct     1140 cttttctgagg aaaacactgg aaaaacctac ttctttgttg ctaacaaata ctggaggtat     1200
gatgaatata acgatctat ggatccaagt tatcccaaaa tgatagcaca tgactttcct     1260
ggaattggcc acaaagttga tgcagttttc atgaaagatg attttttcta tttctttcat     1320
ggaacaagac aatacaaatt tgatcctaaa acgaagagaa ttttgactct ccagaaagct     1380
aatagctggt tcaactgcag gaaaaattga                                     1410

<210> SEQ ID NO 99
<211> LENGTH: 1743
<212> TYPE: DNA
<213> ORGANISM: Homo sapiens
<300> PUBLICATION INFORMATION:
<302> TITLE: MMP10
<310> PATENT DOCUMENT NUMBER: XM006269

<400> SEQUENCE: 99
aaagaaggta agggcagtga gaatgatgca tcttgcattc cttgtgctgt tgtgtctgcc      60
agtctgctct gcctatcctc tgagtggggc agcaaaagag gaggactcca acaaggatct     120
tgcccagcaa tacctagaaa agtactacaa cctcgaaaag gatgtgaaac agtttagaag     180
aaaggacagt aatctcattg ttaaaaaaat ccaaggaatg cagaagttcc ttgggttgga     240
ggtgacaggg aagctagaca ctgacactct ggaggtgatg cgcaagccca gtgtggagt     300 tcctgacgtt ggtcacttca gctcctttcc tggcatgccg aagtggagga aacccacct     360 tacatacagg attgtgaatt atacaccaga tttgccaaga gatgctgttg attctgccat     420
tgagaaagct ctgaaagtct gggaagaggt gactccactc acattctcca ggctgtatga     480
aggagaggct gatataatga tctctttgc agttaaagaa catggagact tttactcttt     540
tgatggccca ggacacagtt tggctcatgc ctacccacct ggacctgggc tttatggaga     600
tattcacttt gatgatgatg aaaaatggac agaagatgca tcaggcacca atttattcct     660
cgttgctgct catgaacttg gccactccct ggggctcttt cactcagcca acactgaagc     720
tttgatgtac ccactctaca actcattcac agagctcgcc cagttccgcc tttcgcaaga     780
tgatgtgaat ggcattcagt ctctctacgg acctcccct gcctctactg aggaacccct     840
ggtgcccaca aaatctgttc cttcgggatc tgagatgcca gccaagtgtg atcctgcttt     900
gtccttcgat gccatcagca ctctgagggg agaatatctg ttctttaaag acagatattt     960
ttggcgaaga tcccactgga acctgaacc tgaatttcat ttgatttctg cattttggcc    1020
ctctcttcca tcatatttgg atgctgcata tgaagttaac agcagggaca ccgtttttat    1080
ttttaaagga aatgagttct gggccatcag aggaaatgag gtacaagcag gttatccaag    1140
aggcatccat accctgggtt ttcctccaac cataaggaaa attgatgcag ctgttctga    1200
```

```
caaggaaaag aagaaaacat acttctttgc agcggacaaa tactggagat tgatgaaaa      1260 tagccagtcc atggagcaag gcttccctag actaatagct gatgactttc caggagttga      1320
gcctaaggtt gatgctgtat tacaggcatt tggattttc tacttcttca gtggatcatc      1380
acagtttgag tttgacccca atgccaggat ggtgacacac atattaaaga gtaacagctg      1440
gttacattgc taggcgagat aggggggaaga cagatatggg tgtttttaat aaatctaata      1500
attattcatc taatgtatta tgagccaaaa tggttaattt ttcctgcatg ttctgtgact      1560
gaagaagatg agccttgcag atatctgcat gtgtcatgaa aatgtttct ggaattcttc        1620 acttgctttt gaattgcact gaacagaatt aagaaatact catgtgcaat aggtgagaga      1680
atgtattttc atagatgtgt tattacttcc tcaataaaaa gttttatttt gggcctgttc      1740
ctt                                                                    1743

<210> SEQ ID NO 100
<211> LENGTH: 1467
<212> TYPE: DNA
<213> ORGANISM: Homo sapiens
<300> PUBLICATION INFORMATION:
<302> TITLE: MMP11
<310> PATENT DOCUMENT NUMBER: XM009873

<400> SEQUENCE: 100
atggctccgg ccgcctggct ccgcagcgcg gccgcgcgcg ccctcctgcc cccgatgctg        60
ctgctgctgc tccagccgcc gccgctgctg gcccgggctc tgccgccgga cgcccaccac       120
ctccatgccg agaggagggg gccacagccc tggcatgcag ccctgcccag tagcccggca       180 cctgccctg ccacgcagga agccccccgg cctgccagca gctcaggcc tccccgctgt          240 ggcgtgcccg acccatctga tgggctgagt gcccgcaacc gacagaagag gttcgtgctt        300
tctggcgggc gctgggagaa acggacctc acctacagga tccttcggtt cccatggcag        360
ttggtgcagg agcaggtgcg gcagacgatg gcagaggccc taaaggtatg gagcgatgtg      420
acgccactca cctttactga ggtgcacgag ggccgtgctg acatcatgat cgacttcgcc       480
aggtactggc atgggacga cctgccgttt gatgggcctg ggggcatcct ggcccatgcc       540 ttcttccca agactcaccg agaagggat gtccacttcg actatgatga acctggact         600 atcggggatg accagggcac agacctgctg caggtggcag cccatgaatt tggccacgtg      660
ctggggctgc agcacacaac agcagccaag gccctgatgt ccgccttcta caccttccgc      720
tacccactga gtcctcagcc agatgactgc agggggcgttc aacacctata tggccagccc    780
tggcccactg tcacctccag gaccccagcc ctgggccccc aggctgggat agacaccaat     840
gagattgcac cgctggagcc agacgccccg ccagatgcct gtgaggcctc ctttgacgcg     900
gtctccacca tccgaggcga gctctttttc ttcaaagcgg gctttgtgtg gcgcctccgt     960
gggggccagc tgcagcccgg ctaccagca ttggcctctc gccactggca gggactgccc     1020
agccctgtgg acgctgcctt cgaggatgcc cagggccaca tttggttctt ccaaggtgct    1080
cagtactggg tgtacgacgg tgaaaagcca gtcctgggcc ccgcacccct caccgagctg     1140
ggcctggtga ggttcccggt ccatgctgcc ttggtctggg tcccgagaa gaacaagatc      1200 tacttcttcc gaggcagga ctactggcgt ttccaccca gcaccggcg tgtagacagt      1260 cccgtgcccc gcagggccac tgactggaga ggggtgccct ctgagatcga cgctgccttc     1320
caggatgctg atggctatgc ctacttcctg cgcggccgcc tctactggaa gtttgaccct      1380
gtgaaggtga aggctctgga aggcttcccc cgtctcgtgg gtcctgactt ctttggctgt     1440
```

```
gccgagcctg ccaacacttt cctctga                                     1467

<210> SEQ ID NO 101
<211> LENGTH: 1653
<212> TYPE: DNA
<213> ORGANISM: Homo sapiens
<220> FEATURE:
<221> NAME/KEY: misc_feature
<222> LOCATION: (626)..(925)
<223> OTHER INFORMATION: n=A, T, G, C or gap
<300> PUBLICATION INFORMATION:
<302> TITLE: MMP12
<310> PATENT DOCUMENT NUMBER: XM006272

<400> SEQUENCE: 101
atgaagtttc ttctaatact gctcctgcag gccactgctt ctggagctct tcccctgaac     60
agctctacaa gcctggaaaa aaataatgtg ctatttggtg agagatactt agaaaaattt    120
tatggccttg agataaacaa acttccagtg acaaaaatga atatagtgg aaacttaatg     180 aaggaaaaaa tccaagaaat gcagcacttc ttgggtctga agtgaccgg caactggac      240 acatctaccc tggagatgat gcacgcacct cgatgtggag tccccgatgt ccatcatttc    300
agggaaatgc caggggggcc cgtatggagg aaacattata tcacctacag aatcaataat    360
tacacacctg acatgaaccg tgaggatgtt gactacgcaa tccggaaagc tttccaagta    420
tggagtaatg ttacccccctt gaaattcagc aagattaaca caggcatggc tgacattttg    480 gtggttttg cccgtggagc tcatggagac ttccatgctt tgatggcaa aggtggaatc     540 ctagcccatg cttttggacc tggatctggc attggagggg atgcacattt cgatgaggac    600
gaattctgga ctacacattc aggagnnnnn nnnnnnnnnn nnnnnnnnnn nnnnnnnnn     660 nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnngagag gatccaaagg ccgtaatgtt ccccacctac    960
aaatatgttg acatcaacac atttcgcctc tctgctgatg acatacgtgg cattcagtcc    1020
ctgtatggag acccaaaaga gaaccaacgc ttgccaaatc ctgacaattc agraccagct    1080
ctctgtgacc ccaatttgag ttttgatgct gtcactaccg tgggaaataa gatcttttc    1140 ttcaaagaca ggttcttctg gctgaaggtt tctgagagac aaagaccag tgttaattta    1200 atttcttcct tatggccaac cttgccatcg gcattgaag ctgcttatga aattgaagcc    1260
agaaatcaag ttttctttt taaagatgac aaatactggt taattagcaa tttaagacca    1320
gagccaaatt atcccaagag catacattct tttggttttc ctaactttgt gaaaaaatt    1380 gatgcagctg ttttttaaccc acgtttttat aggacctact tctttgtaga taaccagtat    1440
tggaggtatg atgaaaggag acagatgatg gaccctggtt atcccaaact gattaccaag    1500
aacttccaag gaatcgggcc taaaattgat gcagtcttct actctaaaaa caaatactac    1560
tatttcttcc aaggatctaa ccaatttgaa tatgacttcc tactccaacg tatcaccaaa    1620
acactgaaaa gcaatagctg gtttggttgt tag                               1653

<210> SEQ ID NO 102
<211> LENGTH: 1416
<212> TYPE: DNA
<213> ORGANISM: Homo sapiens
```

<400> SEQUENCE: 102

```
atgcatccag gggtcctggc tgccttcctc ttcttgagct ggactcattg tcgggccctg      60
cccctteeca gtggtggtga tgaagatgat ttgtctgagg aagacctcca gtttgcagag     120
cgctacctga tcatacta ccatcctaca aatctcgcgg gaatcctgaa ggagaatgca       180
gcaagctcca tgactgagag gctccgagaa atgcagtctt tcttcggctt agaggtgact     240
ggcaaacttg acgataacac cttagatgtc atgaaaaagc caagatgcgg ggttcctgat     300
gtgggtgaat acaatgtttt ccctcgaact cttaaatggt ccaaaatgaa tttaacctac     360
agaattgtga attacacccc tgatatgact cattctgaag tcgaaaaggc attcaaaaaa     420
gccttcaaag tttggtccga tgtaactcct ctgaattttta ccagacttca cgatggcatt     480
gctgacatca tgatctcttt tggaattaag gagcatggcg acttctaccc atttgatggg     540
ccctctggcc tgctggctca tgcttttcct cctgggccaa attatggagg agatgcccat     600
tttgatgatg atgaaacctg acaagtagt tccaaaggct acaacttgtt tcttgttgct     660
gcgcatgagt tcggccactc cttaggtctt gaccactcca aggacctgg agcactcatg     720
tttcctatct acacctacac cggcaaaagc cactttatgc ttcctgatga cgatgtacaa     780
gggatccagt ctctctatgg tccaggagat gaagacccca accctaaaca tccaaaaacg     840
ccagacaaat gtgacccttc cttatccctt gatgccatta ccagtctccg aggagaaaca     900
atgatcttta agacagatt cttctggcgc ctgcatcctc agcaggttga tgcggagctg     960
ttttttaacga aatcattttg gccagaactt cccaaccgta ttgatgctgc atatgagcac    1020
ccttctcatg acctcatctt catcttcaga ggtagaaaat tttgggctct taatggttat    1080
gacattctgg aaggttatcc caaaaaaata tctgaactgg gtcttccaaa agaagttaag    1140
aagataagtg cagctgttca ctttgaggat acaggcaaga ctctcctgtt ctcaggaaac    1200
caggtctgga gatatgatga tactaaccat attatggata agactatccc agactaata    1260
gaagaagact cccaggaat tggtgataaa gtagatgctg tctatgagaa aaatggttat    1320
atctattttt tcaacggacc catacagttt gaatacagca tctggagtaa ccgtattgtt    1380
cgcgtcatgc cagcaaattc cattttgtgg tgttaa                              1416
```

<210> SEQ ID NO 103
<211> LENGTH: 1749
<212> TYPE: DNA
<213> ORGANISM: Homo sapiens
<300> PUBLICATION INFORMATION:
<302> TITLE: MMP14
<310> PATENT DOCUMENT NUMBER: NM004995

<400> SEQUENCE: 103

```
atgtctcccg ccccaagacc cccccgttgt ctcctgctcc cctgctcac gctcggcacc      60
gcgctcgcct cccctcggctc ggcccaaagc agcagcttca gccccgaagc ctggctacag    120
caatatggct acctgcctcc cggggaccta cgtacccaca cacagcgctc acccccagtca   180
ctctcagcgg ccatcgctgc catgcagaag ttttacggct gcaagtaac aggcaaagct    240
gatgcagaca ccatgaaggc catgaggcgc cccgatgtg tgttccaga caagtttggg     300
gctgagatca aggccaatgt tcgaaggaag cgctacgcca tccagggtct caatggcaa     360
cataatgaaa tcactttctg catccagaat acaccccca aggtgggcga gtatgccaca    420
tacgaggcca ttcgcaaggc gttccgcgtg tgggagagtg ccacaccact gcgcttccgc    480
gaggtgccct atgcctacat ccgtgagggc catgagaagc aggccgacat catgatcttc    540
```

-continued

```
tttgccgagg gcttccatgg cgacagcacg cccttcgatg gtgagggcgg cttcctggcc      600
catgcctact tcccaggccc caacattgga ggagacaccc actttgactc tgccgagcct      660
tggactgtca ggaatgagga tctgaatgga aatgacatct tcctggtggc tgtgcacgag      720
ctgggccatg ccctggggct cgagcattcc agtgacccct cggccatcat ggcacccttt      780
taccagtgga tggacacgga gaattttgtg ctgcccgatg atgaccgccg ggcatccag       840
caactttatg ggggtgagtc agggttcccc accaagatgc cccctcaacc caggactacc      900
tcccggcctt ctgttcctga taaacccaaa aaccccacct atgggcccaa catctgtgac      960
gggaactttg acaccgtggc catgctccga ggggagatgt ttgtcttcaa ggagcgctgg     1020
ttctggcggg tgaggaataa ccaagtgatg gatggatacc caatgcccat ggccagttc      1080
tggcggggcc tgcctgcgtc catcaacact gcctacgaga ggaaggatgg caaattcgtc     1140
ttcttcaaag agacaagca ttgggtgttt gatgaggcgt ccctggaacc tggctacccc     1200
aagcacatta aggagctggg ccgagggctg cctaccgaca agattgatgc tgctctcttc     1260
tggatgccca atggaaagac ctacttcttc cgtggaaaca agtactaccg tttcaacgaa     1320
gagctcaggg cagtggatag cgagtacccc aagaacatca agtctgggga agggatccct     1380
gagtctccca gagggtcatt catgggcagc gatgaagtct tcacttactt ctacaagggg     1440
aacaaatact ggaaattcaa caaccagaag ctgaaggtag aaccgggcta ccccaagtca     1500
gccctgaggg actggatggg ctgcccatcg ggaggccggc cggatgaggg gactgaggag     1560
gagacggagg tgatcatcat tgaggtggac gaggagggcg gcggggcggt gagcgcggct     1620
gccgtggtgc tgcccgtgct gctgctgctc ctggtgctgg cggtgggcct tgcagtcttc     1680
ttcttcagac gccatgggac ccccaggcga ctgctctact ccagcgttc cctgctggac     1740
aaggtctga                                                            1749
```

<210> SEQ ID NO 104
<211> LENGTH: 2010
<212> TYPE: DNA
<213> ORGANISM: Homo sapiens
<300> PUBLICATION INFORMATION:
<302> TITLE: MMP15
<310> PATENT DOCUMENT NUMBER: NM002428

<400> SEQUENCE: 104

```
atgggcagcg acccgagcgc gcccggacgg ccgggctgga cgggcagcct cctcggcgac      60
cgggaggagg cggcgcggcc gcgactgctg ccgctgctcc tggtgcttct gggctgcctg     120
ggccttggcg tagcggccga agacgcggag gtccatgccg agaactggct gcggctttat     180
ggctacctgc ctcagcccag ccgccatatg tccaccatgc gttccgccca gatcttggcc     240
tcggcccttg cagagatgca gcgcttctac gggatcccag tcaccggtgt gctcgacgaa     300
gagaccaagg agtggatgaa gcggccccgc tgtgggggtgc cagaccagtt cggggtacga     360
gtgaaagcca acctgcggcg gcgtcggaag cgctacgccc tcaccgggag gaagtggaac     420
aaccaccatc tgacctttag catccagaac tacacggaga gttgggctg gtaccactcg     480
atggaggcgg tgcgcagggc cttccgcgtg tgggagcagg ccacgcccct ggtcttccag     540
gaggtgccct atgaggacat ccggctgcgc cgacagaagg aggccgacat catggtactc     600
tttgcctctg gcttccacgg cgacagctcg ccgtttgatg gcaccggtgg ctttctggcc     660
cacgccatt tccctggccc cggcctaggc ggggacaccc attttgacgc agatgagccc     720
tggaccttct ccagcactga cctgcatgga aacaacctct tcctggtggc agtgcatgag     780
```

-continued

| | |
|---|---|
| ctgggccacg cgctggggct ggagcactcc agcaaccoca atgccatcat ggcgccgttc | 840 |
| taccagtgga aggacgttga caacttcaag ctgcccgagg acgatctccg tggcatccag | 900 |
| cagctctacg gtaccccaga cggtcagcca cagcctaccc agcctctccc cactgtgacg | 960 |
| ccacggcggc caggccggcc tgaccaccgg ccgcccggc ctccccagcc accacccca | 1020 |
| ggtgggaagc cagagcggcc cccaaagccg gccccccag tccagccccg agccacagag | 1080 |
| cggcccgacc agtatggccc caacatctgc gacggggact ttgacacagt ggccatgctt | 1140 |
| cgcggggaga tgttcgtgtt caagggccgc tggttctggc gagtccggca caaccgcgtc | 1200 |
| ctggacaact atcccatgcc catcgggcac ttctggcgtg gtctgcccgg tgacatcagt | 1260 |
| gctgcctacg agcgccaaga cggtcgtttt gtcttttca aaggtgaccg ctactggctc | 1320 |
| tttcgagaag cgaacctgga gcccggctac ccacagccgc tgaccagcta tggcctgggc | 1380 |
| atcccctatg accgcattga cacggccatc tggtgggagc ccacaggcca caccttcttc | 1440 |
| ttccaagagg acaggtactg gcgcttcaac gaggagacac agcgtggaga ccctgggtac | 1500 |
| cccaagccca tcagtgtctg gcaggggatc cctgcctccc ctaaagggc cttcctgagc | 1560 |
| aatgacgcag cctacaccta cttctacaag ggcaccaaat actggaaatt cgacaatgag | 1620 |
| cgcctgcgga tggagcccgg ctaccccaag tccatcctgc gggacttcat gggctgccag | 1680 |
| gagcacgtgg agccaggccc ccgatggccc gacgtggccc ggccgcccctt caaccccac | 1740 |
| ggggtgcag agcccggggc ggacagcgca gagggcgacg tgggggatgg ggatggggac | 1800 |
| tttggggccg gggtcaacaa ggacggggc agccgcgtgg tggtgcagat ggaggaggtg | 1860 |
| gcacggacgg tgaacgtggt gatggtgctg gtgccactgc tgctgctgct ctgcgtcctg | 1920 |
| ggcctcacct acgcgctggt gcagatgcag cgcaagggtg cgccacgtgt cctgctttac | 1980 |
| tgcaagcgct cgctgcagga gtgggtctga | 2010 |

<210> SEQ ID NO 105
<211> LENGTH: 1824
<212> TYPE: DNA
<213> ORGANISM: Homo sapiens
<300> PUBLICATION INFORMATION:
<302> TITLE: MMP16
<310> PATENT DOCUMENT NUMBER: NM005941

<400> SEQUENCE: 105

| | |
|---|---|
| atgatcttac tcacattcag cactggaaga cggttggatt tcgtgcatca ttcgggggtg | 60 |
| tttttcttgc aaaccttgct ttggatttta tgtgctacag tctgcggaac ggagcagtat | 120 |
| ttcaatgtgg aggtttggtt acaaaagtac ggctaccttc caccgactga ccccagaatg | 180 |
| tcagtgctgc gctctgcaga gaccatgcag tctgccctag ctgccatgca gcagttctat | 240 |
| ggcattaaca tgacaggaaa agtggacaga aacacaattg actggatgaa gaagccccga | 300 |
| tgcggtgtac ctgaccagac aagaggtagc tccaaatttc atattcgtcg aaagcgatat | 360 |
| gcattgacag gacagaaatg gcagcacaag cacatcactt acagtataaa gaacgtaact | 420 |
| ccaaaagtag agaccctga ctcgtaaa gctattcgcc gtgcctttga tgtgtggcag | 480 |
| aatgtaactc ctctgacatt tgaagaagtt ccctacagtg aattagaaaa tggcaaacgt | 540 |
| gatgtggata taaccattat ttttgcatct ggtttccatg ggacagctc tcccttgat | 600 |
| ggagagggag gattttggc acatgcctac ttccctggac aggaattggg aggagatacc | 660 |
| cattttgact cagatgagcc atggacacta ggaaatccta atcatgatgg aaatgactta | 720 |
| tttcttgtag cagtccatga actgggacat gctctgggat tggagcattc caatgacccc | 780 |

| | |
|---|---:|
| actgccatca tggctccatt ttaccagtac atggaaacag acaacttcaa actacctaat | 840 |
| gatgatttac agggcatcca gaaaatatat ggtccacctg acaagattcc tccacctaca | 900 |
| agacctctac cgacagtgcc cccacaccgc tctattcctc cggctgaccc aaggaaaaat | 960 |
| gacaggccaa aacctcctcg gcctccaacc ggcagaccct cctatcccgg agccaaaccc | 1020 |
| aacatctgtg atgggaactt taacactcta gctattcttc gtcgtgagat gtttgttttc | 1080 |
| aaggaccagt ggttttggcg agtgagaaac acagggtga tggatggata cccaatgcaa | 1140 |
| attacttact tctggcgggg cttgcctcct agtatcgatg cagtttatga aaatagcgac | 1200 |
| gggaattttg tgttctttaa aggtaacaaa tattgggtgt tcaaggatac aactcttcaa | 1260 |
| cctggttacc ctcatgactt gataacccct ggaagtggaa ttcccctca tggtattgat | 1320 |
| tcagccattt ggtgggagga cgtcgggaaa acctatttct tcaagggaga cagatattgg | 1380 |
| agatatagtg aagaaatgaa acaatggac cctggctatc ccaagccaat cacagtctgg | 1440 |
| aaagggatcc ctgaatctcc tcaggagca tttgtacaca agaaaatgg ctttacgtat | 1500 |
| ttctacaaag gaaaggagta ttggaaattc aacaaccaga tactcaaggt agaacctgga | 1560 |
| catccaagat ccatcctcaa ggattttatg ggctgtgatg gaccaacaga cagagttaaa | 1620 |
| gaaggacaca gcccaccaga tgatgtagac attgtcatca aactggacaa cacagccagc | 1680 |
| actgtgaaag ccatagctat tgtcattccc tgcatcttgg ccttatgcct ccttgtattg | 1740 |
| gtttacactg tgttccagtt caagaggaaa ggaacacccc gccacatact gtactgtaaa | 1800 |
| cgctctatgc aagagtgggt gtga | 1824 |

<210> SEQ ID NO 106
<211> LENGTH: 1560
<212> TYPE: DNA
<213> ORGANISM: Homo sapiens
<300> PUBLICATION INFORMATION:
<302> TITLE: MMP17
<310> PATENT DOCUMENT NUMBER: NM004141

<400> SEQUENCE: 106

| | |
|---|---:|
| atgcagcagt ttggtggcct ggaggccacc ggcatcctgg acgaggccac cctggccctg | 60 |
| atgaaaaccc cacgctgctc cctgccagac ctccctgtcc tgacccaggc tcgcaggaga | 120 |
| cgccaggctc cagcccccac caagtggaac aagaggaacc tgtcgtggag ggtccggacg | 180 |
| ttcccacggg actcaccact ggggcacgac acggtgcgtg cactcatgta ctacgccctc | 240 |
| aaggtctgga gcgacattgc gcccctgaac ttccacgagg tggcgggcag caccgccgac | 300 |
| atccagatcg acttctccaa ggccgaccat aacgacggct accccttcga cggccccggc | 360 |
| ggcaccgtgg cccacgcctt cttccccggc accaccaca ccgccgggga cacccactt | 420 |
| gacgatgacg aggcctggac cttccgctcc tcggatgccc acgggatgga cctgtttgca | 480 |
| gtggctgtcc acgagtttgg ccacgccatt gggttaagcc atgtggccgc tgcacactcc | 540 |
| atcatgcggc cgtactacca gggcccggtg ggtgacccgc tgcgctacgg gctcccctac | 600 |
| gaggacaagt gcgcgtctg gcagctgtac ggtgtgcggg agtctgtgtc tcccacggcg | 660 |
| cagcccgagg agcctcccct gctgccggag cccccagaca accggtccag cgccccgccc | 720 |
| aggaaggacg tgcccacag atgcagcact cactttgacg cggtggccca gatccggggt | 780 |
| gaagctttct tcttcaaagg caagtacttc tggcggctga cgcgggaccg gcacctggtg | 840 |
| tccctgcagc cggcacagat gcaccgcttc tggcggggcc tgccgctgca cctggacagc | 900 |
| gtggacgccg tgtacgagcg caccagcgac cacaagatcg tcttctttaa aggagacagg | 960 |

-continued

| | | | |
|---|---|---|---|
| tactgggtgt | tcaaggacaa | taacgtagag | gaaggatacc cgcgccccgt ctccgacttc | 1020 |
| agcctcccgc | ctggcggcat | cgacgctgcc | ttctcctggg cccacaatga caggacttat | 1080 |
| ttctttaagg | accagctgta | ctggcgctac | gatgaccaca cgaggcacat ggaccccggc | 1140 |
| taccccgccc | agagccccct | gtggaggggt | gtccccagca cgctggacga cgccatgcgc | 1200 |
| tggtccgacg | tgcctcctta | cttcttccgt | ggccaggagt actggaaagt gctggatggc | 1260 |
| gagctggagg | tggcacccgg | gtacccacag | tccacggccc gggactggct ggtgtgtgga | 1320 |
| gactcacagg | ccgatggatc | tgtgctgcg | ggcgtggacg cggcagaggg gccccgcgcc | 1380 |
| cctccaggac | aacatgacca | gagccgctcg | gaggacggtt acgaggtctg ctcatgcacc | 1440 |
| tctgggcat | cctctccccc | ggggccccca | ggcccactgg tggctgccac catgctgctg | 1500 |
| ctgctgccgc | cactgtcacc | aggcgccctg | tggacagcgg cccaggccct gacgctatga | 1560 |

```
<210> SEQ ID NO 107
<211> LENGTH: 1983
<212> TYPE: DNA
<213> ORGANISM: Homo sapiens
<300> PUBLICATION INFORMATION:
<302> TITLE: MMP2
<310> PATENT DOCUMENT NUMBER: NM004530

<400> SEQUENCE: 107
```

| | | | |
|---|---|---|---|
| atggaggcgc | taatggcccg | gggcgcgctc | acgggtcccc tgagggcgct ctgtctcctg | 60 |
| ggctgcctgc | tgagccacgc | cgccgccgcg | ccgtcgccca tcatcaagtt ccccggcgat | 120 |
| gtcgccccca | aaacggacaa | agagttggca | gtgcaatacc tgaacacctt ctatggctgc | 180 |
| cccaaggaga | gctgcaacct | gtttgtgctg | aaggacacac taagaagat gcagaagttc | 240 |
| tttggactgc | cccagacagg | tgatcttgac | cagaatacca tcgagaccat gcggaagcca | 300 |
| cgctgcggca | acccagatgt | ggccaactac | aacttcttcc ctcgcaagcc caagtgggac | 360 |
| aagaaccaga | tcacatacag | gatcattggc | tacacacctg atctggaccc agagacagtg | 420 |
| gatgatgcct | ttgctcgtgc | cttccaagtc | tggagcgatg tgaccccact gcggttttct | 480 |
| cgaatccatg | atggagaggc | agacatcatg | atcaactttg ccgctggga gcatggcgat | 540 |
| ggataccct | tgacggtaa | ggacggactc | ctggctcatg ccttcgcccc aggcactggt | 600 |
| gttgggggag | actcccattt | tgatgacgat | gagctatgga ccttgggaga aggccaagtg | 660 |
| gtccgtgtga | agtatggcaa | cgccgatggg | gagtactgca gttcccctt cttgttcaat | 720 |
| ggcaaggagt | acaacagctg | cactgatact | ggccgcagcg atggcttcct ctggtgctcc | 780 |
| accacctaca | actttgagaa | ggatggcaag | tacggcttct gtccccatga agccctgttc | 840 |
| accatgggcg | gcaacgctga | aggacagccc | tgcaagtttc cattccgctt ccagggcaca | 900 |
| tcctatgaca | gctgcaccac | tgagggccgc | acggatggct accgctggtg cggcaccact | 960 |
| gaggactacg | accgcgacaa | gaagtatggc | ttctgccctg agaccgccat gtccactgtt | 1020 |
| ggtgggaact | cagaaggtgc | cccctgtgtc | ttcccttca ctttcctggg caacaaatat | 1080 |
| gagagctgca | ccagccgcgg | ccgcagtgac | ggaaagatgt ggtgtgcgac cacagccaac | 1140 |
| tacgatgacg | accgcaagtg | gggcttctgc | cctgaccaag gtacagcct gttcctcgtg | 1200 |
| gcagcccacg | agtttggcca | cgccatgggg | ctggagcact ccaagaccc tggggccctg | 1260 |
| atggcaccca | tttacaccta | caccaagaac | ttccgtctgt cccaggatga catcaagggc | 1320 |
| attcaggagc | tctatggggc | ctctcctgac | attgaccttg gcaccggccc cacccccaca | 1380 |
| ctgggccctg | tcactcctga | gatctgcaaa | caggacattg tatttgatgg catcgctcag | 1440 |

-continued

```
atccgtggtg agatcttctt cttcaaggac cggttcattt ggcggactgt gacgccacgt   1500
gacaagccca tggggcccct gctggtggcc acattctggc ctgagctccc ggaaaagatt   1560
gatgcggtat acgaggcccc acaggaggag aaggctgtgt tctttgcagg gaatgaatac   1620
tggatctact cagccagcac cctggagcga gggtacccca agccactgac cagcctggga   1680 ctgcccctg atgtccagcg agtggatgcc gcctttaact ggagcaaaaa caagaagaca    1740
tacatctttg ctggagacaa attctggaga tacaatgagg tgaagaagaa aatggatcct   1800
ggctttccca agctcatcgc agatgcctgg aatgccatcc ccgataacct ggatgccgtc   1860
gtggacctgc agggcggcgg tcacagctac ttcttcaagg gtgcctatta cctgaagctg   1920
gagaaccaaa gtctgaagag cgtgaagttt ggaagcatca atccgactg gctaggctgc    1980 tga                                                                1983

<210> SEQ ID NO 108
<211> LENGTH: 1434
<212> TYPE: DNA
<213> ORGANISM: Homo sapiens
<300> PUBLICATION INFORMATION:
<302> TITLE: MMP2
<310> PATENT DOCUMENT NUMBER: XM006271
<300> PUBLICATION INFORMATION:
<302> TITLE: MMP3
<310> PATENT DOCUMENT NUMBER: XM006271

<400> SEQUENCE: 108
atgaagagtc ttccaatcct actgttgctg tgcgtggcag tttgctcagc ctatccattg     60
gatggagctg caaggggtga ggacaccagc atgaacttg ttcagaaata tctagaaaac    120
tactacgacc tcgaaaaaga tgtgaaacag tttgttagga aaggacag tggtcctgtt     180 gttaaaaaaa tccgagaaat gcagaagttc cttggattgg aggtgacggg gaagctggac    240
tccgacactc tggaggtgat gcgcaagccc aggtgtggaa ttcctgacgt tggtcacttc    300 agaaccttc ctggcatccc gaagtggagg aaaacccacc ttacatacag gattgtgaat    360
tatacaccag atttgccaaa agatgctgtt gattctgctg ttgagaaagc tctgaaagtc    420
tgggaagagg tgactccact cacattctcc aggctgtatg aaggagaggc tgatataatg    480
atctcttttg cagttagaga acatggagac ttttacccctt tgatggacc tggaaatgtt    540 ttggcccatg cctatgcccc tgggccaggg attaatggag atgcccactt tgatgatgat    600
gaacaatgga caaaggatac aacagggacc aatttattc tcgttgctgc tcatgaaatt    660
ggccactccc tgggtctctt tcactcagcc aacactgaag ctttgatgta cccactctat    720
cactcactca cagacctgac tcggttccgc ctgtctcaag atgatataaa tggcattcag    780
tccctctatg gacctccccc tgactcccct gagacccccc tggtacccac ggaacctgtc    840
cctccagaac ctgggacgcc agccaactgt gatcctgctt gtccttttga tgctgtcagc    900
actctgaggg gagaaatcct gatctttaaa gacaggcact tttggcgcaa atccctcagg    960
aagcttgaac ctgaattgca tttgatctct tcattttggc catctcttcc ttcaggcgtg   1020
gatgccgcat atgaagttac tagcaaggac ctcgttttca tttttaaagg aaatcaattc   1080
tgggccatca gaggaaatga ggtacgagct ggatacccaa gaggcatcca caccctaggt   1140
ttccctccaa ccgtgaggaa atcgatgca gccatttctg ataaggaaaa gaacaaaaca   1200 tatttcttg tagaggacaa atactggaga tttgatgaga agaaattc catggagcca    1260 ggcttcccca agcaaatagc tgaagacttt ccagggattg actcaaagat tgatgctgtt   1320
```

| | |
|---|---|
| tttgaagaat ttgggttctt ttatttcttt actggatctt cacagttgga gtttgaccca | 1380 |
| aatgcaaaga aagtgacaca cactttgaag agtaacagct ggcttaattg ttga | 1434 |

<210> SEQ ID NO 109
<211> LENGTH: 1404
<212> TYPE: DNA
<213> ORGANISM: Homo sapiens
<300> PUBLICATION INFORMATION:
<302> TITLE: MMP8
<310> PATENT DOCUMENT NUMBER: NM002424

<400> SEQUENCE: 109

| | |
|---|---|
| atgttctccc tgaagacgct tccatttctg ctcttactcc atgtgcagat ttccaaggcc | 60 |
| tttcctgtat cttctaaaga gaaaaataca aaaactgttc aggactacct ggaaaagttc | 120 |
| taccaattac caagcaacca gtatcagtct acaaggaaga atggcactaa tgtgatcgtt | 180 |
| gaaaagctta agaaatgca gcgatttttt gggttgaatg tgacggggaa gccaaatgag | 240 |
| gaaactctgg acatgatgaa aaagcctcgc tgtggagtgc ctgacagtgg tggttttatg | 300 |
| ttaaccccag gaaaccccaa gtgggaacgc actaacttga cctacaggat tcgaaactat | 360 |
| accccacagc tgtcagaggc tgaggtagaa agagctatca aggatgcctt tgaactctgg | 420 |
| agtgttgcat cacctctcat cttcaccagg atctcacagg gagaggcaga tatcaacatt | 480 |
| gcttttacc aaagagatca cggtgacaat tctccatttg atggacccaa tggaatcctt | 540 |
| gctcatgcct tcagccagg ccaaggtatt ggaggagatg ctcattttga tgccgaagaa | 600 |
| acatggacca acacctccgc aaattacaac ttgtttcttg ttgctgctca tgaatttggc | 660 |
| cattctttgg ggctcgctca ctcctctgac cctggtgcct tgatgtatcc caactatgct | 720 |
| ttcagggaaa ccagcaacta ctcactccct caagatgaca tcgatggcat tcaggccatc | 780 |
| tatggacttt caagcaaccc tatccaacct actggaccaa gcacacccaa accctgtgac | 840 |
| cccagtttga catttgatgc tatcaccaca ctccgtggag aaatacttt ctttaaagac | 900 |
| aggtacttct ggagaaggca tcctcagcta caaagagtcg aaatgaattt tatttctcta | 960 |
| ttctggccat cccttccaac tggtatacag gctgcttatg aagattttga cagagacctc | 1020 |
| atttttcctat ttaaaggcaa ccaatactgg gctctgagtg ctatgatat tctgcaaggt | 1080 |
| tatcccaagg atatatcaaa ctatggcttc cccagcagcg tccaagcaat tgacgcagct | 1140 |
| gttttctaca gaagtaaaac atacttcttt gtaaatgacc aattctggag atatgataac | 1200 |
| caaagacaat tcatggagcc aggttatccc aaaagcatat caggtgcctt tccaggaata | 1260 |
| gagagtaaag ttgatgcagt tttccagcaa gaacatttct tccatgtctt cagtggacca | 1320 |
| agatattacg catttgatct tattgctcag agagttacca gagttgcaag aggcaataaa | 1380 |
| tggcttaact gtagatatgg ctga | 1404 |

<210> SEQ ID NO 110
<211> LENGTH: 2124
<212> TYPE: DNA
<213> ORGANISM: Homo sapiens
<300> PUBLICATION INFORMATION:
<302> TITLE: MMP9
<310> PATENT DOCUMENT NUMBER: XM009491

<400> SEQUENCE: 110

| | |
|---|---|
| atgagcctct ggcagcccct ggtcctggtg ctcctggtgc tgggctgctg ctttgctgcc | 60 |
| cccagacagc gccagtccac ccttgtgctc ttccctggag acctgagaac caatctcacc | 120 |
| gacaggcagc tggcagagga ataccttac cgctatggtt acactcgggt ggcagagatg | 180 |

```
cgtggagagt cgaaatctct ggggcctgcg ctgctgcttc tccagaagca actgtccctg      240
cccgagaccg gtgagctgga tagcgccacg ctgaaggcca tgcgaacccc acggtgcggg      300
gtcccagacc tgggcagatt ccaaaccttt gagggcgacc tcaagtggca ccaccacaac      360
atcacctatt ggatccaaaa ctactcggaa gacttgccgc gggcggtgat tgacgacgcc      420
tttgcccgcg ccttcgcact gtggagcgcg gtgacgccgc tcaccttcac tcgcgtgtac      480
agccgggacg cagacatcgt catccagttt ggtgtcgcgg agcacggaga cgggtatccc      540
ttcgacggga aggacgggct cctggcacac gcctttcctc ctggccccgg cattcaggga      600
gacgcccatt tcgacgatga cgagttgtgg tccctgggca agggcgtcgt ggttccaact      660
cggtttggaa acgcagatgg cgcggcctgc cacttcccct tcatcttcga gggccgctcc      720
tactctgcct gcaccaccga cggtcgctcc gacggcttgc cctggtgcag taccacggcc      780
aactacgaca ccgacgaccg gtttggcttc tgccccagcg agagactcta cacccaggac      840
ggcaatgctg atgggaaacc ctgccagttt ccattcatct tccaaggcca atcctactcc      900
gcctgcacca cggacggtcg ctccgacggc taccgctggt gcgccaccac cgccaactac      960
gaccgggaca agctcttcgg cttctgcccg acccgagctg actcgacggt gatgggggc     1020 aactcggcgg gggagctgtg cgtcttcccc ttcactttcc tgggtaagga gtactcgacc     1080
tgtaccagcg agggccgcgg agatgggcgc ctctggtgcg ctaccacctc gaactttgac     1140
agcgacaaga gtggggcttc tgcccggac caaggataca gtttgttcct cgtggcggcg     1200
catgagttcg gccacgcgct gggcttagat cattcctcag tgccggaggc gctcatgtac     1260
cctatgtacc gcttcactga ggggccccc ttgcataagg acgacgtgaa tggcatccgg     1320
cacctctatg gtcctcgccc tgaacctgag ccacggcctc caaccaccac cacaccgcag     1380
cccacggctc ccccgacggt ctgccccacc ggaccccca ctgtccaccc ctcagagcgc     1440
cccacagctg gccccacagg tcccccctca gctggcccca caggtccccc cactgctggc     1500
ccttctacgg ccactactgt gcctttgagt ccggtggacg atgcctgcaa cgtgaacatc     1560
ttcgacgcca tcgcggagat tgggaaccag ctgtatttgt tcaaggatgg gaagtactgg     1620
cgattctctg agggcagggg gagccggccg cagggcccct tccttatcgc cgacaagtgg     1680
cccgcgctgc cccgcaagct ggactcggtc tttgaggagc ggctctccaa gaagcttttc     1740
ttcttctctg ggcgccaggt gtgggtgtac acaggcgcgt cggtgctggg cccgaggcgt     1800
ctggacaagc tgggcctggg agccgacgtg gcccaggtga ccggggccct ccggagtggc     1860 aggggggaaga tgctgctgtt cagcgggcgg cgcctctgga ggttcgacgt gaaggcgcag     1920 atgtggatc cccggagcgc cagcgaggtg accggatgt tccccggggt gcctttggac     1980
acgcacgacg tcttccagta ccgagagaaa gcctatttct gccaggaccg cttctactgg     2040
cgcgtgagtt cccggagtga gttgaaccag gtggaccaag tgggctacgt gacctatgac     2100
atcctgcagt gccctgagga ctag                                            2124
```

<210> SEQ ID NO 111
<211> LENGTH: 2019
<212> TYPE: DNA
<213> ORGANISM: Homo sapiens
<300> PUBLICATION INFORMATION:
<302> TITLE: PKC alpha
<310> PATENT DOCUMENT NUMBER: NM002737

<400> SEQUENCE: 111

```
atggctgacg tttccccggg caacgactcc acggcgtctc aggacgtggc caaccgcttc       60
```

```
gcccgcaaag gggcgctgag gcagaagaac gtgcacgagg tgaaggacca caaattcatc    120
gcgcgcttct tcaagcagcc caccttctgc agccactgca ccgacttcat ctggggtttt    180
gggaaacaag gcttccagtg ccaagtttgc tgttttgtgg tccacaagag gtgccatgaa    240
tttgttactt tttcttgtcc gggtgcggat aagggacccg acactgatga ccccaggagc    300
aagcacaagt tcaaaatcca cacttacgga agccccacct tctgcgatca ctgtgggtca    360
ctgctctatg gacttatcca tcaagggatg aaatgtgaca cctgcgatat gaacgttcac    420
aagcaatgcg tcatcaatgt ccccagcctc tgcggaatgg atcacactga agaggggg     480 cggatttacc taaaggctga ggttgctgat gaaaagctcc atgtcacagt acgagatgca    540
aaaaatctaa tccctatgga tccaaacggg ctttcagatc cttatgtgaa gctgaaactt    600
attcctgatc caagaatga aagcaagcaa aaaccaaaa ccatccgctc cacactaaat     660
ccgcagtgga atgagtcctt tacattcaaa ttgaaacctt cagacaaaga ccgacgactg    720
tctgtagaaa tctgggactg ggatcgaaca acaaggaatg acttcatggg atcccttcc     780 tttggagttt cggagctgat gaagatgccg ccagtggat ggtacaagtt gcttaaccaa     840
gaagaaggtg agtactacaa cgtacccatt ccggaagggg acgaggaagg aaacatggaa    900
ctcaggcaga aattcgagaa agccaaactt ggccctgctg caacaaagt catcagtccc     960 tctgaagaca ggaaacaacc ttccaacaac cttgaccgag tgaaactcac ggacttcaat   1020
ttcctcatgg tgttgggaaa ggggagtttt ggaaaggtga tgcttgccga caggaagggc   1080
acagaagaac tgtatgcaat caaaatcctg aagaaggatg tggtgattca ggatgatgac   1140
gtggagtgca ccatggtaga aaagcgagtc ttggccctgc ttgacaaacc cccgttcttg   1200
acgcagctgc actcctgctt ccagacagtg gatcggctgt acttcgtcat ggaatatgtc   1260
aacggtgggg acctcatgta ccacattcag caagtaggaa aatttaagga accacaagca   1320
gtattctatg cggcagagat ttccatcgga ttgttctttc ttcataaaag aggaatcatt   1380
tatagggatc tgaagttaga taacgtcatg ttggattcag aaggacatat caaaattgct   1440
gactttggga tgtgcaagga acacatgatg gatgagtca cgaccaggac cttctgtggg   1500
actccagatt atatcgcccc agagataatc gcttatcagc cgtatggaaa atctgtggac   1560
tggtgggcct atgcgtcct gttgtatgaa atgcttgccg gcagcctcc atttgatggt     1620 gaagatgaag acgagctatt tcagtctatc atggagcaca acgtttccta tccaaaatcc   1680
ttgtccaagg aggctgtttc tatctgcaaa ggactgatga ccaaacaccc agccaagcgg   1740
ctgggctgtg ggcctgaggg ggagagggac gtgagagagc atgccttctt ccggaggatc   1800
gactgggaaa aactggagaa cagggagatc cagccaccat tcaagcccaa agtgtgtggc   1860
aaaggagcag agaactttga caagttcttc acacgaggac agcccgtctt aacaccacct   1920
gatcagctgg ttattgctaa catagaccag tctgattttg aagggttctc gtatgtcaac   1980
ccccagtttg tgcaccccat cttacagagt gcagtatga                          2019

<210> SEQ ID NO 112
<211> LENGTH: 2022
<212> TYPE: DNA
<213> ORGANISM: Homo sapiens
<300> PUBLICATION INFORMATION:
<302> TITLE: PKC beta
<310> PATENT DOCUMENT NUMBER: X07109

<400> SEQUENCE: 112
atggctgacc cggctgcggg gccgccgccg agcgagggcg aggagagcac cgtgcgcttc    60
```

```
gcccgcaaag gcgccctccg gcagaagaac gtgcatgagg tcaagaacca caaattcacc      120
gcccgcttct tcaagcagcc caccttctgc agccactgca ccgacttcat ctggggcttc      180
gggaagcagg gattccagtg ccaagtttgc tgctttgtgg tgcacaagcg gtgccatgaa      240
tttgtcacat tctcctgccc tggcgctgac aagggtccag cctccgatga cccccgcagc      300
aaacacaagt taagatccac acgtactcc agccccacgt tttgtgacca ctgtgggtca       360
ctgctgtatg gactcatcca ccaggggatg aaatgtgaca cctgcatgat gaatgtgcac      420
aagcgctgcg tgatgaatgt tcccagcctg tgtggcacgg accacacgga gcgccgcggc      480
cgcatctaca tccaggccca catcgacagg gacgtcctca ttgtcctcgt aagagatgct      540
aaaaaccttg tacctatgga ccccaatggc ctgtcagatc cctacgtaaa actgaaactg      600
attcccgatc ccaaaagtga gagcaaacag aagaccaaaa ccatcaaatg ctccctcaac      660
cctgagtgga atgagacatt tagatttcag ctgaaagaat cggacaaaga cagaagactg      720
tcagtagaga tttgggattg ggatttgacc agcaggaatg acttcatggg atctttgtcc      780
tttgggattt ctgaacttca gaaggccagt gttgatggct ggtttaagtt actgagccag      840
gaggaaggcg agtacttcaa tgtgcctgtg ccaccagaag gaagtgaggc caatgaagaa      900
ctgcggcaga aatttgagag ggccaagatc agtcagggaa ccaaggtccc ggaagaaaag      960
acgaccaaca ctgtctccaa atttgacaac aatggcaaca gagaccggat gaaactgacc     1020 gatttttaact tcctaatggt gctggggaaa ggcagctttg gcaaggtcat gctttcagaa     1080
cgaaaaggca cagatgagct ctatgctgtg aagatcctga agaaggacgt tgtgatccaa     1140
gatgatgacg tggagtgcac tatggtggag aagcgggtgt tggccctgcc tgggaagccg     1200
cccttcctga cccagctcca ctcctgcttc cagaccatgg accgcctgta ctttgtgatg     1260
gagtacgtga atggggcga cctcatgtat cacatccagc aagtcggccg gttcaaggag     1320 cccatgctg tatttacgc tgcagaaatt gccatcggtc tgttcttctt acagagtaag      1380
ggcatcattt accgtgacct aaaacttgac aacgtgatgc tcgattctga gggacacatc     1440
aagattgccg attttggcat gtgtaaggaa acatctggg atggggtgac aaccaagaca      1500
ttctgtggca ctccagacta catcgccccc gagataattg cttatcagcc ctatgggaag      1560
tccgtggatt ggtgggcatt tggagtcctg ctgtatgaaa tgttggctgg gcaggcaccc      1620
tttgaagggg aggatgaaga tgaactcttc caatccatca tggaacacaa cgtagcctat      1680
cccaagtcta tgtccaagga agctgtggcc atctgcaaag gctgatgac caaacaccca      1740 ggcaaacgtc tgggttgtgg acctgaaggc gaacgtgata tcaaagagca tgcattttc     1800 cggtatattg attgggagaa acttgaacgc aaagagatcc agccccctta taagccaaaa      1860
gcttgtgggc gaaatgctga aaacttcgac cgattttca cccgccatcc accagtccta      1920
acacctcccg accaggaagt catcaggaat attgaccaat cagaattcga aggatttccc      1980
tttgttaact ctgaattttt aaaacccgaa gtcaagagct aa                        2022
```

<210> SEQ ID NO 113
<211> LENGTH: 2031
<212> TYPE: DNA
<213> ORGANISM: Homo sapiens
<300> PUBLICATION INFORMATION:
<302> TITLE: PKC delta
<310> PATENT DOCUMENT NUMBER: NM006254

<400> SEQUENCE: 113

```
atggcgccgt tcctgcgcat cgccttcaac tcctatgagc tgggctccct gcaggccgag        60
```

-continued

```
gacgaggcga accagcccgtt ctgtgccgtg aagatgaagg aggcgctcag cacagagcgt    120
gggaaaacac tggtgcagaa gaagccgacc atgtatcctg agtggaagtc gacgttcgat    180
gcccacatct atgaggggcg cgtcatccag attgtgctaa tgcgggcagc agaggagcca    240
gtgtctgagg tgaccgtggg tgtgtcggtg ctggccgagc gctgcaagaa gaacaatggc    300
aaggctgagt tctggctgga cctgcagcct caggccaagg tgttgatgtc tgttcagtat    360
ttcctggagg acgtggattg caaacaatct atgcgcagtg aggacgaggc caagttccca    420
acgatgaacc gccgcggagc catcaaacag gccaaaatcc actacatcaa gaaccatgag    480
tttatcgcca ccttctttgg gcaacccacc ttctgttctg tgtgcaaaga ctttgtctgg    540
ggcctcaaca gcaaggcta caaatgcagg caatgtaacg ctgccatcca caagaaatgc    600
atcgacaaga tcatcggcag atgcactggc accgcggcca cagccggga cactatattc    660 cagaaagaac gcttcaacat cgacatgccg caccgcttca aggttcacaa ctacatgagc    720
cccaccttct gtgaccactg cggcagcctg ctctggggac tggtgaagca gggattaaag    780
tgtgaagact gcggcatgaa tgtgcaccat aaatgccggg agaaggtggc caacctctgc    840
ggcatcaacc agaagctttt ggctgaggcc ttgaaccaag tcacccagag agcctcccgg    900
agatcagact cagcctcctc agagcctgtt gggatatatc aggtttcga agaagacc     960 ggagttgctg gggaggacat gcaagacaac agtgggacct acggcaagat ctgggagggc   1020
agcagcaagt gcaacatcaa caacttcatc ttccacaagg tcctgggcaa aggcagcttc   1080
gggaaggtgc tgcttggaga gctgaagggc agaggagagt actctgccat caaggccctc   1140
aagaaggatg tggtcctgat cgacgacgac gtggagtgca ccatggttga agagcgggtg   1200
ctgacacttg ccgcagagaa tcccttctc acccacctca tctgcacctt ccagaccaag   1260
gaccacctgt tctttgtgat ggagttcctc aacggggggg acctgatgta ccacatccag   1320
gacaaaggcc gctttgaact ctaccgtgcc acgtttatg ccgctgagat aatgtgtgga   1380
ctgcagtttc tacacagcaa gggcatcatt tacaggacc tcaaactgga caatgtgctg   1440
ttggaccggg atgccacat caagattgcc gactttggga tgtgcaaaga gaacatattc   1500
ggggagagcc gggccagcac cttctgcggc acccctgact atatcgcccc tgagatccta   1560
cagggcctga gtacacatt tctctgtgac tggtggtctt cgggggtcct tctgtacgag   1620
atgctcattg ccagtccccc cttccatggt gatgatgagg atgaactctt cgagtccatc   1680
cgtgtggaca cgccacatta tcccgctgg atcaccaagg agtccaagga catcctggag   1740
aagctctttg aagggaacc aaccaagagg ctgggaatga cgggaaacat caaaatccac   1800
cccttcttca agaccataaa ctggactctg ctggaaaagc ggaggttgga gccacccttc   1860
aggcccaaag tgaagtcacc cagagactac agtaactttg accaggagtt cctgaacgag   1920
aaggcgcgcc tctcctacag cgacaagaac ctcatcgact ccatggacca gtctgcattc   1980
gctggcttct cctttgtgaa ccccaaattc gagcacctcc tggaagattg a           2031
```

<210> SEQ ID NO 114
<211> LENGTH: 2049
<212> TYPE: DNA
<213> ORGANISM: Homo sapiens
<300> PUBLICATION INFORMATION:
<302> TITLE: PKC eta
<310> PATENT DOCUMENT NUMBER: NM006255

<400> SEQUENCE: 114

```
atgtcgtctg gcaccatgaa gttcaatggc tatttgaggg tccgcatcgg tgaggcagtg    60
```

-continued

| | | |
|---|---|---|
| gggctgcagc ccacccgctg gtccctgcgc cactcgctct tcaagaaggg ccaccagctg | 120 | |
| ctggacccct atctgacggt gagcgtggac caggtgcgcg tgggccagac cagcaccaag | 180 | |
| cagaagacca caaacccac gtacaacgag gagttttgcg ctaacgtcac cgacggcggc | 240 | |
| cacctcgagt tggccgtctt ccacgagacc cccctgggct acgacttcgt ggccaactgc | 300 | |
| accctgcagt tccaggagct cgtcggcacg accggcgcct cggacacctt cgagggttgg | 360 | |
| gtggatctcg agccagaggg gaaagtattt gtggtaataa cccttaccgg gagtttcact | 420 | |
| gaagctactc tccagagaga ccggatcttc aaacatttta ccaggaagcg ccaaagggct | 480 | |
| atgcgaaggc gagtccacca gatcaatgga cacaagttca tggccacgta tctgaggcag | 540 | |
| cccacctact gctctcactg cagggagttt atctggggag tgtttgggaa cagggttat | 600 | |
| cagtgccaag tgtgcacctg tgtcgtccat aaacgctgcc atcatctaat tgttacagcc | 660 | |
| tgtacttgcc aaaacaatat taacaaagtg gattcaaaga ttgcagaaca gaggttcggg | 720 | |
| atcaacatcc cacacaagtt cagcatccac aactacaaag tgccaacatt ctgcgatcac | 780 | |
| tgtggctcac tgctctgggg aataatgcga caaggacttc agtgtaaaat atgtaaaatg | 840 | |
| aatgtgcata ttcgatgtca agcgaacgtg gcccctaact gtggggtaaa tgcggtggaa | 900 | |
| cttgccaaga ccctggcagg gatgggtctc caacccggaa atatttctcc aacctcgaaa | 960 | |
| ctcgttttcca gatcgaccct aagacgacag ggaaaggaga gcagcaaaga aggaaatggg | 1020 | |
| attggggtta attcttccaa ccgacttggt atcgacaact ttgagttcat ccgagtgttg | 1080 | |
| gggaagggga gttttgggaa ggtgatgctt gcaagagtaa aagaaacagg agacctctat | 1140 | |
| gctgtgaagg tgctgaagaa ggacgtgatt ctgctggatg atgatgtgga atgcaccatg | 1200 | |
| accgagaaaa ggatcctgtc tctggcccgc aatcaccct tcctcactca gttgttctgc | 1260 | |
| tgctttcaga cccccgatcg tctgtttttt gtgatggagt ttgtgaatgg gggtgacttg | 1320 | |
| atgttccaca ttcagaagtc tcgtcgtttt gatgaagcac gagctcgctt ctatgctgca | 1380 | |
| gaaatcattt cggctctcat gttcctccat gataaaggaa tcatctatag agatctgaaa | 1440 | |
| ctggacaatg tcctgttgga ccacgagggt cactgtaaac tggcagactt cggaatgtgc | 1500 | |
| aaggagggga tttgcaatgg tgtcaccacg gccacattct gtggcacgcc agactatatc | 1560 | |
| gctccagaga tcctccagga aatgctgtac gggcctgcag tagactggtg ggcaatgggc | 1620 | |
| gtgttgctct atgagatgct ctgtggtcac gcgccttttg aggcagagaa tgaagatgac | 1680 | |
| ctctttgagg ccatactgaa tgatgaggtg gtctacccta cctggctcca tgaagatgcc | 1740 | |
| acagggatcc taaaatcttt catgaccaag aaccccacca tgcgcttggg cagcctgact | 1800 | |
| cagggaggcg agcacgccat cttgagacat ccttttttta aggaaatcga ctgggccag | 1860 | |
| ctgaaccatc gccaaataga accgcctttc agacccagaa tcaaatcccg agaagatgtc | 1920 | |
| agtaattttg accctgactt cataaaggaa gagccagttt taactccaat tgatgaggga | 1980 | |
| catcttccaa tgattaacca ggatgagttt agaaactttt cctatgtgtc tccagaattg | 2040 | |
| caaccatag | 2049 | |

<210> SEQ ID NO 115
<211> LENGTH: 948
<212> TYPE: DNA
<213> ORGANISM: Homo sapiens
<300> PUBLICATION INFORMATION:
<302> TITLE: PKC epsilon
<310> PATENT DOCUMENT NUMBER: XM002370

<400> SEQUENCE: 115

-continued

```
atgttggcag aactcaaggg caaagatgaa gtatatgctg tgaaggtctt aaagaaggac      60
gtcatccttc aggatgatga cgtggactgc acaatgacag agaagaggat tttggctctg     120
gcacggaaac acccgtacct tacccaactc tactgctgct ccagaccaa ggaccgcctc      180 tttttcgtca tggaatatgt aaatggtgga gacctcatgt ttcagattca gcgctcccga    240
aaattcgacg agcctcgttc acggttctat gctgcagagg tcacatcggc cctcatgttc    300
ctccaccagc atggagtcat ctacagggat ttgaaactgg acaacatcct tctggatgca    360
gaaggtcact gcaagctggc tgacttcggg atgtgcaagg aagggattct gaatggtgtg    420
acgaccacca cgttctgtgg gactcctgac tacatagctc ctgagatcct gcaggagttg    480
gagtatggcc cctccgtgga ctggtgggcc ctggggggtgc tgatgtacga gatgatggct   540
ggacagcctc cctttgaggc cgacaatgag gacgacctat ttgagtccat cctccatgac    600
gacgtgctgt acccagtctg gctcagcaag gaggctgtca gcatcttgaa agctttcatg    660
acgaagaatc cccacaagcg cctgggctgt gtggcatcgc agaatggcga ggacgccatc    720
aagcagcacc cattcttcaa agagattgac tgggtgctcc tggagcagaa gaagatcaag    780
ccacccttca aaccacgcat taaaaccaaa agagacgtca ataattttga ccaagacttt    840
acccgggaag agccggtact cacccttgtg gacgaagcaa ttgtaaagca gatcaaccag    900
gaggaattca aaggtttctc ctactttggt gaagacctga tgcccctga              948
```

<210> SEQ ID NO 116
<211> LENGTH: 1764
<212> TYPE: DNA
<213> ORGANISM: Homo sapiens
<300> PUBLICATION INFORMATION:
<302> TITLE: PKC iota
<310> PATENT DOCUMENT NUMBER: NM002740

<400> SEQUENCE: 116

```
atgtcccaca cggtcgcagg cggcggcagc ggggaccatt cccaccaggt ccgggtgaaa     60
gcctactacc gcggggatat catgataaca cattttgaac cttccatctc ctttgagggc   120
ctttgcaatg aggttcgaga catgtgttct tttgacaacg aacagctctt caccatgaaa   180
tggatagatg aggaaggaga cccgtgtaca gtatcatctc agttggagtt agaagaagcc   240
tttagacttt atgagctaaa caaggattct gaactcttga ttcatgtgtt cccttgtgta   300
ccagaacgtc ctgggatgcc ttgtccagga gaagataaat ccatctaccg tagaggtgca   360
cgccgctgga gaaagcttta ttgtgccaat ggccacactt tccaagccaa gcgtttcaac   420
aggcgtgctc actgtgccat ctgcacagac cgaatatggg gacttggacg ccaaggatat   480
aagtgcatca actgcaaact cttggttcat aagaagtgcc ataaactcgt cacaattgaa   540
tgtgggcggc attctttgcc acaggaacca gtgatgccca tggatcagtc atccatgcat   600
tctgaccatg cacagacagt aattccatat aatccttcaa gtcatgagag tttggatcaa   660
gttggtgaag aaaaagaggc aatgaacacc agggaaagtg gcaaagcttc atccagtcta   720
ggtcttcagg attttgattt gctccgggta ataggaagag gaagttatgc caaagtactg   780
ttggttcgat taaaaaaaac agatcgtatt tatgcaatga agttgtgaa aaaagagctt   840 gttaatgatg atgaggatat tgattggta cagacagaga gcatgtgtt tgagcaggca   900 tccaatcatc ctttccttgt tgggctgcat tcttgctttc agacagaaag cagattgttc   960
tttgttatag agtatgtaaa tggagggac ctaatgtttc atatgcagcg acaaagaaaa   1020
cttcctgaag aacatgccag attttactct gcagaaatca gtctagcatt aaattatctt  1080
```

```
catgagcgag ggataattta tagagatttg aaactggaca atgtattact ggactctgaa    1140
ggccacatta aactcactga ctacggcatg tgtaaggaag gattacggcc aggagataca    1200
accagcactt tctgtggtac tcctaattac attgctcctg aaattttaag aggagaagat    1260
tatggtttca gtgttgactg gtgggctctt ggagtgctca tgtttgagat gatggcagga    1320
aggtctccat ttgatattgt tgggagctcc gataaccctg accagaacac agaggattat    1380
ctcttccaag ttattttgga aaaacaaatt cgcataccac gttctctgtc tgtaaaagct    1440
gcaagtgttc tgaagagttt tcttaataag accctaagg aacgattggg ttgtcatcct    1500
caaacaggat ttgctgatat tcagggacac ccgttcttcc gaaatgttga ttgggatatg    1560
atggagcaaa acaggtggt acctccctt aaaccaaata tttctgggga atttggtttg    1620
gacaactttg attctcagtt tactaatgaa cctgtccagc tcactccaga tgacgatgac    1680
attgtgagga agattgatca gtctgaattt gaaggttttg agtatatcaa tcctctttg    1740 atgtctgcag aagaatgtgt ctga                                           1764

<210> SEQ ID NO 117
<211> LENGTH: 2451
<212> TYPE: DNA
<213> ORGANISM: Homo sapiens
<300> PUBLICATION INFORMATION:
<302> TITLE: PKC mu
<310> PATENT DOCUMENT NUMBER: XM007234

<400> SEQUENCE: 117
atgtatgata agatcctgct ttttcgccat gaccctacct ctgaaaacat ccttcagctg      60
gtgaaagcgg ccagtgatat ccaggaaggc gatcttattg aagtggtctt gtcagcttcc     120
gccacctttg aagactttca gattcgtccc cacgctctct tgttcattc atacagagct     180 ccagctttct gtgatcactg tggagaaatg ctgtgggggc tggtacgtca aggtcttaaa     240
tgtgaagggt gtggtctgaa ttaccataag agatgtgcat ttaaaatacc caacaattgc     300
agcggtgtga ggcggagaag gctctcaaac gtttccctca ctggggtcag caccatccgc     360
acatcatctg ctgaactctc tacaagtgcc cctgatgagc cccttctgca aaaatcacca     420
tcagagtcgt ttattggtcg agagaagagg tcaaattctc aatcatacat ggacgacca    480 attcacttg acaagatttt gatgtctaaa gttaaagtgc cgcacacatt tgtcatccac     540
tcctacaccc ggcccacagt gtgccagtac tgcaagaagc ttctgaaggg gcttttcagg     600
cagggcttgc agtgcaaaga ttgcagattc aactgccata acgttgtgc accgaaagta     660 ccaaacaact gccttggcga agtgaccatt aatggagatt tgcttagccc tggggcagag     720
tctgatgtgg tcatggaaga agggagtgat gacaatgata gtgaaaggaa cagtgggctc     780
atggatgata tggaagaagc aatggtccaa gatgcagaga tggcaatggc agagtgccag     840
aacgacagtg gcgagatgca agatccagac ccagaccacg aggacgccaa cagaaccatc     900
agtccatcaa caagcaacaa tatcccactc atgagggtag tgcagtctgt caaacacacg     960
aagaggaaaa gcagcacagt catgaaagaa ggatggatgg tccactacac cagcaaggac    1020
acgctgcgga acggcacta ttggagattg gatagcaaat gtattaccct ctttcagaat    1080
gacacaggaa gcaggtacta caaggaaatt ccttttatctg aaattttgtc tctgaaccca    1140
gtaaaaactt cagctttaat tcctaatggg gccaatcctc attgtttcga aatcactacg    1200
gcaaatgtag tgtattatgt gggagaaaat gtggtcaatc cttccagccc atcaccaaat    1260
aacagtgttc tcaccagtgg cgttggtgca gatgtggcca ggatgtggga gatagccatc    1320
```

```
cagcatgccc ttatgccgt cattcccaag ggctcctccg tgggtacagg aaccaacttg      1380
cacagagata tctctgtgag tatttcagta tcaaattgcc agattcaaga aaatgtggac      1440
atcagcacag tatatcagat ttttcctgat gaagtactgg gttctggaca gtttggaatt      1500
gtttatggag gaaacatcg taaaacagga agagatgtag ctattaaaat cattgacaaa      1560
ttacgatttc aacaaaaca agaaagccag cttcgtaatg aggttgcaat tctacagaac      1620
cttcatcacc ctggtgttgt aaatttggag tgtatgtttg agacgcctga agagtgttt      1680 gttgttatgg aaaaactcca tggagacatg ctggaaatga tcttgtcaag tgaaaagggc      1740
aggttgccag agcacataac gaagttttta attactcaga tactcgtggc tttgcggcac      1800
cttcatttta aaaatatcgt tcactgtgac ctcaaaccag aaaatgtgtt gctagcctca      1860
gctgatcctt ttcctcaggt gaaactttgt gattttggtt ttgcccggat cattggagag      1920
aagtctttcc ggaggtcagt ggtgggtacc cccgcttacc tggctcctga ggtcctaagg      1980
aacaagggct acaatcgctc tctagacatg tggtctgttg gggtcatcat ctatgtaagc      2040
ctaagcggca cattcccatt taatgaagat gaagacatac acgaccaaat tcagaatgca      2100
gctttcatgt atccaccaaa tccctggaag gaaatatctc atgaagccat tgatcttatc      2160
aacaatttgc tgcaagtaaa aatgagaaag cgctacagtg tggataagac cttgagccac      2220
ccttggctac aggactatca gacctggtta gatttgcgag agctggaatg caaaatcggg      2280
gagcgctaca tcacccatga aagtgatgac ctgaggtggg agaagtatgc aggcgagcag      2340
gggctgcagt accccacaca cctgatcaat ccaagtgcta gccacagtga cactcctgag      2400
actgaagaaa cagaaatgaa agccctcggt gagcgtgtca gcatcctatg a              2451
```

<210> SEQ ID NO 118
<211> LENGTH: 2673
<212> TYPE: DNA
<213> ORGANISM: Homo sapiens
<300> PUBLICATION INFORMATION:
<302> TITLE: PKC nu
<310> PATENT DOCUMENT NUMBER: NM005813

<400> SEQUENCE: 118

```
atgtctgcaa ataattcccc tccatcagcc cagaagtctg tattacccac agctattcct        60
gctgtgcttc cagctgcttc tccgtgttca agtcctaaga cgggactctc tgcccgactc       120
tctaatggaa gcttcagtgc accatcactc accaactcca gaggctcagt gcatacagtt       180
tcatttctac tgcaaattgg cctcacacgg gagagtgtta ccattgaagc ccaggaactg       240
tctttatctg ctgtcaagga tcttgtgtgc tccatagttt atcaaaagtt tccagagtgt       300
ggattctttg gcatgtatga caaaattctt ctctttcgcc atgacatgaa ctcagaaaac       360
attttgcagc tgattacctc agcagatgaa atacatgaag gagacctagt ggaagtggtt       420
ctttcagctt tagccacagt agaagacttc cagattcgtc acatactctc tatgtacat       480 tcttacaaag ctcctacttt ctgtgattac tgtggtgaga tgctgtgggg attggtacgt       540
caaggactga aatgtgaagg ctgtggatta aattaccata acgatgtgc cttcaagatt       600 ccaaataact gtagtggagt aagaaagaga cgtctgtcaa atgtatcttt accaggaccc       660
ggcctctcag ttccaagacc cctacagcct gaatatgtag cccttcccag tgaagagtca       720
catgtccacc aggaaccaag taagagaatt ccttcttgga gtggtcgccc aatctggatg       780
gaaaagatgg taatgtgcag agtgaaagtt ccacacacat ttgctgttca ctcttacacc       840
cgtcccacga tatgtcagta ctgcaagcgg ttactgaaag gcctctttcg ccaaggaatg       900
```

```
cagtgtaaag attgcaaatt caactgccat aaacgctgtg catcaaaagt accaagagac      960
tgccttggag aggttacttt caatggagaa ccttccagtc tgggaacaga tacagatata     1020
ccaatggata ttgacaataa tgacataaat agtgatagta gtcggggttt ggatgacaca     1080
gaagagccat cacccccaga agataagatg ttcttcttgg atccatctga tctcgatgtg     1140
gaaagagatg aagaagccgt taaaacaatc agtccatcaa caagcaataa tattccgcta     1200
atgagggttg tacaatccat caagcacaca aagaggaaga gcagcacaat ggtgaaggaa     1260
gggtggatgg tccattacac cagcagggat aacctgagaa agaggcatta ttggagactt     1320
gacagcaaat gtctaacatt atttcagaat gaatctggat caaagtatta taaggaaatt     1380
ccactttcag aaattctccg catatcttca ccacgagatt tcacaaacat ttcacaaggc     1440
agcaatccac actgttttga aatcattact gatactatgg tatacttcgt tggtgagaac     1500
aatggggaca gctctcataa tcctgttctt gctgccactg gagttggact tgatgtagca     1560
cagagctggg aaaaagcaat tcgccaagcc ctcatgcctg ttactcctca agcaagtgtt     1620
tgcacttctc cagggcaagg aaagatcac aaagatttgt ctacaagtat ctctgtatct     1680
aattgtcaga ttcaggagaa tgtggatatc agtactgttt accagatctt tgcagatgag     1740
gtgcttggtt caggccagtt tggcatcgtt tatggaggaa acatagaaa gactgggagg     1800 gatgtggcta ttaaagtaat tgataagatg agattcccca caaaacaaga aagtcaactc     1860
cgtaatgaag tggctatttt acagaatttg caccatcctg ggattgtaaa cctggaatgt     1920
atgtttgaaa ccccagaacg agtctttgta gtaatgaaa agctgcatgg agatatgttg     1980
gaaatgattc tatccagtga gaaaagtcgg cttccagaac gaattactaa attcatggtc     2040
acacagatac ttgttgcttt gaggaatctg cattttaaga atattgtgca ctgtgattta     2100
aagccagaaa atgtgctgct tgcatcagca gagccatttc tcaggtgaa gctgtgtgac     2160 tttggatttg cacgcatcat tggtgaaaag tcattcagga gatctgtggt aggaactcca     2220
gcatacttag cccctgaagt tctccggagc aaaggttaca accgttccct agatatgtgg     2280
tcagtgggag ttatcatcta tgtgagcctc agtggcacat ttcctttaa tgaggatgaa     2340 gatataaatg accaaatcca aaatgctgca tttatgtacc caccaaatcc atggagagaa     2400
atttctggtg aagcaattga tctgataaac aatctgcttc aagtgaagat gagaaaacgt     2460
tacagtgttg acaaatctct tagtcatccc tggctacagg actatcagac ttggcttgac     2520
cttagagaat ttgaaactcg cattggagaa cgttacatta cacatgaaag tgatgatgct     2580
cgctgggaaa tacatgcata cacacataac cttgtatacc caaagcactt cattatggct     2640
cctaatccag atgatatgga agaagatcct taa                                  2673

<210> SEQ ID NO 119
<211> LENGTH: 2121
<212> TYPE: DNA
<213> ORGANISM: Homo sapiens
<300> PUBLICATION INFORMATION:
<302> TITLE: PKC tau
<310> PATENT DOCUMENT NUMBER: NM006257

<400> SEQUENCE: 119
atgtcgccat tcttcggat tggcttgtcc aactttgact gcgggtcctg ccagtcttgt       60
cagggcgagg ctgttaaccc ttactgtgct gtgctcgtca agagtatgt cgaatcagag      120 aacgggcaga tgtatatcca gaaaaagcct accatgtacc cacctggga cagcactttt      180 gatgcccata tcaacaaggg aagagtcatg cagatcattg tgaaaggcaa aaacgtggac      240
```

-continued

```
ctcatctctg aaaccaccgt ggagctctac tcgctggctg agaggtgcag gaagaacaac      300
gggaagacag aaatatggtt agagctgaaa cctcaaggcc gaatgctaat gaatgcaaga      360
tactttctgg aaatgagtga cacaaaggac atgaatgaat tgagacgga aggcttcttt       420 gctttgcatc agcgccgggg tgccatcaag caggcaaagg tccaccacgt caagtgccac      480
gagttcactg ccaccttctt cccacagccc acattttgct ctgtctgcca cgagtttgtc     540
tggggcctga acaaacaggg ctaccagtgc cgacaatgca atgcagcaat tcacaagaag     600
tgtattgata agttatagc aaagtgcaca ggatcagcta tcaatagccg agaaaccatg       660
ttccacaagg agagattcaa aattgacatg ccacacagat ttaaagtcta caattacaag     720
agcccgacct tctgtgaaca ctgtgggacc ctgctgtggg gactggcacg gcaaggactc     780
aagtgtgatg catgtggcat gaatgtgcat catagatgcc agacaaaggt ggccaacctt     840
tgtggcataa accagaagct aatggctgaa gcgctggcca tgattgagag cactcaacag     900
gctcgctgct taagagatac tgaacagatc ttcagagaag gtccggttga aattggtctc     960
ccatgctcca tcaaaaatga agcaaggccg ccatgtttac cgacaccggg aaaaagagag    1020
cctcagggca tttcctggga gtctccgttg gatgaggtgg ataaaatgtg ccatcttcca    1080
gaacctgaac tgaacaaaga aagaccatct ctgcagatta aactaaaaat tgaggatttt    1140
atcttgcaca aaatgttggg gaaaggaagt tttggcaagg tcttcctggc agaattcaag    1200
aaaaccaatc aattttcgc aataaaggcc ttaaagaaag atgtggtctt gatggacgat    1260
gatgttgagt gcacgatggt agagaagaga gttctttcct tggcctggga gcatccgttt    1320
ctgacgcaca tgttttgtac attccagacc aaggaaaacc tcttttttgt gatggagtac    1380
ctcaacggag gggacttaat gtaccacatc caaagctgcc acaagttcga cctttccaga    1440
gcgacgtttt atgctgctga aatcattctt ggtctgcagt tccttcattc caaaggaata    1500
gtctacaggg acctgaagct agataacatc ctgttagaca aagatggaca tatcaagatc    1560
gcggattttg gaatgtgcaa ggagaacatg ttaggagatg ccaagacgaa taccttctgt    1620
gggacacctg actacatcgc cccagagatc ttgctgggtc agaaatacaa ccactctgtg    1680
gactggtggt ccttcggggt tctcctttat gaaatgctga ttggtcagtc gccttttccac   1740 gggcaggatg aggaggagct cttccactcc atccgcatgg acaatccctt ttacccacgg    1800
tggctggaga aggaagcaaa ggaccttctg gtgaagctct tcgtgcgaga acctgagaag    1860
aggctgggcg tgagggggaga catccgccag caccctttgt ttcggagat caactgggag   1920 gaacttgaac ggaaggagat tgacccaccg ttccggccga aagtgaaatc accatttgac    1980
tgcagcaatt tcgacaaaga attcttaaac gagaagcccc ggctgtcatt tgccgacaga    2040
gcactgatca acagcatgga ccagaatatg ttcaggaact ttttccttcat gaaccccggg    2100 atggagcggc tgatatcctg a                                              2121
```

<210> SEQ ID NO 120
<211> LENGTH: 1779
<212> TYPE: DNA
<213> ORGANISM: Homo sapiens
<300> PUBLICATION INFORMATION:
<302> TITLE: PKC zeta
<310> PATENT DOCUMENT NUMBER: NM2744

<400> SEQUENCE: 120

```
atgcccagca ggaccgaccc caagatggaa gggagcggcg gccgcgtccg cctcaaggcg      60
cattacgggg gggacatctt catcaccagc gtggacgccg ccacgacctt cgaggagctc     120
```

-continued

```
tgtgaggaag tgagagacat gtgtcgtctg caccagcagc acccgctcac cctcaagtgg    180
gtggacagcg aaggtgaccc ttgcacggtg tcctcccaga tggagctgga agaggctttc    240
cgcctggccc gtcagtgcag ggatgaaggc ctcatcattc atgttttccc gagcacccct    300
gagcagcctg gcctgccatg tccgggagaa acaaatcta tctaccgccg ggagccaga     360 agatggagga agctgtaccg tgccaacggc acctcttcc aagccaagcg ctttaacagg     420
agagcgtact gcggtcagtg cagcgagagg atatgggcc tcgcgaggca aggctacagg     480
tgcatcaact gcaaactgct ggtccataag cgctgccacg gcctcgtccc gctgacctgc    540
aggaagcata tggattctgt catgccttcc caagagcctc cagtagacga caagaacgag    600
gacgccgacc ttccttccga ggagacagat ggaattgctt acatttcctc atcccggaag    660
catgacagca ttaaagacga ctcggaggac cttaagccag ttatcgatgg gatggatgga    720
atcaaaatct ctcaggggct tgggctgcag gactttgacc taatcagagt catcgggcgc    780
gggagctacg ccaaggttct cctggtgcgg ttgaagaaga atgaccaaat ttacgccatg    840
aaagtggtga agaaagagct ggtgcatgat gacgaggata ttgactgggt acagacagag    900
aagcacgtgt ttgagcaggc atccagcaac cccttcctgg tcggattaca ctcctgcttc    960
cagacgacaa gtcggttgtt cctggtcatt gagtacgtca acggcgggga cctgatgttc    1020
cacatgcaga ggcagaggaa gctccctgag gagcacgcca ggttctacgc ggccgagatc    1080
tgcatcgccc tcaacttcct gcacgagagg gggatcatct acaggaccct gaagctggac    1140
aacgtcctcc tggatgcgga cgggcacatc aagctcacag actacggcat gtgcaaggaa    1200
ggcctgggcc ctggtgacac aacgagcact ttctgcggaa ccccgaatta catcgccccc    1260
gaaatcctgc ggggagagga gtacgggttc agcgtggact ggtgggcgct gggagtcctc    1320
atgtttgaga tgatggccgg gcgctccccg ttcgacatca tcaccgacaa cccggacatg    1380
aacacagagg actacctttt ccaagtgatc ctggagaagc ccatccggat cccccggttc    1440
ctgtccgtca agcctcccca tgttttaaaa ggattttta ataaggaccc caaagagagg     1500
ctcggctgcc ggccacagac tggatttct gacatcaagt cccacgcgtt cttccgcagc    1560
atagactggg acttgctgga aagaagcag gcgctccctc cattccagcc acagatcaca    1620
gacgactacg tctgacaa ctttgacaca cagttcacca gcgagcccgt gcagctgacc      1680
ccagacgatg aggatgccat aaagaggatc gaccagtcag agttcgaagg ctttgagtat    1740
atcaacccat tattgctgtc caccgaggag tcggtgtga                           1779
```

<210> SEQ ID NO 121
<211> LENGTH: 576
<212> TYPE: DNA
<213> ORGANISM: Homo sapiens
<300> PUBLICATION INFORMATION:
<302> TITLE: VEGF
<310> PATENT DOCUMENT NUMBER: NM003376

<400> SEQUENCE: 121

```
atgaactttc tgctgtcttg ggtgcattgg agccttgcct tgctgctcta cctccaccat     60
gccaagtggt cccaggctgc acccatggca gaaggaggag ggcagaatca tcacgaagtg    120
gtgaagttca tggatgtcta tcagcgcagc tactgccatc caatcgagac cctggtggac    180
atcttccagg agtaccctga tgagatcgag tacatcttca agccatcctg tgtgccctg    240 atgcgatgcg ggggctgctg caatgacgag ggcctggagt gtgtgcccac tgaggagtcc    300
aacatcacca tgcagattat gcggatcaaa cctcaccaag gccagcacat aggagagatg    360
```

```
agcttcctac agcacaacaa atgtgaatgc agaccaaaga aagatagagc aagacaagaa    420
aatccctgtg ggccttgctc agagcggaga aagcatttgt ttgtacaaga tccgcagacg    480
tgtaaatgtt cctgcaaaaa cacagactcg cgttgcaagg cgaggcagct tgagttaaac    540
gaacgtactt gcagatgtga caagccgagg cggtga                              576
```

<210> SEQ ID NO 122
<211> LENGTH: 624
<212> TYPE: DNA
<213> ORGANISM: Homo sapiens
<300> PUBLICATION INFORMATION:
<302> TITLE: VEGF B
<310> PATENT DOCUMENT NUMBER: NM003377

<400> SEQUENCE: 122

```
atgagccctc tgctccgccg cctgctgctc gccgcactcc tgcagctggc ccccgcccag     60
gcccctgtct cccagcctga tgccctggc caccagagga agtggtgtc atggatagat      120 gtgtatactc gcgctacctg ccagccccgg gaggtggtgg tgcccttgac tgtggagctc    180
atgggcaccg tggccaaaca gctggtgccc agctgcgtga ctgtgcagcg ctgtggtggc    240
tgctgccctg acgatggcct ggagtgtgtg cccactgggc agcaccaagt ccggatgcag    300
atcctcatga tccggtaccc gagcagtcag ctggggggaga tgtccctgga agaaacagc    360 cagtgtgaat gcagacctaa aaaaaaggac agtgctgtga gccagacag ggctgccact     420 ccccaccacc gtccccagcc ccgttctgtt ccgggctggg actctgcccc cggagcaccc    480
tccccagctg acatcaccca tcccactcca gccccaggcc cctctgccca cgctgcaccc    540
agcaccacca cgcccctgac ccccggacct gccgccgccg ctgccgacgc cgcagcttcc    600
tccgttgcca agggcggggc ttag                                          624
```

<210> SEQ ID NO 123
<211> LENGTH: 1260
<212> TYPE: DNA
<213> ORGANISM: Homo sapiens
<300> PUBLICATION INFORMATION:
<302> TITLE: VEGF C
<310> PATENT DOCUMENT NUMBER: NM005429

<400> SEQUENCE: 123

```
atgcacttgc tgggcttctt ctctgtggcg tgttctctgc tcgccgctgc gctgctcccg     60
ggtcctcgcg aggcgcccgc cgccgccgcc gccttcgagt ccggactcga cctctcggac    120
gcggagcccg acgcgggcga ggccacggct tatgcaagca agatctgga ggagcagtta    180 cggtctgtgt ccagtgtaga tgaactcatg actgtactct acccagaata ttggaaaatg    240
tacaagtgtc agctaaggaa aggaggctgg caacataaca gagaacaggc caacctcaac    300
tcaaggacag aagagactat aaaatttgct gcagcacatt ataatacaga gatcttgaaa    360
agtattgata tgagtggag aaagactcaa tgcatgccac gggaggtgtg tatagatgtg    420
gggaaggagt ttggagtcgc gacaaacacc ttctttaaac ctccatgtgt gtccgtctac    480
agatgtgggg gttgctgcaa tagtgagggg ctgcagtgca tgaacaccag cacgagctac    540
ctcagcaaga cgttatttga attacagtg cctctctctc aaggccccaa accagtaaca    600
atcagttttg ccaatcacac ttcctgccga tgcatgtcta aactggatgt ttacagacaa    660
gttcattcca ttattagacg ttccctgcca gcaacactac cacagtgtca ggcagcgaac    720
aagacctgcc ccaccaatta catgtggaat aatcacatct gcagatgcct ggctcaggaa    780
```

```
gattttatgt tttcctcgga tgctggagat gactcaacag atggattcca tgacatctgt      840
ggaccaaaca aggagctgga tgaagagacc tgtcagtgtg tctgcagagc ggggcttcgg      900
cctgccagct gtggacccca caagaactga acagaaact catgccagtg tgtctgtaaa       960
aacaaactct tccccagcca atgtggggcc aaccgagaat tgatgaaaa cacatgccag      1020 tgtgtatgta aagaacctg ccccagaaat caacccctaa atcctggaaa atgtgcctgt      1080
gaatgtacag aaagtccaca gaaatgcttg ttaaaaggaa agaagttcca ccaccaaaca     1140
tgcagctgtt acagacggcc atgtacgaac cgccagaagg cttgtgagcc aggattttca     1200
tatagtgaag aagtgtgtcg ttgtgtccct tcatattgga aaagaccaca aatgagctaa     1260
```

<210> SEQ ID NO 124
<211> LENGTH: 1074
<212> TYPE: DNA
<213> ORGANISM: Homo sapiens
<300> PUBLICATION INFORMATION:
<302> TITLE: VEGF D
<310> PATENT DOCUMENT NUMBER: AJ000185

<400> SEQUENCE: 124

```
atattcaaaa tgtacagaga gtgggtagtg gtgaatgttt tcatgatgtt gtacgtccag       60
ctggtgcagg gctccagtaa tgaacatgga ccagtgaagc gatcatctca gtccacattg      120
gaacgatctg aacagcagat cagggctgct tctagtttgg aggaactact tcgaattact      180
cactctgagg actggaagct gtggagatgc aggctgaggc tcaaaagttt taccagtatg      240
gactctcgct cagcatccca tcggtccact aggtttgcgg caacttttcta tgacattgaa      300 acactaaaag ttatagatga agaatggcaa agaactcagt gcagccctag agaaacgtgc      360
gtggaggtgg ccagtgagct ggggaagagt accaacacat tcttcaagcc cccttgtgtg      420
aacgtgttcc gatgtggtgg ctgttgcaat gaagagagcc ttatctgtat gaacaccagc      480
acctcgtaca tttccaaaca gctctttgag atatcagtgc ctttgacatc agtacctgaa      540
ttagtgcctg ttaaagttgc caatcataca ggttgtaagt gcttgccaac agcccccgc       600 catccatact caattatcag aagatccatc cagatccctg aagaagatcg ctgttcccat      660
tccaagaaac tctgtcctat tgacatgcta tgggatagca acaaatgtaa atgtgtttg      720 caggaggaaa atccacttgc tggaacagaa gaccactctc atctccagga accagctctc      780
tgtgggccac acatgatgtt tgacgaagat cgttgcgagt gtgtctgtaa aacaccatgt      840
cccaaagatc taatccagca ccccaaaaac tgcagttgct ttgagtgcaa agaaagtctg      900
gagacctgct gccagaagca caagctatt tacccagaca cctgcagctg tgaggacaga      960 tgccccttc ataccagacc atgtgcaagt ggcaaaacag catgtgcaaa gcattgccgc     1020
tttccaaagg agaaaagggc tgcccagggg ccccacagcc gaaagaatcc ttga           1074
```

<210> SEQ ID NO 125
<211> LENGTH: 1314
<212> TYPE: DNA
<213> ORGANISM: Homo sapiens
<300> PUBLICATION INFORMATION:
<302> TITLE: E2F
<310> PATENT DOCUMENT NUMBER: M96577

<400> SEQUENCE: 125

```
atggccttgg ccggggcccc tgcgggcggc ccatgcgcgc ggcgctgga ggccctgctc       60 ggggccggcg cgctgcggct gctcgactcc tcgcagatcg tcatcatctc cgccgcgcag      120
gacgccagcg ccccgccggc tcccaccggc ccgcggcgc ccgccgccgg ccctgcgac       180
```

```
cctgacctgc tgctcttcgc cacaccgcag gcgccccggc ccacacccag tgcgccgcgg    240
cccgcgctcg gccgcccgcc ggtgaagcgg aggctggacc tggaaactga ccatcagtac    300
ctggccgaga gcagtgggcc agctcggggc agaggccgcc atccaggaaa aggtgtgaaa    360
tccccggggg agaagtcacg ctatgagacc tcactgaatc tgaccaccaa gcgcttcctg    420
gagctgctga ccactcggc tgacggtgtc gtcgacctga actgggctgc cgaggtgctg    480
aaggtgcaga gcggcgcat ctatgacatc accaacgtcc ttgagggcat ccagctcatt    540
gccaagaagt ccaagaacca catccagtgg ctgggcagcc acaccacagt gggcgtcggc    600
ggacggcttg agggggttgac ccaggacctc cgacagctgc aggagagcga gcagcagctg    660
gaccacctga tgaatatctg tactacgcag ctgcgcctgc tctccgagga cactgacagc    720
cagcgcctgg cctacgtgac gtgtcaggac cttcgtagca ttgcagaccc tgcagagcag    780
atggttatgg tgatcaaagc ccctcctgag acccagctcc aagccgtgga ctcttcggag    840
aactttcaga tctcccttaa gagcaaacaa ggcccgatcg atgttttcct gtgccctgag    900
gagaccgtag gtgggatcag ccctgggaag accccatccc aggaggtcac ttctgaggag    960
gagaacaggg ccactgactc tgccaccata gtgtcaccac caccatcatc tccccctca    1020 tccctcacca cagatcccag ccagtctcta ctcagcctgg agcaagaacc gctgttgtcc    1080
cggatgggca gcctgcgggc tcccgtggac gaggaccgc tgtccccgct ggtggcggcc    1140
gactcgctcc tggagcatgt gcgggaggac ttctccggcc tcctccctga ggagttcatc    1200
agcctttccc caccccacga ggccctcgac taccacttcg gcctcgagga gggcgagggc    1260
atcagagacc tcttcgactg tgactttggg gacctcaccc cctggatttc ctga         1314

<210> SEQ ID NO 126
<211> LENGTH: 166
<212> TYPE: DNA
<213> ORGANISM: Human papillomavirus
<300> PUBLICATION INFORMATION:
<302> TITLE: EBER-1
<310> PATENT DOCUMENT NUMBER: Jo2078

<400> SEQUENCE: 126
ggacctacgc tgccctagag gttttgctag ggaggagacg tgtgtggctg tagccacccg     60
tcccgggtac aagtcccggg tggtgaggac ggtgtctgtg gttgtcttcc cagactctgc    120
tttctgccgt cttcggtcaa gtaccagctg gtggtccgca tgtttt                   166

<210> SEQ ID NO 127
<211> LENGTH: 172
<212> TYPE: DNA
<213> ORGANISM: Hepatitis C virus
<300> PUBLICATION INFORMATION:
<302> TITLE: EBER-2
<310> PATENT DOCUMENT NUMBER: J02078

<400> SEQUENCE: 127
ggacagccgt tgccctagtg gtttcggaca caccgccaac gctcagtgcg gtgctaccga     60
cccgaggtca agtcccgggg gaggagaaga gaggcttccc gcctagagca tttgcaagtc    120
aggattctct aatccctctg ggagaagggt attcggcttg ccgctatttt tt            172

<210> SEQ ID NO 128
<211> LENGTH: 651
<212> TYPE: DNA
<213> ORGANISM: Hepatitis C virus
<300> PUBLICATION INFORMATION:
```

```
<302> TITLE: NS2
<310> PATENT DOCUMENT NUMBER: AJ238799

<400> SEQUENCE: 128
atggaccggg agatggcagc atcgtgcgga ggcgcggttt tcgtaggtct gatactcttg      60
accttgtcac cgcactataa gctgttcctc gctaggctca tatggtggtt acaatatttt     120
atcaccaggg ccgaggcaca cttgcaagtg tggatccccc ccctcaacgt tcgggggggc     180
cgcgatgccg tcatcctcct cacgtgcgcg atccacccag agctaatctt taccatcacc     240
aaaatcttgc tcgccatact cggtccactc atggtgctcc aggctggtat aaccaaagtg     300
ccgtacttcg tgcgcgcaca cgggctcatt cgtgcatgca tgctggtgcg aaggttgct     360
gggggtcatt atgtccaaat ggctctcatg aagttggccg cactgacagg tacgtacgtt     420
tatgaccatc tcaccccact gcgggactgg gcccacgcgg cctacgagac ccttgcggtg     480
gcagttgagc ccgtcgtctt ctctgatatg gagaccaagg ttatcacctg ggggcagac     540
accgcggcgt gtgggacat catcttgggc ctgcccgtct ccgcccgcag ggggagggag     600
atacatctgg accggcaga cagccttgaa gggcaggggt ggcgactcct c               651

<210> SEQ ID NO 129
<211> LENGTH: 161
<212> TYPE: DNA
<213> ORGANISM: Hepatitis C virus
<300> PUBLICATION INFORMATION:
<302> TITLE: NS4A
<310> PATENT DOCUMENT NUMBER: AJ238799

<400> SEQUENCE: 129
gcacctgggt gctggtaggc ggagtcctag cagctctggc cgcgtattgc ctgacaacag     60
gcagcgtggt cattgtgggc aggatcatct tgtccggaaa gccggccatc attcccgaca    120
gggaagtcct ttaccgggag ttcgatgaga tggaagagtg c                        161

<210> SEQ ID NO 130
<211> LENGTH: 783
<212> TYPE: DNA
<213> ORGANISM: Hepatitis C virus
<300> PUBLICATION INFORMATION:
<302> TITLE: NS4B
<310> PATENT DOCUMENT NUMBER: AJ238799

<400> SEQUENCE: 130
gcctcacacc tcccttacat cgaacaggga atgcagctcg ccgaacaatt caaacagaag    60
gcaatcgggt tgctgcaaac agccaccaag caagcggagg ctgctgctcc cgtggtggaa    120
tccaagtggc ggaccctcga agccttctgg gcgaagcata tgtggaattt catcagcggg    180
atacaatatt tagcaggctt gtccactctg cctggcaacc ccgcgatagc atcactgatg    240
gcattcacag cctctatcac cagcccgctc accaccaac ataccctcct gtttaacatc     300
ctgggggat gggtggccgc caacttgct cctcccagcg ctgcttctgc tttcgtaggc     360
gccggcatcg ctggagcggc tgttggcagc ataggccttg ggaaggtgct tgtggatatt    420
ttggcaggtt atggagcagg ggtggcaggc gcgctcgtgg cctttaaggt catgagcggc    480
gagatgcct ccaccgagga cctggttaac ctactccctg ctatcctctc ccctggcgcc     540
ctagtcgtcg gggtcgtgtg cgcagcgata ctgcgtcggc acgtgggccc aggggagggg    600
gctgtgcagt ggatgaaccg gctgatagcg ttcgcttcgc ggggtaacca cgtctccccc    660
acgcactatg tgcctgagag cgacgctgca gcacgtgtca ctcagatcct ctctagtctt    720
```

```
accatcactc agctgctgaa gaggcttcac cagtggatca acgaggactg ctccacgcca    780
tgc                                                                  783

<210> SEQ ID NO 131
<211> LENGTH: 1341
<212> TYPE: DNA
<213> ORGANISM: Hepatitis C virus
<300> PUBLICATION INFORMATION:
<302> TITLE: NS5A
<310> PATENT DOCUMENT NUMBER: AJ238799

<400> SEQUENCE: 131
tccggctcgt ggctaagaga tgtttgggat tggatatgca cggtgttgac tgatttcaag     60
acctggctcc agtccaagct cctgccgcga ttgccgggag tcccttctt ctcatgtcaa    120 cgtgggtaca agggagtctg gcggggcgac ggcatcatgc aaaccacctg cccatgtgga   180
gcacagatca ccggacatgt gaaaaacggt tccatgagga tcgtggggcc taggacctgt   240
agtaacacgt ggcatggaac attccccatt aacgcgtaca ccacgggccc ctgcacgccc   300
tccccggcgc caaattattc tagggcgctg tggcgggtgg ctgctgagga gtacgtggag   360
gttacgcggg tgggggattt ccactacgtg acggcatga ccactgacaa cgtaaagtgc    420
ccgtgtcagg ttccggcccc cgaattcttc acagaagtgg atggggtgcg gttgcacagg   480
tacgctccag cgtgcaaacc cctcctacgg gaggaggtca cattcctggt cgggctcaat   540
caatacctgg ttgggtcaca gctcccatgc gagcccgaac cggacgtagc agtgctcact   600
tccatgctca ccgaccccctc ccacattacg gcggagacgc taagcgtag gctgccagg    660 ggatctcccc cctccttggc cagctcatca gctagccagc tgtctgcgcc ttccttgaag   720
gcaacatgca ctacccgtca tgactccccg gacgctgacc tcatcgaggc caacctcctg   780
tggcggcagg agatgggcgg gaacatcacc gcgtggagt cagaaaataa ggtagtaatt   840
ttggactctt cgagccgct ccaagcggag gaggatgaga gggaagtatc cgttccggcg    900
gagatcctgc ggaggtccag gaaattccct cgagcgatgc ccatatgggc acgcccggat   960 tacaacccctc cactgttaga gtcctggaag gacccggact acgtccctcc agtggtacac  1020
gggtgtccat tgccgcctgc caaggccccct ccgataccac ctccacggag gaagaggacg  1080
gttgtcctgt cagaatctac cgtgtcttct gccttggcgg agctcgccac aaagaccttc  1140
ggcagctccg aatcgtcggc cgtcgacagc ggcacggcaa cggcctctcc tgaccagccc  1200
tccgacgacg gcgacgcggg atccgacgtt gagtcgtact cctccatgcc ccccccttgag  1260 ggggagccgg gggatcccga tctcagcgac gggtcttggt ctaccgtaag cgaggaggct  1320
agtgaggacg tcgtctgctg c                                             1341

<210> SEQ ID NO 132
<211> LENGTH: 1772
<212> TYPE: DNA
<213> ORGANISM: Hepatitis C virus
<300> PUBLICATION INFORMATION:
<302> TITLE: NS5B
<310> PATENT DOCUMENT NUMBER: AJ238799

<400> SEQUENCE: 132
tcgatgtcct acacatggac aggcgccctg atcacgccat cgctgcgga ggaaaccaag     60 ctgcccatca atgcactgag caactctttg ctccgtcacc acaacttggt ctatgctaca   120
acatctcgca gcgcaagcct gcggcagaag aaggtcacct tgacagact gcaggtcctg    180 acgaccact accgggacgt gctcaaggag atgaaggcga aggcgtccac agttaaggct   240
```

-continued

```
aaacttctat ccgtggagga agcctgtaag ctgacgcccc cacattcggc cagatctaaa    300
tttggctatg gggcaaagga cgtccggaac ctatccagca aggccgttaa ccacatccgc    360
tccgtgtgga aggacttgct ggaagacact gagacaccaa ttgacaccac catcatggca    420
aaaaatgagg ttttctgcgt ccaaccagag aaggggggcc gcaagccagc tcgccttatc    480
gtattcccag atttgggggt tcgtgtgtgc gagaaaatgg ccctttacga tgtggtctcc    540
accctccctc aggccgtgat gggctcttca tacggattcc aatactctcc tggacagcgg    600
gtcgagttcc tggtgaatgc ctggaaagcg aagaaatgcc ctatgggctt cgcatatgac    660
acccgctgtt ttgactcaac ggtcactgag aatgacatcc gtgttgagga gtcaatctac    720
caatgttgtg acttggcccc cgaagccaga caggccataa ggtcgctcac agagcggctt    780
tacatcgggg gccccctgac taattctaaa gggcagaact gcggctatcg ccggtgccgc    840
gcgagcggtg tactgacgac cagctgcggt aatacccctca catgttactt gaaggccgct    900
gcggcctgtc gagctgcgaa gctccaggac tgcacgatgc tcgtatgcgg agacgacctt    960
gtcgttatct gtgaaagcgc ggggacccaa gaggacgagg cgagcctacg ggccttcacg   1020
gaggctatga ctagatactc tgccccccct ggggacccgc ccaaaccaga atacgacttg   1080
gagttgataa catcatgctc ctccaatgtg tcagtcgcgc acgatgcatc tggcaaaagg   1140
gtgtactatc tcacccgtga ccccaccacc cccttgcgc gggctgcgtg ggagacagct   1200
agacacactc cagtcaattc ctggctaggc aacatcatca tgtatgcgcc caccttgtgg   1260
gcaaggatga tcctgatgac tcatttcttc tccatccttc tagctcagga acaacttgaa   1320
aaagccctag attgtcagat ctacggggcc tgttactcca ttgagccact tgacctacct   1380
cagatcattc aacgactcca tggccttagc gcattttcac tccatagtta ctctccaggt   1440
gagatcaata gggtggcttc atgcctcagg aaacttgggg taccgccctt gcgagtctgg   1500
agacatcggg ccagaagtgt ccgcgctagg ctactgtccc aggggggag ggctgccact   1560 tgtggcaagt acctcttcaa ctgggcagta aggaccaagc tcaaactcac tccaatcccg   1620
gctgcgtccc agttggattt atccagctgg ttcgttgctg gttacagcgg gggagacata   1680
tatcacagcc tgtctcgtgc ccgaccccgc tggttcatgt ggtgcctact cctactttct   1740
gtaggggtag gcatctatct actccccaac cg                                 1772
```

```
<210> SEQ ID NO 133
<211> LENGTH: 1892
<212> TYPE: DNA
<213> ORGANISM: Hepatitis C virus
<300> PUBLICATION INFORMATION:
<302> TITLE: NS3
<310> PATENT DOCUMENT NUMBER: AJ238799

<400> SEQUENCE: 133
```

```
cgcctattac ggcctactcc caacagacgc gaggcctact tggctgcatc atcactagcc     60
tcacaggccg ggacaggaac caggtcgagg gggaggtcca gtggtctcc accgcaacac    120 aatctttcct ggcgacctgc gtcaatgcg tgtgttggac tgtctatcat ggtgccggct    180
caaagaccct tgccggccca aagggcccaa tcacccaaat gtacaccaat gtgaccagg    240 acctcgtcgc ctggcaagcg cccccgggg cgcgttcctt gacaccatgc acctgcggca    300
gctcggacct ttacttggtc acgaggcatg ccgatgtcat tccggtgcgc cggcggggcg    360
acagcagggg gagcctactc tccccaggcc ccgtctccta cttgaaggc tcttcgggcg    420 gtccactgct ctgcccctcg gggcacgctg tgggcatctt tcgggctgcc gtgtgcaccc    480
```

```
gaggggttgc gaaggcggtg gactttgtac ccgtcgagtc tatggaaacc actatgcggt      540
ccccggtctt cacggacaac tcgtcccctc cggccgtacc gcagacattc caggtggccc      600
atctacacgc ccctactggt agcggcaaga gcactaaggt gccggctgcg tatgcagccc      660
aagggtataa ggtgcttgtc ctgaacccgt ccgtcgccgc caccctaggt ttcggggcgt      720
atatgtctaa ggcacatggt atcgacccta acatcagaac cggggtaagg accatcacca      780
cgggtgcccc catcacgtac tccacctatg gcaagtttct tgccgacggt ggttgctctg      840
ggggcgccta tgacatcata atatgtgatg agtgccactc aactgactcg accactatcc      900
tgggcatcgg cacagtcctg gaccaagcgg agacggctgg agcgcgactc gtcgtgctcg      960
ccaccgctac gcctccggga tcggtcaccg tgccacatcc aaacatcgag gaggtggctc     1020
tgtccagcac tggagaaatc ccctttatg gcaaagccat ccccatcgag accatcaagg     1080
gggggaggca cctcattttc tgccattcca agaagaaatg tgatgagctc gccgcgaagc     1140
tgtccggcct cggactcaat gctgtagcat attaccgggg ccttgatgta tccgtcatac     1200
caactagcgg agacgtcatt gtcgtagcaa cggacgctct aatgacgggc tttaccggcg     1260
atttcgactc agtgatcgac tgcaatacat gtgtcaccca gacagtcgac ttcagcctgg     1320
acccgacctt caccattgag acgacgaccg tgccacaaga cgcggtgtca cgctcgcagc     1380
ggcgaggcag gactggtagg ggcaggatgg gcatttacag gtttgtgact ccaggagaac     1440
ggccctcggg catgttcgat cctcggttc tgtgcgagtg ctatgacgcg ggctgtgctt     1500
ggtacgagct cacgcccgcc gagacctcag ttaggttgcg ggcttaccta aacacaccag     1560
ggttgcccgt ctgccaggac catctggagt tctgggagag cgtctttaca ggcctcaccc     1620
acatagacgc ccatttcttg tcccagacta agcaggcagg agacaacttc ccctacctgg     1680
tagcatacca ggctacggtg tgcgccaggg ctcaggctcc acctccatcg tgggaccaaa     1740
tgtggaagtg tctcatacgg ctaaagccta cgctgcacgg gccaacgccc ctgctgtata     1800
ggctgggagc cgttcaaaac gaggttacta ccacacaccc cataaccaaa tacatcatgg     1860
catgcatgtc ggctgacctg gaggtcgtca cg                                   1892

<210> SEQ ID NO 134
<211> LENGTH: 822
<212> TYPE: DNA
<213> ORGANISM: Homo sapiens
<300> PUBLICATION INFORMATION:
<302> TITLE: stmn cell factor
<310> PATENT DOCUMENT NUMBER: M59964

<400> SEQUENCE: 134
atgaagaaga cacaaacttg gattctcact tgcatttatc ttcagctgct cctatttaat       60
cctctcgtca aaactgaagg gatctgcagg aatcgtgtga ctaataatgt aaaagacgtc      120
actaaattgg tggcaaatct tccaaaagac tacatgataa ccctcaaata tgtccccggg      180
atggatgttt tgccaagtca ttgttggata agcgagatgg tagtacaatt gtcagacagc      240
ttgactgatc ttctggacaa gttttcaaat atttctgaag gcttgagtaa ttattccatc      300
atagacaaac ttgtgaatat agtcgatgac cttgtggagt gcgtcaaaga aaactcatct      360
aaggatctaa aaaaatcatt caagagccca gaacccaggc tctttactcc tgaagaattc      420
tttagaattt ttaatagatc cattgatgcc ttcaaggact tgtgtagtgg atctgaaact      480
agtgattgtg tggtttcttc aacattaagt cctgagaaag attccagagt cagtgtcaca      540
aaaccattta tgttaccccc tgttgcagcc agctcccctta ggaatgacag cagtagcagt      600
```

| | |
|---|---|
| aataggaagg ccaaaaatcc ccctggagac tccagcctac actgggcagc catggcattg | 660 |
| ccagcattgt tttctcttat aattggcttt gcttttggag ccttatactg gaagaagaga | 720 |
| cagccaagtc ttacaagggc agttgaaaat atacaaatta atgaagagga taatgagata | 780 |
| agtatgttgc aagagaaaga gagagagttt caagaagtgt aa | 822 |

<210> SEQ ID NO 135
<211> LENGTH: 483
<212> TYPE: DNA
<213> ORGANISM: Homo sapiens
<300> PUBLICATION INFORMATION:
<302> TITLE: TGFalpha
<310> PATENT DOCUMENT NUMBER: AF123238

<400> SEQUENCE: 135

| | |
|---|---|
| atggtcccct cggctggaca gctcgccctg ttcgctctgg gtattgtgtt ggctgcgtgc | 60 |
| caggccttgg agaacagcac gtccccgctg agtgcagacc cgcccgtggc tgcagcagtg | 120 |
| gtgtcccatt ttaatgactg cccagattcc cacactcagt tctgcttcca tggaacctgc | 180 |
| aggttttttgg tgcaggagga caagccagca tgtgtctgcc attctgggta cgttggtgca | 240 |
| cgctgtgagc atgcggacct cctggccgtg gtggctgcca gccagaagaa gcaggccatc | 300 |
| accgccttgg tggtggtctc atcgtggcc ctggctgtcc ttatcatcac atgtgtgctg | 360 |
| atacactgct gccaggtccg aaaacactgt gagtggtgcc gggccctcat ctgccggcac | 420 |
| gagaagccca cgccctcct gaagggaaga accgcttgct gccactcaga aacagtggtc | 480 |
| tga | 483 |

<210> SEQ ID NO 136
<211> LENGTH: 1071
<212> TYPE: DNA
<213> ORGANISM: Homo sapiens
<300> PUBLICATION INFORMATION:
<302> TITLE: GD3 synthase
<310> PATENT DOCUMENT NUMBER: NM003034

<400> SEQUENCE: 136

| | |
|---|---|
| atgagcccct gcgggcgggc ccggcgacaa acgtccagag gggccatggc tgtactggcg | 60 |
| tggaagttcc gcggacccg gctgccatg ggagccagtg ccctctgtgt cgtggtcctc | 120 |
| tgttggctct acatcttccc cgtctaccgg ctgcccaacg agaaagagat cgtgcagggg | 180 |
| gtgctgcaac agggcacggc gtggaggagg aaccagaccg cggccagagc gttcaggaaa | 240 |
| caaatggaag actgctgcga ccctgcccat ctctttgcta tgactaaaat gaattcccct | 300 |
| atggggaaga gcatgtggta tgacggggag tttttatact cattcaccat tgacaattca | 360 |
| acttactctc tcttcccaca ggcaaccca ttccagctgc cattgaagaa atgcgcggtg | 420 |
| gtgggaaatg gtgggattct gaagaagagt ggctgtggcc gtcaaataga tgaagcaaat | 480 |
| tttgtcatgc gatgcaatct ccctccttg tcaagtgaat acactaagga tgttggatcc | 540 |
| aaaagtcagt tagtgacagc taatcccagc ataattcggc aaaggtttca gaaccttctg | 600 |
| tggtccagaa agacatttgt ggacaacatg aaaatctata accacagtta catctacatg | 660 |
| cctgcctttt ctatgaagac aggaacagag ccatctttga gggttattat tacactgtca | 720 |
| gatgttggtg ccaatcaaac agtgctgttt gccaaccca acttttctgcg tagcattgga | 780 |
| aagttctgga aaaagtagagg aatccatgcc aagcgcctgt ccacaggact tttttctggtg | 840 |
| agcgcagctc tgggtctctg tgaagaggtg gccatctatg gcttctggcc cttctctgtg | 900 |

```
aatatgcatg agcagcccat cagccaccac tactatgaca acgtcttacc cttttctggc    960
ttccatgcca tgcccgagga atttctccaa ctctggtatc ttcataaaat cggtgcactg    1020
agaatgcagc tggacccatg tgaagatacc tcactccagc ccacttccta g             1071

<210> SEQ ID NO 137
<211> LENGTH: 744
<212> TYPE: DNA
<213> ORGANISM: Homo sapiens
<300> PUBLICATION INFORMATION:
<302> TITLE: FGF14
<310> PATENT DOCUMENT NUMBER: NM004115

<400> SEQUENCE: 137
atggccgcgg ccatcgctag cggcttgatc cgccagaagc ggcaggcgcg ggagcagcac    60
tgggaccggc cgtctgccag caggaggcgg agcagcccca gcaagaaccg cgggctctgc    120
aacggcaacc tggtggatat cttctccaaa gtgcgcatct tcggcctcaa gaagcgcagg    180
ttgcggcgcc aagatcccca gctcaagggt atagtgacca ggttatattg caggcaaggc    240
tactacttgc aaatgcaccc cgatggagct ctcgatggaa ccaaggatga cagcactaat    300
tctacactct tcaacctcat accagtggga ctacgtgttg ttgccatcca gggagtgaaa    360
acagggttgt atatagccat gaatggaaaa ggttacctct acccatcaga acttttttacc    420 cctgaatgca gtttaaaga atctgttttt gaaaattatt atgtaatcta ctcatccatg    480
ttgtacagac aacaggaatc tggtagagcc tggtttttgg gattaaataa ggaagggcaa    540
gctatgaaag ggaacagagt aaagaaaacc aaaccagcag ctcatttttct acccaagcca    600 ttggaagttg ccatgtaccg agaaccatct ttgcatgatg ttggggaaac ggtcccgaag    660
cctggggtga cgccaagtaa aagcacagt gcgtctgcaa taatgaatgg aggcaaacca    720
gtcaacaaga gtaagacaac atag                                            744

<210> SEQ ID NO 138
<211> LENGTH: 1503
<212> TYPE: DNA
<213> ORGANISM: Human immunodeficiency virus
<300> PUBLICATION INFORMATION:
<302> TITLE: gag (HIV)
<310> PATENT DOCUMENT NUMBER: NC001802

<400> SEQUENCE: 138
atgggtgcga gagcgtcagt attaagcggg ggagaattag atcgatggga aaaaattcgg    60
ttaaggccag ggggaaagaa aaaatataaa ttaaaacata tagtatgggc aagcagggag    120
ctagaacgat tcgcagttaa tcctggcctg ttagaaacat cagaaggctg tagacaaata    180
ctgggacagc tacaaccatc ccttcagaca ggatcagaag aacttagatc attatataat    240
acagtagcaa ccctctattg tgtgcatcaa aggatagaga taaaagacac caaggaagct    300
ttagacaaga tagaggaaga gcaaaacaaa agtaagaaaa agcacagca agcagcagct    360 gacacaggac acagcaatca ggtcagccaa aattacccta tagtgcagaa catccagggg    420
caaatggtac atcaggccat atcacctaga actttaaatg catgggtaaa agtagtagaa    480
gagaaggctt tcagcccaga agtgataccc atgttttcag cattatcaga aggagccacc    540
ccacaagatt taaacaccat gctaaacaca gtggggggac atcaagcagc catgcaaatg    600
ttaaaagaga ccatcaatga ggaagctgca gaatgggata gagtgcatcc agtgcatgca    660
gggcctattg caccaggcca gatgagagaa ccaaggggaa gtgacatagc aggaactact    720
agtacccttc aggaacaaat aggatggatg acaaataatc cacctatccc agtaggagaa    780
```

| | |
|---|---|
| atttataaaa gatggataat cctgggatta aataaaatag taagaatgta tagccctacc | 840 |
| agcattctgg acataagaca aggaccaaag gaacccttta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt caggagtag gaggacccgg ccataaggca | 1080 |
| agagttttgg ctgaagcaat gagccaagta acaaattcag ctaccataat gatgcagaga | 1140 |
| ggcaatttta ggaaccaaag aaagattgtt aagtgtttca attgtggcaa agaagggcac | 1200 |
| acagccagaa attgcagggc ccctaggaaa aagggctgtt ggaaatgtgg aaaggaagga | 1260 |
| caccaaatga aagattgtac tgagagacag gctaattttt tagggaagat ctggccttcc | 1320 |
| tacaagggaa ggccagggaa ttttcttcag agcagaccag agccaacagc cccaccagaa | 1380 |
| gagagcttca ggtctggggt agagacaaca actccccctc agaagcagga gccgatagac | 1440 |
| aaggaactgt atcctttaac ttccctcagg tcactctttg gcaacgaccc ctcgtcacaa | 1500 |
| taa | 1503 |

<210> SEQ ID NO 139
<211> LENGTH: 1101
<212> TYPE: DNA
<213> ORGANISM: Human immunodeficiency virus
<300> PUBLICATION INFORMATION:
<302> TITLE: TARBP2
<310> PATENT DOCUMENT NUMBER: NM004178

<400> SEQUENCE: 139

| | |
|---|---|
| atgagtgaag aggagcaagg ctccggcact accacgggct gcgggctgcc tagtatagag | 60 |
| caaatgctgg ccgccaaccc aggcaagacc ccgatcagcc ttctgcagga gtatgggacc | 120 |
| agaatagga gacgcctgt gtacgacctt ctcaaagccg agggccaagc ccaccagcct | 180 |
| aatttcacct tccgggtcac cgttggcgac accagctgca ctggtcaggg ccccagcaag | 240 |
| aaggcagcca agcacaaggc agctgaggtg gccctcaaac acctcaaagg ggggagcatg | 300 |
| ctggagccgg ccctggagga cagcagttct ttttctcccc tagactcttc actgcctgag | 360 |
| gacattccgg tttttactgc tgcagcagct gctaccccag ttccatctgt agtcctaacc | 420 |
| aggagccccc ccatggaact gcagccccct gtctccccctc agcagtctga gtgcaacccc | 480 |
| gttggtgctc tgcaggagct ggtggtgcag aaaggctggc ggttgccgga gtacacagtg | 540 |
| acccaggagt ctgggccagc ccaccgcaaa gaattcacca tgacctgtcg agtggagcgt | 600 |
| ttcattgaga ttgggagtgg cacttccaaa aaattggcaa gcggaatgc ggcggccaaa | 660 |
| atgctgcttc gagtgcacac ggtgcctctg gatgcccggg atggcaatga ggtggagcct | 720 |
| gatgatgacc acttctccat tggtgtgggc ttccgcctgg atggtcttcg aaaccggggc | 780 |
| ccaggttgca cctgggattc tctacgaaat tcagtaggag agaagatcct gtccctccgc | 840 |
| agttgctccc tgggctccct gggtgccctg gccctgcct gctgccgtgt cctcagtgag | 900 |
| ctctctgagg agcaggcctt tcacgtcagc tacctggata ttgaggagct gagcctgagt | 960 |
| ggactctgcc agtgcctggt ggaactgtcc acccagccgg ccactgtgtg tcatggctct | 1020 |
| gcaaccacca gggaggcagc ccgtggtgag gctgcccgcc gtgccctgca gtacctcaag | 1080 |
| atcatggcag gcagcaagtg a | 1101 |

<210> SEQ ID NO 140
<211> LENGTH: 219

<212> TYPE: DNA
<213> ORGANISM: Human immunodeficiency virus
<300> PUBLICATION INFORMATION:
<302> TITLE: TAT (HIV)
<310> PATENT DOCUMENT NUMBER: U44023

<400> SEQUENCE: 140

```
atggagccag tagatcctag cctagagccc tggaagcatc caggaagtca gcctaagact      60
gcttgtacca cttgctattg taaagagtgt tgctttcatt gccaagtttg tttcataaca     120
aaaggcttag gcatctccta tggcaggaag aagcggagac agcgacgaag aactcctcaa     180
ggtcatcaga ctaatcaagt ttctctatca aagcagtaa                            219
```

<210> SEQ ID NO 141
<211> LENGTH: 22
<212> TYPE: RNA
<213> ORGANISM: Synthetic sequence
<220> FEATURE:
<223> OTHER INFORMATION: Description of the synthetic sequence: sense
      strand (R1A) of a dsRNA that is homologous to an MDR1 sequence

<400> SEQUENCE: 141

```
ccaucucgaa aagaaguuaa ga                                               22
```

<210> SEQ ID NO 142
<211> LENGTH: 24
<212> TYPE: RNA
<213> ORGANISM: Synthetic sequence
<220> FEATURE:
<223> OTHER INFORMATION: Description of the synthetic sequence:
      antisense strand (R1B) of a dsRNA, that it
      complementary to an MDR1 sequence

<400> SEQUENCE: 142

```
ucuuaacuuc uuuucgagau gggu                                             24
```

<210> SEQ ID NO 143
<211> LENGTH: 22
<212> TYPE: RNA
<213> ORGANISM: Synthetic sequence
<220> FEATURE:
<223> OTHER INFORMATION: Description of the synthetic sequence: sense
      strand (R2A) of a dsRNA that is homologous to an MDR1 sequence

<400> SEQUENCE: 143

```
uauagguucc aggcuugcug ua                                               22
```

<210> SEQ ID NO 144
<211> LENGTH: 22
<212> TYPE: RNA
<213> ORGANISM: Synthetic sequence
<220> FEATURE:
<223> OTHER INFORMATION: Description of the synthetic sequence: sense
      strand (R3A) of a dsRNA that is homologous to an MDR1 sequence

<400> SEQUENCE: 144

```
ccagagaagg ccgcaccugc au                                               22
```

<210> SEQ ID NO 145
<211> LENGTH: 24
<212> TYPE: RNA
<213> ORGANISM: Synthetic sequence
<220> FEATURE:
<223> OTHER INFORMATION: Description of the synthetic sequence:
      antisense strand (R3B) of a dsRNA, that it
      complementary to an MDR1 sequence

```
<400> SEQUENCE: 145
augcaggugc ggccuucucu ggcu                                          24

<210> SEQ ID NO 146
<211> LENGTH: 21
<212> TYPE: RNA
<213> ORGANISM: Synthetic sequence
<220> FEATURE:
<223> OTHER INFORMATION: Description of the synthetic sequence: sense
      strand (R4A) of a dsRNA that is homologous to an MDR1 sequence

<400> SEQUENCE: 146
ccaucucgaa aagaaguuaa g                                             21

<210> SEQ ID NO 147
<211> LENGTH: 21
<212> TYPE: RNA
<213> ORGANISM: Synthetic sequence
<220> FEATURE:
<223> OTHER INFORMATION: Description of the synthetic sequence:
      antisense strand (R4B) of a dsRNA, that it
      complementary to an MDR1 sequence

<400> SEQUENCE: 147
uaacuucuuu ucgagaugggu u                                            21

<210> SEQ ID NO 148
<211> LENGTH: 22
<212> TYPE: RNA
<213> ORGANISM: Synthetic sequence
<220> FEATURE:
<223> OTHER INFORMATION: Description of the synthetic sequence: sense
      strand (S1A) of a dsRNA, that is homologous to the YFP- and
      GFP sequence, respectively

<400> SEQUENCE: 148
ccacaugaag cagcacgacu uc                                            22

<210> SEQ ID NO 149
<211> LENGTH: 22
<212> TYPE: RNA
<213> ORGANISM: Synthetic sequence
<220> FEATURE:
<223> OTHER INFORMATION: Description of the synthetic sequence:
      antisense strand(S1B) of a dsRNA that is
      complementary to the YFP- and GFP sequence, respectively

<400> SEQUENCE: 149
gaagucgugc ugcuucaugu gg                                            22

<210> SEQ ID NO 150
<211> LENGTH: 21
<212> TYPE: RNA
<213> ORGANISM: Synthetic sequence
<220> FEATURE:
<223> OTHER INFORMATION: Description of the synthetic sequence:
      antisense strand(S7A) of a dsRNA that is homologous
      to the YFP- and GFP sequence, respectively

<400> SEQUENCE: 150
ccacaugaag cagcacgacu u                                             21

<210> SEQ ID NO 151
<211> LENGTH: 21
<212> TYPE: RNA
<213> ORGANISM: Synthetic sequence
<220> FEATURE:
```

```
<223> OTHER INFORMATION: Description of the synthetic sequence:
      antisense strand(S7B) of a dsRNA, that is
      complementary to the YFP- and GFP sequence, respectively

<400> SEQUENCE: 151
gucgugcugc uucauguggu c                                              21

<210> SEQ ID NO 152
<211> LENGTH: 24
<212> TYPE: RNA
<213> ORGANISM: Synthetic sequence
<220> FEATURE:
<223> OTHER INFORMATION: Description of the synthetic sequence:
      antisense strand(R2B) of a dsRNA that is
      complementary to the MDR-1 sequence

<400> SEQUENCE: 152
uacagcaagc cuggaaccua uagc                                           24

<210> SEQ ID NO 153
<211> LENGTH: 22
<212> TYPE: RNA
<213> ORGANISM: Synthetic sequence
<220> FEATURE:
<223> OTHER INFORMATION: Description of the synthetic sequence: sense
      strand (K1A) of a dsRNA that is homologous to the 5'-UTR of
      the neomycin sequence

<400> SEQUENCE: 153
acaggaugag gaucguuucg ca                                             22

<210> SEQ ID NO 154
<211> LENGTH: 22
<212> TYPE: RNA
<213> ORGANISM: Synthetic sequence
<220> FEATURE:
<223> OTHER INFORMATION: Description of the synthetic sequence:
      antisense strand(K1B) of a dsRNA that is
      complementary to the 5'-UTR of the neomycin sequence

<400> SEQUENCE: 154
ugcgaaacga uccucauccu gu                                             22

<210> SEQ ID NO 155
<211> LENGTH: 21
<212> TYPE: RNA
<213> ORGANISM: Synthetic sequence
<220> FEATURE:
<223> OTHER INFORMATION: Description of the synthetic sequence: sense
      strand (K3A) of a dsRNA that is homologous to the 5'-UTR of the
      neomycin sequence

<400> SEQUENCE: 155
gaugaggauc guuucgcaug a                                              21

<210> SEQ ID NO 156
<211> LENGTH: 21
<212> TYPE: RNA
<213> ORGANISM: Synthetic sequence
<220> FEATURE:
<223> OTHER INFORMATION: Description of the synthetic sequence:
      antisense strand(K3B) of a dsRNA that
      complementary to the 5'-UTR of the neomycin sequence

<400> SEQUENCE: 156
augcgaaacg auccucaucc u                                              21
```

```
<210> SEQ ID NO 157
<211> LENGTH: 24
<212> TYPE: RNA
<213> ORGANISM: Synthetic sequence
<220> FEATURE:
<223> OTHER INFORMATION: Description of the synthetic sequence: sense
      strand (K2A) of a dsRNA that is homologous to the 5'-UTR of the
      neomycin sequence

<400> SEQUENCE: 157
acaggaugag gaucguuucg caug                                            24

<210> SEQ ID NO 158
<211> LENGTH: 24
<212> TYPE: RNA
<213> ORGANISM: Synthetic sequence
<220> FEATURE:
<223> OTHER INFORMATION: Description of the synthetic sequence:
      antisense strand(K2B) of a dsRNA that is
      complementary to the 5'-UTR of the neomycin sequence

<400> SEQUENCE: 158
ugcgaaacga uccucauccu gucu                                            24

<210> SEQ ID NO 159
<211> LENGTH: 24
<212> TYPE: RNA
<213> ORGANISM: Synthetic sequence
<220> FEATURE:
<223> OTHER INFORMATION: Description of the synthetic sequence:
      antisense strand(S4B) of a dsRNA that is
      complementary to the YFP- and GFP sequence, respectively

<400> SEQUENCE: 159
gaagucgugc ugcuucaugu gguc                                            24

<210> SEQ ID NO 160
<211> LENGTH: 24
<212> TYPE: RNA
<213> ORGANISM: Synthetic sequence
<220> FEATURE:
<223> OTHER INFORMATION: Description of the synthetic sequence: sense
      strand (PKC1 A) of a dsRNA that is homologous to the
      proteinkinase C sequence

<400> SEQUENCE: 160
cuucuccgcc ucacaccgcu gcaa                                            24

<210> SEQ ID NO 161
<211> LENGTH: 22
<212> TYPE: RNA
<213> ORGANISM: Synthetic sequence
<220> FEATURE:
<223> OTHER INFORMATION: Description of the synthetic sequence:
      antisense strand(PKC2 B) of a dsRNA that is
      complementary to the proteinkinase C sequence

<400> SEQUENCE: 161
gcagcggugu gaggcggaga ag                                              22

<210> SEQ ID NO 162
<211> LENGTH: 21
<212> TYPE: RNA
<213> ORGANISM: Synthetic sequence
<220> FEATURE:
<223> OTHER INFORMATION: Description of the synthetic sequence:
      antisense strand(S12B) of a dsRNA that is
      complementary to the YFP- and GFP sequence, respectively
```

-continued

```
<400> SEQUENCE: 162
aagucgugcu gcuucaugug g                                          21

<210> SEQ ID NO 163
<211> LENGTH: 23
<212> TYPE: RNA
<213> ORGANISM: Synthetic sequence
<220> FEATURE:
<223> OTHER INFORMATION: Description of the synthetic sequence:
      antisense strand(S11B) of a dsRNA that is
      complementary to the YFP- and GFP sequence, respectively

<400> SEQUENCE: 163
aagucgugcu gcuucaugug guc                                        23

<210> SEQ ID NO 164
<211> LENGTH: 20
<212> TYPE: RNA
<213> ORGANISM: Synthetic sequence
<220> FEATURE:
<223> OTHER INFORMATION: Description of the synthetic sequence: sense
      strand (S13A) of a dsRNA that is homologous to the YFP- and
      GFP sequence, respectively

<400> SEQUENCE: 164
ccacaugaag cagcacgacu                                            20

<210> SEQ ID NO 165
<211> LENGTH: 22
<212> TYPE: RNA
<213> ORGANISM: Synthetic sequence
<220> FEATURE:
<223> OTHER INFORMATION: Description of the synthetic sequence:
      antisense strand(S13B) of a dsRNA that is
      complementary to the YFP- and GFP sequence, respectively

<400> SEQUENCE: 165
agucgugcug cuucaugugg uc                                         22

<210> SEQ ID NO 166
<211> LENGTH: 20
<212> TYPE: RNA
<213> ORGANISM: Synthetic sequence
<220> FEATURE:
<223> OTHER INFORMATION: Description of the synthetic sequence:
      antisense strand(S14B) of a dsRNA that is
      complementary to the YFP- and GFP sequence, respectively

<400> SEQUENCE: 166
agucgugcug cuucaugugg                                            20

<210> SEQ ID NO 167
<211> LENGTH: 24
<212> TYPE: RNA
<213> ORGANISM: Synthetic sequence
<220> FEATURE:
<223> OTHER INFORMATION: Description of the synthetic sequence: sense
      strand (S4A) of a dsRNA that is homologous to the YFP- and
      GFP sequence, respectively

<400> SEQUENCE: 167
ccacaugaag cagcacgacu ucuu                                       24

<210> SEQ ID NO 168
<211> LENGTH: 21
<212> TYPE: RNA
<213> ORGANISM: Synthetic sequence
```

```
<220> FEATURE:
<223> OTHER INFORMATION: Description of the synthetic sequence: sense
      strand (ES-7A) of a dsRNA that is homologous to the human
      EGFR sequence

<400> SEQUENCE: 168
aacaccgcag caugucaaga u                                           21

<210> SEQ ID NO 169
<211> LENGTH: 21
<212> TYPE: RNA
<213> ORGANISM: Synthetic sequence
<220> FEATURE:
<223> OTHER INFORMATION: Description of the synthetic sequence:
      antisense strand(ES-7B) of a dsRNA that is
      complementary to the human EGFR sequence

<400> SEQUENCE: 169
cuugacaugc ugcgguguuu u                                           21

<210> SEQ ID NO 170
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-8A) of a dsRNA that is homologous to the human
      EGFR sequence

<400> SEQUENCE: 170
aaguuaaaau ucccgucgcu au                                          22

<210> SEQ ID NO 171
<211> LENGTH: 22
<212> TYPE: RNA
<213> ORGANISM: Synthetic sequence
<220> FEATURE:
<223> OTHER INFORMATION: Description of the synthetic sequence:
      antisense strand(ES-8B) of a dsRNA that is
      complementary to the human EGFR sequence

<400> SEQUENCE: 171
ugauagcgac gggaauuuua ac                                          22

<210> SEQ ID NO 172
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-2A) of a dsRNA that is homologous to the human
      EGFR sequence

<400> SEQUENCE: 172
agugugaucc aagcugcccc aa                                          22

<210> SEQ ID NO 173
<211> LENGTH: 24
<212> TYPE: RNA
<213> ORGANISM: Synthetic sequence
<220> FEATURE:
<223> OTHER INFORMATION: Description of the synthetic sequence:
      antisense strand(ES-5B) of a dsRNA that is
      complementary to the human EGFR sequence

<400> SEQUENCE: 173
uugggacagc uuggaucaca cuuu                                        24
```

We claim:

1. A double-stranded ribonucleic acid (dsRNA) for inhibiting the expression of a target gene in a cell in vitro, comprising a complementary RNA strand and a sense RNA strand, wherein the sense RNA strand comprises a nucleotide sequence which is substantially identical to the corresponding part of the target gene, wherein the complementary RNA strand comprises a complementary nucleotide sequence which is complementary to an mRNA transcript formed during expression of the target gene, wherein the complementary strand specifically hybridizes with the mRNA transcript, wherein the complementary RNA strand comprises a 3'-end and a 5'-end, wherein the 3'-end has a nucleotide overhang of 1 to 4 nucleotides and wherein the dsRNA at the 5'-end of the complementary RNA strand is blunt, and wherein the dsRNA is less than 25 base pairs in length and wherein the two RNA strands of the dsRNA are separate and non-linked, and wherein the target gene comprises a sequence of SEQ ID NO:51.

2. The dsRNA of claim 1, wherein the nucleotide overhang is 1 or 2 nucleotides in length.

3. The dsRNA of claim 1, wherein the nucleotides of the nucleotide overhang are replaced with nucleoside thiophosphates.

4. A method of inhibiting the expression of a target gene in a cell in vitro, the method comprising:
(a) introducing into the cell a double-stranded ribonucleic acid (dsRNA) for inhibiting the expression of a target gene in a cell in vitro, wherein the dsRNA comprises a complementary RNA strand and a sense RNA strand, wherein the sense RNA strand comprises a nucleotide sequence which is substantially identical to the corresponding part of the target gene, wherein the complementary RNA strand comprises a complementary nucleotide sequence which is complementary to an mRNA transcript formed during expression of the target gene, wherein the complementary strand specifically hybridizes with the mRNA transcript, wherein the complementary RNA strand comprises a 3'-end and a 5'-end, wherein the 3'-end has a nucleotide overhang of 1 to 4 nucleotides and wherein the dsRNA at the 5'-end of the complementary RNA strand is blunt, and wherein the dsRNA less than 25 base pairs in length and wherein the two RNA strands of the dsRNA are separate and non-linked, and wherein the target gene comprises a sequence of SEQ ID NO:51; and
(b) maintaining the cell produced in step (a) for a time sufficient to obtain degradation of the mRNA transcript of the target gene, thereby inhibiting expression of the target gene in the cell.

5. The method of claim 4, wherein the nucleotide overhang is 1 or 2 nucleotides in length.

6. The method of claim 4, wherein the nucleotides of the nucleotide overhang are replaced with nucleoside thiophosphates.

* * * * *

UNITED STATES PATENT AND TRADEMARK OFFICE
CERTIFICATE OF CORRECTION

PATENT NO. : 7,829,693 B2  Page 1 of 1
APPLICATION NO. : 10/384339
DATED : November 9, 2010
INVENTOR(S) : Roland Kreutzer et al.

It is certified that error appears in the above-identified patent and that said Letters Patent is hereby corrected as shown below:

In claim 4, Column 278, Line 15, insert --is-- between "dsRNA" and "less".

Signed and Sealed this
Twelfth Day of April, 2011

David J. Kappos
*Director of the United States Patent and Trademark Office*